(12) United States Patent
Sadhu et al.

(10) Patent No.: US 6,949,535 B2
(45) Date of Patent: Sep. 27, 2005

(54) INHIBITORS OF HUMAN PHOSPHATIDYL-INOSITOL 3-KINASE DELTA

(75) Inventors: Chanchal Sadhu, Bothell, WA (US); Ken Dick, Bothell, WA (US); Jennifer Treiberg, Bothell, WA (US); C. Gregory Sowell, Mukilteo, WA (US); Edward A. Kesicki, Bothell, WA (US); Amy Oliver, Bothell, WA (US)

(73) Assignee: ICOS Corporation, Bothell, WA (US)

(*) Notice: Subject to any disclaimer, the term of this patent is extended or adjusted under 35 U.S.C. 154(b) by 61 days.

(21) Appl. No.: 10/697,912

(22) Filed: Oct. 30, 2003

(65) Prior Publication Data

US 2004/0266780 A1 Dec. 30, 2004

Related U.S. Application Data

(60) Division of application No. 10/027,591, filed on Oct. 19, 2001, now Pat. No. 6,667,300, which is a continuation-in-part of application No. 09/841,341, filed on Apr. 24, 2001, now Pat. No. 6,518,277.
(60) Provisional application No. 60/199,655, filed on Apr. 25, 2000, and provisional application No. 60/238,057, filed on Oct. 5, 2000.

(51) Int. Cl.[7] ..................... A61K 31/33; A61K 31/517; C07D 239/72; C07D 473/00
(52) U.S. Cl. ................. 514/183; 514/266.1; 514/266.2; 514/266.23; 514/266.3; 544/264; 544/265; 544/283; 544/287; 544/290; 544/319
(58) Field of Search ................ 514/183, 266.1, 514/266.2, 266, 266.3; 544/264, 265, 283, 287, 290, 319

(56) References Cited

U.S. PATENT DOCUMENTS

| | | | |
|---|---|---|---|
| 3,322,756 A | 5/1967 | Ruschig et al. | 260/247.2 |
| 3,984,555 A | 10/1976 | Amschler et al. | 424/251 |
| 4,183,931 A | 1/1980 | Wolfe et al. | 424/251 |
| 4,225,489 A | 9/1980 | Rolf et al. | 260/154 |
| 5,378,725 A | 1/1995 | Bonjouklian et al. | 514/453 |
| 5,480,906 A | 1/1996 | Creemer et al. | 514/453 |
| 5,858,753 A | 1/1999 | Chantry et al. | 435/194 |
| 6,046,049 A | 4/2000 | Monia et al. | 435/375 |

FOREIGN PATENT DOCUMENTS

| | | | |
|---|---|---|---|
| EP | 0 675 124 | 4/1995 | ......... C07D/473/30 |
| EP | 0 884 310 | 12/1998 | |
| EP | 0 900 568 | 3/1999 | |
| GB | 1356763 | 12/1974 | |
| JP | 55 118918 | 9/1980 | |
| JP | 55 118917 | 12/1980 | |

(Continued)

OTHER PUBLICATIONS

Y-T. Chang et al., "Inositol phospholipid pathway inhibitors and regulators," *Exp. Opin. Ther. Patents*, 11, (1) pp. 45–59 (2001).

(Continued)

*Primary Examiner*—Richard L. Raymond
*Assistant Examiner*—Sudhaker B. Patel
(74) *Attorney, Agent, or Firm*—Marshall, Gerstein & Borun LLP

(57) ABSTRACT

Methods of inhibiting phosphatidylinositol 3-kinase delta isoform (PI3Kδ) activity, and methods of treating diseases, such as disorders of immunity and inflammation, in which PI3Kδ plays a role in leukocyte function are disclosed. Preferably, the methods employ active agents that selectively inhibit PI3Kδ, while not significantly inhibiting activity of other PI3K isoforms. Compounds are provided that inhibit PI3Kδ activity, including compounds that selectively inhibit PI3Kδ activity. Methods of using PI3Kδ inhibitory compounds to inhibit cancer cell growth or proliferation are also provided. Accordingly, the invention provides methods of using PI3Kδ inhibitory compounds to inhibit PI3Kδ-mediated processes in vitro and in vivo.

15 Claims, 9 Drawing Sheets

FOREIGN PATENT DOCUMENTS

| | | | | |
|---|---|---|---|---|
| JP | 56 2322 | 1/1981 | | |
| WO | WO 94/17090 | 4/1994 | ......... | C07H/19/167 |
| WO | 9524379 | * 9/1995 | | |
| WO | WO 96/04923 | 2/1996 | .......... | A61K/31/70 |
| WO | WO 96/25488 | 8/1996 | ............ | C12N/9/12 |
| WO | WO 97/41097 | 11/1997 | | |
| WO | WO 97/46688 | 12/1997 | ........... | C12N/15/54 |
| WO | WO 98/33802 | 8/1998 | ......... | C07F/9/6512 |
| WO | WO 99/08501 | 2/1999 | | |
| WO | WO 99/34804 | 7/1999 | .......... | A61K/31/52 |
| WO | WO 01/00881 | 1/2001 | ............ | C12Q/1/68 |
| WO | WO 01/81346 | 5/2001 | | |
| WO | WO 01/53266 | 7/2001 | ......... | C07D/215/38 |
| WO | WO 01/57034 | 8/2001 | ......... | C07D/413/06 |
| WO | WO 01/30768 | 11/2001 | | |

OTHER PUBLICATIONS

Computer Search (8 pages).

J. Downward, "A target for PI(3) kinase," *Nature, 376*, pp. 553–554 (1995).

S. Volinia et al., "Molecular cloning, cDNA sequence, and chromosomal localization of the human phosphatidylinositol 3–kinase p110α (PIK3CA) gene," *Genomics, 24*, pp. 472–477 (1994).

B. Vanhaesebroeck et al., "A novel human phosphoinositide 3–kinase," *FASEB Journal, 10*, p. A1395 (1996).

Boudewijn et al., "Protein kinase B (c–Akt) in phosphatidylinositol–3–OH kinase signal transduction," *Nature, 376*, pp. 599–602 (1995).

Eichholtz et al., "A myristoylated pseudosubstrate peptide, a novel protein kinase C inhibitor," *J. Biol. Chem., 268*, pp. 1982–1986 (1993).

Hiles et al., "Phosphatidylinositol 3–kinase: Structure and expression of the 100 kd catalytic subunit," *Cell, 70*, pp. 419–429 (1992).

Hu et al., "Cloning of a novel, ubiquitously expressed human phosphatidylinositol 3–kinase and identification of its binding site on p85," *Mol. Cell. Biol., 13*, pp. 7677–7688 (1993).

Hu et al., "Ras–dependent induction of cellular responses by constitutively active phosphatidylinositol–3 kinase," *Science, 268*, pp. 100–102 (1995).

T. Hunter, "When is a lipid kinase not a lipid kinase? When it is a protein kinase," *Cell, 83*, pp. 1–4 (1995).

Otsu et al., "Characterization of two 85 kd proteins that associate with receptor tyrosine kinases, middle–T/pp60$^{c-STC}$ complexes, and PI3–kinase," *Cell, 65*, pp. 91–104 (1991).

Pages et al., "Binding of phosphatidyl–inositol–D–OH kinase to CD28 is required for T–cell signalling," *Nature, 369*, pp. 327–329 (1994).

Panayotou et al., "Phosphatidyl–inositol 3–kinase: A key enzyme in diverse signalling processes," *Trends in Cell Biol., 2*, pp. 358–360 (1992).

P.J. Parker, "PI 3–kinase puts GTP on the Rac," *Current Biology, 5*, pp. 577–579 (1995).

Rameh et al., "Phosphatidylinositol (3,4,5)$P_3$ interacts with SH2 domains and modulates PI 3–kinase associate with tyrosine–phosphorylated proteins," *Cell, 83*, pp. 821–830 (1995).

Rodriguez–Viciana et al., "Activation of phosphoinositide 3–kinase by interaction ewith ras and by point mutation," *EMBO Journal., 15*, pp. 2442–2451 (1996).

C.E. Rudd, "Upstream–downstream" CD28 cosignaling pathways and T cell function, *Immunity, 4*, pp. 527–534 (1996).

Stephens et al., "Characterization of a phosphatidylinositol-specific phosphoinositide 3–kinase from mammalian cells," *Current Biology, 4*, pp. 203–214 (1994).

Stoyanov et al., "Cloning and characterization of a G protein–activated human phosphoinositied–3 kinase," *Science, 269*, pp. 690–693 (1995).

Thelan et al., "Wortmannin binds specifically to 1–phosphatidylinositol 3–kinase while inhibiting guanine nucleotide–binding protein–coupled receptor signaling in neutrophil leukocytes," *Proc. Natl. Acad. Sci. USA., 91*, pp. 4960–4964 (1994).

Volinia et al., "Chromosomal localization of human p85α, a subunit of phosphatidylinositol 3–kinase, and its homologous p85β," *Oncogene, 7*, pp. 789–793 (1992).

Yao et al., "Requirement for phosphatidylinositol–3 kinase in the prevention of apoptosis by nerve growth factor," *Science, 267*, pp. 2003–2006 (1995).

D. Chantry et al, "p110δ, a novel phosphatidylinositol 3–kinase catalytic subunit that associates with p85 and is expressed predominantly in leukocytes," *J. Biological Chemistry, 272(31)*, pp. 19236–19241 (1997).

Genbank Accession No. U57843, "Human phosphatidylinositol 3–kinase delta catalytic subunit mRNA," deposited by A.J. Morris, dated May 10, 1997.

B. Vanhaesebroeck et al., "p110δ, a novel phosphoinositide 3–kinase in leukocytes," *Proc. Natl. Acad. Sci., USA, 94*, pp. 4330–4335 (1997).

S. Volinia et al., "A human phosphatidylinositol 3–kinase complex related to the yeast Vps34p–Vps15p protein sorting system," *EMBO J., 14(14)*, pp. 3339–3348 (1995).

Carnero et al., Wortmannin, an inhibitor of phosphatidyl–inositol 3–kinase, induces oocyte maturation through a MPF–MAPK–dependent pathway, *FEB Letters, 422*, pp. 155–159 (1998).

Ager et al., "Synthesis and central Nervous system activity of quinazolinones methaqualone," J. Medicinal Chem., 20/3, 379–86 (1977).

CAS Abstract DN 86:83505–1977:83505, pp. 111–118.

T.L. Rathman et al., American Chemical Society, 45, pp. 2169–2176 (1980).

Ismail et al., Chemical Abstracts, vol. 98, No. 1, p. 406 (1983).

Parasharya et al., Chemical Abstracts, vol. 121, No. 9, p. 1065 (1994).

Barakat et al., Chemical Abstracts, vol. 124, No. 21, p. 1334 (1996).

Chern et al., Chemical Abstracts, vol. 129, No. 16, p. 676 (1998).

El–Feky et al., Chemical Abstracts, vol. 131, No. 23, p. 497 (1999).

El–Feky et al., Chemical Abstracts, vol. 106, No. 13, p. 650 (1987).

M.F. Hassan et al., Chinese Journal of Chemistry, vol. 9, No. 3, pp. 262–269 (1991).

Chemical Abstract 106:102196.

* cited by examiner

SEQUENCE LISTING

<160> NUMBER OF SEQ ID NOS: 6

<210> SEQ ID NO 1
<211> LENGTH: 5220
<212> TYPE: DNA
<213> ORGANISM: Human p110delta complete cDNA
<220> FEATURE:
<221> NAME/KEY: CDS
<222> LOCATION: (196)..(3327)

<400> SEQUENCE: 1

```
cagtcgctcc gagcggccgc gagcagagcc gcccagccct gtcagctgcg ccgggacgat      60
aaggagtcag gccagggcgg gatgacactc attgattcta aagcatcttt aatctgccag     120
gcggaggggg ctttgctggt ctttcttgga ctattccaga gaggacaact gtcatctggg     180
aagtaacaac gcagg atg ccc cct ggg gtg gac tgc ccc atg gaa ttc tgg      231
                 Met Pro Pro Gly Val Asp Cys Pro Met Glu Phe Trp
                  1               5                  10 acc aag gag gag aat cag agc gtt gtg gtt gac ttc ctg ctg ccc aca       279
Thr Lys Glu Glu Asn Gln Ser Val Val Val Asp Phe Leu Leu Pro Thr
         15                  20                  25 ggg gtc tac ctg aac ttc cct gtg tcc cgc aat gcc aac ctc agc acc       327
Gly Val Tyr Leu Asn Phe Pro Val Ser Arg Asn Ala Asn Leu Ser Thr
     30                  35                  40 atc aag cag ctg ctg tgg cac cgc gcc cag tat gag ccg ctc ttc cac       375
Ile Lys Gln Leu Leu Trp His Arg Ala Gln Tyr Glu Pro Leu Phe His
 45                  50                  55                  60 atg ctc agt ggc ccc gag gcc tat gtg ttc acc tgc atc aac cag aca       423
Met Leu Ser Gly Pro Glu Ala Tyr Val Phe Thr Cys Ile Asn Gln Thr
                 65                  70                  75 gcg gag cag caa gag ctg gag gac gag caa cgg cgt ctg tgt gac gtg       471
Ala Glu Gln Gln Glu Leu Glu Asp Glu Gln Arg Arg Leu Cys Asp Val
             80                  85                  90 cag ccc ttc ctg ccc gtc ctg cgc ctg gtg gcc cgt gag ggc gac cgc       519
Gln Pro Phe Leu Pro Val Leu Arg Leu Val Ala Arg Glu Gly Asp Arg
         95                 100                 105 gtg aag aag ctc atc aac tca cag atc agc ctc ctc atc ggc aaa ggc       567
Val Lys Lys Leu Ile Asn Ser Gln Ile Ser Leu Leu Ile Gly Lys Gly
    110                 115                 120 ctc cac gag ttt gac tcc ttg tgc gac cca gaa gtg aac gac ttt cgc       615
Leu His Glu Phe Asp Ser Leu Cys Asp Pro Glu Val Asn Asp Phe Arg
125                 130                 135                 140 gcc aag atg tgc caa ttc tgc gag gag gcg gcc gcc cgc cgg cag cag       663
Ala Lys Met Cys Gln Phe Cys Glu Glu Ala Ala Ala Arg Arg Gln Gln
                145                 150                 155 ctg ggc tgg gag gcc tgg ctg cag tac agt ttc ccc ctg cag ctg gag       711
Leu Gly Trp Glu Ala Trp Leu Gln Tyr Ser Phe Pro Leu Gln Leu Glu
                160                 165                 170 ccc tcg gct caa acc tgg ggg cct ggt acc ctg cgg ctc ccg aac cgg       759
Pro Ser Ala Gln Thr Trp Gly Pro Gly Thr Leu Arg Leu Pro Asn Arg
            175                 180                 185 gcc ctt ctg gtc aac gtt aag ttt gag ggc agc gag gag agc ttc acc       807
Ala Leu Leu Val Asn Val Lys Phe Glu Gly Ser Glu Glu Ser Phe Thr
        190                 195                 200
```

-continued

| | | |
|---|---|---|
| ttc cag gtg tcc acc aag gac gtg ccg ctg gcg ctg atg gcc tgt gcc<br>Phe Gln Val Ser Thr Lys Asp Val Pro Leu Ala Leu Met Ala Cys Ala<br>205                        210                      215                      220 | 855 | |
| ctg cgg aag aag gcc aca gtg ttc cgg cag ccg ctg gtg gag cag ccg<br>Leu Arg Lys Lys Ala Thr Val Phe Arg Gln Pro Leu Val Glu Gln Pro<br>                        225                      230                      235 | 903 | |
| gaa gac tac acg ctg cag gtg aac ggc agg cat gag tac ctg tat ggc<br>Glu Asp Tyr Thr Leu Gln Val Asn Gly Arg His Glu Tyr Leu Tyr Gly<br>        240                      245                      250 | 951 | |
| aac tac ccg ctc tgc cag ttc cag tac atc tgc agc tgc ctg cac agt<br>Asn Tyr Pro Leu Cys Gln Phe Gln Tyr Ile Cys Ser Cys Leu His Ser<br>                255                      260                      265 | 999 | |
| ggg ttg acc cct cac ctg acc atg gtc cat tcc tcc tcc atc ctc gcc<br>Gly Leu Thr Pro His Leu Thr Met Val His Ser Ser Ser Ile Leu Ala<br>270                        275                      280 | 1047 | |
| atg cgg gat gag cag agc aac cct gcc ccc cag gtc cag aaa ccg cgt<br>Met Arg Asp Glu Gln Ser Asn Pro Ala Pro Gln Val Gln Lys Pro Arg<br>285                        290                      295                      300 | 1095 | |
| gcc aaa cca cct ccc att cct gcg aag aag cct tcc tct gtg tcc ctg<br>Ala Lys Pro Pro Pro Ile Pro Ala Lys Lys Pro Ser Ser Val Ser Leu<br>                        305                      310                      315 | 1143 | |
| tgg tcc ctg gag cag ccg ttc cgc atc gag ctc atc cag ggc agc aaa<br>Trp Ser Leu Glu Gln Pro Phe Arg Ile Glu Leu Ile Gln Gly Ser Lys<br>                        320                      325                      330 | 1191 | |
| gtg aac gcc gac gag cgg atg aag ctg gtg gtg cag gcc ggg ctt ttc<br>Val Asn Ala Asp Glu Arg Met Lys Leu Val Val Gln Ala Gly Leu Phe<br>        335                      340                      345 | 1239 | |
| cac ggc aac gag atg ctg tgc aag acg gtg tcc agc tcg gag gtg agc<br>His Gly Asn Glu Met Leu Cys Lys Thr Val Ser Ser Ser Glu Val Ser<br>350                        355                      360 | 1287 | |
| gtg tgc tcg gag ccc gtg tgg aag cag cgg ctg gag ttc gac atc aac<br>Val Cys Ser Glu Pro Val Trp Lys Gln Arg Leu Glu Phe Asp Ile Asn<br>365                        370                      375                      380 | 1335 | |
| atc tgc gac ctg ccc cgc atg gcc cgt ctc tgc ttt gcg ctg tac gcc<br>Ile Cys Asp Leu Pro Arg Met Ala Arg Leu Cys Phe Ala Leu Tyr Ala<br>                        385                      390                      395 | 1383 | |
| gtg atc gag aaa gcc aag aag gct cgc tcc acc aag aag aag tcc aag<br>Val Ile Glu Lys Ala Lys Lys Ala Arg Ser Thr Lys Lys Lys Ser Lys<br>                400                      405                      410 | 1431 | |
| aag gcg gac tgc ccc att gcc tgg gcc aac ctc atg ctg ttt gac tac<br>Lys Ala Asp Cys Pro Ile Ala Trp Ala Asn Leu Met Leu Phe Asp Tyr<br>        415                      420                      425 | 1479 | |
| aag gac cag ctt aag acc ggg gaa cgc tgc ctc tac atg tgg ccc tcc<br>Lys Asp Gln Leu Lys Thr Gly Glu Arg Cys Leu Tyr Met Trp Pro Ser<br>430                        435                      440 | 1527 | |
| gtc cca gat gag aag ggc gag ctg ctg aac ccc acg ggc act gtg cgc<br>Val Pro Asp Glu Lys Gly Glu Leu Leu Asn Pro Thr Gly Thr Val Arg<br>445                        450                      455                      460 | 1575 | |
| agt aac ccc aac acg gat agc gcc gct gcc ctg ctc atc tgc ctg ccc<br>Ser Asn Pro Asn Thr Asp Ser Ala Ala Ala Leu Leu Ile Cys Leu Pro<br>                        465                      470                      475 | 1623 | |
| gag gtg gcc ccg cac ccc gtg tac tac ccc gcc ctg gag aag atc ttg<br>Glu Val Ala Pro His Pro Val Tyr Tyr Pro Ala Leu Glu Lys Ile Leu<br>                        480                      485                      490 | 1671 | |
| gag ctg ggg cga cac agc gag tgt gtg cat gtc acc gag gag gag cag<br>Glu Leu Gly Arg His Ser Glu Cys Val His Val Thr Glu Glu Glu Gln<br>        495                      500                      505 | 1719 | |
| ctg cag ctg cgg gaa atc ctg gag cgg cgg ggg tct ggg gag ctg tat<br>Leu Gln Leu Arg Glu Ile Leu Glu Arg Arg Gly Ser Gly Glu Leu Tyr<br>510                        515                      520 | 1767 | |

```
gag cac gag aag gac ctg gtg tgg aag ctg cgg cat gaa gtc cag gag     1815
Glu His Glu Lys Asp Leu Val Trp Lys Leu Arg His Glu Val Gln Glu
525                 530                 535                 540 cac ttc ccg gag gcg cta gcc cgg ctg ctg ctc gtc acc aag tgg aac     1863
His Phe Pro Glu Ala Leu Ala Arg Leu Leu Leu Val Thr Lys Trp Asn
                545                 550                 555 aag cat gag gat gtg gcc cag atg ctc tac ctg ctg tgc tcc tgg ccg     1911
Lys His Glu Asp Val Ala Gln Met Leu Tyr Leu Leu Cys Ser Trp Pro
            560                 565                 570 gag ctg ccc gtc ctg agc gcc ctg gag ctg cta gac ttc agc ttc ccc     1959
Glu Leu Pro Val Leu Ser Ala Leu Glu Leu Leu Asp Phe Ser Phe Pro
        575                 580                 585 gat tgc cac gta ggc tcc ttc gcc atc aag tcg ctg cgg aaa ctg acg     2007
Asp Cys His Val Gly Ser Phe Ala Ile Lys Ser Leu Arg Lys Leu Thr
    590                 595                 600 gac gat gag ctg ttc cag tac ctg ctg cag ctg gtg cag gtg ctc aag     2055
Asp Asp Glu Leu Phe Gln Tyr Leu Leu Gln Leu Val Gln Val Leu Lys
605                 610                 615                 620 tac gag tcc tac ctg gac tgc gag ctg acc aaa ttc ctg ctg gac cgg     2103
Tyr Glu Ser Tyr Leu Asp Cys Glu Leu Thr Lys Phe Leu Leu Asp Arg
                625                 630                 635 gcc ctg gcc aac cgc aag atc ggc cac ttc ctt ttc tgg cac ctc cgc     2151
Ala Leu Ala Asn Arg Lys Ile Gly His Phe Leu Phe Trp His Leu Arg
            640                 645                 650 tcc gag atg cac gtg ccg tcg gtg gcc ctg cgc ttc ggc ctc atc ctg     2199
Ser Glu Met His Val Pro Ser Val Ala Leu Arg Phe Gly Leu Ile Leu
        655                 660                 665 gag gcc tac tgc agg ggc agc acc cac cac atg aag gtg ctg atg aag     2247
Glu Ala Tyr Cys Arg Gly Ser Thr His His Met Lys Val Leu Met Lys
    670                 675                 680 cag ggg gaa gca ctg agc aaa ctg aag gcc ctg aat gac ttc gtc aag     2295
Gln Gly Glu Ala Leu Ser Lys Leu Lys Ala Leu Asn Asp Phe Val Lys
685                 690                 695                 700 ctg agc tct cag aag acc ccc aag ccc cag acc aag gag ctg atg cac     2343
Leu Ser Ser Gln Lys Thr Pro Lys Pro Gln Thr Lys Glu Leu Met His
                705                 710                 715 ttg tgc atg cgg cag gag gcc tac cta gag gcc ctc tcc cac ctg cag     2391
Leu Cys Met Arg Gln Glu Ala Tyr Leu Glu Ala Leu Ser His Leu Gln
            720                 725                 730 tcc cca ctc gac ccc agc acc ctg ctg gct gaa gtc tgc gtg gag cag     2439
Ser Pro Leu Asp Pro Ser Thr Leu Leu Ala Glu Val Cys Val Glu Gln
        735                 740                 745 tgc acc ttc atg gac tcc aag atg aag ccc ctg tgg atc atg tac agc     2487
Cys Thr Phe Met Asp Ser Lys Met Lys Pro Leu Trp Ile Met Tyr Ser
    750                 755                 760 aac gag gag gca ggc agc ggc ggc agc gtg ggc atc atc ttt aag aac     2535
Asn Glu Glu Ala Gly Ser Gly Gly Ser Val Gly Ile Ile Phe Lys Asn
765                 770                 775                 780 ggg gat gac ctc cgg cag gac atg ctg acc ctg cag atg atc cag ctc     2583
Gly Asp Asp Leu Arg Gln Asp Met Leu Thr Leu Gln Met Ile Gln Leu
                785                 790                 795 atg gac gtc ctg tgg aag cag gag ggg ctg gac ctg agg atg acc ccc     2631
Met Asp Val Leu Trp Lys Gln Glu Gly Leu Asp Leu Arg Met Thr Pro
            800                 805                 810 tat ggc tgc ctc ccc acc ggg gac cgc aca ggc ctc att gag gtg gta     2679
Tyr Gly Cys Leu Pro Thr Gly Asp Arg Thr Gly Leu Ile Glu Val Val
        815                 820                 825 ctc cgt tca gac acc atc gcc aac atc caa ctc aac aag agc aac atg     2727
Leu Arg Ser Asp Thr Ile Ala Asn Ile Gln Leu Asn Lys Ser Asn Met
```

-continued

| | | |
|---|---|---|
| gca gcc aca gcc gcc ttc aac aag gat gcc ctg ctc aac tgg ctg aag<br>Ala Ala Thr Ala Ala Phe Asn Lys Asp Ala Leu Leu Asn Trp Leu Lys<br>845                        850                        855                        860 | 2775 |

(positions 830, 835, 840 headers above)

```
                830                 835                840
gca gcc aca gcc gcc ttc aac aag gat gcc ctg ctc aac tgg ctg aag      2775
Ala Ala Thr Ala Ala Phe Asn Lys Asp Ala Leu Leu Asn Trp Leu Lys
845                 850                 855                 860 tcc aag aac ccg ggg gag gcc ctg gat cga gcc att gag gag ttc acc      2823
Ser Lys Asn Pro Gly Glu Ala Leu Asp Arg Ala Ile Glu Glu Phe Thr
                    865                 870                 875 ctc tcc tgt gct ggc tat tgt gtg gcc aca tat gtg ctg ggc att ggc      2871
Leu Ser Cys Ala Gly Tyr Cys Val Ala Thr Tyr Val Leu Gly Ile Gly
                        880                 885                 890 gat cgg cac agc gac aac atc atg atc cga gag agt ggg cag ctg ttc      2919
Asp Arg His Ser Asp Asn Ile Met Ile Arg Glu Ser Gly Gln Leu Phe
                895                 900                 905 cac att gat ttt ggc cac ttt ctg ggg aat ttc aag acc aag ttt gga      2967
His Ile Asp Phe Gly His Phe Leu Gly Asn Phe Lys Thr Lys Phe Gly
    910                 915                 920 atc aac cgc gag cgt gtc cca ttc atc ctc acc tat gac ttt gtc cat      3015
Ile Asn Arg Glu Arg Val Pro Phe Ile Leu Thr Tyr Asp Phe Val His
925                 930                 935                 940 gtg att cag cag ggg aag act aat aat agt gag aaa ttt gaa cgg ttc      3063
Val Ile Gln Gln Gly Lys Thr Asn Asn Ser Glu Lys Phe Glu Arg Phe
                    945                 950                 955 cgg ggc tac tgt gaa agg gcc tac acc atc ctg cgg cgc cac ggg ctt      3111
Arg Gly Tyr Cys Glu Arg Ala Tyr Thr Ile Leu Arg Arg His Gly Leu
                960                 965                 970 ctc ttc ctc cac ctc ttt gcc ctg atg cgg gcg gca ggc ctg cct gag      3159
Leu Phe Leu His Leu Phe Ala Leu Met Arg Ala Ala Gly Leu Pro Glu
                975                 980                 985 ctc agc tgc tcc aaa gac atc cag tat ctc aag gac  tcc ctg gca ctg     3207
Leu Ser Cys Ser Lys Asp Ile Gln Tyr Leu Lys Asp  Ser Leu Ala Leu
                    990                 995                 1000 ggg aaa aca gag gag gag gca ctg aag cac ttc  cga gtg aag ttt         3252
Gly Lys Thr Glu Glu Glu Ala Leu Lys His Phe  Arg Val Lys Phe
1005                1010                1015 aac gaa gcc ctc cgt gag agc tgg aaa acc aaa  gtg aac tgg ctg         3297
Asn Glu Ala Leu Arg Glu Ser Trp Lys Thr Lys  Val Asn Trp Leu
1020                1025                1030 gcc cac aac gtg tcc aaa gac aac agg cag tagtggctcc tcccagccct        3347
Ala His Asn Val Ser Lys Asp Asn Arg Gln
1035                1040 gggcccaaga ggaggcggct gcgggtcgtg gggaccaagc acattggtcc taaagggct     3407 gaagagcctg aactgcacct aacgggaaag aaccgacatg gctgccttt gtttacactg     3467 gttatttatt tatgacttga aatagtttaa ggagctaaac agccataaac ggaaacgcct    3527
ccttcattca gcggcggtgc tgggcccccc gaggctgcac ctggctctcg gctgaggatt    3587
gtcaccccaa gtcttccagc tggtggatct gggcccagca agactgttc tcctcccgag     3647 ggaaccttct tcccaggcct cccgccagac tgcctgggtc ctggcgcctg gcggtcacct    3707
ggtgcctact gtccgacagg atgcctcgat cctcgtgcga cccacccctgt gtatcctccc   3767 tagactgagt tctggcagct ccccgaggca gccggggtac cctctagatt cagggatgct    3827
tgctctccac ttttcaagtg ggtcttgggt acgagaattc cctcatcttt ctctactgta    3887
```

```
aagtgatttt gtttgcaggt aagaaaataa tagatgactc accacacctc tacggctggg    3947
gagatcaggc ccagccccat aaaggagaat ctacgctggt cctcaggacg tgttaaagag    4007
atctgggcct catgtagctc accccggtca cgcatgaagg caaaagcagg tcagaagcga    4067
atactctgcc attatctcaa aaatctttt tttttttttt ttgagatggg gtcttcctct     4127
gttgcccagg ctggagtgca gtggtgcaat cttggctcac tgtaacctcc gcctcccagg    4187
ttcaagtgat tcttcttgcc tcagcctcct gagtagctgg gattacaggt gtgcaccacc    4247
cgtacccagc taattttgt attttagtag agacggggt ttcaccatgt tggctgggct      4307
ggtctcgaac tcctgacctc aggtgatcca cccgcctgag cctcccaaag tgctgggatt    4367
acaggcatga gccaccacgc ccggcccact ctgccattgt ctaagccacc tctgaaagca    4427
ggttttaaca aaggatgag gccagaactc ttccagaacc atcacctttg ggaacctgct     4487
gtgagagtgc tgaggtacca gaagtgtgag aacgagggg cgtgctggga tctttctctc     4547
tgactatact tagtttgaaa tggtgcaggc ttagtcttaa gcctccaaag gcctggattt    4607
gagcagcttt agaaatgcag gttctagggc ttctcccagc cttcagaagc caactaactc    4667
tgcagatggg gctaggactg tgggctttta gcagcccaca ggtgatccta acatatcagg    4727
ccatggactc aggacctgcc cggtgatgct gttgatttct caaaggtctt ccaaaactca    4787
acagagccag aagtagccgc ccgctcagcg gctcaggtgc cagctctgtt ctgattcacc    4847
aggggtccgt cagtagtcat tgccacccgc ggggcacctc cctggccaca cgcctgttcc    4907
cagcaagtgc tgaaactcac tagaccgtct gcctgtttcg aaatggggaa agccgtgcgt    4967
gcgcgttatt tatttaagtg cgcctgtgtg cgcgggtgtg ggagcacact ttgcaaagcc    5027
acagcgtttc tggttttggg tgtacagtct tgtgtgcctg gcgagaagaa tattttctat    5087 tttttttaagt catttcatgt ttctgtctgg ggaaggcaag ttagttaagt atcactgatg   5147
tgggttgaga ccagcactct gtgaaacctt gaaatgagaa gtaaaggcag atgaaaagaa    5207
aaaaaaaaaa aaa                                                       5220
```

<210> SEQ ID NO 2
<211> LENGTH: 1044
<212> TYPE: PRT
<213> ORGANISM: Human p110delta protein

<400> SEQUENCE: 2

```
Met Pro Pro Gly Val Asp Cys Pro Met Glu Phe Trp Thr Lys Glu Glu
1               5                   10                  15
```

-continued

```
Asn Gln Ser Val Val Asp Phe Leu Leu Pro Thr Gly Val Tyr Leu
             20                  25                  30

Asn Phe Pro Val Ser Arg Asn Ala Asn Leu Ser Thr Ile Lys Gln Leu
             35                  40                  45

Leu Trp His Arg Ala Gln Tyr Glu Pro Leu Phe His Met Leu Ser Gly
         50                  55                  60

Pro Glu Ala Tyr Val Phe Thr Cys Ile Asn Gln Thr Ala Glu Gln Gln
 65                  70                  75                  80

Glu Leu Glu Asp Glu Gln Arg Arg Leu Cys Asp Val Gln Pro Phe Leu
                 85                  90                  95

Pro Val Leu Arg Leu Val Ala Arg Glu Gly Asp Arg Val Lys Lys Leu
             100                 105                 110

Ile Asn Ser Gln Ile Ser Leu Leu Ile Gly Lys Gly Leu His Glu Phe
             115                 120                 125

Asp Ser Leu Cys Asp Pro Glu Val Asn Asp Phe Arg Ala Lys Met Cys
         130                 135                 140

Gln Phe Cys Glu Glu Ala Ala Ala Arg Arg Gln Gln Leu Gly Trp Glu
145                 150                 155                 160

Ala Trp Leu Gln Tyr Ser Phe Pro Leu Gln Leu Glu Pro Ser Ala Gln
                 165                 170                 175

Thr Trp Gly Pro Gly Thr Leu Arg Leu Pro Asn Arg Ala Leu Leu Val
             180                 185                 190

Asn Val Lys Phe Glu Gly Ser Glu Glu Ser Phe Thr Phe Gln Val Ser
             195                 200                 205

Thr Lys Asp Val Pro Leu Ala Leu Met Ala Cys Ala Leu Arg Lys Lys
         210                 215                 220

Ala Thr Val Phe Arg Gln Pro Leu Val Glu Gln Pro Glu Asp Tyr Thr
225                 230                 235                 240

Leu Gln Val Asn Gly Arg His Glu Tyr Leu Tyr Gly Asn Tyr Pro Leu
                 245                 250                 255

Cys Gln Phe Gln Tyr Ile Cys Ser Cys Leu His Ser Gly Leu Thr Pro
             260                 265                 270

His Leu Thr Met Val His Ser Ser Ile Leu Ala Met Arg Asp Glu
         275                 280                 285

Gln Ser Asn Pro Ala Pro Gln Val Gln Lys Pro Arg Ala Lys Pro Pro
         290                 295                 300

Pro Ile Pro Ala Lys Lys Pro Ser Ser Val Ser Leu Trp Ser Leu Glu
305                 310                 315                 320

Gln Pro Phe Arg Ile Glu Leu Ile Gln Gly Ser Lys Val Asn Ala Asp
                 325                 330                 335

Glu Arg Met Lys Leu Val Val Gln Ala Gly Leu Phe His Gly Asn Glu
             340                 345                 350

Met Leu Cys Lys Thr Val Ser Ser Ser Glu Val Ser Val Cys Ser Glu
         355                 360                 365

Pro Val Trp Lys Gln Arg Leu Glu Phe Asp Ile Asn Ile Cys Asp Leu
     370                 375                 380

Pro Arg Met Ala Arg Leu Cys Phe Ala Leu Tyr Ala Val Ile Glu Lys
385                 390                 395                 400

Ala Lys Lys Ala Arg Ser Thr Lys Lys Ser Lys Lys Ala Asp Cys
                 405                 410                 415

Pro Ile Ala Trp Ala Asn Leu Met Leu Phe Asp Tyr Lys Asp Gln Leu
             420                 425                 430
```

```
Lys Thr Gly Glu Arg Cys Leu Tyr Met Trp Pro Ser Val Pro Asp Glu
        435                 440                 445
Lys Gly Glu Leu Leu Asn Pro Thr Gly Thr Val Arg Ser Asn Pro Asn
        450                 455                 460
Thr Asp Ser Ala Ala Leu Leu Ile Cys Leu Pro Glu Val Ala Pro
465                 470                 475                 480
His Pro Val Tyr Tyr Pro Ala Leu Glu Lys Ile Leu Glu Leu Gly Arg
                485                 490                 495
His Ser Glu Cys Val His Val Thr Glu Glu Gln Leu Gln Leu Arg
                500                 505                 510
Glu Ile Leu Glu Arg Arg Gly Ser Gly Glu Leu Tyr Glu His Glu Lys
        515                 520                 525
Asp Leu Val Trp Lys Leu Arg His Glu Val Gln Glu His Phe Pro Glu
530                 535                 540
Ala Leu Ala Arg Leu Leu Leu Val Thr Lys Trp Asn Lys His Glu Asp
545                 550                 555                 560
Val Ala Gln Met Leu Tyr Leu Leu Cys Ser Trp Pro Glu Leu Pro Val
                565                 570                 575
Leu Ser Ala Leu Glu Leu Leu Asp Phe Ser Phe Pro Asp Cys His Val
                580                 585                 590
Gly Ser Phe Ala Ile Lys Ser Leu Arg Lys Leu Thr Asp Asp Glu Leu
                595                 600                 605
Phe Gln Tyr Leu Leu Gln Leu Val Gln Val Leu Lys Tyr Glu Ser Tyr
                610                 615                 620
Leu Asp Cys Glu Leu Thr Lys Phe Leu Leu Asp Arg Ala Leu Ala Asn
625                 630                 635                 640
Arg Lys Ile Gly His Phe Leu Phe Trp His Leu Arg Ser Glu Met His
                645                 650                 655
Val Pro Ser Val Ala Leu Arg Phe Gly Leu Ile Leu Glu Ala Tyr Cys
                660                 665                 670
Arg Gly Ser Thr His His Met Lys Val Leu Met Lys Gln Gly Glu Ala
                675                 680                 685
Leu Ser Lys Leu Lys Ala Leu Asn Asp Phe Val Lys Leu Ser Ser Gln
        690                 695                 700
Lys Thr Pro Lys Pro Gln Thr Lys Glu Leu Met His Leu Cys Met Arg
705                 710                 715                 720
Gln Glu Ala Tyr Leu Glu Ala Leu Ser His Leu Gln Ser Pro Leu Asp
                725                 730                 735
Pro Ser Thr Leu Leu Ala Glu Val Cys Val Glu Gln Cys Thr Phe Met
                740                 745                 750
Asp Ser Lys Met Lys Pro Leu Trp Ile Met Tyr Ser Asn Glu Glu Ala
                755                 760                 765
Gly Ser Gly Gly Ser Val Gly Ile Ile Phe Lys Asn Gly Asp Asp Leu
        770                 775                 780
Arg Gln Asp Met Leu Thr Leu Gln Met Ile Gln Leu Met Asp Val Leu
785                 790                 795                 800
Trp Lys Gln Glu Gly Leu Asp Leu Arg Met Thr Pro Tyr Gly Cys Leu
                805                 810                 815
Pro Thr Gly Asp Arg Thr Gly Leu Ile Glu Val Val Leu Arg Ser Asp
                820                 825                 830
Thr Ile Ala Asn Ile Gln Leu Asn Lys Ser Asn Met Ala Ala Thr Ala
                835                 840                 845
Ala Phe Asn Lys Asp Ala Leu Leu Asn Trp Leu Lys Ser Lys Asn Pro
```

-continued

```
                    850                 855                 860
Gly Glu Ala Leu Asp Arg Ala Ile Glu Phe Thr Leu Ser Cys Ala
865                 870                 875                 880

Gly Tyr Cys Val Ala Thr Tyr Val Leu Gly Ile Gly Asp Arg His Ser
                    885                 890                 895

Asp Asn Ile Met Ile Arg Glu Ser Gly Gln Leu Phe His Ile Asp Phe
                900                 905                 910

Gly His Phe Leu Gly Asn Phe Lys Thr Lys Phe Gly Ile Asn Arg Glu
            915                 920                 925

Arg Val Pro Phe Ile Leu Thr Tyr Asp Phe Val His Val Ile Gln Gln
    930                 935                 940

Gly Lys Thr Asn Asn Ser Glu Lys Phe Glu Arg Phe Arg Gly Tyr Cys
945                 950                 955                 960

Glu Arg Ala Tyr Thr Ile Leu Arg Arg His Gly Leu Leu Phe Leu His
                    965                 970                 975

Leu Phe Ala Leu Met Arg Ala Ala Gly Leu Pro Glu Leu Ser Cys Ser
                980                 985                 990

Lys Asp Ile Gln Tyr Leu Lys Asp Ser Leu Ala Leu Gly Lys Thr Glu
            995                 1000                1005

Glu Glu Ala Leu Lys His Phe Arg Val Lys Phe Asn Glu Ala Leu
    1010                1015                1020

Arg Glu Ser Trp Lys Thr Lys Val Asn Trp Leu Ala His Asn Val
    1025                1030                1035

Ser Lys Asp Asn Arg Gln
    1040

<210> SEQ ID NO 3
<211> LENGTH: 69
<212> TYPE: DNA
<213> ORGANISM: 5' Primer for p110beta

<400> SEQUENCE: 3
gatcgaattc ggcgccacca tggactacaa ggacgacgat gacaagtgct tcagtttcat    60
aatgcctcc                                                            69

<210> SEQ ID NO 4
<211> LENGTH: 42
<212> TYPE: DNA
<213> ORGANISM: 3' Primer for p110beta

<400> SEQUENCE: 4
gatcgcggcc gcttaagatc tgtagtcttt ccgaactgtg tg                       42

<210> SEQ ID NO 5
<211> LENGTH: 40
<212> TYPE: DNA
<213> ORGANISM: 5' Primer for p110gamma

<400> SEQUENCE: 5
agaatgcggc cgcatggagc tggagaacta taaacagccc                          40

<210> SEQ ID NO 6
<211> LENGTH: 37
```

```
<212> TYPE: DNA
<213> ORGANISM: 3' Primer for p110gamma

<400> SEQUENCE: 6
cgcggatcct taggctgaat gtttctctcc ttgtttg                    37
```

INHIBITORS OF HUMAN PHOSPHATIDYL-INOSITOL 3-KINASE DELTA

CROSS-REFERENCE TO RELATED APPLICATIONS

This application is a divisional of U.S. Ser. No. 10/027,591, filed Oct. 19, 2001, now U.S. Pat. No. 6,667,300, which is a continuation-in-part of U.S. patent application Ser. No. 09/841,341, filed Apr. 24, 2001, now U.S. Pat. No. 6,518,277, which claims the benefit of: U.S. provisional application Ser. No. 60/199,655, filed Apr. 25, 2000 and U.S. provisional application Ser. No. 60/238,057, filed Oct. 5, 2000.

FIELD OF THE INVENTION

The present invention relates generally to phosphatidylinositol 3-kinase (PI3K) enzymes, and more particularly to selective inhibitors of PI3K activity and to methods of using such materials.

BACKGROUND OF THE INVENTION

Cell signaling via 3'-phosphorylated phosphoinositides has been implicated in a variety of cellular processes, e.g., malignant transformation, growth factor signaling, inflammation, and immunity (see Rameh et al., *J. Biol Chem*, 274:8347–8350 (1999) for a review). The enzyme responsible for generating these phosphorylated signaling products, phosphatidylinositol 3-kinase (PI 3-kinase; PI3K), was originally identified as an activity associated with viral oncoproteins and growth factor receptor tyrosine kinases that phosphorylates phosphatidylinositol (PI) and its phosphorylated derivatives at the 3'-hydroxyl of the inositol ring (Panayotou et al., *Trends Cell Biol* 2:358–60 (1992)).

The levels of phosphatidylinositol-3,4,5-triphosphate (PIP3), the primary product of PI 3-kinase activation, increase upon treatment of cells with a variety of agonists. PI 3-kinase activation, therefore, is believed to be involved in a range of cellular responses including cell growth, differentiation, and apoptosis (Parker et al., *Current Biology*, 5:577–99 (1995); Yao et al., *Science*, 267:2003–05 (1995)). Though the downstream targets of phosphorylated lipids generated following PI 3-kinase activation have not been well characterized, emerging evidence suggests that pleckstrin-homology domain- and FYVE-finger domain-containing proteins are activated when binding to various phosphatidylinositol lipids (Sternmark et al., *J Cell Sci*, 112:4175–83 (1999); Lemmon et al., *Trends Cell Biol*, 7:237–42 (1997)). In vitro, some isoforms of protein kinase C (PKC) are directly activated by PIP3, and the PKC-related protein kinase, PKB, has been shown to be activated by PI 3-kinase (Burgering et al., *Nature*, 376:599–602 (1995)).

Presently, the PI 3-kinase enzyme family has been divided into three classes based on their substrate specificities. Class I PI3Ks can phosphorylate phosphatidylinositol (PI), phosphatidylinositol-4-phosphate, and phosphatidylinositol-4,5-biphosphate (PIP2) to produce phosphatidylinositol-3-phosphate (PIP), phosphatidylinositol-3,4-biphosphate, and phosphatidylinositol-3,4,5-triphosphate, respectively. Class II PI3Ks phosphorylate PI and phosphatidylinositol-4-phosphate, whereas Class III PI3Ks can only phosphorylate PI.

The initial purification and molecular cloning of PI 3-kinase revealed that it was a heterodimer consisting of p85 and p110 subunits (Otsu et al., *Cell*, 65:91–104 (1991); Hiles et al., *Cell*, 70:419–29 (1992)). Since then, four distinct Class I PI3Ks have been identified, designated PI3K $\alpha$, $\beta$, $\delta$, and $\gamma$, each consisting of a distinct 110 kDa catalytic subunit and a regulatory subunit. More specifically, three of the catalytic subunits, i.e., p110$\alpha$, p110$\beta$ and p100$\delta$, each interact with the same regulatory subunit, p85; whereas p110$\gamma$ interacts with a distinct regulatory subunit, p110. As described below, the patterns of expression of each of these PI3Ks in human cells and tissues are also distinct. Though a wealth of information has been accumulated in recent past on the cellular functions of PI 3-kinases in general, the roles played by the individual isoforms are largely unknown.

Cloning of bovine p110$\alpha$ has been described. This protein was identified as related to the *Saccharomyces cerevisiae* protein: Vps34p, a protein involved in vacuolar protein processing. The recombinant p110$\alpha$ product was also shown to associate with p85$\alpha$, to yield a PI3K activity in transfected COS-1 cells. See Hiles et al., *Cell*, 70, 419–29 (1992).

The cloning of a second human p110 isoform, designated p110$\beta$, is described in Hu et al., *Mol Cell Biol*, 13:7677–88 (1993). This isoform is said to associate with p85 in cells, and to be ubiquitously expressed, as p110$\beta$ mRNA has been found in numerous human and mouse tissues as well as in human umbilical vein endothelial cells, Jurkat human leukemic T cells, 293 human embryonic kidney cells, mouse 3T3 fibroblasts, HeLa cells, and NBT2 rat bladder carcinoma cells. Such wide expression suggests that this isoform is broadly important in signaling pathways.

Identification of the p100$\delta$ isoform of PI 3-kinase is described in Chantry et al., *J Biol Chem*, 272:19236–41 (1997). It was observed that the human p110$\delta$ isoform is expressed in a tissue-restricted fashion. It is expressed at high levels in lymphocytes and lymphoid tissues, suggesting that the protein might play a role in PI 3-kinase-mediated signaling in the immune system. Details concerning the P110$\delta$ isoform also can be found in U.S. Pat. Nos. 5,858,753; 5,822,910; and 5,985,589. See also, Vanhaesebroeck et al., *Proc Natl Acad Sci USA*, 94:4330–5 (1997), and international publication WO 97/46688.

In each of the PI3K$\alpha$, $\beta$, and $\delta$ subtypes, the p85 subunit acts to localize PI 3-kinase to the plasma membrane by the interaction of its SH2 domain with phosphorylated tyrosine residues (present in an appropriate sequence context) in target proteins (Rameh et al., *Cell*, 83:821–30 (1995)). Two isoforms of p85 have been identified, p85$\alpha$, which is ubiquitously expressed, and p85$\beta$, which is primarily found in the brain and lymphoid tissues (Volinia et al., *Oncogene*, 7:789–93 (1992)). Association of the p85 subunit to the PI 3-kinase p110$\alpha$, $\beta$, or $\delta$ catalytic subunits appears to be required for the catalytic activity and stability of these enzymes. In addition, the binding of Ras proteins also upregulates PI 3-kinase activity.

The cloning of p110$\gamma$ revealed still further complexity within the PI3K family of enzymes (Stoyanov et al., *Science*, 269:690–93 (1995)). The p110$\gamma$ isoform is closely related to p110$\alpha$ and p110$\beta$ (45–48% identity in the catalytic domain), but as noted does not make use of p85 as a targeting subunit. Instead, p110$\gamma$ contains an additional domain termed a "pleckstrin homology domain" near its amino terminus. This domain allows interaction of p110$\gamma$ with the $\beta\gamma$ subunits of heterotrimeric G proteins and this interaction appears to regulate its activity.

The p101 regulatory subunit for PI3Kgamma was originally cloned in swine, and the human ortholog identified subsequently (Krugmann et al., *J Biol Chem*, 274:17152–8 (1999)). Interaction between the N-terminal region of p101 with the N-terminal region of p110$\gamma$ appears to be critical for the PI3K$\gamma$ activation through G$\beta\gamma$ mentioned above.

A constitutively active PI3K polypeptide is described in international publication WO 96/25488. This publication discloses preparation of a chimeric fusion protein in which a 102-residue fragment of p85 known as the inter-SH2 (iSH2) region is fused through a linker region to the N-terminus of murine p110. The p85 iSH2 domain apparently is able to activate PI3K activity in a manner comparable to intact p85 (Klippel et al., *Mol Cell Biol*, 14:2675–85 (1994)).

Thus, PI 3-kinases can be defined by their amino acid identity or by their activity. Additional members of this growing gene family include more distantly related lipid and protein kinases including Vps34 TOR1, and TOR2 of *Saccharomyces cerevisiae* (and their mammalian homologs such as FRAP and mTOR), the ataxia telangiectasia gene product (ATR) and the catalytic subunit of DNA-dependent protein kinase (DNA-PK). See generally, Hunter, *Cell*, 83:1–4 (1995).

PI 3-kinase also appears to be involved in a number of aspects of leukocyte activation. A p85-associated PI 3-kinase activity has been shown to physically associate with the cytoplasmic domain of CD28, which is an important costimulatory molecule for the activation of T-cells in response to antigen (Pages et al., *Nature*, 369:327–29 (1994); Rudd, Immunity, 4:527–34 (1996)). Activation of T cells through CD28 lowers the threshold for activation by antigen and increases the magnitude and duration of the proliferative response. These effects are linked to increases in the transcription of a number of genes including interleukin-2 (IL2), an important T cell growth factor (Fraser et al., *Science*, 251:313–16 (1991)). Mutation of CD28 such that it can no longer interact with PI 3-kinase leads to a failure to initiate IL2 production, suggesting a critical role for PI 3-kinase in T cell activation.

Specific inhibitors against individual members of a family of enzymes provide invaluable tools for deciphering functions of each enzyme. Two compounds, LY294002 and wortmannin, have been widely used as PI 3-kinase inhibitors. These compounds, however, are nonspecific PI3K inhibitors, as they do not distinguish among the four members of Class I PI 3-kinases. For example, the $IC_{50}$ values of wortmannin against each of the various Class I PI 3-kinases are in the range of 1–10 nM. Similarly, the $IC_{50}$ values for LY294002 against each of these PI 3-kinases is about 1 µM (Fruman et al., *Ann Rev Biochem*, 67:481–507 (1998)). Hence, the utility of these compounds in studying the roles of individual Class I PI 3-kinases is limited.

Based on studies using wortmannin, there is evidence that PI 3-kinase function also is required for some aspects of leukocyte signaling through G-protein coupled receptors (Thelen et al., *Proc Natl Acad Sci USA*, 91:4960–64 (1994)). Moreover, it has been shown that wortmannin and LY294002 block neutrophil migration and superoxide release. However, inasmuch as these compounds do not distinguish among the various isoforms of PI3K, it remains unclear which particular PI3K isoform or isoforms are involved in these phenomena.

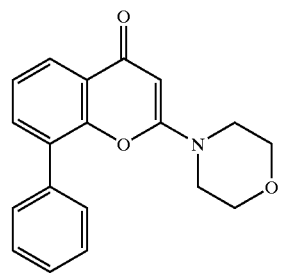

LY294002

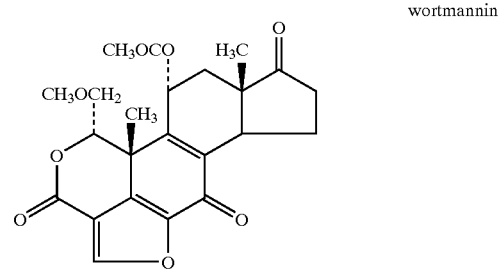

wortmannin

In view of the above considerations, it is clear that existing knowledge is lacking with respect to structural and functional features of the PI 3-kinase enzymes, including subcellular localization, activation states, substrate affinities, and the like. Moreover, the functions that these enzymes perform in both normal and diseased tissues remains to be elucidated. In particular, the function of PI3Kδ in leukocytes has not previously been characterized, and knowledge concerning its function in human physiology remains limited. The coexpression in these tissues of other PI3K isoforms has heretofore confounded efforts to segregate the activities of each enzyme. Furthermore, separation of the activities of the various PI3K isozymes may not be possible without identification of inhibitors that demonstrate selective inhibition characteristics. Indeed, Applicants are not presently aware that such selective, or better, specific, inhibitors of PI3K isozymes have been demonstrated.

Thus, there exists a need in the art for further structural characterization of the PI3Kδ polypeptide. There also exists a need for functional characterization of PI3Kδ. Furthermore, our understanding of PI3Kδ requires further elaboration of the structural interactions of p110δ, both with its regulatory subunit and with other proteins in the cell. There also remains a need for selective or specific inhibitors of PI3K isozymes, in order that the functions of each isozyme can be better characterized. In particular, selective or specific inhibitors of PI3Kδ are desirable for exploring the role of this isozyme and for development of pharmaceuticals to modulate the activity of the isozyme.

One aspect of the present invention is to provide compounds that can inhibit the biological activity of human PI3Kδ. Another aspect of the invention is to provide compounds that inhibit PI3Kδ selectively while having relatively low inhibitory potency against the other PI3K isoforms. Another aspect of the invention is to provide methods of characterizing the function of human PI3Kδ. Another aspect of the invention is to provide methods of selectively modulating human PI3Kδ activity, and thereby promoting medical treatment of diseases mediated by PI3Kδ dysfunction. Other aspects and advantages of the invention will be readily apparent to the artisan having ordinary skill in the art.

SUMMARY OF THE INVENTION

It has now been discovered that these and other aspects can be achieved by the present invention, which, in one aspect, is a method for disrupting leukocyte function, comprising contacting leukocytes with a compound that selectively inhibits phosphatidylinositol 3-kinase delta (PI3Kδ) activity in the leukocytes. According to the method, the leukocytes can comprise cells selected from the group consisting of neutrophils, B lymphocytes, T lymphocytes, and basophils.

For example, in cases in which the leukocytes comprise neutrophils, the method can comprise disrupting at least one neutrophil function selected from the group consisting of stimulated superoxide release, stimulated exocytosis, and chemotactic migration. Preferably, the method does not substantially disrupt bacterial phagocytosis or bacterial killing by the neutrophils. In cases wherein the leukocytes comprise B lymphocytes, the method can comprise disrupting proliferation of the B lymphocytes or antibody production by the B lymphocytes. In cases wherein the leukocytes comprise T lymphocytes, the method can comprise disrupting proliferation of the T lymphocytes. In cases wherein the leukocytes comprise basophils, the method can comprise disrupting histamine release by the basophils.

In the methods of the invention wherein a selective PI3Kδ inhibitor is employed, it is preferred that the compound be at least about 10-fold selective for inhibition of PI3Kδ relative to other Type I P13K isoforms in a cell-based assay. More preferably, the compound is at least about 20-fold selective for inhibition of PI3Kδ relative to other Type I PI3K isoforms in a cell-based assay. Still more preferably, the compound is at least about 50-fold selective for inhibition of PI3Kδ relative to other Type I PI3K isoforms in a biochemical assay.

Preferred selective compounds useful according to the methods include compounds having the structure (I):

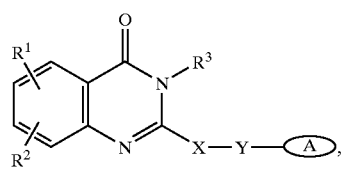

(I)

wherein A is an optionally substituted monocyclic or bicyclic ring system containing at least two nitrogen atoms, and at least one ring of the system is aromatic;

X is selected from the group consisting of $C(R^b)_2$, $CH_2CHR^b$, and $CH=C(R^b)$;

Y is selected from the group consisting of null, S, SO, $SO_2$, NH, O, C(=O), OC(=O), C(=O)O, and NHC(=O)$CH_2S$;

$R^1$ and $R^2$, independently, are selected from the group consisting of hydrogen, $C_{1-6}$alkyl, aryl, heteroaryl, halo, NHC(=O)$C_{1-3}$alkyleneN$(R^a)_2$, $NO_2$, $OR^a$, $CF_3$, $OCF_3$, $N(R^a)_2$, CN, OC(=O)$R^a$, C(=O)$R^a$, C(=O)O$R^a$, aryl$OR^b$, Het, $NR^a$C(=O)$C_{1-3}$alkyleneC(=O)O$R^a$, aryl$OC_{1-3}$-alkyleneN$(R^a)_2$, arylOC(=O)$R^a$, $C_{1-4}$alkyleneC(=O)O$R^a$, $OC_{1-4}$alkyleneC(=O)O$R^a$, $C_{1-4}$alkyleneOC$_{1-4}$alkyleneC(=O)O$R^a$, C(=O)$NR^a SO_2 R^a$, $C_{1-4}$alkyleneN$(R^a)_2$, $C_{2-6}$alkenyleneN$(R^a)_2$, C(=O)$NR^a C_{1-4}$alkyleneO$R^a$, C(=O)$NR^a C_{1-4}$alkyleneHet, $OC_{2-4}$-alkyleneN$(R^a)_2$, $OC_{1-4}$alkyleneCH(O$R^b$)$CH_2 N(R^a)_2$, $C_{1-4}$alkyleneHet, $OC_{2-4}$alkyleneO$R^a$, $OC_{2-4}$alkyleneNR$^a$C(=O)O$R^a$, $NR^a C_{1-4}$alkyleneN$(R^a)_2$, $NR^a$C(=O)$R^a$, $NR^a$C(=O) $N(R^a)_2$, N(SO$_2 C_{1-4}$alkyl)$_2$, NR$^a$(SO$_2 C_{1-4}$alkyl), SO$_2 N(R^a)_2$, $OSO_2 CF_3$, $C_{1-3}$alkylenearyl, $C_{1-4}$alkyleneHet, $C_{1-6}$alkyleneO$R^b$, $C_{1-3}$alkyleneN$(R^a)_2$, C(=O)$N(R^a)_2$, NHC(=O)$C_1$–$C_3$alkylenearyl, $C_{3-8}$cycloalkyl, $C_{3-8}$heterocycloalkyl, arylOC$_{1-3}$-alkyleneN$(R^a)_2$, arylOC(=O)$R^b$, NHC(=O)$C_{1-3}$alkyleneC$_{3-8}$-heterocycloalkyl, NHC(=O)$C_{1-3}$alkyleneHet, $OC_{1-4}$alkyleneOC$_{1-4}$alkyleneC(=O)O$R^b$, C(=O)$C_{1-4}$alkyleneHet, and NHC(=O)halo$C_{1-6}$alkyl;

or $R^1$ and $R^2$ are taken together to form a 3- or 4-membered alkylene or alkenylene chain component of a 5- or 6-membered ring, optionally containing at least one heteroatom;

$R^3$ is selected from the group consisting of optionally substituted hydrogen, $C_{1-6}$alkyl, $C_{3-8}$cycloalkyl, $C_{3-8}$heterocycloalkyl, $C_{1-4}$alkylenecycloalkyl, $C_{2-6}$alkenyl, $C_{1-3}$alkylenearyl, aryl$C_{1-3}$alkyl, C(=O)$R^a$, aryl, heteroaryl, C(=O)O$R^a$, C(=O)$N(R^a)_2$, C(=S)$N(R^a)_2$, SO$_2 R^a$, SO$_2 N(R^a)_2$, S(=O)$R^a$, S(=O)$N(R^a)_2$, C(=O)$NR^a C_{1-4}$-alkyleneO$R^a$, C(=O)$NR^a C_{1-4}$alkyleneHet, C(=O)$C_{1-4}$alkylenearyl, C(=O)$C_{1-4}$alkyleneheteroaryl, $C_{1-4}$alkylenearyl optionally substituted with one or more of halo, SO$_2 N(R^a)_2$, $N(R^a)_2$, C(=O)O$R^a$, $NR^a SO_2 CF_3$, CN, NO$_2$, C(=O)$R^a$, O$R^a$, $C_{1-4}$alkyleneN$(R^a)_2$, and OC$_{1-4}$alkyleneN$(R^a)_2$, $C_{1-4}$-alkyleneheteroaryl, $C_{1-4}$alkyleneHet, $C_{1-4}$alkyleneC(=O)—$C_{1-4}$alkylenearyl, $C_{1-4}$alkyleneC(=O)$C_{1-4}$alkyleneheteroaryl, $C_{1-4}$alkyleneC(=O)Het, $C_{1-4}$alkyleneC(=O)$N(R^a)_2$, $C_{1-4}$alkyleneO$R^a$, $C_{1-4}$alkyleneNR$^a$C(=O)$R^a$, $C_{1-4}$alkyleneOC$_{1-4}$alkyleneO$R^a$, $C_{1-4}$alkyleneN$(R^a)_2$, $C_{1-4}$alkyleneC(=O)—O$R^a$, and $C_{1-4}$alkyleneOC$_{1-4}$alkyleneC(=O)O$R^a$;

$R^a$ is selected from the group consisting of hydrogen, $C_{1-6}$alkyl, $C_{3-8}$cycloalkyl, $C_{3-8}$heterocycloalkyl, $C_{1-3}$alkyleneN$(R^c)_2$, aryl, aryl$C_{1-3}$alkyl, $C_{1-3}$-alkylenearyl, heteroaryl, heteroaryl$C_{1-3}$alkyl, and $C_{1-3}$alkyleneheteroaryl;

or two $R^a$ groups are taken together to form a 5- or 6-membered ring, optionally containing at least one heteroatom;

$R^b$ is selected from the group consisting of hydrogen, $C_{1-6}$alkyl, heteroC$_{1-3}$alkyl, $C_{1-3}$alkylene-heteroC$_{1-3}$alkyl, arylheteroC$_{1-3}$alkyl, aryl, heteroaryl, aryl$C_{1-3}$alkyl, heteroaryl$C_{1-3}$alkyl, $C_{1-3}$alkylenearyl, and $C_{1-3}$alkyleneheteroaryl;

$R^c$ is selected from the group consisting of hydrogen, $C_{1-6}$alkyl, $C_{3-8}$cycloalkyl, aryl, and heteroaryl;

Het is a 5- or 6-membered heterocyclic ring, saturated or partially or fully unsaturated, containing at least one heteroatom selected from the group consisting of oxygen, nitrogen, and sulfur, and optionally substituted with $C_{1-4}$alkyl or C(=O)O$R^a$;

and pharmaceutically acceptable salts and solvates (e.g., hydrates) thereof, wherein the compound has at least about a 10-fold selective inhibition for PI3Kδ relative other Type-I PI3K isoforms in a cell-based assay.

In another embodiment, the invention is a method for treating a medical condition mediated by neutrophils, comprising administering to an animal in need thereof an effective amount of a compound that selectively inhibits phosphatidylinositol 3-kinase delta (PI3Kδ) activity in the neutrophils. Exemplary medical conditions that can be treated according to the method include those conditions characterized by an undesirable neutrophil function selected from the group consisting of stimulated superoxide release, stimulated exocytosis, and chemotactic migration. Preferably, according to the method, phagocytic activity or bacterial killing by the neutrophils is substantially uninhibited.

In another embodiment, the invention is a method for disrupting a function of osteoclasts comprising contacting osteoclasts with a compound that selectively inhibits phosphatidylinositol 3-kinase delta (PI3Kδ) activity in the osteoclasts. According to the method, the compound can comprise a moiety that preferentially binds to bone.

In another embodiment, the invention is a method of ameliorating a bone-resorption disorder in an animal in need thereof comprising administering to the animal an effective amount of a compound that inhibits phosphatidylinositol 3-kinase delta (PI3Kδ) activity in osteoclasts of the animal. A preferred bone-resorption disorder amenable to treatment according to the method is osteoporosis.

In another embodiment, the invention is a method for inhibiting the growth or proliferation of cancer cells of hematopoietic origin, comprising contacting the cancer cells with a compound that selectively inhibits phosphatidylinositol 3-kinase delta (PI3Kδ) activity in the cancer cells. The method can be advantageous in inhibiting the growth or proliferation of cancers selected from the group consisting of lymphomas, multiple myelomas, and leukemias.

In another embodiment, the invention is a method of inhibiting kinase activity of a phosphatidylinositol 3-kinase delta (PI3Kδ) polypeptide, comprising contacting the PI3Kδ polypeptide with a compound having the generic structure (I).

Preferred compounds useful according to the method include compounds selected from the group consisting of:

(II)

wherein Y is selected from the group consisting of null, S, and NH;

$R^4$ is selected from the group consisting of H, halo, $NO_2$, OH, $OCH_3$, $CH_3$, and $CF_3$;

$R^5$ is selected from the group consisting of H, $OCH_3$, and halo;

or $R^4$ and $R^5$ together with C-6 and C-7 of the quinazoline ring system define a 5- or 6-membered aromatic ring optionally containing one or more O, N, or S atoms;

$R^6$ is selected from the group consisting of $C_1$–$C_6$alkyl, phenyl, halophenyl, alkoxyphenyl, alkylphenyl, biphenyl, benzyl, pyridinyl, 4-methylpiperazinyl, $C(=O)OC_2H_5$, and morpholinyl;

$R^d$, independently, is selected from the group consisting of $NH_2$, halo, $C_{1-3}$alkyl, $S(C_{1-3}$alkyl), OH, $NH(C_{1-3}$alkyl), $N(C_{1-3}$alkyl)$_2$, $NH(C_{1-3}$alkylenephenyl), and q is 1 or 2, provided that at least one of $R^4$ and $R^5$ is other than H when $R^6$ is phenyl or 2-chlorophenyl.

More preferably, the compound is selected from the group consisting of:

(III)

wherein Y is selected from the group consisting of null, S, and NH;

$R^7$ is selected from the group consisting of H, halo, OH, $OCH_3$, $CH_3$, and $CF_3$;

$R^8$ is selected from the group consisting of is H, $OCH_3$, and halo;

or $R^7$ and $R^8$ together with C-6 and C-7 of the quinazoline ring system define a 5- or 6-membered aromatic ring optionally containing one or more O, N, or S atoms;

$R^9$ is selected from the group consisting of $C_1$–$C_6$alkyl, phenyl, halophenyl, alkylphenyl, biphenyl, benzyl, pyridinyl, 4-methylpiperazinyl, $C(=O)$—$OC_2H_5$, and morpholinyl;

$R^d$, independently, is selected from the group consisting of $NH_2$, halo, $C_{1-3}$alkyl, $S(C_{1-3}$alkyl), OH, $NH(C_{1-3}$alkyl), $N(C_{1-3}$alkyl)$_2$, $NH(C_{1-3}$alkylenephenyl); and q is 1 or 2, provided that at least one of $R^7$ and $R^8$ is different from 6-halo or 6,7-dimethoxy groups, and that $R^9$ is different from 4-chlorophenyl.

In another embodiment, the invention is a method for disrupting leukocyte function, comprising contacting leukocytes with a compound having a general structure (I).

In another embodiment, the invention is a class of compounds that have been observed to inhibit PI3Kδ activity in biochemical and cell-based assays, and are expected to exhibit therapeutic benefit in medical conditions in which PI3Kδ activity is excessive or undesirable. Thus, the invention provides a class of compounds having the structure (II).

Preferably, the compounds have a general structure (IV)

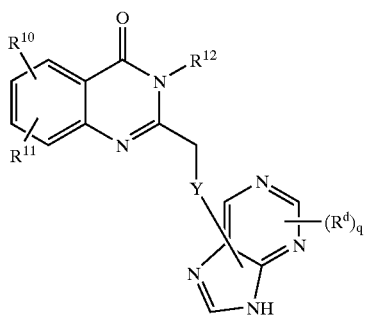

(IV)

wherein Y is selected from the group consisting of null, S, and NH;

$R^{10}$ is selected from the group consisting of H, halo, OH, $OCH_3$, $CH_3$, and $CF_3$;

$R^{11}$ is selected from the group consisting of H, $OCH_3$, and halo;

or $R^{10}$ and $R^{11}$ together with C-6 and C-7 of the quinazoline ring system define a 5- or 6-membered aromatic ring optionally containing one or more O, N, or S atoms;

$R^{12}$ is selected from the group consisting of $C_1$–$C_6$alkyl, phenyl, halophenyl, alkylphenyl, biphenyl, benzyl, pyridinyl, 4-methylpiperazinyl, $C(=O)C_2H_5$, and morpholinyl;

$R^d$, independently, is selected from the group consisting of $NH_2$, halo, $C_{1-3}$alkyl, $S(C_{1-3}alkyl)$, OH, $NH(C_{1-3}alkyl)$, $N(C_{1-3}alkyl)_2$, $NH(C_{1-3}alkylenephenyl)$, and q is 1 or 2, provided that:

(a) at least one of $R^{10}$ and $R^{11}$ is different from 6-halo or 6,7-dimethoxy groups;

(b) $R^{12}$ is different from 4-chlorophenyl; and (c) at least one of $R^{10}$ and $R^{11}$ is different from H when $R^{12}$ is phenyl or 2-chlorophenyl and X is S.

These and other features and advantages of the present invention will be appreciated from the detailed description and examples that are set forth herein. The detailed description and examples are provided to enhance the understanding of the invention, but are not intended to limit the scope of the invention.

DETAILED DESCRIPTION OF THE PREFERRED EMBODIMENTS

Figure 1:
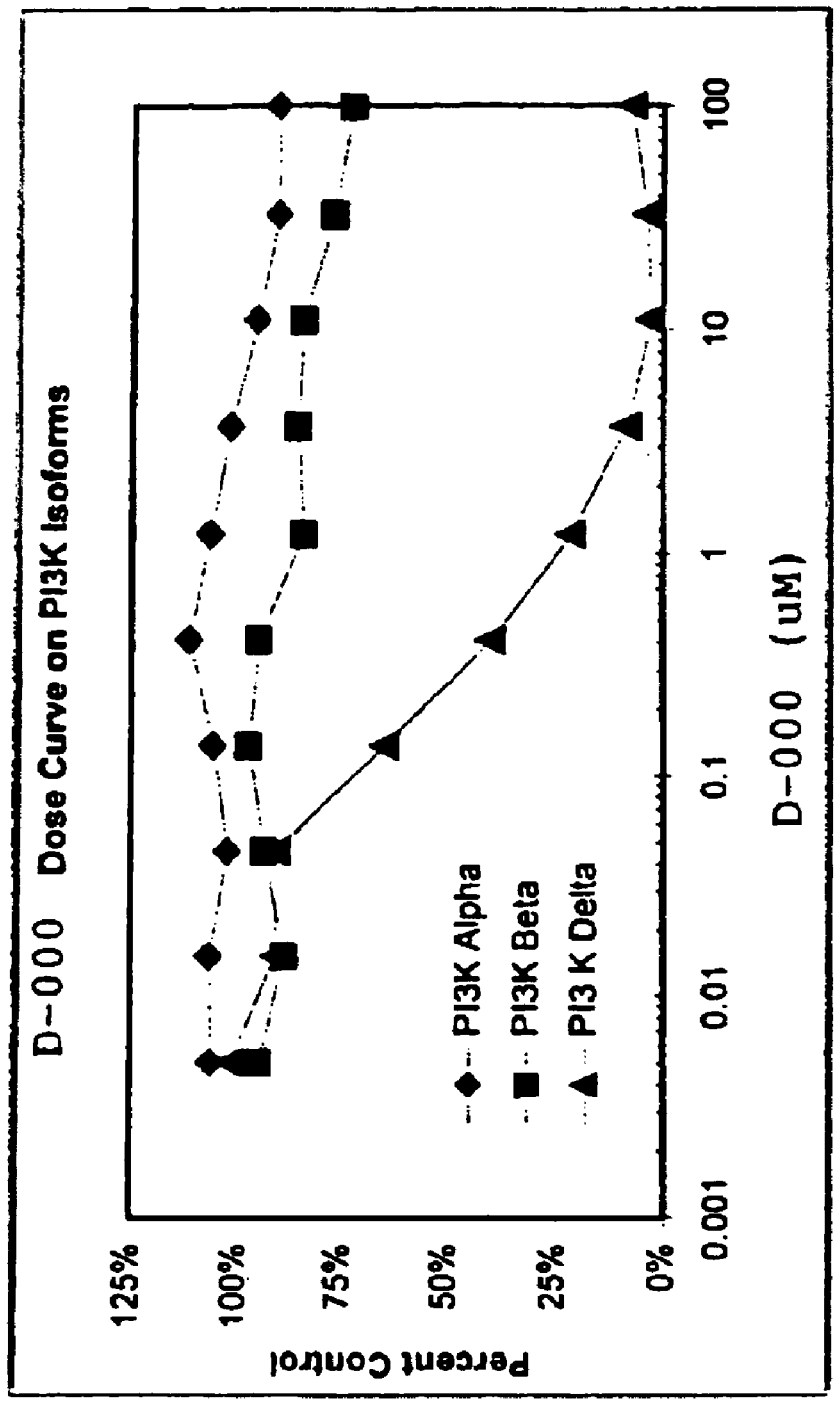
FIG. 1 shows the effect of a selective PI3Kδ inhibitor of the invention on the activity of three PI3K isoforms.

The invention provides compounds that selectively inhibit the activity of PI3Kδ. The invention further provides methods of inhibiting PI3Kδ activity, including methods of selectively modulating the activity of the PI3Kδ isozyme in cells, especially leukocytes, osteoclasts, and cancer cells. The methods include in vitro, in vivo, and ex vivo applications.

Of particular benefit are methods of selectively modulating PI3Kδ activity in the clinical setting in order to ameliorate disease or disorders mediated by PI3Kδ activity. Thus, treatment of diseases or disorders characterized by excessive or inappropriate PI3Kδ activity can be treated through use of selective modulators of PI3Kδ according to the invention.

Other methods of the invention include enabling the further characterization of the physiological role of the isozyme. Moreover, the invention provides pharmaceutical compositions comprising selective PI3Kδ inhibitors. Also provided are articles of manufacture comprising a selective PI3Kδ inhibitor compound (or a pharmaceutical composition comprising the compound) and instructions for using the compound. Details of these and other useful embodiments of the invention are now described.

The methods described herein benefit from the use of compounds that selectively inhibit, and preferably specifically inhibit, the activity of PI3Kδ in cells, including cells in vitro, in vivo, or ex vivo. Cells useful in the methods include those that express endogenous PI3Kδ, wherein endogenous indicates that the cells express PI3Kδ absent recombinant introduction into the cells of one or more polynucleotides encoding a PI3Kδ polypeptide or a biologically active fragment thereof. Methods also encompass use of cells that express exogenous PI3Kδ, wherein one or more polynucleotides encoding PI3Kδ or a biologically active fragment thereof have been introduced into the cell using recombinant procedures.

Of particular advantage, the cells can be in vivo, i.e., in a living subject, e.g., an animal or human, wherein a PI3Kδ inhibitor can be used as a therapeutic to inhibit PI3Kδ activity in the subject. Alternatively, the cells can be isolated as discrete cells or in a tissue, for ex vivo or in vitro methods. In vitro methods also encompassed by the invention can comprise the step of contacting a PI3Kδ enzyme or a biologically active fragment thereof with an inhibitor compound of the invention. The PI3Kδ enzyme can include a purified and isolated enzyme, wherein the enzyme is isolated from a natural source (e.g., cells or tissues that normally express a PI3Kδ polypeptide absent modification by recombinant technology) or isolated from cells modified by recombinant techniques to express exogenous enzyme.

The term "selective PI3Kδ inhibitor" as used herein refers to a compound that inhibits the PI3Kδ isozyme more effectively than other isozymes of the PI3K family. A "selective PI3Kδ inhibitor" compound is understood to be more selective for PI3Kδ than compounds conventionally and generically designated PI3K inhibitors, e.g., wortmannin or LY294002. Concomitantly, wortmannin and LY294002 are deemed "nonselective PI3K inhibitors." Compounds of any type that selectively negatively regulate PI3Kδ expression or activity can be used as selective PI3Kδ inhibitors in the methods of the invention. Moreover, compounds of any type that selectively negatively regulate PI3Kδ expression or activity and that possess acceptable pharmacological properties can be used as selective PI3Kδ inhibitors in the therapeutic methods of the invention.

The relative efficacies of compounds as inhibitors of an enzyme activity (or other biological activity) can be established by determining the concentrations at which each compound inhibits the activity to a predefined extent and then comparing the results. Typically, the preferred determination is the concentration that inhibits 50% of the activity in a biochemical assay, i.e., the 50% inhibitory concentration or "$IC_{50}$." $IC_{50}$ determinations can be accomplished using conventional techniques known in the art. In general, an $IC_{50}$ can be determined by measuring the activity of a given enzyme in the presence of a range of concentrations of the inhibitor under study. The experimentally obtained values of enzyme activity then are plotted against the inhibitor concentrations used. The concentration of the inhibitor that shows 50% enzyme activity (as compared to the activity in the absence of any inhibitor) is taken as the $IC_{50}$ value. Analogously, other inhibitory concentrations can be defined through appropriate determinations of activity. For example, in some settings it can be desirable to establish a 90% inhibitory concentration, i.e., $IC_{90}$, etc.

Accordingly, a "selective PI3Kδ inhibitor" alternatively can be understood to refer to a compound that exhibits a 50% inhibitory concentration ($IC_{50}$ with respect to PI3Kδ that is at least at least 10-fold, preferably at least 20-fold, and more preferably at least 30-fold, lower than the $IC_{50}$ value with respect to any or all of the other Class I PI3K family members. The term "specific PI3Kδ inhibitor" can be understood to refer to a selective PI3Kδ inhibitor compound that exhibits an $IC_{50}$ with respect to PI3Kδ that is at least 50-fold, preferably at least 100-fold, more preferably at least 200-fold, and still more preferably at least 500-fold, lower than the $IC_{50}$ with respect to any or all of the other PI3K Class I family members.

Among other things, the invention provides methods of inhibiting leukocyte function. More particularly, the invention provides methods of inhibiting or suppressing functions of neutrophils and T and B lymphocytes. With respect to neutrophils, it has unexpectedly been found that inhibition of PI3Kδ activity inhibits functions of neutrophils. For example, it has been observed that the compounds of the invention elicit inhibition of classical neutrophil functions such as stimulated superoxide release, stimulated exocytosis, and chemotactic migration. However, it has been further observed that the method of the invention permits suppression of certain functions of neutrophils, while not substantially affecting other functions of these cells. For example, it has been observed that phagocytosis of bacteria by neutrophils is not substantially inhibited by the selective PI3Kδ inhibitor compounds of the invention.

Thus, the invention includes methods for inhibiting neutrophil functions, without substantially inhibiting phagocytosis of bacteria. Neutrophil functions suitable for inhibition according to the method include any function that is mediated by PI3Kδ activity or expression. Such functions include, without limitation, stimulated superoxide release, stimulated exocytosis or degranulation, chemotactic migration, adhesion to vascular endothelium (e.g., tethering/rolling of neutrophils, triggering of neutrophil activity, and/or latching of neutrophils to endothelium), transmural diapedesis or emigration through the endothelium to peripheral tissues. In general, these functions can be collectively termed "inflammatory functions," as they are typically related to neutrophil response to inflammation. The inflammatory functions of neutrophils can be distinguished from the bacterial killing functions exhibited by these cells, e.g., phagocytosis and killing of bacteria. Accordingly, the invention further includes methods of treating disease states in which one or more of the inflammatory functions of neutrophils are abnormal or undesirable.

It has further been established through the invention that PI3Kδ plays a role in the stimulated proliferation of lymphocytes, including B cells and T cells. Moreover, PI3Kδ appears to play a role in stimulated secretion of antibodies by B cells. Selective PI3Kδ inhibitor compounds of the invention have been employed to establish that these phenomena can be abrogated by inhibition of PI3Kδ. Thus, the invention includes methods of inhibiting lymphocyte proliferation, and methods of inhibiting antibody production by B lymphocytes. Other methods enabled by the invention include methods of treating disease states in which one or more of these lymphocyte functions are abnormal or undesirable.

It has now been determined that PI3Kδ activity can be inhibited selectively or specifically to facilitate treatment of a PI3Kδ-mediated disease while reducing or eliminating complications that are typically associated with concomitant inhibition of the activity of other Class I PI 3-kinases. To illustrate this embodiment, methods of the invention can be practiced using members of a class of compounds that have been found to exhibit selective inhibition of PI3Kδ relative to other PI3K isoforms.

The methods of this embodiment can be practiced using compounds having the general structure (III). Preferred methods employ compounds that have been empirically determined to exhibit at least 10-fold selective inhibition of PI3Kδ relative to other PI3K isoforms. For example, the methods can be practiced using the following compounds:

3-(2-isopropylphenyl)-5-methyl-2-(9H-purin-6-ylsulfanylmethyl)-3H-quinazolin-4-one;
5-chloro-2-(9H-purin-6-ylsulfanylmethyl)-3-o-tolyl-3H-quinazolin-4-one;
5-chloro-3-(2-fluorophenyl)-2-(9H-purin-6-ylsulfanylmethyl)-3H-quinazolin-4-one;
3-(2-fluorophenyl)-5-methyl-2-(9H-purin-6-ylsulfanylmethyl)-3H-quinazolin-4-one;
3-(2-methoxyphenyl)-5-methyl-2-(9H-purin-y-ylsulfanylmethyl-3H-quinazolin-4-one;
3-(2,6-dichlorophenyl)-5-methyl-2-(9H-purin-6-ylsulfanylmethyl)-3H-quinazolin-4-one;
3-(2-chlorophenyl)-6-fluoro-2-(9h-purin-6-ylsulfanylmethyl)-3H-quinazolin-4-one;
5-chloro-3-(2-chlorophenyl)-2-(9H-purin-6-ylsulfanylmethyl)-3H-quinazolin-4-one;
3-(2-chlorophenyl)-5-methyl-2-(9H-purin-6-ylsulfanylmethyl)-3H-quinazolin-4-one;
3-(3-methoxyphenyl-2-(9H-purin-6-ylsulfanylmethyl-3H-quinazolin-4-one;
3-(2-chlorophenyl)-5-fluoro-2-(9H-purin-6-ylsulfanylmethyl)-3H-quinazolin-4-one;
3-benzyl-2-(9H-purin-6-ylsulfanylmethyl)-3H-quinazolin-4-one;
3-butyl-2-(9H-purin-6-ylsulfanylmethyl)-3H-quinazolin-4-one;
3-(2-chlorophenyl)-7-fluoro-2-(9H-purin-6-ylsulfanylmethyl)-3H-quinazolin-4-one;
3-morpholin-4-yl-2-(9H-purin-6-ylsulfanylmethyl)-3H-quinazolin-4-one, acetate salt;

8-chloro-3-(2-chlorophenyl)-2-(9H-purin-6-ylsulfanylmethyl)-3H-quinazolin-4-one;

3-(2-chlorophenyl)-6,7-difluoro-2-(9H-purin-6-ylsulfanylmethyl)-3H-quinazolin-4-one;

3-(2-methoxyphenyl-2-(9H-purin-6-ylsulfanylmethyl)-3H-quinazolin-4-one;

6-chloro-3-(2-chlorophenyl)-2-(9H-purin-6-ylsulfanylmethyl)-3H-quinazolin-4-one;

3-(3-chlorophenyl)-2-(9H-purin-6-ylsulfanylmethyl)-3H-quinazolin-4-one;

2-(9H-purin-6-ylsulfanylmethyl)-3-pyridin-4-yl-3H-quinazolin-4-one;

3-(2-chlorophenyl)-2-(9H-purin-6-ylsulfanylmethyl) trifluoromethyl-3H-quinazolin-4-one;

3-benzyl-5-fluoro-2-(9H-purin-6-ylsulfanylmethyl)-3H-quinazolin-4-one;

3-(4-methylpiperazin-1-yl)-2-(9H-purin-6-ylsulfanylmethyl)-3H-quinazolin-4-one, acetate salt;

3-(2-chlorophenyl)-6-hydroxy-2-(9H-purin-6-ylsulfanylmethyl)-3H-quinazolin-4-one;

[5-fluoro-4-oxo-2-(9H-purin-6-ylsulfanylmethyl)-4H-quinazolin-3-yl]acetic acid ethyl ester;

3-(2,4-dimethoxyphenyl)-2-(9H-purin-6-ylsulfanylmethyl)-3H-quinazolin-4-one;

3-biphenyl-2-yl-5-chloro-2-(9H-purin-6-ylsulfanylmethyl)-3H-quinazolin-4-one;

2-(6-aminopurin-9-ylmethyl)-3-(2-isopropylphenyl)-5-methyl-3H-quinazolin-4-one;

2-(6-aminopurin-9-ylmethyl)-5-methyl-3-o-tolyl-3H-quinazolin-4-one;

2-(6-aminopurin-9-ylmethyl)-3-biphenyl-2-yl-5-chloro-3H-quinazolin-4-one;

5-chloro-3-(2-methoxyphenyl)-2-(9H-purin-6-ylsulfanylmethyl)-3H-quinazolin-4-one;

2-(6-aminopurin-9-ylmethyl)-3-(2-fluorophenyl)-5-methyl-3H-quinazolin-4-one;

2-(6-aminopurin-9-ylmethyl)-5-chloro-3-(2-fluorophenyl)-3H-quinazolin-4-one;

2-(6-aminopurin-9-ylmethyl)-8-chloro-3-(2-chlorophenyl)-3H-quinazolin-4-one;

2-(6-aminopurin-9-ylmethyl)-5-chloro-3-(2-chlorophenyl)-3H-quinazolin-4-one;

2-(6-aminopurin-9-ylmethyl)-3-(2-chlorophenyl)-5-methyl-3H-quinazolin-4-one;

2-(6-aminopurin-9-ylmethyl)-3-(2-chlorophenyl)-5-fluoro-3H-quinazolin-4-one;

2-(6-aminopurin-9-ylmethyl)-3-benzyl-5-fluoro-3H-quinazolin-4-one;

2-(6-aminopurin-9-ylmethyl)-3-butyl-3H-quinazolin-4-one;

2-(6-aminopurin-9-ylmethyl)-3-morpholin-4-yl-3H-quinazolin-4-one;

2-(6-aminopurin-9-ylmethyl)-3-(2-chlorophenyl)-7-fluoro-3H-quinazolin-4-one;

3-(2-chlorophenyl)-2-(9H-purin-6-ylsulfanylmethyl)-3H-quinazolin-4-one;

3-phenyl-2-(9H-purin-6-ylsulfanylmethyl)-3H-quinazolin-4-one;

2-(6-aminopurin-9-ylmethyl)-5-chloro-3-(2-isopropylphenyl)-3H-quinazolin-4-one; and 2-(6-aminopurin-9-ylmethyl)-5-chloro-3-o-tolyl-3H-quinazolin-4-one.

It has further been determined that the methods of the invention can be advantageously practiced using members of a class of compounds that exhibit PI3Kδ inhibitory activity, thereby facilitating inhibitions of PI3Kδ activity in diseases mediated thereby. For example, in this embodiment, the methods of the invention can be practiced using compounds having the general structure (I).

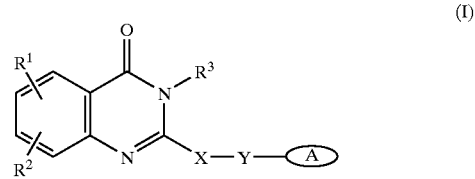

wherein A is an optionally substituted monocyclic or bicyclic ring system containing at least two nitrogen atoms, and at least one ring of the system is aromatic;

X is selected from the group consisting of $C(R^b)_2$, $CH_2CHR^b$, and $CH=C(R^b)$;

Y is selected from the group consisting of null, S, SO, $SO_2$, NH, O, C(=O), OC(=O), C(=O)O, and NHC(=O) $CH_2S$;

$R^1$ and $R^2$, independently, are selected from the group consisting of hydrogen, $C_{1-6}$alkyl, aryl, heteroaryl, halo, $NHC(=O)C_{1-3}$alkyleneN$(R^a)_2$, $NO_2$, $OR^a$, $CF_3$, $OCF_3$, $N(R^a)_2$, CN, $OC(=O)R^a$, $C(=O)R^a$, $C(=O)OR^a$, aryl$OR^b$, Het, $NR^aC(=O)C_{1-3}$alkyleneC$(=O)OR^a$, aryl$OC_{1-3}$-alkyleneN$(R^a)_2$, aryl$OC(=O)R^a$, $C_{1-4}$alkyleneC$(=O)OR^a$, $OC_{1-4}$alkyleneC$(=O)OR^a$, $C_{1-4}$alkyleneOC$_{1-4}$alkyleneC$(=O)OR^a$, $C(=O)NR^aSO_2R^a$, $C_{1-4}$alkyleneN$(R^a)_2$, $C_{2-6}$alkenyleneN$(R^a)_2$, $C(=O)NR^aC_{1-4}$alkyleneOR^a$, $C(=O)NR^aC_{1-4}$-alkyleneHet, $OC_{2-4}$-alkyleneN$(R^a)_2$, $OC_{1-4}$alkyleneCH$(OR^b)CH_2N(R^a)_2$, $OC_{1-4}$-alkyleneHet, $OC_{2-4}$alkyleneOR^a$, $OC_{2-4}$alkyleneNR$^aC(=O)OR^a$, $NR^aC_{1-4}$alkyleneN$(R^a)_2$, $NR^aC(=O)R^a$, $NR^aC(=O)N(R^a)_2$, $N(SO_2C_{1-4}$alkyl)$_2$, $NR^a(SO_2C_{1-4}$alkyl), $SO_2N(R^a)_2$, $OSO_2CF_3$, $C_{1-3}$alkylenearyl, $C_{1-4}$alkyleneHet, $C_{1-6}$alkyleneOR^b$, $C_{1-3}$alkyleneN$(R^a)_2$, $C(=O)N(R^a)_2$, $NHC(=O)C_1-C_3$alkylenearyl, $C_{3-8}$ cycloalkyl, $C_{3-8}$heterocycloalkyl, aryl$OC_{1-3}$-alkyleneN$(R^a)_2$, arylOC$(=O)R^b$, $NHC(=O)C_{1-3}$alkyleneC$_{3-8}$-heterocycloalkyl, $NHC(=O)C_{1-3}$alkyleneHet, $OC_{1-4}$alkyleneOC$_{1-4}$alkyleneC$(=O)OR^b$, $C(=O)C_{1-4}$alkyleneHet, and $NHC(=O)$halo$C_{1-6}$alkyl;

or $R^1$ and $R^2$ are taken together to form a 3- or 4-membered alkylene or alkenylene chain component of a 5- or 6-membered ring, optionally containing at least one heteroatom;

$R^3$ is selected from the group consisting of optionally substituted hydrogen, $C_{1-6}$alkyl, $C_{3-8}$cycloalkyl, $C_{3-8}$heterocycloalkyl, $C_{1-4}$alkylenecycloalkyl, $C_{2-6}$alkenyl, $C_{1-3}$alkylenearyl, aryl$C_{1-3}$alkyl, $C(=O)R^a$, aryl, heteroaryl, $C(=O)OR^a$, $C(=O)N(R^a)_2$, $C(=S)N(R^a)_2$, $SO_2R^a$, $SO_2N(R^a)_2$, $S(=O)R^a$, $S(=O)N(R^a)_2$, $C(=O)NR^aC_{1-4}$-alkyleneOR^a$, $C(=O)NR^aC_{1-4}$alkyleneHet, $C(=O)C_{1-4}$alkylenearyl, $C(=O)C_{1-4}$alkyleneheteroaryl, $C_{1-4}$alkylenearyl optionally substituted with one or more of halo $SO_2N(R^a)_2$, $N(R^a)_2$, $C(=O)OR^a$, $NR^aSO_2CF_3$, CN, $NO_2$, $C(=O)R^a$, $OR^a$, $C_{1-4}$alkyleneN$(R^a)_2$, and $OC_{1-4}$alkyleneN$(R^a)_2$, $C_{1-4}$alkyleneheteroaryl, $C_{1-4}$alkyleneHet, $C_{1-4}$alkyleneC$(=O)C_{1-4}$alkylenearyl, $C_{1-4}$alkyleneC$(=O)$ $C_{1-4}$alkyleneheteroaryl, $C_{1-4}$alkyleneC$(=O)$Het, $C_{1-4}$alkyleneC$(=O)—N(R^a)_2$, $C_{1-4}$alkyleneOR^a$, $C_{1-4}$alkyleneNR$^aC(=O)R^a$, $C_{1-4}$alkyleneOC$_{1-4}$alkyleneOR^a$, $C_{1-4}$alkyleneN$(R^a)_2$, $C_{1-4}$alkyleneC$(=O)OR^a$, and $C_{1-4}$alkyleneOC$_{1-4}$alkyleneC $(=O)OR^a$;

$R^a$ is selected from the group consisting of hydrogen, $C_{1-6}$alkyl, $C_{3-8}$cycloalkyl, $C_{3-8}$heterocycloalkyl, $C_{1-3}$alkyleneN$(R^c)_2$, aryl, aryl$C_{1-3}$alkyl, $C_{1-3}$alkylenearyl, heteroaryl, heteroaryl$C_{1-3}$alkyl, and $C_{1-3}$alkyleneheteroaryl;

or two $R^a$ groups are taken together to form a 5- or 6-membered ring, optionally containing at least one heteroatom;

R$^b$ is selected from the group consisting of hydrogen, C$_{1-6}$alkyl, heteroC$_{1-3}$alkyl, C$_{1-3}$alkyleneheteroC$_{1-3}$alkyl, arylheteroC$_{1-3}$alkyl, aryl, heteroaryl, arylC$_{1-3}$alkyl, heteroarylC$_{1-3}$alkyl, C$_{1-3}$alkylenearyl, and C$_{1-3}$alkyleneheteroaryl;

R$^c$ is selected from the group consisting of hydrogen, C$_{1-6}$alkyl, C$_{3-8}$cycloalkyl, aryl, and heteroaryl;

Het is a 5- or 6-membered heterocyclic ring, saturated or partially or fully unsaturated, containing at least one heteroatom selected from the group consisting of oxygen, nitrogen, and sulfur, and optionally substituted with C$_{1-4}$alkyl or C(=O)OR$^a$;

and pharmaceutically acceptable salts and solvates (e.g., hydrates) thereof.

For example, methods of the invention can employ compounds that possess PI3Kδ inhibitory activity, as follows:

3-(2-isopropylphenyl)-5-methyl-2-(9H-purin-6-ylsulfanylmethyl)-3H-quinazolin-4-one;

5-chloro-2-(9H-purin-6-ylsulfanylmethyl)-3-o-tolyl-3H-quinazolin-4-one;

5-chloro-3-(2-fluorophenyl)-2-(9H-purin-6-ylsulfanylmethyl)-3H-quinazolin-4-one;

3-(2-fluorophenyl)-5-methyl-2-(9H-purin-6-ylsulfanylmethyl)-3H-quinazolin-4-one;

3-(2-methoxyphenyl)-5-methyl-2-(9H-purin-6-ylsulfanylmethyl)-3H-quinazolin-4-one;

3-(2,6-dichlorophenyl)-5-methyl-2-(9H-purin-6-ylsulfanylmethyl)-3H-quinazolin-4-one;

3-(2-chlorophenyl)-6-fluoro-2-(9H-purin-6-ylsulfanylmethyl)-3h-quinazolin-4-one;

5-chloro-3-(2-chlorophenyl)-2-(9H-purin-6-ylsulfanylmethyl)-3H-quinazolin-4-one;

3-(2-chlorophenyl)-5-methyl-2-(9H-purin-6-ylsulfanylmethyl)-3H-quinazolin-4-one;

3-(2-methoxyphenyl)-2-(9H-purin-6-ylsulfanylmethyl)-3H-quinazolin-4-one;

3-(2-chlorophenyl)-5-fluoro-2-(9H-purin-6-ylsulfanylmethyl)-3H-quinazolin-4-one;

3-benzyl-2-(9H-purin-6-ylsulfanylmethyl)-3H-quinazolin-4-one;

3-butyl-2-(9H-purin-6-ylsulfanylmethyl)-3H-quinazolin-4-one;

3-(2-chlorophenyl)-7-fluoro-2-(9H-purin-6-ylsulfanylmethyl)-3H-quinazolin-4-one;

3-morpholin-4-yl-2-(9H-purin-6-ylsulfanylmethyl)-3H-quinazolin-4-one, acetate salt;

8-chloro-3-(2-chlorophenyl)-2-(9H-purin-6-ylsulfanylmethyl)-3H-quinazolin-4-one;

3-(2-chlorophenyl)-6,7-difluoro-2-(9H-purin-6-ylsulfanylmethyl)-3H-quinazolin-4-one;

3-(3-methoxyphenyl)-2-(9H-purin-6-ylsulfanylmethyl)-3H-quinazolin-4-one;

6-chloro-3-(2-chlorophenyl)-2-(9H-purin-6-ylsulfanylmethyl)-3H-quinazolin-4-one;

3-(3-chlorophenyl)-2-(9H-purin-6-ylsulfanylmethyl)-3H-quinazolin-4-one;

2-(9H-purin-6-ylsulfanylmethyl)-3-pyridin-4-yl-3H-quinazolin-4-one;

3-(2-chlorophenyl)-2-(9H-purin-6-ylsulfanylmethyl) trifluoromethyl-3H-quinazolin-4-one;

3-benzyl-5-fluoro-2-(9H-purin-6-ylsulfanylmethyl)-3H-quinazolin-4-one;

3-(4-methylpiperazin-1-yl)-2-(9H-purin-6-ylsulfanylmethyl)-3H-quinazolin-4-one, acetate salt;

3-(2-chlorophenyl)-6-hydroxy-2-(9H-purin-6-ylsulfanylmethyl)-3H-quinazolin-4-one;

[5-fluoro-4-oxo-2-(9H-purin-6-ylsulfanylmethyl)-4H-quinazolin-3-yl]acetic acid ethyl ester;

3-biphenyl-2-yl-5-chloro-2-(9H-purin-6-ylsulfanylmethyl)-3H-quinazolin-4-one;

5-chloro-3-(2-methoxyphenyl)-2-(9H-purin-6-ylsulfanylmethyl)-3H-quinazolin-4-one;

2-(6-aminopurin-9-ylmethyl)-3-(2-isopropylphenyl)-5-methyl-3H-quinazolin-4-one;

2-(6-aminopurin-9-ylmethyl)-5-methyl-3-o-tolyl-3H-quinazolin-4-one;

2-(6-aminopurin-9-ylmethyl)-3-biphenyl-2-yl-t-chloro-3H-quinazolin-4-one;

2-(6-aminopurin-9-ylmethyl)-3-(2-fluorophenyl)-5-methyl-3H-quinazolin-4-one;

2-(6-aminopurin-9-ylmethyl)-5-chloro-3-(2-fluorophenyl)-3H-quinazolin-4-one;

2-(6-aminopurin-9-ylmethyl)-8-chloro-3-(2-chlorophenyl)-3H-quinazolin-4-one;

2-(6-aminopurin-9-ylmethyl)-5-chloro-3-(2-chlorophenyl)-3H-quinazolin-4-one;

2-(6-aminopurin-9-ylmethyl)-3-(2-chlorophenyl)-5-methyl-3H-quinazolin-4-one;

2-(6-aminopurin-9-ylmethyl)-3-(2-chlorophenyl)-5-fluoro-3H-quinazolin-4-one;

2-(6-aminopurin-9-ylmethyl)-3-benzyl-5-fluoro-3H-quinazolin-4-one;

2-(6-aminopurin-9-ylmethyl)-3-butyl-3H-quinazolin-4-one;

2-(6-aminopurin-9-ylmethyl)-3-morpholin-4-yl-3H-quinazolin-4-one;

2-(6-aminopurin-9-ylmethyl)-3-(2-chlorophenyl)-7-fluoro-3H-quinazolin-4-one;

3-(2-chlorophenyl)-2-(9H-purin-6-ylsulfanylmethyl)-3H-quinazolin-4-one;

3-phenyl-2-(9H-purin-6-ylsulfanylmethyl)-3H-quinazolin-4-one;

2-(6-aminopurin-9-ylmethyl)-5-chloro-3-(2-chlorophenyl)-3H-quinazolin-4-one;

3-(4-chlorophenyl)-2-(9H-purin-6-ylsulfanylmethyl)-3H-quinazolin-4-one;

3-(2-chlorophenyl)-6,7-dimethoxy-2-(9H-purin-6-ylsulfanylmethyl)-3H-quinazolin-4-one;

3-(2-chlorophenyl)-7-nitro-2-(9H-purin-6-ylsulfanylmethyl)-3H-quinazolin-4-one;

2-(6-aminopurin-9-ylmethyl)-6-bromo-3-(2-chlorophenyl)-3H-quinazolin-4-one;

2-(6-aminopurin-9-ylmethyl)-3-(2-chlorophenyl)-6,7-dimethoxy-3H-quinazolin-4-one;

6-bromo-3-(2-chlorophenyl)-2-(9H-purin-6-ylsulfanylmethyl)-3H-quinazolin-4-one;

3-(2-chlorophenyl)-2-(9H-purin-6-ylsulfanylmethyl)-3H-benzo[g]quinazolin-4-one;

2-(6-aminopurin-9-ylmethyl)-5-chloro-3-o-tolyl-3H-quinazolin-4-one; and 2-(6-aminopurin-9-ylmethyl)-5-chloro-3-(2-methoxyphenyl)-3H-quinazolin-4-one.

The invention further provides compounds that are selective inhibitors of PI3Kδ activity. The compounds exhibit inhibition of PI3Kδ in biochemical assays, and selectively disrupt function of PI3Kδ-expressing cells in cell-based assays. As described elsewhere herein, the compounds of the invention have been demonstrated to inhibit certain functions in neutrophils and other leukocytes, as well as functions of osteoclasts.

In general, compounds provided by the invention have the general structure (I), a pharmaceutically acceptable salt thereof, or a prodrug thereof:

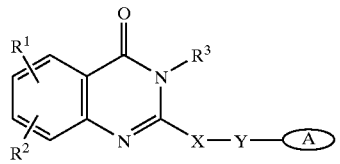

(I)

wherein A is an optionally substituted monocyclic or bicyclic ring system containing at least two nitrogen atoms, and at least one ring of the system is aromatic;

X is selected from the group consisting of $C(R^b)_2$, $CH_2CHR^b$, and $CH=C(R^b)$;

Y is selected from the group consisting of null, S, SO, $SO_2$, NH, $OC(=O)$, $OC(=O)$, $C(=O)O$, and $NHC(=O)$ $CH_2S$;

$R^1$ and $R^2$, independently, are selected from the group consisting of hydrogen, $C_{1-6}$alkyl, aryl, heteroaryl, halo, $NHC(=O)C_3$alkyleneN$(R^a)_2$, $NO_2$, $OR^a$, $CF_3$, $OCF_3$, $N(R^a)_2$, CN, $OC(=O)R^a$, $C(=O)R^a$, $C(=O)OR^a$, aryl$OR^b$, Het, $NR^aC(=O)C_{1-3}$alkyleneC$(=O)OR^a$, aryl$OC_{1-3}$-alkyleneN$(R^a)_2$, aryl$OC(=O)R^a$, $C_{1-4}$alkyleneC$(=O)OR^a$, $OC_{1-4}$alkyleneC$(=O)OR^a$, $C_{1-4}$alkyleneOC$_{1-4}$alkyleneC$(=O)OR^a$, $C(=O)NR^aSO_2R^a$, $C_{1-4}$alkyleneN$(R^a)_2$, $C_{2-6}$alkenyleneN$(R^a)_2$, $C(=O)NR^aC_{1-4}$alkyleneOR$^a$, $C(=O)NR^aC_{1-4}$alkyleneHet, $OC_{2-4}$-alkyleneN$(R^a)_2$, $OC_{1-4}$alkyleneCH(OR$^b$)CH$_2$N$(R^a)_2$, $OC_{1-4}$alkyleneHet, $OC_{2-4}$alkyleneOR$^a$, $OC_{2-4}$ alkyleneNR$^a$C$(=O)OR^a$, $NR^aC_{1-4}$alkyleneN$(R^a)_2$, $NR^aC(=O)R^a$, $NR^aC(=O)N(R^a)_2$, $N(SO_2C_{1-4}$alkyl)$_2$, $NR^a(SO_2C_{1-4}$alkyl), $SO_2N(R^a)_2$, $OSO_2CF_3$, $C_{1-3}$alkylenearyl, $C_{1-4}$alkyleneHet, $C_{1-6}$alkyleneOR$^b$, $C_{1-3}$alkyleneN$(R^a)_2$, $C(=O)N(R^a)_2$, $NHC(=O)C_1-C_3$alkylenearyl, $C_{3-8}$cycloalkyl, $C_{3-8}$heterocycloalkyl, aryl$OC_{1-3}$-alkyleneN$(R^a)_2$, arylOC$(=O)R^b$, $NHC(=O)C_{1-3}$alkyleneC$_{3-8}$-heterocycloalkyl, $NHC(=O)C_{1-3}$alkyleneHet, $OC_{1-4}$alkyleneOC$_{1-4}$alkyleneC$(=O)OR^b$, $C(=O)C_{1-4}$alkyleneHet, and $NHC(=O)$ halo$C_{1-6}$ alkyl;

or $R^1$ and $R^2$ are taken together to form a 3- or 4-membered alkylene or alkenylene chain component of a 5- or 6-membered ring, optionally containing at least one heteroatom;

$R^3$ is selected from the group consisting of optionally substituted hydrogen, $C_{1-6}$alkyl, $C_{3-8}$cycloalkyl, $C_{3-8}$heterocycloalkyl, $C_{1-4}$alkylenecycloalkyl, $C_{2-6}$alkenyl, $C_{1-3}$alkylenearyl, aryl$C_{1-3}$alkyl, $C(=O)R^a$, aryl, heteroaryl, $C(=O)OR^a$, $C(=O)N(R^a)_2$, $C(=S)N(R^a)_2$, $SO_2R^a$, $SO_2N(R^a)_2$, $S(=O)R^a$, $S(=O)N(R^a)_2$, $C(=O)NR^aC_{1-4}$alkyleneOR$^a$, $C(=O)NR^aC_{1-4}$alkyleneHet, $C(=O)C_{1-4}$alkylenearyl, $C(=O)C_{1-4}$alkyleneheteroaryl, $C_{1-4}$alkylenearyl optionally substituted with one or more of halo $SO_2N(R^a)_2$, $N(R^a)_2$, $C(=O)OR^a$, $NR^aSO_2CF_3$, CN, $NO_2$, $C(=O)R^a$, $OR^a$, $C_{1-4}$alkyleneN$(R^a)_2$, and $OC_{1-4}$alkyleneN$(R^a)_2$, $C_{1-4}$-alkyleneheteroaryl, $C_{1-4}$alkyleneHet, $C_{1-4}$alkyleneC$(=O)$—$C_{1-4}$alkylenearyl, $C_{1-4}$alkyleneC$(=O)C_{1-4}$alkyleneheteroaryl, $C_{1-4}$alkyleneC$(=O)$Het, $C_{1-4}$alkyleneC$(=O)N(R^a)_2$, $C_{1-4}$alkyleneOR$^a$, $C_{1-4}$alkyleneNR$^a$C$(=O)R^a$, $C_{1-4}$alkyleneOC$_{1-4}$alkyleneOR$^a$, $C_{1-4}$alkyleneN$(R^a)_2$, $C_{1-4}$alkyleneC$(=O)$—OR$^a$, and $C_{1-4}$alkyleneOC$_{1-4}$alkyleneC$(=O)OR^a$;

$R^a$ is selected from the group consisting of hydrogen, $C_{1-6}$alkyl, $C_{3-8}$cycloalkyl, $C_{3-8}$heterocycloalkyl, $C_{1-3}$alkyleneN$(R^c)_2$, aryl, aryl$C_{1-3}$alkyl, $C_{1-3}$alkylenearyl, heteroaryl, heteroaryl$C_{1-3}$alkyl, and $C_{1-3}$alkyleneheteroaryl;

or two $R^a$ groups are taken together to form a 5- or 6-membered ring, optionally containing at least one heteroatom;

$R^b$ is selected from the group consisting of hydrogen, $C_{1-6}$alkyl, hetero$C_{1-3}$alkyl, $C_{1-3}$alkyleneheteroC$_{1-3}$alkyl, arylheteroC$_{1-3}$alkyl, aryl, heteroaryl, aryl$C_{1-3}$alkyl, heteroaryl$C_{1-3}$alkyl, $C_{1-3}$alkylenearyl, and $C_{1-3}$alkyleneheteroaryl;

$R^c$ is selected from the group consisting of hydrogen, $C_{1-6}$alkyl, $C_{3-8}$cycloalkyl, aryl, and heteroaryl;

Het is a 5- or 6-membered heterocyclic ring, saturated or partially or fully unsaturated, containing at least one heteroatom selected from the group consisting of oxygen, nitrogen, and sulfur, and optionally substituted with $C_{1-4}$alkyl or $C(=O)OR^a$;

and pharmaceutically acceptable salts and solvates (e.g., hydrates) thereof.

As used herein, the term "alkyl" is defined as straight chained and branched hydrocarbon groups containing the indicated number of carbon atoms, typically methyl, ethyl, and straight chain and branched propyl and butyl groups. The hydrocarbon group can contain up to 16 carbon atoms, preferably one to eight carbon atoms. The term "alkyl" includes "bridged alkyl," i.e., a $C_6$–$C_{16}$ bicyclic or polycyclic hydrocarbon group, for example, norbornyl, adamantyl, bicyclo[2.2.2]octyl, bicyclo-[2.2.1]heptyl, bicyclo[3.2.1] octyl, or decahydro-naphthyl. The term "cycloalkyl" is defined as a cyclic $C_3$–$C_8$ hydrocarbon group, e.g., cyclopropyl, cyclobutyl, cyclohexyl, and cyclopentyl.

The term "alkenyl" is defined identically as "alkyl," except for containing a carbon-carbon double bond. "Cycloalkenyl" is defined similarly to cycloalkyl, except a carbon-carbon double bond is present in the ring.

The term "alkylene" is defined as an alkyl group having a substituent. For example, the term "$C_{1-3}$alkylenearyl" refers to an alkyl group containing one to three carbon atoms, and substituted with an aryl group.

The term "hetero$C_{1-3}$alkyl" is defined as a $C_{1-3}$alkyl group further containing a heteroatom selected from O, S, and NR$^a$. For example, —CH$_2$OCH$_3$ or —CH$_2$CH$_2$SCH$_3$. The term "arylheteroC$_{1-3}$alkyl" refers to an aryl group having a heteroC$_{1-3}$alkyl substituent.

The term "halo" or "halogen" is defined herein to include fluorine, bromine, chlorine, and iodine.

The term "haloalkyl" is defined herein as an alkyl group substituted with one or more halo substituents, either fluoro, chloro, bromo, iodo, or combinations thereof. Similarly, "halocycloalkyl" is defined as a cycloalkyl group having one or more halo substituents.

The term "aryl," alone or in combination, is defined herein as a monocyclic or polycyclic aromatic group, preferably a monocyclic or bicyclic aromatic group, e.g., phenyl or naphthyl. Unless otherwise indicated, an "aryl" group can be unsubstituted or substituted, for example, with one or more, and in particular one to three, halo, alkyl, phenyl, hydroxyalkyl, alkoxy, alkoxyalkyl, haloalkyl, nitro, amino, alkylamino, acylamino, alkylthio, alkylsulfinyl, and alkylsulfonyl. Exemplary aryl groups include phenyl, naphthyl, biphenyl, tetra-hydronaphthyl, chlorophenyl, fluorophenyl, aminophenyl, methylphenyl, methoxyphenyl, trifluoromethylphenyl, nitrophenyl, carboxyphenyl, and the like. The terms "arylC$_{1-3}$alkyl" and "heteroarylC$_{1-3}$alkyl" are defined as an aryl or heteroaryl group having a $C_{1-3}$alkyl substituent.

The term "heteroaryl" is defined herein as a monocyclic or bicyclic ring system containing one or two aromatic rings and containing at least one nitrogen, oxygen, or sulfur atom in an aromatic ring, and which can be unsubstituted or substituted, for example, with one or more, and in particular one to three, substituents, like halo, alkyl, hydroxy, hydroxyalkyl, alkoxy, alkoxyalkyl, haloalkyl, nitro, amino, alkylamino, acylamino, alkylthio, alkylsulfinyl, and alkylsulfonyl. Examples of heteroaryl groups include thienyl, furyl, pyridyl, oxazolyl, quinolyl, isoquinolyl, indolyl, triazolyl, isothiazolyl, isoxazolyl, imidizolyl, benzothiazolyl, pyrazinyl, pyrimidinyl, thiazolyl, and thiadiazolyl.

The term "Het" is defined as monocyclic, bicyclic, and tricyclic groups containing one or more heteroatoms selected from the group consisting of oxygen, nitrogen, and sulfur. A "Het" group also can contain an oxo group (=O) attached to the ring. Nonlimiting examples of Het groups include 1,3-dioxolane, 2-pyrazoline, pyrazolidine, pyrrolidine, piperazine, a pyrroline, 2H-pyran, 4H-pyran, morpholine, thiopholine, piperidine, 1,4-dithiane, and 1,4-dioxane.

The term "hydroxy" is defined as —OH.

The term "alkoxy" is defined as —OR, wherein R is alkyl.

The term "alkoxyalkyl" is defined as an alkyl group wherein a hydrogen has been replaced by an alkoxy group. The term "(alkylthio)alkyl" is defined similarly as alkoxyalkyl, except a sulfur atom, rather than an oxygen atom, is present.

The term "hydroxyalkyl" is defined as a hydroxy group appended to an alkyl group.

The term "amino" is defined as —$NH_2$, and the term "alkylamino" is defined as —$NR_2$, wherein at least one R is alkyl and the second R is alkyl or hydrogen.

The term "acylamino" is defined as RC(=O)N, wherein R is alkyl or aryl.

The term "alkylthio" is defined as —SR, wherein R is alkyl.

The term "alkylsulfinyl" is defined as R—$SO_2$, wherein R is alkyl.

The term "amino" is defined as —$NH_2$, and the term "alkylamino" is defined as —$NR_2$, wherein at least one R is alkyl and the second R is alkyl or hydrogen.

The term "acylamino" is defined as RC(=O)N, wherein R is alkyl or aryl.

The term "alkylthio" is defined as —SR, wherein R is alkyl.

The term "alkylsulfinyl" is defined as R—$SO_2$, wherein R is alkyl.

The term "alkylsulfonyl" is defined as R—$SO_3$, wherein R is alkyl.

The term "nitro" is defined as —$NO_2$.

The term "trifluoromethyl" is defined as —$CF_3$.

The term "trifluoromethoxy" is defined as —$OCF_3$.

The term "cyano" is defined as —CN.

In preferred embodiments, X is selected from the group consisting of $CH_2$, $CH_2CH_2$, CH=CH, CH($CH_3$), CH($CH_2CH_3$), $CH_2CH(CH_3)$, and C($CH_3$)$_2$. In further preferred embodiments, Y is selected from the group consisting of null, S, and NH.

The A ring can be monocyclic or bicyclic. Monocyclic A ring systems are aromatic. Bicyclic A ring systems contain at least one aromatic ring, but both rings can be aromatic. Examples of A ring systems include, but are not limited to, imidazolyl, pyrazolyl, 1,2,3-triazolyl, pyridizinyl, pyrimidinyl, pyrazinyl, 1,3,5-triazinyl, purinyl, cinnolinyl, phthalazinyl, quinazolinyl, quinoxalinyl, 1,8-naphthyridinyl, pteridinyl, 1H-indazolyl, and benzimidazolyl.

In a preferred group of compounds of formula (I), A is represented by an optionally substituted ring system selected from the group consisting of

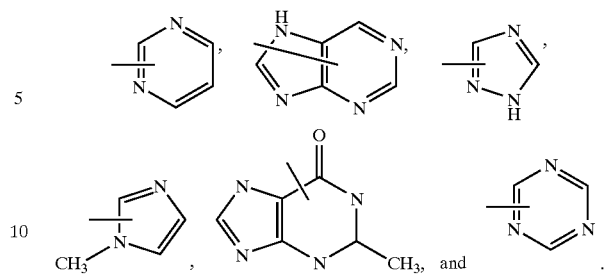

The A ring system optionally can be substituted with one to three, and preferably one to two, substituents selected from the group consisting of N($R^a$)$_2$, halo, $C_{1-3}$alkyl, S($C_{1-3}$alkyl), $OR^a$, and

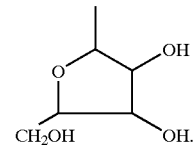

Specific substituents include, but are not limited to, $NH_2$, NH($CH_3$), N($CH_3$)$_2$, $NHCH_2C_6H_5$, NH($C_2H_5$), Cl, F, $CH_3$, $SCH_3$, OH, and

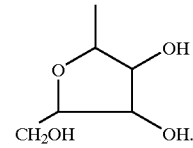

In another preferred group of compounds of formula (I), $R^1$ and $R^2$, independently, are represented by hydrogen, $OR^a$, halo, $C_{1-6}$alkyl, $CF_3$, $NO_2$, N($R^a$)$_2$, $NR^aC_{1-3}$alkyleneN($R^a$)$_2$, and $OC_{1-3}$alkylene$OR^a$. Specific substituents include, but are not limited to, H, $OCH_3$, Cl, Br, F, $CH_3$, $CF_3$, $NO_2$, OH, N($CH_3$)$_2$,

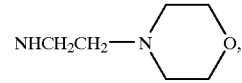

and O($CH_2$)$_2$$OCH_2C_6H_5$. $R^1$ and $R^2$ also can be taken together to form a ring, for example, a phenyl ring.

In a preferred embodiment, $R^3$ is selected from the group consisting of optionally substituted $C_{1-6}$alkyl, aryl, heteroaryl, $C_{3-8}$cycloalkyl, $C_{3-8}$heterocycloalkyl, C(=O)$OR^a$, $C_{1-4}$alkyleneHet, $C_{1-4}$alkylenecycloalkyl, $C_{1-4}$alkylenearyl, $C_{1-4}$alkyleneC(=O)$C_{1-4}$-alkylenearyl, $C_{1-4}$alkyleneC(=O)$OR^a$, $C_{1-4}$alkyleneC(=O)N($R^a$)$_2$, $C_{1-4}$alkyleneC(=O)Het, $C_{1-4}$alkyleneN($R^a$)$_2$, and $C_{1-4}$alkylene$NR^aC$(=O)$R^a$. Specific $R^3$ groups include, but are not limited to

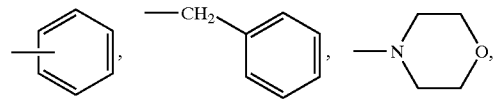

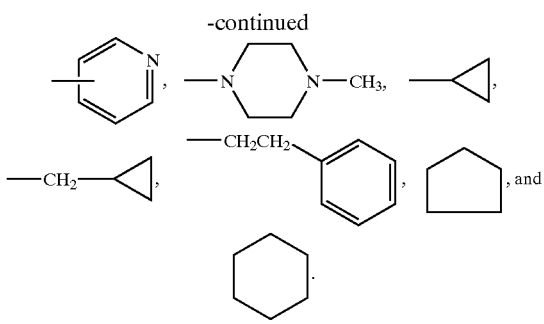

The R³ group can be substituted with one to three substituents, for example, halo, OR$^a$, C$_{1-6}$alkyl, aryl, heteroaryl, NO$_2$, N(R$^a$)$_2$, NR$^a$SO$_2$CF$_3$, NR$^a$C(=O)R$^a$, C(=O)OR$^a$, N(R$^a$)C$_{1-4}$alkylene(R$^a$)$_2$, SO$_2$N(R$^a$)$_2$, CN, C(=O)R$^a$, C$_{1-4}$alkyleneN(R$^a$)$_2$, OC$_{1-4}$alkyleneC≡CR$^a$, OC$_{1-4}$alkyleneC(=O)N(R$^a$)$_2$, OC$_{1-4}$alkylenearyl, OC$_{1-4}$alkyleneheteroaryl, OC$_{1-4}$alkyleneHet, OC$_{1-4}$alkylene N(R$^a$)$_2$, and N(R$^a$)—C$_{1-4}$alkyleneN(R$^a$)$_2$. Specific substituents for the R³ group include, but are not limited to, Cl, F, CH$_3$, CH(CH$_3$)$_2$, OH, OCH$_3$, O(CH$_2$)$_3$N(CH$_3$)$_2$, OCH$_2$C≡CH, OCH$_2$C(=O)—NH$_2$, C$_6$H$_5$, NO$_2$, NH$_2$, NHC(=O)CH$_3$, CO$_2$H, N(CH$_3$)CH$_2$CH$_2$N—(CH$_3$)$_2$, and

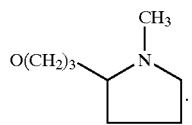

As used herein, the quinazoline ring structure, and numbering of the ring structure, is

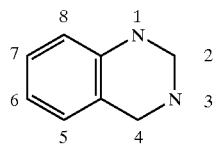

The purine ring structure, and numbering of the ring structure, is

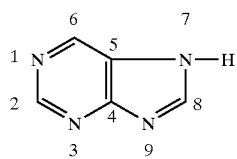

The compounds provided by the invention are exemplified as follows:

3-(2-isopropylphenyl)-5-methyl-2-(9H-purin-6-ylsulfanylmethyl)-3H-quinazolin-4-one;
5-chloro-2-(9H-purin-6-ylsulfanylmethyl)-3-o-tolyl-3H-quinazolin-4-one;
5-chloro-3-(2-fluorophenyl)-2-(9H-purin-6-ylsulfanylmethyl)-3H-quinazolin-4-one;
3-(2-fluorophenyl)-5-methyl-2-(9H-purin-6-ylsulfanylmethyl)-3H-quinazolin-4-one;
3-(2-methoxyphenyl)-5-methyl-2-(9H-purin-6-ylsulfanylmethyl)-3H-quinazolin-4-one;
3-(2,6-dichlorophenyl)-5-methyl-2-(9H-purin-6-ylsulfanylmethyl)-3H-quinazolin-4-one;
3-(2-chlorophenyl)-6-fluoro-2-(9H-purin-6-ylsulfanylmethyl)-3h-quinazolin-4-one;
5-chloro-3-(2-chlorophenyl)-2-(9H-purin-6-ylsulfanylmethyl)-3H-quinazolin-4-one;
3-(2-chlorophenyl)-5-methyl-2-(9H-purin-6-ylsulfanylmethyl)-3H-quinazolin-4-one;
3-(2-methoxyphenyl)-2-(9H-purin-6-ylsulfanylmethyl)-3H-quinazolin-4-one;
3-(2-chlorophenyl)-5-fluoro-2-(9H-purin-6-ylsulfanylmethyl)-3H-quinazolin-4-one;
3-benzyl-2-(9H-purin-6-ylsulfanylmethyl)-3H-quinazolin-4-one;
3-butyl-2-(9H-purin-6-ylsulfanylmethyl)-3H-quinazolin-4-one;
3-(2-chlorophenyl)-7-fluoro-2-(9H-purin-6-ylsulfanylmethyl)-3H-quinazolin-4-one;
3-morpholin-4-yl-2-(9H-purin-6-ylsulfanylmethyl)-3H-quinazolin-4-one, acetate salt;
8-chloro-3-(2-chlorophenyl)-2-(9H-purin-6-ylsulfanylmethyl)-3H-quinazolin-4-one;
3-(2-chlorophenyl)-6,7-difluoro-2-(9H-purin-6-ylsulfanylmethyl)-3H-quinazolin-4-one;
3-(3-methoxyphenyl)-2-(9H-purin-6-ylsulfanylmethyl)-3H-quinazolin-4-one;
6-chloro-3-(2-chlorophenyl)-2-(9H-purin-6-ylsulfanylmethyl)-3H-quinazolin-4-one;
3-(3-chlorophenyl)-2-(9H-purin-6-ylsulfanylmethyl)-3H-quinazolin-4-one;
2-(9H-purin-6-ylsulfanylmethyl)-3-pyridin-4-yl-3H-quinazolin-4-one;
3-(2-chlorophenyl)-8-trifluoromethyl-2-(9H-purin-6-ylsulfanylmethyl)-3H-quinazolin-4-one;
3-benzyl-5-fluoro-2-(9H-purin-6-ylsulfanylmethyl)-3H-quinazolin-4-one;
3-(4-methylpiperazin-1-yl)-2-(9H-purin-6-ylsulfanylmethyl)-3H-quinazolin-4-one, acetate salt;
3-(2-chlorophenyl)-6-hydroxy-2-(9H-purin-6-ylsulfanylmethyl)-3H-quinazolin-4-one;
[5-fluoro-4-oxo-2-(9H-purin-6-ylsulfanylmethyl)-4H-quinazolin-3-yl]acetic acid ethyl ester;
3-(2-methoxyphenyl)-2-(9H-purin-6-ylsulfanylmethyl)-3H-quinazolin-4-one;
3-biphenyl-2-yl-5-chloro-2-(9H-purin-6-ylsulfanylmethyl)-3H-quinazolin-4-one;
5-chloro-3-(2-methoxyphenyl)-2-(9H-purin-6-ylsulfanylmethyl)-3H-quinazolin-4-one;
2-(6-aminopurin-9-ylmethyl)-3-(2-isopropylphenyl)-5-methyl-3H-quinazolin-4-one;
2-(6-aminopurin-9-ylmethyl)-5-methyl-3-o-tolyl-3H-quinazolin-4-one;
2-(6-aminopurin-9-ylmethyl)-3-biphenyl-2-yl-5-chloro-3H-quinazolin-4-one;
2-(6-aminopurin-9-ylmethyl)-3-(2-fluorophenyl)-5-methyl-3H-quinazolin-4-one;
2-(6-aminopurin-9-ylmethyl)-5-chloro-3-(2-fluorophenyl)-3H-quinazolin-4-one;
2-(6-aminopurin-9-ylmethyl)-8-chloro-3-(2-chlorophenyl)-3H-quinazolin-4-one;
2-(6-aminopurin-9-ylmethyl)-5-chloro-3-(2-chlorophenyl)-3H-quinazolin-4-one;
2-(6-aminopurin-9-ylmethyl)-3-(2-chlorophenyl)-5-methyl-3H-quinazolin-4-one;
2-(6-aminopurin-9-ylmethyl)-3-(2-chlorophenyl)-5-fluoro-3H-quinazolin-4-one;
2-(6-aminopurin-9-ylmethyl)-3-benzyl-5-fluoro-3H-quinazolin-4-one;
2-(6-aminopurin-9-ylmethyl)-3-butyl-3H-quinazolin-4-one;

2-(6-aminopurin-9-ylmethyl)-3-morpholin-4-yl-3H-quinazolin-4-one;
2-(6-aminopurin-9-ylmethyl)-3-(2-chlorophenyl)-7-fluoro-3H-quinazolin-4-one;
2-(6-aminopurin-9-ylmethyl)-6-chloro-3-(2-chlorophenyl)-3H-quinazolin-4-one;
3-(4-chlorophenyl)-2-(9H-purin-6-ylsulfanylmethyl)-3H-quinazolin-4-one;
3-(2-chlorophenyl)-6,7-dimethoxy-2-(9H-purin-6-ylsulfanylmethyl)-3H-quinazoline-4-one;
3-(2-chlorophenyl)-7-nitro-2-(9H-purin-6-ylsulfanylmethyl)-3H-quinazolin-4-one;
2-(6-aminopurin-9-ylmethyl)-6-bromo-3-(2-chlorophenyl)-3H-quinazolin-4-one;
2-(6-aminopurin-9-ylmethyl)-3-(2-chlorophenyl)-6,7-dimethoxy-3H-quinazolin-4-one;
6-bromo-3-(2-chlorophenyl)-2-(9H-purin-6-ylsulfanylmethyl)-3H-quinazolin-4-one;
3-(2-chlorophenyl)-2-(9H-purin-6-ylsulfanylmethyl)-3H-benzo[g]quinazolin-4-one;
2-(6-aminopurin-9-ylmethyl)-5-chloro-3-o-tolyl-3H-quinazolin-4-one; and
2-(6-aminopurin-9-ylmethyl)-5-chloro-3-(2-methoxyphenyl)-3H-quinazolin-4-one.

The preferred compounds provided by the invention have the structure (IV), exemplified as follows:
3-(2-isopropylphenyl)-5-methyl-2-(9H-purin-6-ylsulfanylmethyl)-3H-quinazolin-4-one;
5-chloro-2-(9H-purin-6-ylsulfanylmethyl)-3-o-tolyl-3H-quinazolin-4-one;
5-chloro-3-(2-fluorophenyl)-2-(9H-purin-6-ylsulfanylmethyl)-3H-quinazolin-4-one;
3-(2-fluorophenyl)-5-methyl-2-(9H-purin-6-ylsulfanylmethyl)-3H-quinazolin-4-one;
3-(2,6-dichlorophenyl)-5-methyl-2-(9H-purin-6-ylsulfanylmethyl)-3H-quinazolin-4-one;
3-(2-chlorophenyl)-6-fluoro-2-(9H-purin-6-ylsulfanylmethyl)-3h-quinazolin-4-one;
5-chloro-3-(2-chlorophenyl)-2-(9H-purin-6-ylsulfanylmethyl)-3H-quinazolin-4-one;
3-(2-chlorophenyl)-5-methyl-2-(9H-purin-6-ylsulfanylmethyl)-3H-quinazolin-4-one;
3-(2-chlorophenyl)-5-fluoro-2-(9H-purin-6-ylsulfanylmethyl)-3H-quinazolin-4-one;
3-benzyl-2-(9H-purin-6-ylsulfanylmethyl)-3H-quinazolin-4-one;
3-butyl-2-(9H-purin-6-ylsulfanylmethyl)-3H-quinazolin-4-one;
3-(2-chlorophenyl)-7-fluoro-2-(9H-purin-6-ylsulfanylmethyl)-3H-quinazolin-4-one;
3-morpholin-4-yl-2-(9H-purin-6-ylsulfanylmethyl)-3H-quinazolin-4-one, acetate salt;
8-chloro-3-(2-chlorophenyl)-2-(9H-purin-6-ylsulfanylmethyl)-3H-quinazolin-4-one;
3-(2-chlorophenyl)-6,7-difluoro-2-(9H-purin-6-ylsulfanylmethyl)-3H-quinazolin-4-one;
6-chloro-3-(2-chlorophenyl)-2-(9H-purin-6-ylsulfanylmethyl)-3H-quinazolin-4-one;
3-(3-chlorophenyl)-2-(9H-purin-6-ylsulfanylmethyl)-3H-quinazolin-4-one;
2-(9H-purin-6-ylsulfanylmethyl)-3-pyridin-4-yl-3H-quinazolin-4-one;
3-(2-chlorophenyl)-2-(9H-purin-6-ylsulfanylmethyl)trifluoromethyl-3H-quinazolin-4-one;
3-benzyl-5-fluoro-2-(9H-purin-6-ylsulfanylmethyl)-3H-quinazolin-4-one;
3-(4-methylpiperazin-1-yl)-2-(9H-purin-6-ylsulfanylmethyl)-3H-quinazolin-4-one, acetate salt;
3-(2-chlorophenyl)-6-hydroxy-2-(9H-purin-6-ylsulfanylmethyl)-3H-quinazolin-4-one;
[5-fluoro-4-oxo-2-(9H-purin-6-ylsulfanylmethyl)-4H-quinazolin-3-yl]acetic acid ethyl ester;
3-biphenyl-2-yl-5-chloro-2-(9H-purin-6-ylsulfanylmethyl)-3H-quinazolin-4-one;
2-(6-aminopurin-9-ylmethyl)-3-(2-isopropylphenyl)-5-methyl-3H-quinazolin-4-one;
2-(6-aminopurin-9-ylmethyl)-5-methyl-3-o-tolyl-3H-quinazolin-4-one;
2-(6-aminopurin-9-ylmethyl)-3-biphenyl-2-yl-5-chloro-3H-quinazolin-4-one;
2-(6-aminopurin-9-ylmethyl)-3-(2-fluorophenyl)-5-methyl-3H-quinazolin-4-one;
2-(6-aminopurin-9-ylmethyl)-5-chloro-3-(2-fluorophenyl)-3H-quinazolin-4-one;
2-(6-aminopurin-9-ylmethyl)-8-chloro-3-(2-chlorophenyl)-3H-quinazolin-4-one;
2-(6-aminopurin-9-ylmethyl)-5-chloro-3-(2-chlorophenyl)-3H-quinazolin-4-one;
2-(6-aminopurin-9-ylmethyl)-3-(2-chlorophenyl)-5-methyl-3H-quinazolin-4-one;
2-(6-aminopurin-9-ylmethyl)-3-(2-chlorophenyl)-5-fluoro-3H-quinazolin-4-one;
2-(6-aminopurin-9-ylmethyl)-3-benzyl-5-fluoro-3H-quinazolin-4-one;
2-(6-aminopurin-9-ylmethyl)-3-butyl-3H-quinazolin-4-one;
2-(6-aminopurin-9-ylmethyl)-3-morpholin-4-yl-3H-quinazolin-4-one;
2-(6-aminopurin-9-ylmethyl)-3-(2-chlorophenyl)-7-fluoro-3H-quinazolin-4-one; and
2-(6-aminopurin-9-ylmethyl)-5-chloro-3-o-tolyl-3H-quinazoline-4-one.

It is generally accepted that biological systems can exhibit very sensitive activities with respect to the absolute stereochemical nature of compounds. (See, E. J. Ariens, *Medicinal Research Reviews*, 6:451–466 (1986); E. J. Ariens, *Medicinal Research Reviews*, 7:367–387 (1987); K. W. Fowler, Handbook of Stereoisomers: Therapeutic Drugs, CRC Press, edited by Donald P. Smith, pp. 35–63 (1989); and S. C. Stinson, *Chemical and Engineering News*, 75:38–70 (1997).)

Therefore, the present invention includes all possible stereoisomers and geometric isomers of compounds of structural formulae (I)–(IV), and includes not only racemic compounds, but also the optically active isomers as well. When a compound of structural formulae (I)–(IV) is desired as a single enantiomer, it can be obtained either by resolution of the final product or by stereospecific synthesis from either isomerically pure starting material or use of a chiral auxiliary reagent, for example, see Z. Ma et al., *Tetrahedron: Asymmetry*, 8(6), pages 883–888 (1997). Resolution of the final product, an intermediate, or a starting material can be achieved by any suitable method known in the art. Additionally, in situations where tautomers of the compounds of structural formulae (I)–(IV) are possible, the present invention is intended to include all tautomeric forms of the compounds. Specific stereoisomers exhibit an excellent ability to inhibit kinase activity of PI3Kδ.

The term "prodrug" as used herein refers to compounds that are rapidly transformed in vivo to a compound having structural formula (I) hereinabove, for example, by hydrolysis. Prodrug design is discussed generally in Hardma et al. (Eds.), *Goodman and Gilman's The Pharmacological Basis of Therapeutics*, 9th ed., pp. 11–16 (1996). A thorough discussion is provided in Higuchi et al., *Prodrugs as Novel Delivery Systems*, Vol. 14, ASCD Symposium Series, and in Roche (ed.), *Bioreversible Carriers in Drug Design*, American Pharmaceutical Association and Pergamon Press (1987). Briefly, administration of a drug is followed by elimination from the body or some biotransformation whereby biological activity of the drug is reduced or eliminated. Alternatively, a biotransformation process can lead to a metabolic by-product, which is itself more active or equally active as compared to the drug initially administered. Increased understanding of these biotransformation processes permits the design of so-called "prodrugs," which, following a biotransformation, become more physiologically active in their altered state. Prodrugs, therefore, encompass pharmacologically inactive compounds that are converted to biologically active metabolites.

To illustrate, prodrugs can be converted into a pharmacologically active form through hydrolysis of, for example, an ester or amide linkage, thereby introducing or exposing a functional group on the resultant product. The prodrugs can be designed to react with an endogenous compound to form a water-soluble conjugate that further enhances the pharmacological properties of the compound, for example, increased circulatory half-life. Alternatively, prodrugs can be designed to undergo covalent modification on a functional group with, for example, glucuronic acid, sulfate, glutathione, amino acids, or acetate. The resulting conjugate can be inactivated and excreted in the urine, or rendered more potent than the parent compound. High molecular weight conjugates also can be excreted into the bile, subjected to enzymatic cleavage, and released back into the circulation, thereby effectively increasing the biological half-life of the originally administered compound.

Methods for Identifying Negative Regulators of PI3Kδ Activity

The PI3Kδ protein, as well as fragments thereof possessing biological activity, can be used for screening putative negative regulator compounds in any of a variety of drug screening techniques. A negative regulator of PI3Kδ is a compound that diminishes or abolishes the ability of PI3Kδ to carry out any of its biological functions. An example of such compounds is an agent that decreases the ability of a PI3Kδ polypeptide to phosphorylate phosphatidylinositol or to target appropriate structures within a cell. The selectivity of a compound that negatively regulates PI3Kδ activity can be evaluated by comparing its activity on the PI3Kδ to its activity on other proteins. Selective negative regulators include, for example, antibodies and other proteins or peptides that specifically bind to a PI3Kδ polypeptide, oligonucleotides that specifically bind to PI3Kδ polypeptides, and other nonpeptide compounds (e.g., isolated or synthetic organic molecules) that specifically interact with PI3Kδ polypeptides. Negative regulators also include compounds as described above, but which interact with a specific binding partner of PI3Kδ polypeptides.

Presently preferred targets for the development of selective negative regulators of PI3Kδ include, for example:

(1) cytoplasmic regions of PI3Kδ polypeptides that contact other proteins and/or localize PI3Kδ within a cell;

(2) regions of PI3Kδ polypeptides that bind specific binding partners;

(3) regions of the PI3Kδ polypeptides that bind substrate;

(4) allosteric regulatory sites of the PI3Kδ polypeptides that can or cannot interact directly with the active site upon regulatory signal;

(5) regions of the PI3Kδ polypeptides that mediate multimerization.

For example, one target for development of modulators is the identified regulatory interaction of p85 with p110δ, which can be involved in activation and/or subcellular localization of the p100δ moiety. Still other selective modulators include those that recognize specific regulatory or PI3Kδ-encoding nucleotide sequences. Modulators of PI3Kδ activity can be therapeutically useful in treatment of a wide range of diseases and physiological conditions in which aberrant PI3Kδ activity is involved.

Accordingly, the invention provides methods of characterizing the potency of a test compound as an inhibitor of PI3Kδ polypeptide, said method comprising the steps of (a) measuring activity of a PI3Kδ polypeptide in the presence of a test compound; (b) comparing the activity of the PI3Kδ polypeptide in the presence of the test compound to the activity of the PI3Kδ polypeptide in the presence of an equivalent amount of a reference compound (e.g., a PI3Kδ inhibitor compound of the invention as described herein), wherein a lower activity of the PI3Kδ polypeptide in the presence of the test compound than in the presence of the reference indicates that the test compound is a more potent inhibitor than the reference compound, and a higher activity of the PI3Kδ polypeptide in the presence of the test compound than in the presence of the reference indicates that the test compound is a less potent inhibitor than the reference compound.

The invention further provides methods of characterizing the potency of a test compound as an inhibitor of PI3Kδ polypeptide, comprising the steps of (a) determining an amount of a control compound (e.g., a PI3Kδ inhibitor compound of the invention as described herein) that inhibits an activity of a PI3Kδ polypeptide by a reference percentage of inhibition, thereby defining a reference inhibitory amount for the control compound; (b) determining an amount of a test compound that inhibits an activity of a PI3Kδ polypeptide by a reference percentage of inhibition, thereby defining a reference inhibitory amount for the test compound; (c) comparing the reference inhibitory amount for the test compound to the reference inhibitory amount for the control compound, wherein a lower reference inhibitory amount for the test compound than for the control compound indicates that the test compound is a more potent inhibitor than the control compound, and a higher reference inhibitory amount for the test compound than for the control compound indicates that the test compound is a less potent inhibitor than the control compound. In one aspect, the method uses a reference inhibitory amount which is the amount of the compound than inhibits the activity of the PI3Kδ polypeptide by 50%, 60%, 70%, or 80%. In another aspect the method employs a reference inhibitory amount that is the amount of the compound that inhibits the activity of the PI3Kδ polypeptide by 90%, 95%, or 99%. These methods comprise determining the reference inhibitory amount of the compounds in an in vitro biochemical assay, in an in vitro cell-based assay, or in an in vivo assay.

The invention further provides methods of identifying a negative regulator of PI3Kδ activity, comprising the steps of (i) measuring activity of a PI3Kδ polypeptide in the presence and absence of a test compound, and (ii) identifying as a negative regulator a test compound that decreases PI3Kδ activity and that competes with a compound of the invention for binding to PI3Kδ. Furthermore, the invention provides methods for identifying compounds that inhibit PI3Kδ activity, comprising the steps of (i) contacting a PI3Kδ polypeptide with a compound of the invention in the presence and absence of a test compound, and (ii) identifying a test compound as a negative regulator of PI3Kδ activity wherein the compound competes with a compound of the invention for binding to PI3Kδ. The invention therefore provides a method for screening for candidate negative regulators of PI3Kδ activity and/or to confirm the mode of action of candidate such negative regulators. Such methods can be employed against other PI3K isoforms in parallel to establish comparative activity of the test compound across the isoforms and/or relative to a compound of the invention.

In these methods, the PI3Kδ polypeptide can be a fragment of p110δ that exhibits kinase activity, i.e., a fragment comprising the catalytic site of p110δ. Alternatively, the PI3Kδ polypeptide can be a fragment from the p110δ-binding domain of p85 and provides a method to identify allosteric modulators of PI3Kδ. The methods can be employed in cells expressing cells expressing PI3Kδ or its subunits, either endogenously or exogenously. Accordingly, the polypeptide employed in such methods can be free in solution, affixed to a solid support, modified to be displayed on a cell surface, or located intracellularly. The modulation of activity or the formation of binding complexes between the PI3Kδ polypeptide and the agent being tested then can be measured.

Human PI3K polypeptides are amenable to biochemical or cell-based high throughput screening (HTS) assays according to methods known and practiced in the art, including melanophore assay systems to investigate receptor-ligand interactions, yeast-based assay systems, and mammalian cell expression systems. For a review, see Jayawickreme and Kost, *Curr Opin Biotechnol*, 8:629–34 (1997). Automated and miniaturized HTS assays also are comprehended as described, for example, in Houston and Banks, *Curr Opin Biotechnol*, 8:734–40 (1997).

Such HTS assays are used to screen libraries of compounds to identify particular compounds that exhibit a desired property. Any library of compounds can be used, including chemical libraries, natural product libraries, and combinatorial libraries comprising random or designed oligopeptides, oligonucleotides, or other organic compounds.

Chemical libraries can contain known compounds, proprietary structural analogs of known compounds, or compounds that are identified from natural product screening.

Natural product libraries are collections of materials isolated from naturals sources, typically, microorganisms, animals, plants, or marine organisms. Natural products are isolated from their sources by fermentation of microorganisms followed by isolation and extraction of the fermentation broths or by direct extraction from the microorganisms or tissues (plants or animal) themselves. Natural product libraries include polyketides, nonribosomal peptides, and variants (including nonnaturally occurring variants) thereof. For a review, see Cane et al., *Science*, 282:63–68 (1998).

Combinatorial libraries are composed of large numbers of related compounds, such as peptides, oligonucleotides, or other organic compounds as a mixture. Such compounds are relatively straightforward to design and prepare by traditional automated synthesis protocols, PCR, cloning, or proprietary synthetic methods. Of particular interest are peptide and oligonucleotide combinatorial libraries.

Still other libraries of interest include peptide, protein, peptidomimetic, multiparallel synthetic collection, recombinatorial, and polypeptide libraries. For a review of combinatorial chemistry and libraries created thereby, see Myers, *Curr Opin Biotechnol*, 8:701–07 (1997).

Once compounds have been identified that show activity as negative regulators of PI3Kδ function, a program of optimization can be undertaken in an effort to improve the potency and or selectivity of the activity. This analysis of structure-activity relationships (SAR) typically involves of iterative series of selective modifications of compound structures and their correlation to biochemical or biological activity. Families of related compounds can be designed that all exhibit the desired activity, with certain members of the family, namely those possessing suitable pharmacological profiles, potentially qualifying as therapeutic candidates.

Therapeutic Uses of Inhibitors of PI3Kδ Activity

The invention provides a method for selectively or specifically inhibiting PI3Kδ activity therapeutically or prophylactically. The method comprises administering a selective or specific inhibitor of PI3Kδ activity in an amount effective therefor. This method can be employed in treating humans or animals who are or can be subject to any condition whose symptoms or pathology is mediated by PI3Kδ expression or activity.

"Treating" as used herein refers to preventing a disorder from occurring in an animal that can be predisposed to the disorder, but has not yet been diagnosed as having it; inhibiting the disorder, i.e., arresting its development; relieving the disorder, i.e., causing its regression; or ameliorating the disorder, i.e., reducing the severity of symptoms associated with the disorder. "Disorder" is intended to encompass medical disorders, diseases, conditions, syndromes, and the like, without limitation.

The methods of the invention embrace various modes of treating an animal subject, preferably a mammal, more preferably a primate, and still more preferably a human. Among the mammalian animals that can be treated are, for example, companion animals (pets), including dogs and cats; farm animals, including cattle, horses, sheep, pigs, and goats; laboratory animals, including rats, mice, rabbits, guinea pigs, and nonhuman primates, and zoo specimens. Nonmammalian animals include, for example, birds, fish, reptiles, and amphibians.

In one aspect, the method of the invention can be employed to treat subjects therapeutically or prophylactically who have or can be subject to an inflammatory disorder. One aspect of the present invention derives from the involvement of PI3Kδ in mediating aspects of the inflammatory process. Without intending to be bound by any theory, it is theorized that, because inflammation involves processes are typically mediated by leukocyte (e.g., neutrophil, lymphocyte, etc.) activation and chemotactic transmigration, and because PI3Kδ can mediate such phenomena, antagonists of PI3Kδ can be used to suppress injury associated with inflammation.

"Inflammatory disorder" as used herein can refer to any disease, disorder, or syndrome in which an excessive or unregulated inflammatory response leads to excessive inflammatory symptoms, host tissue damage, or loss of tissue function. "Inflammatory disorder" also refers to a pathological state mediated by influx of leukocytes and/or neutrophil chemotaxis.

"Inflammation" as used herein refers to a localized, protective response elicited by injury or destruction of tissues, which serves to destroy, dilute, or wall off (sequester) both the injurious agent and the injured tissue. Inflammation is notably associated with influx of leukocytes and/or neutrophil chemotaxis. Inflammation can result from infection with pathogenic organisms and viruses and from noninfectious means such as trauma or reperfusion following myocardial infarction or stroke, immune response to foreign antigen, and autoimmune responses. Accordingly, inflammatory disorders amenable to the invention encompass disorders associated with reactions of the specific defense system as well as with reactions of the nonspecific defense system.

As used herein, the term "specific defense system" refers to the component of the immune system that reacts to the presence of specific antigens. Examples of inflammation resulting from a response of the specific defense system include the classical response to foreign antigens, autoimmune diseases, and delayed type hypersensitivity response mediated by T-cells. Chronic inflammatory diseases, the rejection of solid transplanted tissue and organs, e.g., kidney and bone marrow transplants, and graft versus host disease (GVHD), are further examples of inflammatory reactions of the specific defense system.

The term "nonspecific defense system" as used herein refers to inflammatory disorders that are mediated by leukocytes that are incapable of immunological memory (e.g., granulocytes, and macrophages). Examples of inflammation that result, at least in part, from a reaction of the nonspecific defense system include inflammation associated with conditions such as adult (acute) respiratory distress syndrome (ARDS) or multiple organ injury syndromes; reperfusion injury; acute glomerulonephritis; reactive arthritis; dermatoses with acute inflammatory components; acute purulent meningitis or other central nervous system inflammatory disorders such as stroke; thermal injury; inflammatory bowel disease; granulocyte transfusion associated syndromes; and cytokine-induced toxicity.

"Autoimmune disease" as used herein refers to any group of disorders in which tissue injury is associated with humoral or cell-mediated responses to the body's own constituents. "Allergic disease" as used herein refers to any symptoms, tissue damage, or loss of tissue function resulting from allergy. "Arthritic disease" as used herein refers to any disease that is characterized by inflammatory lesions of the joints attributable to a variety of etiologies. "Dermatitis" as used herein refers to any of a large family of diseases of the skin that are characterized by inflammation of the skin attributable to a variety of etiologies. "Transplant rejection" as used herein refers to any immune reaction directed against grafted tissue, such as organs or cells (e.g., bone marrow), characterized by a loss of function of the grafted and surrounding tissues, pain, swelling, leukocytosis, and thrombocytopenia.

The therapeutic methods of the present invention include methods for the treatment of disorders associated with inflammatory cell activation. "Inflammatory cell activation" refers to the induction by a stimulus (including, but not limited to, cytokines, antigens or auto-antibodies) of a proliferative cellular response, the production of soluble mediators (including but not limited to cytokines, oxygen radicals, enzymes, prostanoids, or vasoactive amines), or cell surface expression of new or increased numbers of mediators (including, but not limited to, major histocompatability antigens or cell adhesion molecules) in inflammatory cells (including but not limited to monocytes, macrophages, T lymphocytes, B lymphocytes, granulocytes (i.e., polymorphonuclear leukocytes such as neutrophils, basophils, and eosinophils), mast cells, dendritic cells, Langerhans cells, and endothelial cells). It will be appreciated by persons skilled in the art that the activation of one or a combination of these phenotypes in these cells can contribute to the initiation, perpetuation, or exacerbation of an inflammatory disorder.

The compounds of the invention have been found to inhibit superoxide release by neutrophils. Superoxide is released by neutrophils in response to any of a variety of stimuli, including signals of infection, as a mechanism of cell killing. For example, superoxide release is known to be induced by tumor necrosis factor alpha (TNFα), which is released by macrophages, mast cells, and lymphocytes upon contact with bacterial cell wall components such as lipopolysaccharide (LPS). TNFα is an extraordinarily potent and promiscuous activator of inflammatory processes, being involved in activation of neutrophils and various other cell types, induction of leukocyte/endothelial cell adhesion, pyrexia, enhanced MHC class I production, and stimulation of angiogenesis. Alternatively, superoxide release can be stimulated by formyl-Met-Leu-Phe (fMLP) or other peptides blocked at the N-terminus by formylated methionine. Such peptides are not normally found in eukaryotes, but are fundamentally characteristic of bacteria, and signal the presence of bacteria to the immune system. Leukocytes expressing the fMLP receptor, e.g., neutrophils and macrophages, are stimulated to migrate up gradients of these peptides (i.e., chemotaxis) toward loci of infection. As demonstrated herein, the compounds of the invention inhibit stimulated superoxide release by neutrophils in response to either TNFα or fMLP. Other functions of neutrophils, including stimulated exocytosis and directed chemotactic migration, also have been shown to be inhibited by the PI3Kδ inhibitors of the invention. Accordingly, the compounds of the invention can be expected to be useful in treating disorders, such as inflammatory disorders, that are mediated by any or all of these neutrophil functions.

The present invention enables methods of treating such diseases as arthritic diseases, such as rheumatoid arthritis, monoarticular arthritis, osteoarthritis, gouty arthritis, spondylitis; Behcet disease; sepsis, septic shock, endotoxic shock, gram negative sepsis, gram positive sepsis, and toxic shock syndrome; multiple organ injury syndrome secondary to septicemia, trauma, or hemorrhage; ophthalmic disorders such as allergic conjunctivitis, vernal conjunctivitis, uveitis, and thyroid-associated ophthalmopathy; eosinophilic granuloma; pulmonary or respiratory disorders such as asthma, chronic bronchitis, allergic rhinitis, ARDS, chronic pulmonary inflammatory disease (e.g., chronic obstructive pulmonary disease), silicosis, pulmonary sarcoidosis, pleurisy, alveolitis, vasculitis, emphysema, pneumonia, bronchiectasis, and pulmonary oxygen toxicity; reperfusion injury of the myocardium, brain, or extremities; fibrosis such as cystic fibrosis; keloid formation or scar tissue formation; atherosclerosis; autoimmune diseases, such as systemic lupus erythematosus (SLE), autoimmune thyroiditis, multiple sclerosis, some forms of diabetes, and Reynaud's syndrome; and transplant rejection disorders such as GVHD and allograft rejection; chronic glomerulonephritis; inflammatory bowel diseases such as chronic inflammatory bowel disease (CIBD), Crohn's disease, ulcerative colitis, and necrotizing enterocolitis; inflammatory dermatoses such as contact dermatitis, atopic dermatitis, psoriasis, or urticaria; fever and myalgias due to infection; central or peripheral nervous system inflammatory disorders such as meningitis, encephalitis, and brain or spinal cord injury due to minor trauma; Sjögren's syndrome; diseases involving leukocyte diapedesis; alcoholic hepatitis; bacterial pneumonia; antigen-antibody complex mediated diseases; hypovolemic shock; Type I diabetes mellitus; acute and delayed hypersensitivity; disease states due to leukocyte dyscrasia and metastasis; thermal injury; granulocyte transfusion-associated syndromes; and cytokine-induced toxicity.

The method can have utility in treating subjects who are or can be subject to reperfusion injury, i.e., injury resulting from situations in which a tissue or organ experiences a period of ischemia followed by reperfusion. The term "ischemia" refers to localized tissue anemia due to obstruction of the inflow of arterial blood. Transient ischemia followed by reperfusion characteristically results in neutrophil activation and transmigration through the endothelium of the blood vessels in the affected area. Accumulation of activated neutrophils in turn results in generation of reactive oxygen metabolites, which damage components of the involved tissue or organ. This phenomenon of "reperfusion injury" is commonly associated with conditions such as vascular stroke (including global and focal ischemia), hemorrhagic shock, myocardial ischemia or infarction, organ transplantation, and cerebral vasospasm. To illustrate, reperfusion injury occurs at the termination of cardiac bypass procedures or during cardiac arrest when the heart, once prevented from receiving blood, begins to reperfuse. It is expected that inhibition of PI3Kδ activity will result in reduced amounts of reperfusion injury in such situations.

With respect to the nervous system, global ischemia occurs when blood flow to the entire brain ceases for a period. Global ischemia can result from cardiac arrest. Focal ischemia occurs when a portion of the brain is deprived of its normal blood supply. Focal ischemia can result from thromboembolytic occlusion of a cerebral vessel, traumatic head injury, edema, or brain tumor. Even if transient, both global and focal ischemia can cause widespread neuronal damage. Although nerve tissue damage occurs over hours or even days following the onset of ischemia, some permanent nerve tissue damage can develop in the initial minutes following the cessation of blood flow to the brain.

Ischemia also can occur in the heart in myocardial infarction and other cardiovascular disorders in which the coronary arteries have been obstructed as a result of atherosclerosis, thrombus, or spasm. Accordingly, the invention is believed to be useful for treating cardiac tissue damage, particularly damage resulting from cardiac ischemia or caused by reperfusion injury in mammals.

In another aspect, selective inhibitors of PI3Kδ activity, such as the compounds of the invention, can be employed in methods of treating diseases of bone, especially diseases in which osteoclast function is abnormal or undesirable. As shown in Example 6, below, compounds of the invention inhibit osteoclast function in vitro. Accordingly, the use of such compounds and other PI3Kδ selective inhibitors can be of value in treating osteoporosis, Paget's disease, and related bone resorption disorders.

In a further aspect, the invention includes methods of using PI3Kδ inhibitory compounds to inhibit the growth or proliferation of cancer cells of hematopoietic origin, preferably cancer cells of lymphoid origin, and more preferably cancer cells related to or derived from B lymphocytes or B lymphocyte progenitors. Cancers amenable to treatment using the method of the invention include, without limitation, lymphomas, e.g., malignant neoplasms of lymphoid and reticuloendothelial tissues, such as Burkitt's lymphoma, Hodgkins' lymphoma, non-Hodgkins lymphomas, lymphocytic lymphomas and the like; multiple myelomas; as well as leukemias such as lymphocytic leukemias, chronic myeloid (myelogenous) leukemias, and the like. In a preferred embodiment, PI3Kδ inhibitory compounds can be used to inhibit or control the growth or proliferation of chronic myeloid (myelogenous) leukemia cells.

In another aspect, the invention includes a method for suppressing a function of basophils and/or mast cells, and thereby enabling treatment of diseases or disorders characterized by excessive or undesirable basophil and/or mast cell activity. According to the method, a compound of the invention can be used that selectively inhibits the expression or activity of phosphatidylinositol 3-kinase delta (PI3Kδ) in the basophils and/or mast cells. Preferably, the method employs a PI3Kδ inhibitor in an amount sufficient to inhibit stimulated histamine release by the basophils and/or mast cells. Accordingly, the use of such compounds and other PI3Kδ selective inhibitors can be of value in treating diseases characterized by histamine release, i.e., allergic disorders, including disorders such as chronic obstructive pulmonary disease (COPD), asthma, ARDS, emphysema, and related disorders.

Pharmaceutical Compositions of Inhibitors of PI3Kδ Activity

A compound of the present invention can be administered as the neat chemical, but it is typically preferable to administer the compound in the form of a pharmaceutical composition or formulation. Accordingly, the present invention also provides pharmaceutical compositions that comprise a chemical or biological compound ("agent") that is active as a modulator of PI3Kδ activity and a biocompatible pharmaceutical carrier, adjuvant, or vehicle. The composition can include the agent as the only active moiety or in combination with other agents, such as oligo- or polynucleotides, oligo- or polypeptides, drugs, or hormones mixed with excipient(s) or other pharmaceutically acceptable carriers. Carriers and other ingredients can be deemed pharmaceutically acceptable insofar as they are compatible with other ingredients of the formulation and not deleterious to the recipient thereof.

Techniques for formulation and administration of pharmaceutical compositions can be found in *Remington's Pharmaceutical Sciences,* 18*th Ed.,* Mack Publishing Co, Easton, Pa., 1990. The pharmaceutical compositions of the present invention can be manufactured using any conventional method, e.g., mixing, dissolving, granulating, dragee-making, levigating, emulsifying, encapsulating, entrapping, melt-spinning, spray-drying, or lyophilizing processes. However, the optimal pharmaceutical formulation will be determined by one of skill in the art depending on the route of administration and the desired dosage. Such formulations can influence the physical state, stability, rate of in vivo release, and rate of in vivo clearance of the administered agent. Depending on the condition being treated, these pharmaceutical compositions can be formulated and administered systemically or locally.

The pharmaceutical compositions are formulated to contain suitable pharmaceutically acceptable carriers, and can optionally comprise excipients and auxiliaries that facilitate processing of the active compounds into preparations that can be used pharmaceutically. The administration modality will generally determine the nature of the carrier. For example, formulations for parenteral administration can comprise aqueous solutions of the active compounds in water-soluble form. Carriers suitable for parenteral administration can be selected from among saline, buffered saline, dextrose, water, and other physiologically compatible solutions. Preferred carriers for parenteral administration are physiologically compatible buffers such as Hank's solution, Ringer's solution, or physiologically buffered saline. For tissue or cellular administration, penetrants appropriate to the particular barrier to be permeated are used in the formulation. Such penetrants are generally known in the art. For preparations comprising proteins, the formulation can include stabilizing materials, such as polyols (e.g., sucrose) and/or surfactants (e.g., nonionic surfactants), and the like.

Alternatively, formulations for parenteral use can comprise dispersions or suspensions of the active compounds prepared as appropriate oily injection suspensions. Suitable lipophilic solvents or vehicles include fatty oils, such as sesame oil, and synthetic fatty acid esters, such as ethyl oleate or triglycerides, or liposomes. Aqueous injection suspensions can contain substances that increase the viscosity of the suspension, such as sodium carboxymethylcellulose, sorbitol, or dextran. Optionally, the suspension also can contain suitable stabilizers or agents that increase the solubility of the compounds to allow for the preparation of highly concentrated solutions. Aqueous polymers that provide pH-sensitive solubilization and/or sustained release of the active agent also can be used as coatings or matrix structures, e.g., methacrylic polymers, such as the EUDRAGIT® series available from Röhm America Inc. (Piscataway, N.J.). Emulsions, e.g., oil-in-water and water-in-oil dispersions, also can be used, optionally stabilized by an emulsifying agent or dispersant (surface active materials; surfactants). Suspensions can contain suspending agents such as ethoxylated isostearyl alcohols, polyoxyethlyene sorbitol and sorbitan esters, microcrystalline cellulose, aluminum metahydroxide, bentonite, agar-agar, gum tragacanth, and mixtures thereof.

Liposomes containing the active agent also can be employed for parenteral administration. Liposomes generally are derived from phospholipids or other lipid substances. The compositions in liposome form also can contain other ingredients, such as stabilizers, preservatives, excipients, and the like. Preferred lipids include phospholipids and phosphatidyl cholines (lecithins), both natural and synthetic. Methods of forming liposomes are known in the art. See, e.g., Prescott (Ed.), *Methods in Cell Biology, Vol. XIV*, p. 33, Academic Press, New York (1976).

The pharmaceutical compositions comprising the agent in dosages suitable for oral administration can be formulated using pharmaceutically acceptable carriers well known in the art. The preparations formulated for oral administration can be in the form of tablets, pills, capsules, cachets, dragees, lozenges, liquids, gels, syrups, slurries, elixirs, suspensions, or powders. To illustrate, pharmaceutical preparations for oral use can be obtained by combining the active compounds with a solid excipient, optionally grinding the resulting mixture, and processing the mixture of granules, after adding suitable auxiliaries if desired, to obtain tablets or dragee cores. Oral formulations can employ liquid carriers similar in type to those described for parenteral use, e.g., buffered aqueous solutions, suspensions, and the like.

Preferred oral formulations include tablets, dragees, and gelatin capsules. These preparations can contain one or more excipients, which include, without limitation:

a) diluents, such as sugars, including lactose, dextrose, sucrose, mannitol, or sorbitol;

b) binders, such as magnesium aluminum silicate, starch from corn, wheat, rice, potato, etc.;

c) cellulose materials, such as methylcellulose, hydroxypropylmethyl cellulose, and sodium carboxymethylcellulose, polyvinylpyrrolidone, gums, such as gum arabic and gum tragacanth, and proteins, such as gelatin and collagen;

d) disintegrating or solubilizing agents such as cross-linked polyvinyl pyrrolidone, starches, agar, alginic acid or a salt thereof, such as sodium alginate, or effervescent compositions;

e) lubricants, such as silica, talc, stearic acid or its magnesium or calcium salt, and polyethylene glycol;

f) flavorants and sweeteners;

g) colorants or pigments, e.g., to identify the product or to characterize the quantity (dosage) of active compound; and h) other ingredients, such as preservatives, stabilizers, swelling agents, emulsifying agents, solution promoters, salts for regulating osmotic pressure, and buffers.

Gelatin capsules include push-fit capsules made of gelatin, as well as soft, sealed capsules made of gelatin and a coating such as glycerol or sorbitol. Push-fit capsules can contain the active ingredient(s) mixed with fillers, binders, lubricants, and/or stabilizers, etc. In soft capsules, the active compounds can be dissolved or suspended in suitable fluids, such as fatty oils, liquid paraffin, or liquid polyethylene glycol with or without stabilizers.

Dragee cores can be provided with suitable coatings such as concentrated sugar solutions, which also can contain gum arabic, talc, polyvinyl pyrrolidone, carbopol gel, polyethylene glycol, and/or titanium dioxide, lacquer solutions, and suitable organic solvents or solvent mixtures.

The pharmaceutical composition can be provided as a salt of the active agent. Salts tend to be more soluble in aqueous or other protonic solvents than the corresponding free acid or base forms. Pharmaceutically acceptable salts are well known in the art. Compounds that contain acidic moieties can form pharmaceutically acceptable salts with suitable cations. Suitable pharmaceutically acceptable cations include, for example, alkali metal (e.g., sodium or potassium) and alkaline earth (e.g., calcium or magnesium) cations.

Compounds of structural formula (I) that contain basic moieties can form pharmaceutically acceptable acid addition salts with suitable acids. For example, Berge et al. describe pharmaceutically acceptable salts in detail in *J Pharm Sci*, 66:1 (1977). The salts can be prepared in situ during the final isolation and purification of the compounds of the invention or separately by reacting a free base function with a suitable acid.

Representative acid addition salts include, but are not limited to, acetate, adipate, alginate, citrate, aspartate, benzoate, benzenesulfonate, bisulfate, butyrate, camphorate, camphorol-sulfonate, digluconate, glycerophosphate, hemisulfate, heptanoate, hexanoate, fumarate, hydrochloride, hydrobromide, hydroiodide, 2-hydroxyethanesulfonate (isothionate), lactate, maleate, methanesulfonate or sulfate, nicotinate, 2-naphthalenesulfonate, oxalate, pamoate, pectinate, persulfate, 3-phenylpropionate, picrate, pivalate, propionate, succinate, tartrate, thiocyanate, phosphate or hydrogen phosphate, glutamate, bicarbonate, p-toluenesulfonate, and undecanoate. Examples of acids that can be employed to form pharmaceutically acceptable acid addition salts include, without limitation, such inorganic acids as hydrochloric acid, hydrobromic acid, sulfuric acid, and phosphoric acid, and such organic acids as oxalic acid, maleic acid, succinic acid, and citric acid.

In light of the foregoing, any reference to compounds of the present invention appearing herein is intended to include compounds of structural formula (I)–(IV), as well as pharmaceutically acceptable salts and solvates, and prodrugs, thereof.

Basic addition salts can be prepared in situ during the final isolation and purification of the compounds of the invention or separately by reacting a carboxylic acid-containing moiety with a suitable base such as the hydroxide, carbonate, or bicarbonate of a pharmaceutically acceptable metal cation, or with ammonia or organic primary, secondary, or tertiary amine. Pharmaceutically acceptable basic addition salts include, but are not limited to, cations based on alkali metals or alkaline earth metals such as lithium, sodium, potassium, calcium, magnesium, and aluminum salts and the like, and nontoxic quaternary ammonium and amine cations including ammonium, tetramethylammonium, tetraethylammonium, methylammonium, dimethylammonium, trimethylammonium, ethylammonium, diethylammonium, triethylammonium, and the like. Other representative organic amines useful for the formation of base addition salts include ethylenediamine, ethanolamine, diethanolamine, piperidine, piperazine, and the like.

Basic nitrogen-containing groups can be quaternized with such agents as lower alkyl halides such as methyl, ethyl, propyl, and butyl chlorides, bromides and iodides; dialkyl sulfates like dimethyl, diethyl, dibutyl, and diamyl sulfates; long chain alkyl halides such as decyl, lauryl, myristyl, and stearyl chlorides, bromides, and iodides; arylalkyl halides such as benzyl and phenethyl bromides; and others. Products having modified solubility or dispersibility are thereby obtained.

Compositions comprising a compound of the invention formulated in a pharmaceutical acceptable carrier can be prepared, placed in an appropriate container, and labeled for treatment of an indicated condition. Accordingly, there also is contemplated an article of manufacture, such as a container comprising a dosage form of a compound of the invention and a label containing instructions for use of the compound. Kits are also contemplated under the invention. For example, the kit can comprise a dosage form of a pharmaceutical composition and a package insert containing instructions for use of the composition in treatment of a medical condition. In either case, conditions indicated on the label can include treatment of inflammatory disorders, cancer, etc.

Methods of Administration of Inhibitors of PI3Kδ Activity

Pharmaceutical compositions comprising an inhibitor of PI3Kδ activity can be administered to the subject by any conventional method, including parenteral and enteral techniques. Parenteral administration modalities include those in which the composition is administered by a route other than through the gastrointestinal tract, for example, intravenous, intraarterial, intraperitoneal, intra-medullary, intramuscular, intraarticular, intrathecal, and intraventricular injections. Enteral administration modalities include, for example, oral (including buccal and sublingual) and rectal administration. Transepithelial administration modalities include, for example, transmucosal administration and transdermal administration. Transmucosal administration includes, for example, enteral administration as well as nasal, inhalation, and deep lung administration; vaginal administration; and rectal administration. Transdermal administration includes passive or active transdermal or transcutaneous modalities, including, for example, patches and iontophoresis devices, as well as topical application of pastes, salves, or ointments. Parenteral administration also can be accomplished using a high-pressure technique, e.g., POWDERJECT®.

Surgical techniques include implantation of depot (reservoir) compositions, osmotic pumps, and the like. A preferred route of administration for treatment of inflammation can be local or topical delivery for localized disorders such as arthritis, or systemic delivery for distributed disorders, e.g., intravenous delivery for reperfusion injury or for systemic conditions such as septicemia. For other diseases, including those involving the respiratory tract, e.g., chronic obstructive pulmonary disease, asthma, and emphysema, administration can be accomplished by inhalation or deep lung administration of sprays, aerosols, powders, and the like.

For the treatment of neoplastic diseases, especially leukemias and other distributed cancers, parenteral administration is typically preferred. Formulations of the compounds to optimize them for biodistribution following parenteral administration would be desirable. The PI3Kδ inhibitor compounds can be administered before, during, or after administration of chemotherapy, radiotherapy, and/or surgery.

Moreover, the therapeutic index of the PI3Kδ inhibitor compounds can be enhanced by modifying or derivatizing the compounds for targeted delivery to cancer cells expressing a marker that identifies the cells as such. For example, the compounds can be linked to an antibody that recognizes a marker that is selective or specific for cancer cells, so that the compounds are brought into the vicinity of the cells to exert their effects locally, as previously described (see for example, Pietersz et al., *Immunol Rev,* 129:57 (1992); Trail et al., *Science,* 261:212 (1993); and Rowlinson-Busza et al., *Curr Opin Oncol,* 4:1142 (1992)). Tumor-directed delivery of these compounds enhances the therapeutic benefit by, inter alia, minimizing potential nonspecific toxicities that can result from radiation treatment or chemotherapy. In another aspect, PI3Kδ inhibitor compounds and radioisotopes or chemotherapeutic agents can be conjugated to the same anti-tumor antibody.

For the treatment of bone resorption disorders or osteoclast-mediated disorders, the PI3Kδ inhibitors can be delivered by any suitable method. Focal administration can be desirable, such as by intraarticular injection. In some cases, it can be desirable to couple the compounds to a moiety that can target the compounds to bone. For example, a PI3Kδ inhibitor can be coupled to compounds with high affinity for hydroxyapatite, which is a major constituent of bone. This can be accomplished, for example, by adapting a tetracycline-coupling method developed for targeted delivery of estrogen to bone (Orme et al., *Bioorg Med Chem Lett,* 4(11):1375–80 (1994)).

To be effective therapeutically in modulating central nervous system targets, the agents used in the methods of the invention should readily penetrate the blood brain barrier when peripherally administered. Compounds that cannot penetrate the blood brain barrier, however, can still be effectively administered by an intravenous route.

As noted above, the characteristics of the agent itself and the formulation of the agent can influence the physical state, stability, rate of in vivo release, and rate of in vivo clearance of the administered agent. Such pharmacokinetic and pharmacodynamic information can be collected through preclinical in vitro and in vivo studies, later confirmed in humans during the course of clinical trials. Thus, for any compound used in the method of the invention, a therapeutically effective dose can be estimated initially from biochemical and/or cell-based assays. Then, dosage can be formulated in animal models to achieve a desirable circulating concentration range that modulates PI3Kδ expression or activity. As human studies are conducted, further information will emerge regarding the appropriate dosage levels and duration of treatment for various diseases and conditions.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the "therapeutic index," which typically is expressed as the ratio LD50/ED50. Compounds that exhibit large therapeutic indices, i.e., the toxic dose is substantially higher than the effective dose, are preferred. The data obtained from such cell culture assays and additional animal studies can be used in formulating a range of dosage for human use. The dosage of such compounds lies preferably within a range of circulating concentrations that include the $ED_{50}$ with little or no toxicity.

For the methods of the invention, any effective administration regimen regulating the timing and sequence of doses can be used. Doses of the agent preferably include pharmaceutical dosage units comprising an effective amount of the agent. As used herein, "effective amount" refers to an amount sufficient to modulate PI3Kδ expression or activity and/or derive a measurable change in a physiological parameter of the subject through administration of one or more of the pharmaceutical dosage units.

Exemplary dosage levels for a human subject are of the order of from about 0.001 milligram of active agent per kilogram body weight (mg/kg) to about 100 mg/kg. Typically, dosage units of the active agent comprise from about 0.01 mg to about 10,000 mg, preferably from about 0.1 mg to about 1,000 mg, depending upon the indication, route of administration, etc. Depending on the route of administration, a suitable dose can be calculated according to body weight, body surface area, or organ size. The final dosage regimen will be determined by the attending physician in view of good medical practice, considering various factors that modify the action of drugs, e.g., the agent's specific activity, the identity and severity of the disease state, the responsiveness of the patient, the age, condition, body weight, sex, and diet of the patient, and the severity of any infection. Additional factors that can be taken into account include time and frequency of administration, drug combinations, reaction sensitivities, and tolerance/response to therapy. Further refinement of the dosage appropriate for treatment involving any of the formulations mentioned herein is done routinely by the skilled practitioner without undue experimentation, especially in light of the dosage information and assays disclosed, as well as the pharmacokinetic data observed in human clinical trials. Appropriate dosages can be ascertained through use of established assays for determining concentration of the agent in a body fluid or other sample together with dose response data.

The frequency of dosing will depend on the pharmacokinetic parameters of the agent and the route of administration. Dosage and administration are adjusted to provide sufficient levels of the active moiety or to maintain the desired effect. Accordingly, the pharmaceutical compositions can be administered in a single dose, multiple discrete doses, continuous infusion, sustained release depots, or combinations thereof, as required to maintain desired minimum level of the agent. Short-acting pharmaceutical compositions (i.e., short half-life) can be administered once a day or more than once a day (e.g., two, three, or four times a day). Long acting pharmaceutical compositions might be administered every 3 to 4 days, every week, or once every two weeks. Pumps, such as subcutaneous, intraperitoneal, or subdural pumps, can be preferred for continuous infusion.

The following Examples are provided to further aid in understanding the invention, and presuppose an understanding of conventional methods well-known to those persons having ordinary skill in the art to which the examples pertain, e.g., the construction of vectors and plasmids, the insertion of genes encoding polypeptides into such vectors and plasmids, or the introduction of vectors and plasmids into host cells. Such methods are described in detail in numerous publications including, for example, Sambrook et al., *Molecular Cloning: A Laboratory Manual*, Cold Spring Harbor Laboratory Press (1989), Ausubel et al. (Eds.), *Current Protocols in Molecular Biology*, John Wiley & Sons, Inc. (1994); and Ausubel et al. (Eds.), *Short Protocols in Molecular Biology*, 4th ed., John Wiley & Sons, Inc. (1999). The particular materials and conditions described hereunder are intended to exemplify particular aspects of the invention and should not be construed to limit the reasonable scope thereof.

EXAMPLE 1

Preparation and Purification of Recombinant PI3Kα, β, and δ

Recombinant PI3K heterodimeric complexes consisting of a p110 catalytic subunit and a p85 regulatory subunit were overexpressed using the BACTO-BAC® HT baculovirus expression system (GIBCO/BRL), and then purified for use in biochemical assays. The four Class I PI 3-kinases were cloned into baculovirus vectors as follows:

p110δ: A FLAG®-tagged version of human p110δ (SEQ ID NO:1) (see Chantry et al., *J Biol Chem*, 272:19236–41 (1997)) was subcloned using standard recombinant DNA techniques into the BamH1-Xba1 site of the insect cell expression vector pFastbac HTb (Life Technologies, Gaithersburg, Md.), such that the clone was in frame with the His tag of the vector. The FLAG® system is described in U.S. Pat. Nos. 4,703,004; 4,782,137; 4,851,341; and 5,011,912, and reagents are available from Eastman Kodak Co.

p110α: Similar to the method used for p110δ, described above, a FLAG®-tagged version of p110α (see Volinia et al., *Genomics*, 24(3):427–477 (1994)) was subcloned in BamH1-HindIII sites of pFastbac HTb (Life Technologies) such that the clone was in frame with the His tag of the vector.

p110β: A p110β (see Hu et al., *Mol Cell Biol*, 13:7677–88 (1993)) clone was amplified from the human MARATHON® Ready spleen cDNA library (Clontech, Palo Alto Calif.) according to the manufacturer's protocol using the following primers:

```
5' Primer                               (SEQ ID NO:3)
5'-GATCGAATTCGGCGCCACCATGGACTACAAGGACGATGACAAGTG
   CTTCAGTTTCATAATGCCTCC-3'

3' Primer                               (SEQ ID NO:4)
5'-GATCGCGGCCGCTTAAGATCTGTAGTCTTTCCGAACTGTGTG-3'
```

The 5' primer was built to contain a FLAG® tag in frame with the p110β sequence. After amplification, the FLAG®-p110β sequence was subcloned using standard recombinant techniques into the EcOR1-Not1 sites of pFastbac HTa (Life Technologies), such that the clone was in frame with the His tag of the vector.

p110γ: The p110γ cDNA (see Stoyanov et al., *Science*, 269:690–93 (1995)) was amplified from a human Marathon Ready spleen cDNA library (Clontech) according to the manufacturer's protocol using the following primers:

```
5' Primer                               (SEQ ID NO:5)
5'-AGAATGCGGCCGCATGGAGCTGGAGAACTATAAACAGCCC-3'

3' Primer                               (SEQ ID NO:6)
5'-CGCGGATCCTTAGGCTGAATGTTTCTCTCCTTGTTTG-3'
```

A FLAG® tag was subsequently attached to the 5' end of the p110γ sequence and was cloned in the BamH1-Spe1 sites of pFastbac HTb (Life Technologies) using standard recombinant DNA techniques, with the FLAG®-110γ sequence in-frame with the His tag of the vector.

p85α: A BamH1-EcOR1 fragment of FLAG®-tagged p85 cDNA (see Skolnik et al., *Cell*, 65:83–89 (1991)) was subcloned into the BamH1-EcOR1 sites of the vector pFastbac dual (Life Technologies).

Recombinant baculoviruses containing the above clones were generated using manufacturer's recommended protocol (Life Technologies). Baculoviruses expressing His-tagged p110α, p110β, or p110δ catalytic subunit and p85 subunit were coinfected into Sf21 insect cells. To enrich the heterodimeric enzyme complex, an excess amount of baculovirus expressing p85 subunit was infected, and the His-tagged p110 catalytic subunit complexed with p85 was purified on nickel affinity column. Since p110γ does not associate with p85, Sf21 cells were infected with recombinant baculoviruses expressing His-tagged p110γ only. In an alternate approach, p101 can be cloned into baculovirus, to permit coexpression with its preferred binding partner p110γ.

The 72-hour post-infected Sf21 cells (3 liters) were harvested and homogenized in a hypotonic buffer (20 mM HEPES-KOH, pH 7.8, 5 mM KCl, complete protease inhibitor cocktail (Roche Biochemicals, Indianapolis, Ind.), using a Dounce homogenizer. The homogenates were centrifuged at 1,000×g for 15 min. The supernatants were further centrifuged at 10,000×g for 20 min, followed by ultracentrifugation at 100,000×g for 60 min. The soluble fraction was immediately loaded onto 10 mL of HITRAP® nickel affinity column (Pharmacia, Piscataway, N.J.) equilibrated with 50 mL of Buffer A (50 mM HEPES-KOH, pH 7.8, 0.5 M NaCl, 10 mM imidazole). The column was washed extensively with Buffer A, and eluted with a linear gradient of 10–500 mM imidazole. Free p85 subunit was removed from the column during the washing step and only the heterodimeric enzyme complex eluted at 250 mM imidazole. Aliquots of nickel fractions were analyzed by 10% SDS-polyacrylamide gel electrophoresis (SDS-PAGE), stained with SYPRO® Red (Molecular Probes, Inc., Eugene, Oreg.), and quantitated with STORM® PhosphoImager (Molecular Dynamics, Sunnyvale, Calif.). The active fractions were pooled and directly loaded onto a 5 mL Hi-trap heparin column preequilibrated with Buffer B containing 50 mM HEPES-KOH, pH 7.5, 50 mM NaCl, 2 mM dithiothreitol (DTT). The column was washed with 50 mL of Buffer B and eluted with a linear gradient of 0.05–2 M NaCl. A single peak containing PI3K enzyme complex eluted at 0.8 M NaCl. SDS-polyacrylamide gel analysis showed that the purified PI3K enzyme fractions contained a 1:1 stoichiometric complex of p110 and p85 subunits. The protein profile of the enzyme complex during heparin chromatography corresponded to that of lipid kinase activity. The active fractions were pooled and frozen under liquid nitrogen.

EXAMPLE 2
PI3Kδ High Throughput Screen (HTS) and Selectivity Assay

A high throughput screen of a proprietary chemical library was performed to identify candidate inhibitors of PI3Kδ activity. PI3Kδ catalyzes a phosphotransfer from γ-[$^{32}$P]ATP to PIP$_2$/PS liposomes at the D3' position of the PIP$_2$ lipid inositol ring. This reaction is MgCl$_2$ dependent and is quenched in high molarity potassium phosphate buffer pH 8.0 containing 30 mM EDTA. In the screen, this reaction is performed in the presence or absence of library compounds. The reaction products (and all unlabelled products) are transferred to a 96-well, prewetted PVDF filter plate, filtered, and washed in high molarity potassium phosphate. Scintillant is added to the dried wells and the incorporated radioactivity is quantitated.

The majority of assay operations were performed using a BIOMEK® 1000 robotics workstations (Beckman) and all plates were read using Wallac liquid scintillation plate counter protocols.

The 3× assay stocks of substrate and enzyme were made and stored in a trough (for robotics assays) or a 96-well, V-bottom, polypropylene plate (for manual assays). Reagents were stable for at least 3 hours at room temperature.

The 3× substrate for the HTS contained 0.6 mM Na$_2$ATP, 0.10 mCi/mL γ-[$^{32}$P]ATP (NEN, Pittsburgh, Pa.), 6 μM PIP$_2$/PS liposomes (Avanti Polar Lipids, Inc., Atlanta, Ga.), in 20 mM HEPES, pH 7.4.

The 3× enzyme stock for the HTS contained 1.8 nM PI3Kδ, 150 μg/mL horse IgG (used only as a stabilizer), 15 mM MgCl$_2$, 3 mM DTT in 20 mM HEPES, pH 7.4.

The chemical high throughput screen (HTS) library samples (each containing a pool of 22 compounds) in dimethyl sulfoxide (DMSO) were diluted to 18.75 μM or 37.5 μM in double distilled water, and 20 μL of the dilutions were placed in the wells of a 96-well polypropylene plate for assaying. The negative inhibitor control (or positive enzyme control) was DMSO diluted in water, and the positive inhibitor controls employed concentrations of LY294002 sufficient to provide 50% and 100% inhibition.

To the 20 μL pooled chemical library dilutions, 20 μL of 3× substrate was added. The reaction was initiated with 20 μL of 3× enzyme, incubated at room temperature for 10 minutes. This dilution established a final concentration of 200 μM ATP in the reaction volume. The reaction was stopped with 150 μL quench buffer (1.0 M potassium phosphate pH 8.0, 30 mM EDTA). A portion of the quenched solution (180 μL) was then transferred to a PVDF filter plate (Millipore #MAIP NOB prewetted with sequential 200 μL washes of 100% methanol, water, and finally 1.0 M potassium phosphate pH 8.0 wash buffer).

The PVDF filter plate was aspirated under moderate vacuum (2–5 mm Hg), washed with 5×200 μL of wash buffer, and then dried by aspiration. The filter was subsequently blotted, allowed to air dry completely, and inserted into a Wallac counting cassette with 50 μL of Ecoscint scintillation cocktail added per well. The incorporated radioactivity was quantitated, and data were analyzed, after normalizing to the enzyme positive control (set at 100%), to identify the curve intersection at the 50% inhibition value to estimate IC$_{50}$ values for the inhibitors.

A total of 57 pooled master wells were selected for deconvolution, based on combined criteria of <42% residual activity at the tested concentration, and a total accepted hit rate of no more than 0.2%. At 22 compounds per well, a total of 1254 compounds were identified through this deconvolution and individually assayed at the 1× concentration of 27.7 μM to identify which compounds exhibited the desired activity. From these assays, 73 compounds were selected and assayed further to develop IC$_{50}$ curves. From the IC$_{50}$ curve results, 34 compounds were selected for selectivity assays against PI3Kα and PI3Kβ (see assay protocol in Example 11).

From the selectivity assays, one compound, 3-(2-chlorophenyl)-2-(9H-purin-6-ylsulfanylmethyl)-3H-quinazolin-4-one (Compound D-000), was selected as being a relatively potent and selective compound. Catalog searches and selectivity assays of many analogous compounds of the potent and/or selective hits yielded only one compound that was both an active and selective analogue of D-000. This compound was purchased from Contract Services Corporation (Catalog #7232154) and differed from D-000 in substituting a phenyl group for the 2-chlorophenyl group of D-000.

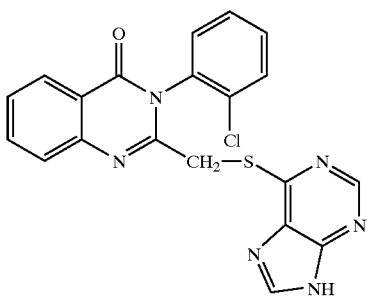

D-000

As described above, the PI 3-kinase inhibitor LY294002 (Calbiochem, La Jolla, Calif.) does not have significant selectivity among the different PI 3-kinase isoforms tested. Under our assay conditions, LY294002 inhibited all three isoforms of PI 3-kinases with an $IC_{50}$ of 0.3 to 1 μM. However, when the compound D-000 was tested against the same PI 3-kinase isoforms distinct selectivity was observed. Specifically, as shown in FIG. 1, D-000 inhibited the activity of the δ isoform of PI3K with an $IC_{50}$ of approximately 0.3 μM, whereas under similar conditions it did not inhibit activities of the α and β isoforms at a limit of 100 μM compound. These results show that D-000 selectively inhibits PI3Kδ activity.

EXAMPLES 3–7

Since PI3Kδ is expressed at significant levels only in leukocytes, it is important to study the effects of the PI3Kδ-selective inhibitor on leukocyte functions. Accordingly, the effects of PI3Kδ inhibition in several types of leukocytes were examined. Neutrophils were examined to determine the effects that selective inhibition of PI3Kδ might elicit (Example 3, below). It surprisingly was found that selective inhibition of PI3Kδ activity appears to be significantly associated with inhibition of some but not all functions characteristic of activated neutrophils. In addition, the effects of PI3Kδ inhibition on B cell and T cell function also were tested (Examples 4–5, below). Moreover, as PI3Kδ also is expressed in osteoclasts, the effect of PI3Kδ inhibition on the function of these specialized cells was studied (Example 6, below).

EXAMPLE 3
Characterization of Role of PI3Kδ in Neutrophil Function

The effects of a PI3Kδ inhibitor of the invention, i.e., D-000, on neutrophil functions such as superoxide generation, elastase exocytosis, chemotaxis, and bacterial killing were tested.

A. Preparation of Neutrophils from Human Blood

Aliquots (8 mL) of heparinized blood from healthy volunteers were layered on 3 mL cushions of 7.3% FICOLL® (Sigma, St. Louis, Mo.) and 15.4% HYPAQUE® (Sigma) and centrifuged at 900 rpm for 30 min at room temperature in a table top centrifuge (Beckman). The neutrophil-rich band just above the FICOLL®-HYPAQUE® cushion was collected and washed with Hanks' balanced salt solution (HBSS) containing 0.1% gelatin. Residual erythrocytes were removed by hypotonic lysis with 0.2% NaCl. The neutrophil preparation was washed twice with HBSS containing 0.1% gelatin and used immediately.

B. Measurement of Superoxide Production from Neutrophils

Superoxide generation is one of the hallmarks of neutrophil activation. A variety of activators potentiate superoxide generation by neutrophils. The effect of the PI3Kδ inhibitor D-000 on superoxide generation by three different agonists: TNF1α, IgG, and fMLP, each representing separate classes of activator, was measured. Superoxide generated by the neutrophils was measured by monitoring the change in absorbance upon reduction of cytochrome C by modification of the method described by Green et al., (pp. 14.5.1–14.5.11 in Supp. 12, *Curr Protocols Immunol* (Eds., Colligan et al.) (1994)), as follows. Individual wells of a 96-well plate were coated overnight at 4° C. with 50 μL of 2 mg/mL solution of human fibrinogen or IgG. The wells were washed with PBS and the following reagents were added to each well: 50 μL of HBSS or superoxide dismutase (1 mg/mL), 50 μL of HBSS or TNF1α (50 ng/mL), 50 μL cytochrome C (2.7 mg/mL), and 100 μL of purified human neutrophil suspension ($2\times10^6$ cells/mL). The plate was centrifuged for 2 min at 200 rpm and absorbance at 550 nm was monitored for 2 hr. To measure the relative amounts of superoxide generated, values obtained from the superoxide dismutase-containing wells were subtracted from all, and normalized to the values obtained from the wells without any inhibitor.

Figure 2:
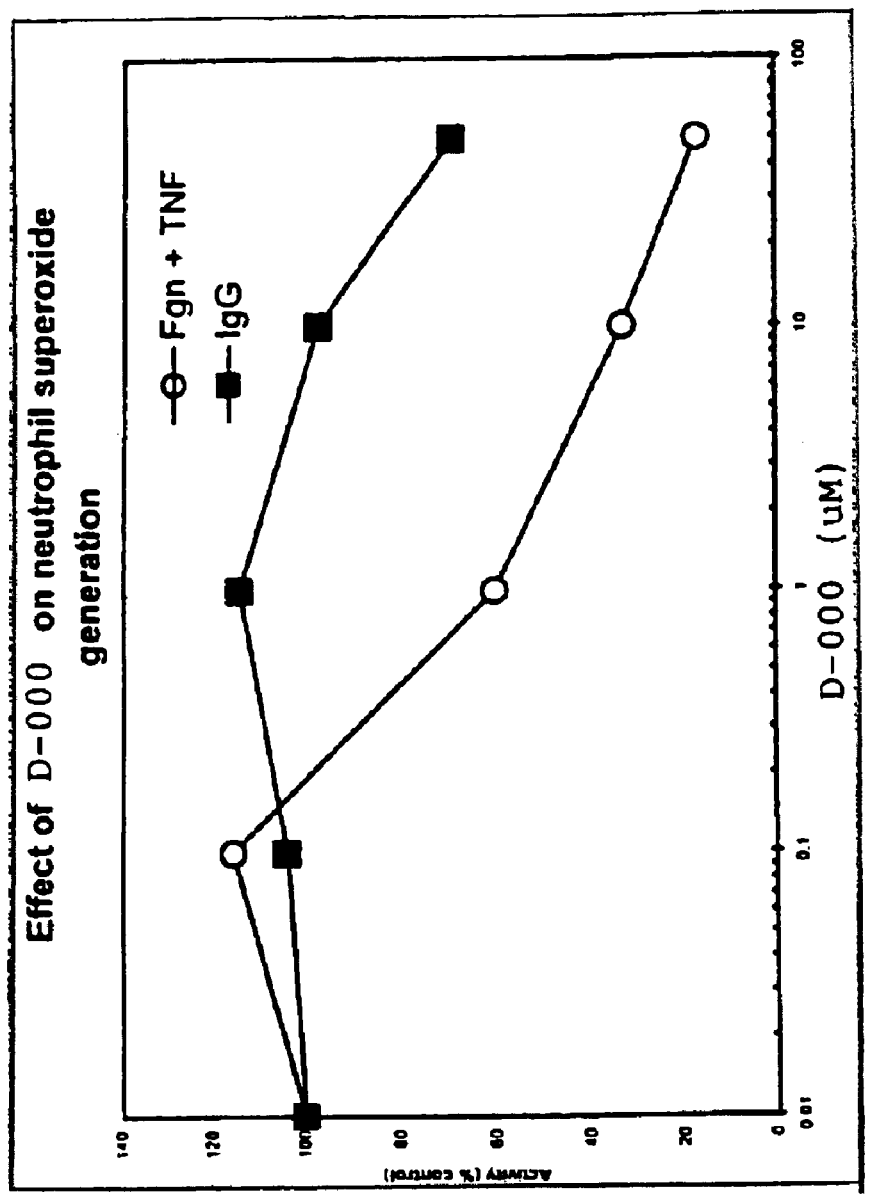
FIG. 2 shows the effect of a selective PI3Kδ inhibitor on superoxide generation by human neutrophils in the presence of TNF or IgG.

As shown in FIG. 2, the PI3Kδ inhibitor D-000 inhibits TNF-induced superoxide generation by neutrophils in a concentration dependent manner. Superoxide generation induced by TNF was reduced to its half-maximal value at about 3 μM D-000. FIG. 2 also reveals that superoxide generation induced by IgG was not significantly inhibited by D-000. In fact, even at 10 μM this PI3Kδ inhibitor did not have any effect on superoxide generation induced by IgG.

Figure 3:
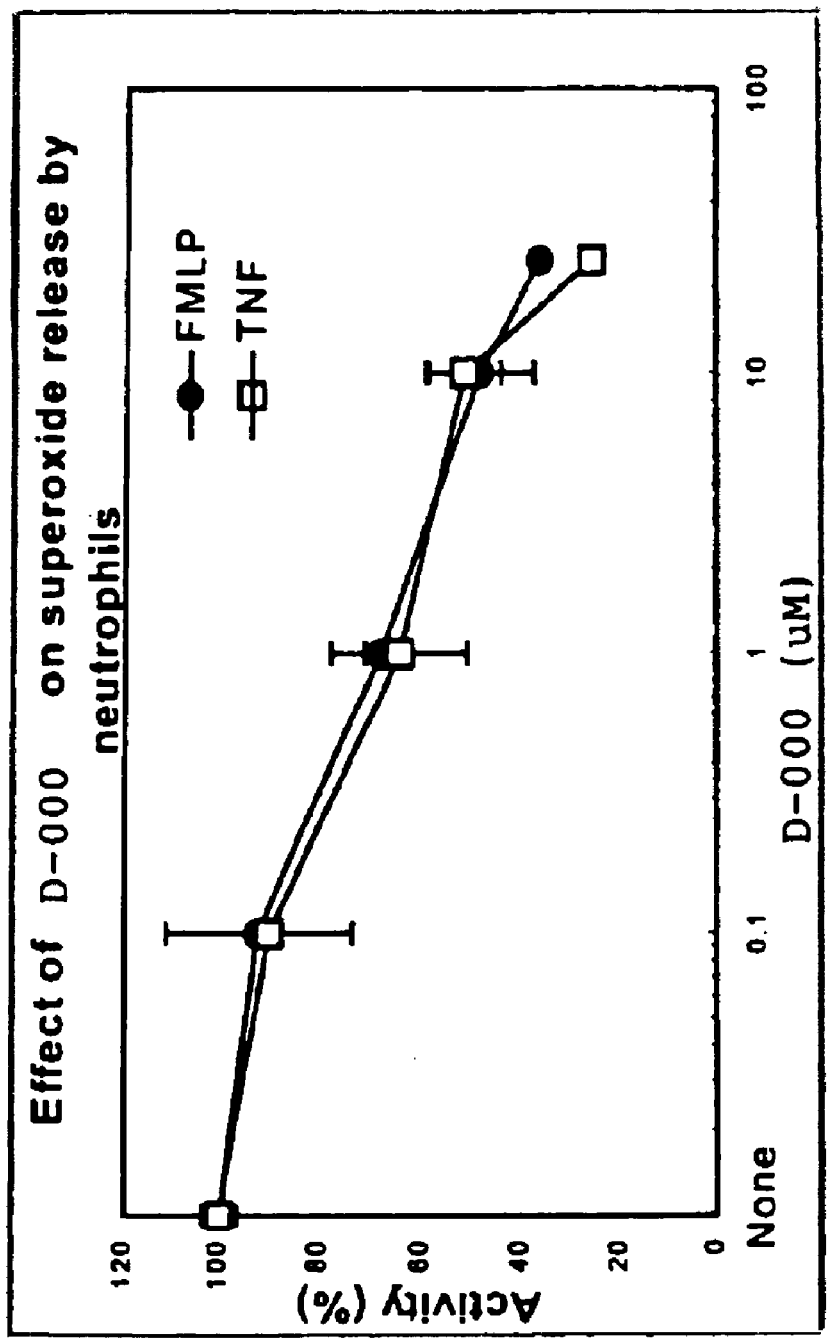
FIG. 3 shows the effect of a selective PI3Kδ inhibitor on superoxide generation by human neutrophils in the presence of TNF or fMLP.

Next, the effect of D-000 on superoxide generation induced by another potent inducer, the bacterial peptide, formylated-Met-Leu-Phe (fMLP) was studied. Like the TNF-induced superoxide generation, fMLP-induced superoxide generation also was inhibited by D-000 (FIG. 3). These results show that the PI3Kδ inhibitor D-000 can prevent stimulus specific induction of superoxide generation by neutrophils, indicating that PI3Kδ is involved in this process.

C. Measurement of Elastase Exocytosis from Neutrophils

Figure 4:
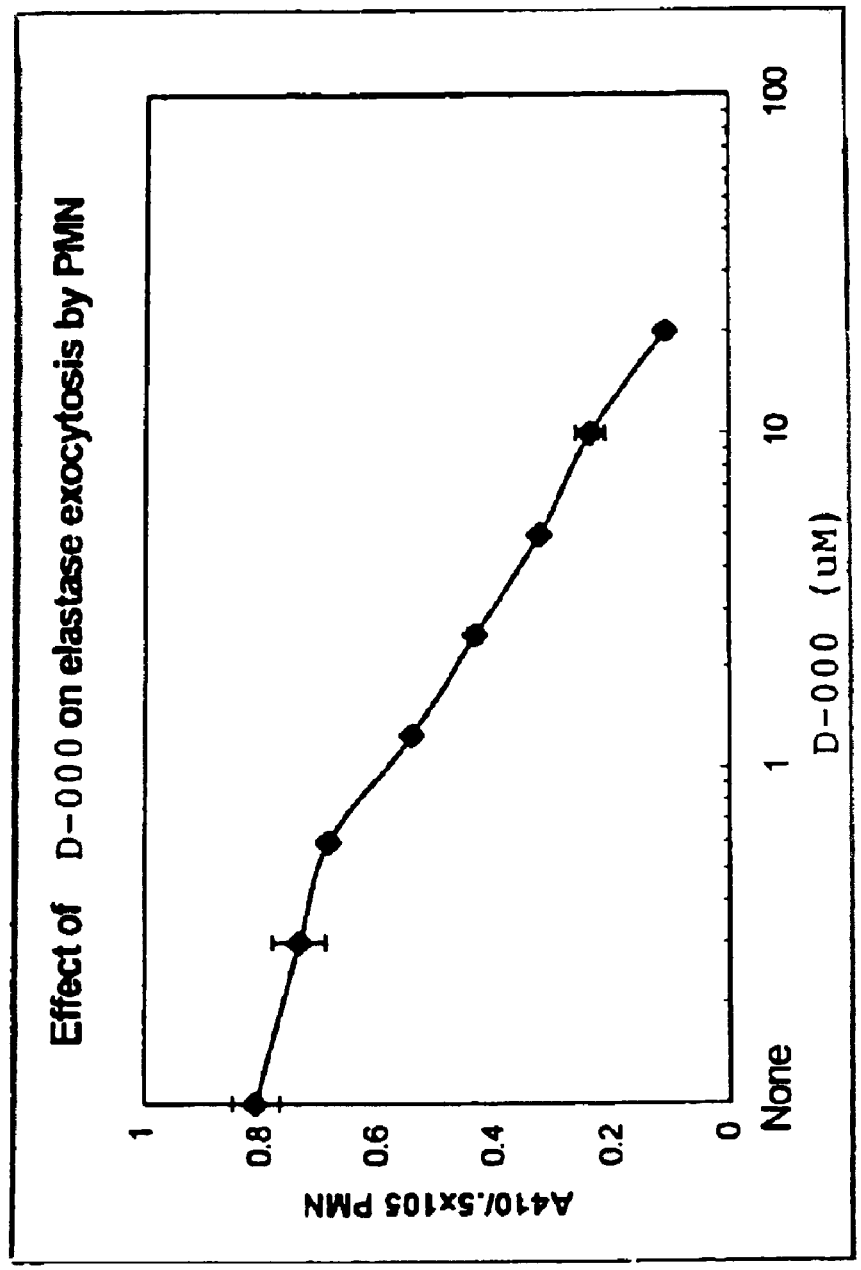
FIG. 4 shows the effect of a selective PI3Kδ inhibitor on elastase exocytosis in the presence of fMLP by human neutrophils.

In addition to superoxide generation, activated neutrophils also respond by releasing several proteases that are responsible for the destruction of tissues and cartilage during inflammation. As an indication of protease release, the effect of D-000 on elastase exocytosis was measured. Elastase exocytosis was quantitated by modification of the procedure described by Ossanna et al. (*J Clin Invest*, 77:1939–1951 (1986)), as follows. Purified human neutrophils ($0.2\times10^6$) (treated with either DMSO or a serial dilution of D-000 in DMSO) were stimulated with fMLP in PBS containing 0.01 mg/mL cytochalasin B, 1.0 μM sodium azide ($NaN_3$), 5 μg/mL L-methionine and 1 μM fMLP for 90 min at 37° C. in a 96-well plate. At the end of the incubation period, the plate was centrifuged for 5 min at 1000 rpm, and 90 μL of the supernatant was transferred to 10 μL of 10 mM solution of an elastase substrate peptide, MeO-suc-Ala-Ala-Pro-Val-pNA, wherein MeO-suc=methoxy-succinyl; pNA=p-nitroanilide (Calbiochem, San Diego, Calif.). Absorbance at 410 nm was monitored for 2 hr in a 96-well plate reader. To measure the relative amounts of elastase excytosed, all absorbance values were normalized to the values without any inhibitor. As shown in FIG. 4, the PI3Kδ inhibitor D-000 inhibits fMLP-induced elastase exocytosis significantly, and does so in a dose-dependent fashion. Inhibition was half-maximal at a concentration of about 2–3 μM D-000.

D. Measurement of fMLP-Induced Human Neutrophil Migration

Neutrophils have the intrinsic capacity to migrate through tissues, and are one of the first cell types to arrive at the sites of inflammation or tissue injury. The effect of D-000 on neutrophil migration towards a concentration gradient of fMLP was measured. The day before the migration assays were performed, 6-well plates were coated with recombinant ICAM-1/Fc fusion protein (Van der Vieren et al., *Immunity*, 3:683–690 (1995)) (25 µg/mL in bicarbonate buffer, pH 9.3) and left overnight at 4° C. After washing, 1% agarose solution, in RPMI-1640 with 0.5% bovine serum albumin (BSA), was added to wells with or without an inhibitor, and plates were placed into a refrigerator before punching holes in the gelled agarose to create plaques (1 central hole surrounded by 6 peripheral ones per well).

Human neutrophils were obtained as described above, and resuspended in RPMI medium supplemented with 0.5% BSA at $5 \times 10^6$ cells/mL. After combining equal volumes of neutrophil suspension and medium (either with DMSO or a serial dilution of the test compound in DMSO), neutrophils were aliquoted into the peripheral holes, while the central hole received fMLP (5 µM). Plates were incubated at 37° C. in the presence of 5% $CO_2$ for 4 hr, followed by termination of migration by the addition of 1% glutaraldehyde solution in D-PBS. After removing the agarose layer, wells were washed with distilled water and dried.

Analysis of neutrophil migration was conducted on a Nikon DIAPHOT® inverted microscope (1× objective) video workstation using the NIH 1.61 program. Using Microsoft Excel and Table Curve 4 (SSPS Inc., Chicago Ill.) programs, a migration index was obtained for each of the studied conditions. Migration index was defined as the area under a curve representing number of migrated neutrophils versus the net distance of migration per cell.

Figure 5:
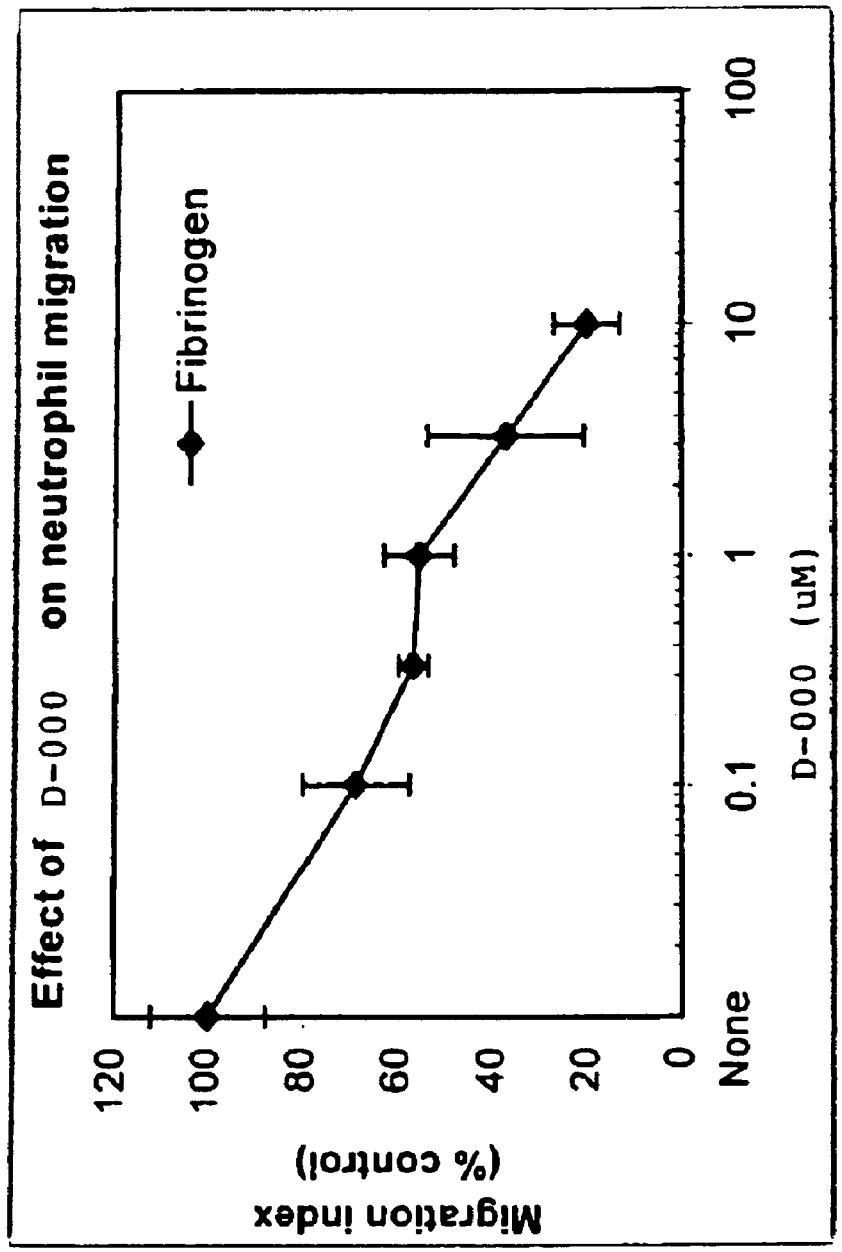
FIG. 5 shows the effect of a selective PI3Kδ inhibitor on fMLP-induced chemotaxis by human neutrophils.

As shown in FIG. 5, the PI3Kδ inhibitor D-000 had a profound effect on neutrophil migration, inhibiting this activity in a dose-dependent manner. The $EC_{50}$ of this compound for inhibition of neutrophil migration in this assay is about 1 µM. Based on a visual inspection of the recorded paths of the cells in this assay, it appears that the total path length for the neutrophils was not significantly affected by the test compound. Rather, the compound affected neutrophil orientation or sense of direction, such that instead of migrating along the axis of the chemoattractant gradient, the cells migrated in an undirected or less directed manner.

E. Measurement of Bactericidal Capacity of Neutrophils

Given that the PI3Kδ inhibitor D-000 affects certain neutrophil functions detailed above, it was of interest to see whether the compound affects neutrophil-mediated bacterial killing. The effect of D-000 on neutrophil-mediated *Staphylococcus aureus* killing was studied according to the method described by Clark and Nauseef (pp. 7.23.4–7.23.6 in Vol. 2, Supp. 6, *Curr Protocols Immunol* (Eds., Colligan et al.) (1994)). Purified human neutrophils ($5 \times 10^6$ cells/mL) (treated with either DMSO or a serial dilution of D-000 in DMSO) were mixed with autologous serum. Overnight-grown *S. aureus* cells were washed, resuspended in HBSS, and added to the serum-opsonized neutrophils at a 10:1 ratio. Neutrophils were allowed to internalize the bacteria by phagocytosis by incubation at 37° C. for 20 min. The noninternalized bacteria were killed by 10 units/mL lysostaphin at 37° C. for 5 min and the total mixture was rotated at 37° C. Samples were withdrawn at various times for up to 90 min and the neutrophils were lysed by dilution in water. Viable bacteria were counted by plating appropriate dilutions on trypticase-soy-agar plate and counting the *S. aureus* colonies after overnight growth.

Figure 6:
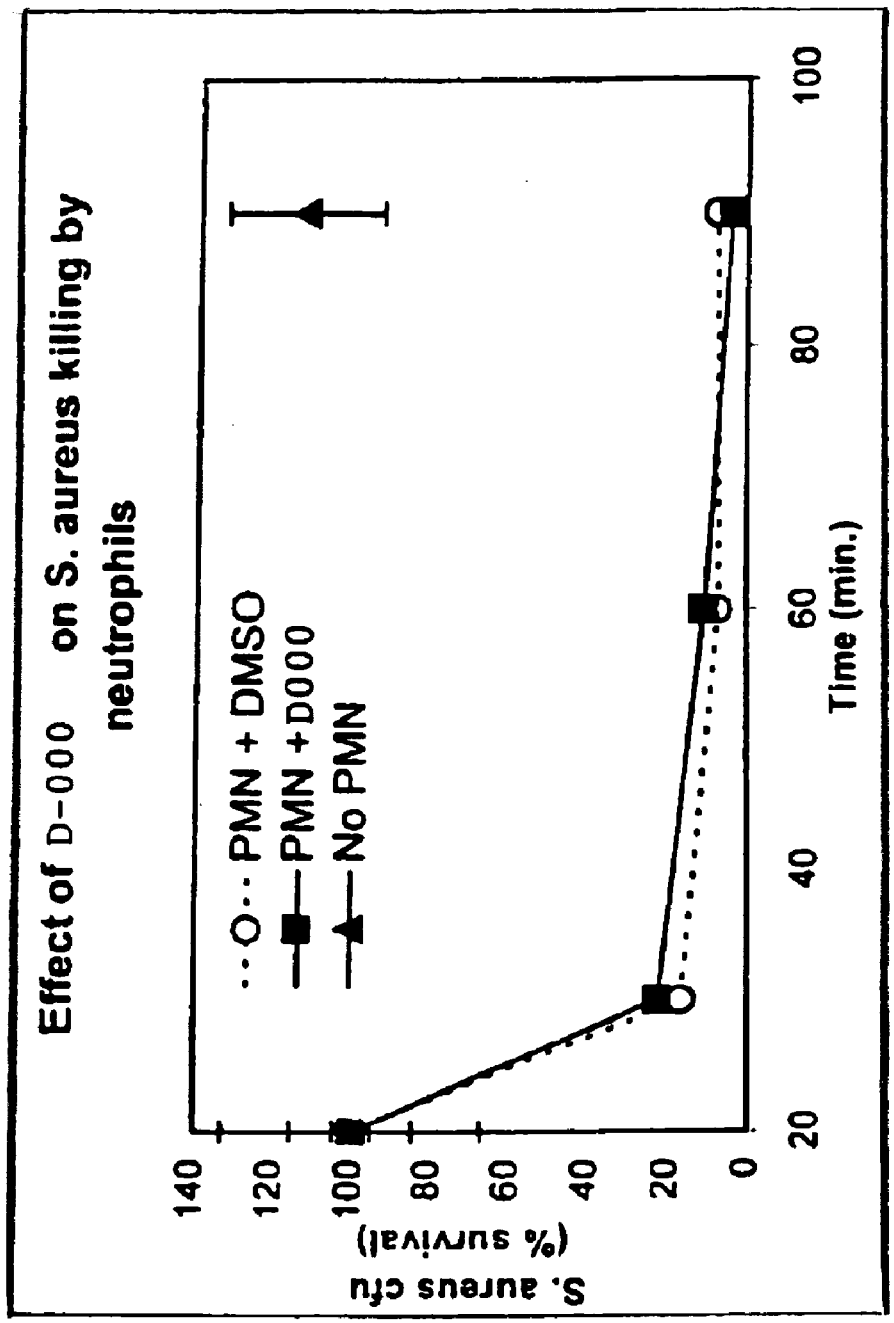
FIG. 6 shows that a selective PI3Kδ inhibitor does not affect phagocytosis and killing of S. aureus by neutrophils.

As shown in FIG. 6, neutrophil-mediated killing of *S. aureus* was similar in samples treated with DMSO (control) and with D-000. These results indicate that the PI3Kδ inhibitor does not significantly affect the ability of neutrophils to kill *S. aureus*, suggesting that PI3Kδ is not involved in this pathway of neutrophil function.

EXAMPLE 4

Characterization of Role of PI3Kδ in B Lymphocyte Function

The effects of the PI 3-kinase inhibitor on B cell functions including classical indices such as antibody production and specific stimulus-induced proliferation also were studied.

A. Preparation and Stimulation of B Cells from Peripheral Human Blood

Heparinized blood (200 mL) from healthy volunteers was mixed with an equal volume of D-PBS, layered on 10×10 mL FICOLL-PAQUE® (Pharmacia), and centrifuged at 1600 rpm for 30 min at room temperature. Peripheral blood mononuclear cells (PBMC) were collected from the FICOLL®/serum interface, overlayed on 10 mL fetal bovine serum (FBS) and centrifuged at 800 rpm for 10 min to remove platelets. After washing, cells were incubated with DYNAL® Antibody Mix (B cell kit) (Dynal Corp., Lake Success, N.Y.) for 20 min at 4–8° C. Following the removal of unbound antibody, PBL were mixed with anti-mouse IgG coated magnetic beads (Dynal) for 20 min at 4–8° C. with gentle shaking followed by elimination of labeled non-B cells on the magnetic bead separator. This procedure was repeated once more. The B cells were resuspended in RPMI-1640 with 10% FBS, and kept on ice until further use.

B. Measurement of Antibody Production by Human B Cells

To study antibody production, B cells were aliquoted at $50-75 \times 10^3$ cells/well into 96-well plate with or without inhibitor, to which IL-2 (100 U/mL) and PANSORBIN® (Calbiochem) *Staphylococcus aureus* cells (1:90,000) were added. Part of the media was removed after 24–36 hr, and fresh media (with or without inhibitor) and IL-2 were added. Cultures were incubated at 37° C., in the presence of a $CO_2$ incubator for additional 7 days. Samples from each condition (in triplicate) were removed, and analyzed for IgG and IgM, as measured by ELISA. Briefly, IMMULON® 4 96-well plates were coated (50 µL/well) with either 150 ng/mL donkey antihuman IgG (H+L) (Jackson ImmunoResearch, West Grove Pa.), or 2 µg/mL donkey antihuman IgG+IgM (H+L) (Jackson ImmunOResearch) in bicarbonate buffer, and left overnight at 4° C. After 3× washing with phosphate buffered saline containing 0.1% TWEEN®-80 (PBST) (350 µL/well), and blocking with 3% goat serum in PBST (100 µL/well) for 1 hr at room temperature, samples (100 µL/well) of B cell spent media diluted in PBST were added. For IgG plates the dilution range was 1:500 to 1:10000, and for IgM 1:50 to 1:1000. After 1 hr, plates were exposed to biotin-conjugated anti-human IgG (100 ng/mL) or antihuman IgM (200 ng/mL) (Jackson ImmunOResearch) for 30 min, following by streptavidin-HRP (1:20000) for 30 min, and finally, to TMB solution (1:100) with $H_2O_2$ (1:10000) for 5 min, with 3×PBST washing between steps. Color development was stopped by $H_2SO_4$ solution, and plates were read on an ELISA plate reader.

Figure 7:
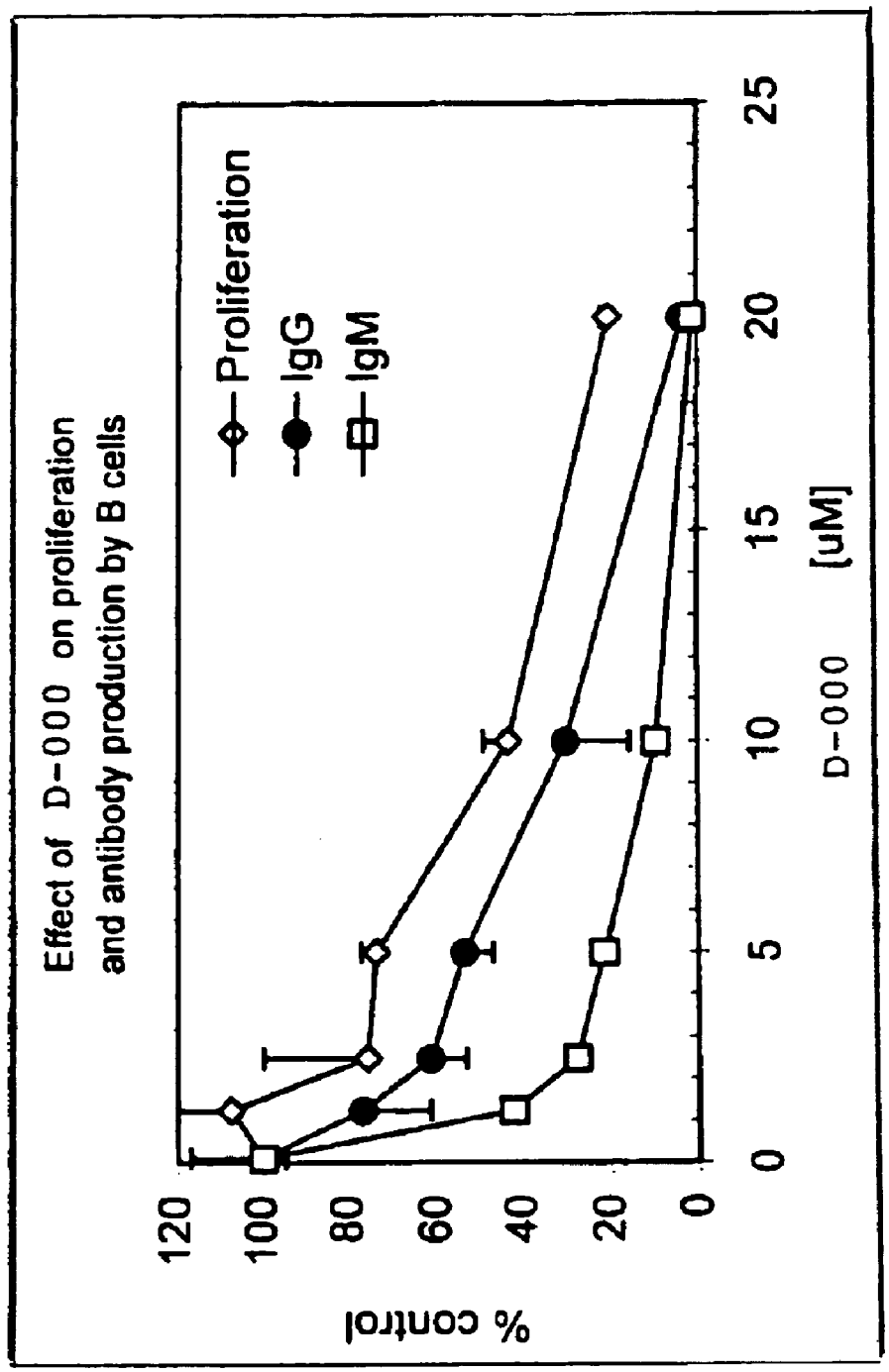
FIG. 7 shows the effect of a selective PI3Kδ inhibitor on proliferation and antibody production by human B lymphocytes.

As shown in FIG. 7, D-000 significantly inhibited antibody production. IgM production was affected more than IgG production: half-maximal inhibition of IgM production was observed at about 1 µM, versus about 7 µM for comparable inhibition of IgG production.

C. Measurement of B Cell Proliferation in Response to Cell Surface IgM Stimulation In the above experiment, the B cells were stimulated using PANSORBIN®. The effect of D-000 on B cell proliferation response when they were stimulated through their cell surface IgM using anti-IgM antibody also was measured. Murine splenocytes (Balb/c) were plated into 96-well microtiter plates at $2 \times 10^5$ cells per well in 10% FBS/RPMI. Appropriate dilutions of test inhibitor in complete medium were added to the cells and the plates were incubated for 30–60 minutes prior to the addition of stimulus. Following the preincubation with test inhibitor an F(ab')$_2$ preparation of goat antibody specific for the µ-chain of mouse IgM was added to the wells at a final concentration of 25 µg/mL. The plates were incubated at 37° C. for 3 days and 1 µCi of [$^3$H]-thymidine was added to each well for the final four hours of culture. The plates were harvested onto fiber filters washed and the incorporation of radio-label was determined using a beta counter (Matrix 96, Packard Instrument Co., Downers Grove, Ill.) and expressed as counts per minute (CPM).

Figure 8:
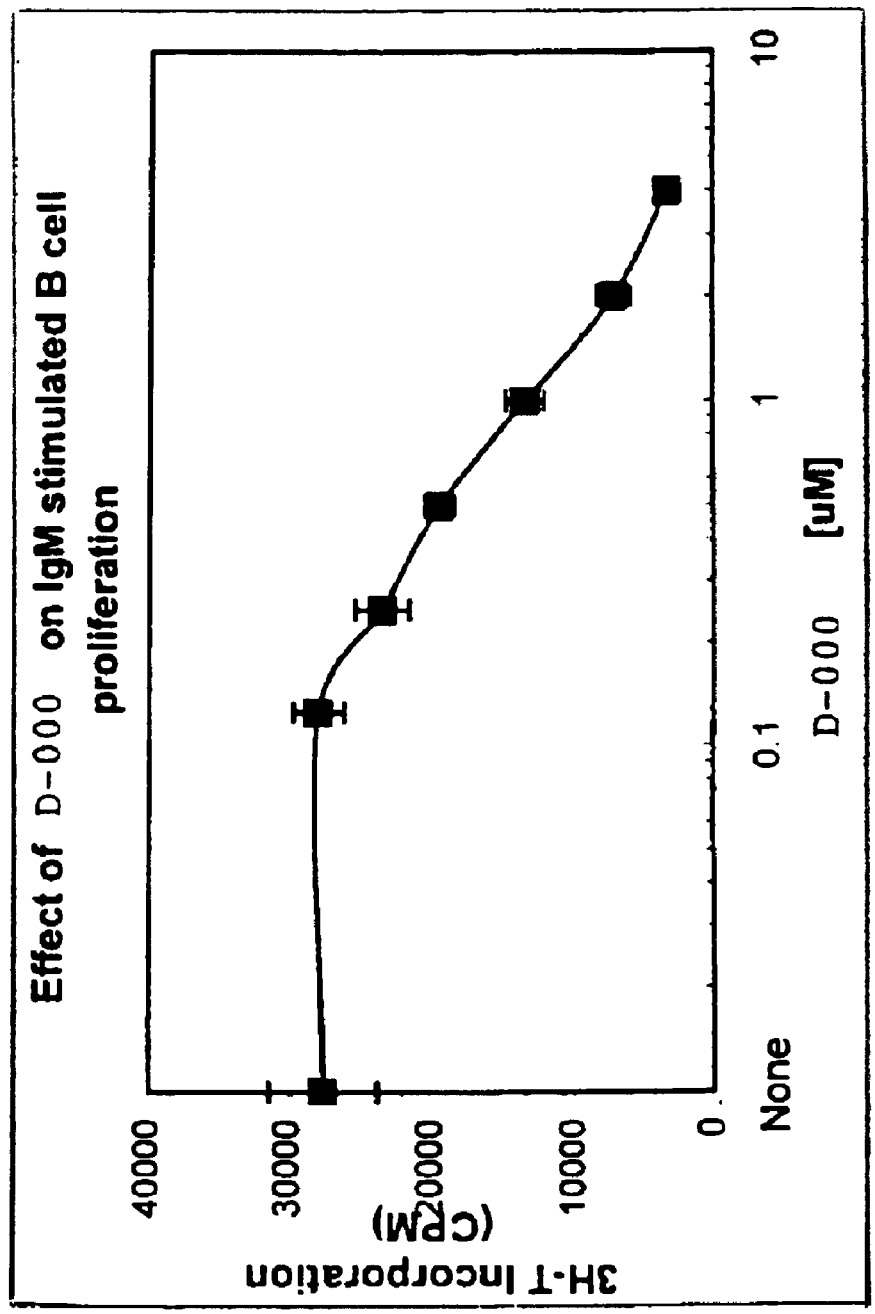
FIG. 8 shows the effect of a selective PI3Kδ inhibitor on anti-IgM stimulated mouse splenic B lymphocyte proliferation.

FIG. 8 shows the effect of D-000 on anti-IgM stimulated proliferation of B cells. The compound inhibited anti-IgM-stimulated B cell proliferation in a dose-dependent manner. At about 1 µM, proliferation was reduced to its half-maximal value.

Because the compound D-000 inhibits B cell proliferation, it is envisioned that this compound and other PI3Kδ inhibitors could be used to suppress undesirable proliferation of B cells in clinical settings. For example, in B cell malignancy, B cells of various stages of differentiation show unregulated proliferation. Based on the results shown above, one can infer that PI3Kδ selective inhibitors could be used to control, limit, or inhibit growth of such cells.

EXAMPLE 5
Characterization of Role of PI3Kδ in T Lymphocyte Function

T cell proliferation in response to costimulation of CD3+ CD28 was measured. T cells were purified from healthy human blood by negative selection using antibody coated magnetic beads according to the manufacturer's protocol (Dynal) and resuspended in RPMI. The cells were treated with either DMSO or a serial dilution of D-000 in DMSO and plated at $1 \times 10^5$ cells/well on a 96-well plate precoated with goat antimouse IgG. Mouse monoclonal anti-CD3 and anti-CD28 antibodies were then added to each well at 0.2 ng/mL and 0.2 µg/mL, respectively. The plate was incubated at 37° C. for 24 hr and [$^3$H]-thymidine (1 µCi/well) was added. After another 18 hr incubation the cells were harvested with an automatic cell harvester, washed and the incorporated radioactivity was quantified.

Although the PI3Kδ inhibitor D-000 inhibited anti-CD3- and anti-CD28-induced proliferation of T cells, its effect is not as strong as its effect on B cells or on some of the functions of neutrophils. Half-maximal inhibition of thymidine incorporation was not achieved at the highest tested concentration, i.e., 10 µM D-000.

EXAMPLE 6
Characterization of Role of PI3Kδ in Osteoclast Function

To analyze the effect of the PI3Kδ inhibitor D-000 on osteoclasts, mouse bone marrow cells were isolated and differentiated them to osteoclasts by treating the cells with Macrophage Colony Stimulating Factor$^{-1}$ (mCSF$^{-1}$) and Osteoprotegerin Ligand (OPGL) in serum-containing medium (αMEM with 10% heat-inactivated FBS; Sigma) for 3 days. On day four, when the osteoclasts had developed, the medium was removed and cells were harvested. The osteoclasts were plated on dentine slices at $10^5$ cells/well in growth medium, i.e., αMEM containing 1% serum and 2% BSA with 55 µg/mL OPGL and 10 ng/mL mCSF-1. After 3 hr, the medium was changed to 1% serum and 1% BSA, with or without osteopontin (25 µg/mL) and the PI3K inhibitors (100 nM). The medium was changed every 24 hours with fresh osteopontin and the inhibitors. At 72 hr, the medium was removed, and the dentine surfaces were washed with water to remove cell debris and stained with acid hematoxylin. Excess stain was washed and the pit depths were quantitated using confocal microscopy.

As shown in Table 1, in two experiments, the PI 3-kinase inhibitors had an inhibitory effect on osteoclast function. Both the nonspecific inhibitors LY294002 and wortmannin inhibited osteoclast activity. However, the PI3Kδ inhibitor D-000 had the most profound effect, as at 100 nM this compound almost completely inhibited the osteoclast activity.

TABLE 1

| Osteopontin (OPN) | D-000 + OPN | LY294002 + OPN | Wortmannin + OPN |
| --- | --- | --- | --- |
| 10 ± 0.5 | 1 | 4.6 ± 0.22 | 5.7 ± 0.6 |
| 9 ± 0.4 | 1 | 5.8 ± 0.5 | 5 ± 0.5 |

EXAMPLE 7
Characterization of Role of PI3Kδ in Basophil Function

Assessment of the effect of a compound of the invention on basophil function was tested using a conventional histamine release assay, generally in accordance with the method described in Miura et al., *J Immunol*, 162:4198–206 (1999). Briefly, enriched basophils were preincubated with test compounds at several concentrations from 0.1 nM to 1,000 nM, for 10 min at 37° C. Then, polyclonal goat antihuman IgE (0.1 µg/mL) or fMLP was added, and allowed to incubate for an additional 30 min. Histamine released into the supernatant was measured using an automated fluorometric technique. Two compounds were tested, shown below.

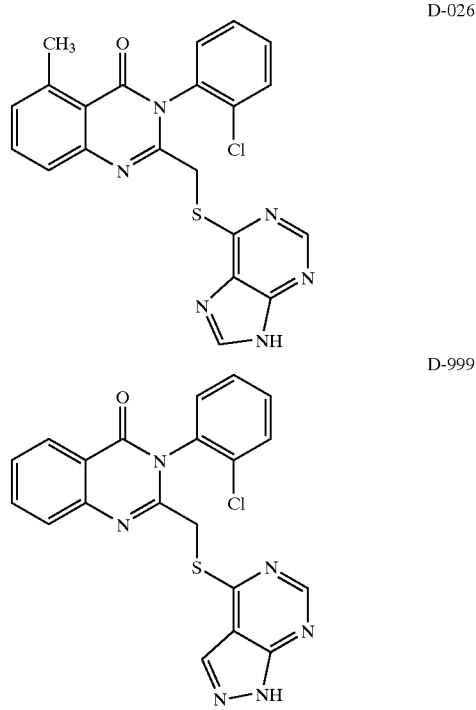

A dose-dependent decrease in histamine release was observed for 3-(2-chlorophenyl)-5-methyl-2-(9H-purin-6-ylsulfanylmethyl)-3H-quinazolin-4-one (D-026) when the basophils were stimulated with anti-IgE. This suppression of histamine release was essentially 100% at 1,000 nM, with an EC$_{50}$ of about 25 nM. Another compound, 3-(2-chlorophenyl)-2-(1H-pyrazolo[3,4-d]pyrimidin-4-ylsulfanylmethyl)-3H-quinazolin-4-one (D-999), in which the purine ring structure is rearranged, was less efficacious in the inhibition of histamine release. Neither compound elicited any effect when the basophils were stimulated with fMLP. For comparison, the nonselective PI3K inhibitor LY294002 was tested at 0.1 nM and 10,000 nM, showing close to 100% inhibition of histamine release at the highest concentration.

These data indicate that inhibitors of PI 3-kinase delta activity can be used to suppress release of histamine, which is one of the mediators of allergy. Since the activity of various PI 3-kinases are required for protein trafficking, secretion, and exocytosis in many cell types, the above data suggest that histamine release by other cells, such as mast cells, also can be disrupted by PI 3-kinase delta-selective inhibitors.

CHEMICAL SYNTHESIS EXAMPLES

Specific nonlimiting examples of compounds of the invention are provided below. It is understood in the art that protecting groups can be employed where necessary in accordance with general principles of synthetic chemistry. These protecting groups are removed in the final steps of the synthesis under basic, acidic, or hydrogenolytic conditions readily apparent to those persons skilled in the art. By employing appropriate manipulation and protection of any chemical functionalities, synthesis of compounds of structural formula (I) not specifically set forth herein can be accomplished by methods analogous to the schemes set forth below.

Unless otherwise noted, all starting materials were obtained from commercial suppliers and used without further purification. All reactions and chromatography fractions were analyzed by thin-layer chromatography (TLC) on 250 mm silica gel plates, visualized with ultraviolet (UV) light or iodine (I$_2$) stain. Products and intermediates were purified by flash chromatography or reverse-phase high performance liquid chromatography.

The following abbreviations are used in the synthetic examples: aq (aqueous), H$_2$O (water), CHCl$_3$ (chloroform), HCl (hydrochloric acid), MeOH (methanol), NaOH (sodium hydroxide), NaOMe (sodium methoxide), TFA (trifluoroacetic acid), K$_2$CO$_3$ (potassium carbonate), SOCl$_2$ (thionyl chloride), CH$_2$Cl$_2$ (methylene chloride), EtOAC (ethyl acetate), DMF (dimethylformamide), EtOH (ethanol), DMSO (dimethyl sulfoxide), NaHCO$_3$ (sodium bicarbonate), TLC (thin layer chromatography), HPLC (high performance liquid chromatography), HOBT (hydroxybenzotriazole), EDC (ethyldiethylaminopropylcarbodiimide), DIEA (diisopropylethylamine), and HOAc (acetic acid).

I. General Procedures

Procedure A

Thionyl chloride was added to a rapidly stirring solution of anthranilic acid or benzoic acid in benzene, and the mixture was stirred at reflux for 5 to 18 hours. The reaction was concentrated in vacuo, and stripped down twice with benzene. The resulting oil was dissolved in CHCl$_3$ and to that solution was added the appropriate aniline. The reaction mixture was heated to reflux and stirred until complete, as determined by TLC, at which point the reaction mixture was cooled to ambient temperature. The precipitate was removed by filtration, and the filtrate concentrated in vacuo. The crude product was purified by chromatography and/or recrystallization from MeOH to provide amides 1a–1r.

Procedure B

To a rapidly stirring suspension of an amide in glacial acetic acid was added chloroacetyl chloride. The reaction mixture was heated to 120° C., and allowed to stir at that temperature until complete, as determined by TLC. After brief cooling, the reaction mixture was concentrated in vacuo. The crude residue was purified by extraction, chromatography, and/or recrystallization to provide chlorides 2a–2r.

Procedure C

A mixture of a chloride, either a nitrogen or a sulfur nucleophile, for example, mercaptopurine monohydrate or adenine, and K$_2$CO$_3$ in DMF was stirred at room temperature for 15–72 hours. The resulting suspension was poured into water, and kept at 4° C. for several hours. The crude solid was filtered, washed with water, and purified by chromatography or recrystallization to provide the final product.

EXAMPLE 8

Preparation of Intermediate Compounds: Amides

2-Amino-N-(2-chlorophenyl)-4,5-dimethoxybenzamide (1a)

Prepared according to Procedure A using 4,5-dimethoxyanthranilic acid (5.0 g, 25.4 mmol) and SOCl$_2$ (5.5 mL, 76.1 mmol) in benzene (100 mL), followed by 2-chloroaniline (6.7 mL, 63.5 mmol) and CHCl$_3$ (75 mL). The product was washed with aqueous NaHCO$_3$ (2×25 mL) and HCl (0.5 M, 75 mL) and purified by chromatography in CH$_2$Cl$_2$ to provide 4.3 g of a brown foam (55%). $^1$H NMR (CDCl$_3$) δ: 8.42 (dd, J=1.5, 8.3 Hz, 1H); 8.32 (br s, 1H); 7.40 (dd, J=1.4, 8.0 Hz, 1H); 7.31 (dt, J=1.4, 7.9 Hz, 1H); 7.05 (dt, J=1.5, 7.7 Hz, 1H); 7.03 (s, 1H); 6.24 (s, 1H); 3.88 (s, 3H); 3.87 (s, 3H). MS (ES): m/z 307.0 (M+).

2-Amino-5-bromo-N-(2-chlorophenyl)benzamide (1b)

Prepared according to Procedure A using 2-amino-5-bromobenzoic acid (5.0 g, 23.1 mmol) and SOCl$_2$ (7.0 mL, 95.9 mmol) in benzene (50 mL), followed by 2-chloroaniline (7.3 mL, 69.3 mmol) and CHCl$_3$ (50 mL). The product was purified by two chromatographies in CH$_2$Cl$_2$ to provide 1.48 g of a yellow orange solid (20%). $^1$H NMR (CDCl$_3$) δ: 8.36 (dd, J=1.2, 8.2 Hz, 1H); 8.20 (br s, 1H); 7.62 (d, J=2.1 Hz, 1H); 7.42 (dd, J=1.3, 8.0 Hz, 1H); 7.34 (dd, J=2.2, 8.8 Hz, 1H); 7.28–7.33 (m, 1H); 7.09 (dt, J=1.4, 7.7 Hz, 1H); 6.62 (d, J=8.7 Hz, 1H); 5.57 (br s, 2H).

2-Amino-N-(2-chlorophenyl)-4-fluorobenzamide (1c)

Prepared according to Procedure A using 2-amino-4-fluorobenzoic acid (1.15 g, 7.41 mmol) and SOCl$_2$ (1.4 mL, 18.5 mmol) in benzene (25 mL), followed by 2-chloroaniline (1.6 mL, 14.8 mmol) and CHCl$_3$ (25 mL). The product was chromatographed in CH$_2$Cl$_2$, then triturated from hexanes to provide 1.02 g of an off-white solid (52%). $^1$H NMR (CDCl$_3$) δ: 12.91 (br s, 1H); 8.72 (dd, J=2.7, 12 Hz, 1H); 8.34 (dd, J=6.4, 9.2 Hz, 1H); 8.29 (dd, J=5.9, 8.8 Hz, 1H); 7.81 (dd, J=6.2, 8.8 Hz, 1H); 7.28 (dt, J=2.4, 8.4 Hz, 1H); 7.21 (dd, J=2.4, 9.0 Hz, 1H); 6.92 (ddd, J=2.4, 7.3, 9.1 Hz, 1H); 6.54 (ddd, J=2.4, 7.8, 8.8 Hz, 1H); 6.45 (dd, J=2.4, 11 Hz, 1H); 5.93 (br s, 2H). MS (ES): m/z 265.0 (M+)

2-Amino-5-chloro-N-(2-chlorophenyl)benzamide (1d)

Prepared according to Procedure A using 2-amino-5-chlorobenzoic acid (2.0 g, 11.7 mmol) and SOCl$_2$ (2.2 mL, 29.2 mmol) in benzene (50 mL), followed by 2-chloroaniline (2.5 mL, 23.3 mmol) and CHCl$_3$ (50 mL). The product was purified by recrystallization from MeOH to provide 1.72 g of a dark yellow solid (52%). $^1$H NMR (CDCl₃) δ: 8.37 (dd, J=1.5, 8.3 Hz, 1H); 8.22 (br s, 1H); 7.48 (d, J=2.3 Hz, 1H); 7.42 (dd, J=1.5, 8.1 Hz, 1H); 7.31 (dt, J=1.4, 7.8 Hz, 1H); 7.22 (dd, J=2.4, 8.8 Hz, 1H); 7.09 (dt, J=1.5, 7.7 Hz, 1H); 6.67 (d, J=8.8 Hz, 1H); 5.56 (br s, 2H)

2-Amino-N-(2-chlorophenyl)-6-fluorobenzamide (1e)

Prepared according to Procedure A using 2-amino-6-fluorobenzoic acid (2.0 g, 12.9 mmol) and SOCl₂ (2.3 mL, 32.2 mmol) in benzene (50 mL), followed by 2-chloroaniline (2.7 mL, 25.8 mmol) and CHCl₃ (50 mL). The product was purified by chromatography in EtOAc/hexanes to provide 2.06 g of a pale orange solid (60%). ¹H NMR (CDCl₃) δ: 9.00 (d, J=17 Hz, 1H); 8.47 (d, J=8.3 Hz, 1H); 7.41 (d, J=8.0 Hz, 1H); 7.30 (t, J=7.9 Hz, 1H); 7.10–7.20 (m, 1H); 7.07 (t, J=7.7 Hz, 1H); 6.49 (d, J=8.3 Hz, 1H); 6.03 (br s, 2H). MS (ES): m/z 265.0 (M+).

2-Amino-6-chloro-N-(2-chlorophenyl)benzamide (1f)

Prepared according to Procedure A using 2-amino-6-chlorobenzoic acid (2.5 g, 14.6 mmol) and SOCl₂ (2.7 mL, 36.4 mmol) in benzene (75 mL), followed by 2-chloroaniline (3.1 mL, 29.1 mmol) and CHCl₃ (75 mL). The product chromatographed in CH₂Cl₂ to provide 1.05 g of a yellow orange solid (26%). ¹H NMR (CDCl₃) δ: 8.54 (d, J=8.1 Hz, 1H); 8.30 (br s, 1H); 7.41 (dd, J=1.5, 8.0 Hz, 1H); 7.33 (t, J=7.8 Hz, 1H); 7.10 (t, J=8.1 Hz, 1H); 7.09 (dt, J=1.6, 7.8 Hz, 1H); 6.78 (dd, J=0.4, 7.9 Hz, 1H); 6.63 (dd, J=0.9, 8.2 Hz, 1H); 4.69 (br s, 2H). MS (ES): m/z 303.0 (M+22), 281.0 (M+).

2-Amino-N-(2-chlorophenyl)-6-methylbenzamide (1 g)

Prepared according to Procedure A using 2-amino-6-methylbenzoic acid (2.5 g, 16.5 mmol) and SOCl₂ (3.0 mL, 41.3 mmol) in benzene (75 mL), followed by 2-chloroaniline (3.5 mL, 33.0 mmol) and CHCl₃ (75 mL). The product was chromatographed in CH₂Cl₂ to provide 2.19 g of a brown oil (51%). ¹H NMR (CDCl₃) δ: 8.58 (d, J=8.1 Hz, 1H); 7.99 (br s, 1H); 7.40 (dd, J=1.4, 8.0 Hz, 1H); 7.34 (t, J=7.7 Hz, 1H); 7.11 (t, J=7.8 Hz, 1H); 7.09 (dt, J=1.5, 7.7 Hz, 1H); 6.64 (d, J=7.5 Hz, 1H); 6.59 (d, J=8.1 Hz, 1H); 4.29 (br s, 2H); 2.45 (s, 3H). MS (ES) m/z 283.0 (M+22).

2-Amino-3-chloro-N-(2-chlorophenyl)benzamide (1 h)

Prepared according to Procedure A using 2-amino-3-chlorobenzoic acid (1.0 g, 5.82 mmol) and SOCl₂ (1.1 mL, 14.6 mmol) in benzene (25 mL), followed by 2-chloroaniline (1.2 mL, 11.7 mmol) and CHCl₃ (25 mL). The product was recrystallized from MeOH to provide 1.29 g of a yellow solid (78%). ¹H NMR (CDCl₃) δ: 8.43 (dd, J=1.4, 8.3 Hz, 1H); 8.30 (br s, 1H); 7.47 (dd, J=1.1, 8.0 Hz, 1H); 7.42 (d, J=8.0 Hz, 2H); 7.33 (dt, J=1.4, 7.9 Hz, 1H); 7.09 (dt, J=1.5, 7.7 Hz, 1H); 6.68 (t, J=7.9 Hz, 1H); 6.13 (br s, 2H). MS (ES): m/z 281.0 (M+).

2-Amino-N-biphenyl-2-yl-6-chlorobenzamide (1i)

Prepared according to Procedure A using 2-amino-6-chlorobenzoic acid (2.0 g, 11.7 mmol) and SOCl₂ (2.1 mL, 29.3 mmol) in benzene (60 mL), followed by 2-aminobiphenylamine (4.15 g, 24.5 mmol) and CHCl₃ (60 mL). The product was chromatographed in CH₂Cl₂ to provide 2.16 g of a foamy dark-amber residue (57%). ¹H NMR (CDCl₃) δ: 8.48 (d, J=8.2 Hz, 1H); 7.79 (br s, 1H); 7.34–7.46 (m, 6H); 7.20–7.30 (m, 2H); 7.00 (t, J=8.1 Hz, 1H); 6.63 (dd, J=0.6, 7.9 Hz, 1H); 6.54 (d, J=8.3 Hz, 1H); 4.58 (br s, 2H). MS (ES): m/z 323.1 (M+).

2-Amino-6-chloro-N-o-tolylbenzamide (1j)

Prepared according to Procedure A using 2-amino-6-chlorobenzoic acid (1.0 g, 5.83 mmol) and SOCl₂ (1.1 mL, 14.6 mmol) in benzene (30 mL), followed by o-toluidine (1.4 mL, 12.8 mmol) and CHCl₃ (30 mL). The product was chromatographed in CH₂CO₂ to provide 840 mg of an oily yellow solid (55%). ¹H NMR (CDCl₃) δ: 7.96 (d, J=7.9 Hz, 1H); 7.60 (br s, 1H); 7.23–7.30 (m, 2H); 7.14 (t, J=7.5 Hz, 1H); 7.11 (t, J=8.3 Hz, 1H); 6.78 (d, J=7.9 Hz, 1H); 6.64 (d, J=8.2 Hz, 1H); 4.73 (br s, 2H); 2.35 (s, 3H). MS (ES): m/z 261.0 (M+).

2-Amino-6-chloro-N-(2-fluorophenyl)benzamide (1k)

Prepared according to Procedure A using 2-amino-6-chlorobenzoic acid (2.0 g, 11.7 mmol) and SOCl₂ (2.1 mL, 29.1 mmol) in benzene (60 mL), followed by 2-fluoroaniline (2.3 mL, 23.4 mmol) and CHCl₃ (60 mL). The product was chromatographed in CH₂Cl₂ to provide 1.05 g of a yellow solid (34%). ¹H NMR (CDCl₃) δ: 8.45 (t, J=8.0 Hz, 1H); 8.01 (br s, 1H); 7.02–7.22 (m, 4H); 6.78 (dd, J=0.5, 7.9 Hz, 1H); 6.64 (dd, J=0.8, 8.2 Hz, 1H); 4.73 (br s, 2H). MS (ES): m/z 265.0 (M+)

2-Amino-6-chloro-N-(2-methoxyphenyl)benzamide (1l)

Prepared according to Procedure A using 2-amino-6-chlorobenzoic acid (2.0 g, 11.7 mmol) and SOCl₂ (2.1 mL, 29.1 mmol) in benzene (60 mL), followed by o-anisidine (2.6 mL, 23.4 mmol) and CHCl₃ (60 mL). The product was chromatographed in CH₂Cl₂ to provide 2.61 g of a dark yellow oil (81%). ¹H NMR (CDCl₃) δ: 8.53 (dd, J=1.7, 7.9 Hz, 1H); 8.39 (br S, 1H); 7.11 (dt, J=1.6, 7.8 Hz, 1H); 7.09 (t, J=8.1 Hz, 1H); 7.02 (dt, J=1.4, 7.8 Hz, 1H); 6.92 (dd, J=1.4, 8.0 Hz, 1H); 6.62 (dd, J=0.9, 8.2 Hz, 1H); 4.66 (br s, 2H); 3.87 (s, 3H). MS (ES): m/z 277.0 (M+).

2-Amino-N-(2-chlorophenyl)-3-trifluoromethylbenzamide (1m)

Prepared according to Procedure A using 3-trifluoromethylanthranilic acid (2.0 g, 9.75 mmol) and SOCl₂ (1.8 mL, 24.4 mmol) in benzene (50 mL), followed by 2-chloroaniline (2.1 mL, 19.5 mmol) and CHCl₃ (50 mL). The product was purified by recrystallization from MeOH to provide 2.38 g yellow crystals (78%). ¹H NMR (CDCl₃) δ: 8.40 (dd, J=1.4, 8.3 Hz, 1H); 8.25 (br s, 1H); 7.71 (d, J=7.8 Hz, 1H); 7.60 (d, J=7.8 Hz, 1H); 7.43 (dd, J=1.4, 8.0 Hz, 1H); 7.34 (dt, J=1.3, 7.9 Hz, 1H); 7.11 (dt, J=1.5, 7.7 Hz, 1H); 6.77 (t, J=7.8 Hz, 1H); 6.24 (br S, 2H). MS (ES): m/z 315.0 (M+)

3-Aminonaphthalene-2-carboxylic acid (2-chlorophenyl)amide (1n)

Prepared according to Procedure A using 3-amino-2-napthoic acid (2.0 g, 10.7 mmol) and SOCl₂ (1.9 mL, 26.7 mmol) in benzene (50 mL), followed by 2-chloroaniline (2.3 mL, 21.4 mmol) and CHCl₃ (50 mL). The product was recrystallized from MeOH to provide 1.71 g of a brown solid (54%). ¹H NMR (CDCl₃) δ: 10.88 (br s, 1H); 9.21 (s, 1H); 8.91 (s, 1H); 8.70 (dd, J=1.0, 8.3 Hz, 1H); 7.95–8.01 (m, 1H); 7.87–7.94 (m, 1H); 7.60–7.68 (m, 2H); 7.41 (dd, J=1.3, 8.0 Hz, 1H); 7.34 (dt, J=1.2, 7.8 Hz, 1H); 7.07 (dt, J=1.4, 7.7 Hz, 1H). MS (ES): m/z 297.1 (M+).

2-Amino-N-(2-chlorophenyl)-4-nitrobenzamide (1o)

Prepared according to Procedure A using 4-nitroanthranilic acid (5.0 g, 27.5 mmol) and SOCl₂ (5.0 mL, 68.6 mmol) in benzene (150 mL), followed by 2-chloroaniline (5.8 mL, 55.0 mmol) and CHCl₃ (150 mL). The product was purified by chromatography in CH₂Cl₂ followed by recrystallization from MeOH to provide 2.20 g of an orange-brown solid (31%). ¹H NMR (CDCl₃) δ: 8.41 (dd, J=1.3, 8.3 Hz, 1H); 8.31 (br s, 1H); 7.67 (d, J=8.6 Hz, 1H); 7.57 (d, J=2.1 Hz, 1H); 7.52 (dd, J=2.2, 8.5 Hz, 1H); 7.44 (dd, J=1.3, 8.1 Hz, 1H); 7.35 (dt, J=1.3, 7.9 Hz, 1H); 7.13 (dt, J=1.4, 7.8 Hz, 1H); 5.88 (br s, 2H). MS (ES): m/z 292.0 (M+)

2-Amino-N-(2-chlorophenyl)-5-hydroxybenzamide (1p)

Prepared according to Procedure A using 2-amino-5-hydroxybenzoic acid (5.0 g, 32.7 mmol) and SOCl₂ (6.0 mL, 81.6 mmol) in benzene (150 mL), followed by 2-chloroaniline (6.9 mL, 65.4 mmol) and CHCl₃ (150 mL). The product was purified by two chromatographies in MeOH/CH₂Cl₂ to provide 990 mg of a brown solid (12%). ¹H NMR (MeOH-d₄) δ: 7.92 (dd, J=1.6, 8.1 Hz, 1H); 7.48 (dd, J=1.5, 7.7 Hz, 1H); 7.34 (dt, J=1.5, 7.7 Hz, 1H); 7.20 (dt, J=1.7, 7.7 Hz, 1H); 7.16 (d, J=2.7 Hz, 1H); 6.83 (dd, J=2.7, 8.7 Hz, 1H); 6.76 (d, J=8.7 Hz, 1H); [6.24 (br s, 2H)). MS (ES): m/z 263.0 (M+).

2-Amino-N-(2-chlorophenyl)-4,5-difluorobenzamide (1q)

Prepared according to Procedure A using 4,5-difluoroanthranilic acid (2.0 g, 11.6 mmol) and SOCl₂ (2.1 mL, 28.9 mmol) in benzene (60 mL), followed by 2-chloroaniline (2.4 mL, 23.2 mmol) and CHCl₃ (60 mL). The product was purified by two chromatographies in CH₂Cl₂ and EtOAc/hexanes to provide 769 mg of a yellow solid (23%). ¹H NMR (CDCl₃) δ: 8.69–8.82 (m, 1H); 8.00 (dd, J=8.4, 9.0 Hz, 1H); 7.90 (dd, J=8.9, 12 Hz, 1H); 7.39 (dd, J=6.8, 10 Hz, 1H); 6.53 (dd, J=6.6, 12 Hz, 1H); 6.41 (br s, 2H); 5.79 (br s, 1H). MS (ES): m/z 283.1 (M+).

2-Amino-N-(2-chlorophenyl)-5-fluorobenzamide (1r)

Prepared according to Procedure A using 2-amino-5-fluorobenzoic acid (1.0 g, 6.45 mmol) and SOCl₂ (1.2 mL, 16.1 mmol) in benzene (30 mL), followed by 2-chloroaniline (1.4 mL, 12.9 mmol) and CHCl₃ (30 mL). The product was triturated from CH₂Cl₂ to provide 985 mg of a mustard-yellow solid (58%). ¹H NMR (CDCl₃) δ: 7.66 (dd, J=2.9, 8.7 Hz, 1H); 7.52–7.55 (m, 1H); 7.32–7.37 (m, 3H); 7.09 (dt, J=3.0, 8.5 Hz, 1H); 6.71 (dd, J=4.3, 8.7 Hz, 1H). MS (ES): m/z 305.0 (M+40).

EXAMPLE 9
Preparation of Intermediate Compounds: Chlorides

2-Chloromethyl-3-(2-chlorophenyl)-6,7-dimethoxy-3H-quinazolin-4-one (2a)

Prepared according to Procedure B with 1a (2.95 g, 9.63 mmol) and chloroacetyl chloride (2.3 mL, 28.9 mmol) in acetic acid (30 mL). Purified by extraction from aq. $K_2CO_3$ and recrystallization from isopropanol to afford 1.61 g of a brown crystalline solid (46%). ¹H NMR (CDCl₃) δ: 7.59–7.66 (m, 2H); 7.45–7.56 (m, 3H); 7.20 (s, 1H); 4.37 (d, J=12 Hz, 1H); 4.08 (d, J=12 Hz, 1H); 4.04 (s, 3H); 4.00 (s, 3H). MS (ES): m/z 365.0 (M+).

6-Bromo-2-chloromethyl-3-(2-chlorophenyl)-3H-quinazolin-4-one (2b)

Prepared according to Procedure B with 1b (500 mg, 1.54 mmol) and chloroacetyl chloride (0.37 mL, 4.61 mmol) in acetic acid (10 mL). Purified by recrystallization from isopropanol to afford 490 mg of an off-white solid (83%). ¹H NMR (CDCl₃) δ: 8.43 (d, J=2.3 Hz, 1H); 7.91 (dd, J=2.3, 8.7 Hz, 1H); 7.67 (d, J=8.7 Hz, 1H); 7.60–7.65 (m, 1H); 7.47–7.56 (m, 2H); 7.52 (t, J=5.3 Hz, 1H); 7.47–7.56 (m, 1H); 4.37 (d, J=12 Hz, 1H), 4.06 (d, J=12 Hz, 1H). MS (ES): m/z 385.0 (M+)

2-Chloromethyl-3-(2-chlorophenyl)-7-fluoro-3H-quinazolin-4-one (2c)

Prepared according to Procedure B with 1c (500 mg, 1.89 mmol) and chloroacetyl chloride (0.45 mL, 5.67 mmol) in acetic acid (10 mL). Purified by extraction from aqueous $K_2CO_3$, followed by recrystallization from isopropanol to afford 501 mg of a yellow crystalline solid (82%). ¹H NMR (CDCl₃) δ: 8.32 (dd, J=6.0, 8.9 Hz, 1H); 7.59–7.66 (m, 1H); 7.50–7.55 (m, 3H); 7.44 (dd, J=2.4, 9.4 Hz, 1H); 7.27 (dt, J=2.5, 8.5 Hz, 1H); 4.37 (d, J=12 Hz, 1H), 4.07 (d, J=12 Hz, 1H). MS (ES): m/z 323.0 (M+).

6-Chloro-2-chloromethyl-3-(2-chlorophenyl)-3H-quinazolin-4-one (2d)

Prepared according to Procedure B with 1d (500 mg, 1.78 mmol) and chloroacetyl chloride (0.42 mL, 5.33 mmol) in acetic acid (10 mL). Purified by recrystallization from isopropanol to afford 555 mg of a yellow solid (92%). ¹H NMR (CDCl₃) δ: 8.27 (d, J=1.9 Hz, 1H); 7.74–7.78 (m, 2H); 7.60–7.66 (m, 1H); 7.48–7.57 (m, 3H); 4.37 (d, J=12 Hz, 1H), 4.07 (d, J=12 Hz, 1H). MS (ES): m/z 339.0 (M+).

2-Chloromethyl-3-(2-chlorophenyl)-5-fluoro-3H-quinazolin-4-one (2e)

Prepared according to Procedure B with 1e (500 mg, 1.89 mmol) and chloroacetyl chloride (0.45 mL, 5.67 mmol) in acetic acid (10 mL). Purified by extraction from aq. $K_2CO_3$ and recrystallization from isopropanol to afford 430 mg of an off-white crystalline solid (70%). ¹H NMR (CDCl₃) δ: 7.76 (dt, J=5.3, 8.2 Hz, 1H); 7.56–7.65 (m, 2H); 7.47–7.56 (m, 3H); 7.16–7.25 (m, 1H); 4.35 (d, J=12 Hz, 1H), 4.07 (d, J=12 Hz, 1H). MS (ES): m/z 323.0 (M+).

5-Chloro-2-chloromethyl-3-(2-chlorophenyl)-3H-quinazolin-4-one (2f)

Prepared according to Procedure B with 1f (1.00 g, 3.56 mmol) and chloroacetyl chloride (0.85 mL, 10.7 mmol) in acetic acid (15 mL). Purified by recrystallization from isopropanol to afford 791 mg of an off-white crystalline solid (65%). ¹H NMR (CDCl₃) δ: 7.70 (s, 1H); 7.68 (d, J=3.8 Hz, 1H); 7.61–7.65 (m, 1H); 7.55 (dd, J=2.7, 6.4 Hz, 1H); 7.51 (d, J=3.1 Hz, 1H); 7.50 (s, 2H); 4.35 (d, J=12 Hz, 1H), 4.05 (d, J=12 Hz, 1H). MS (ES): m/z 339.0 (M+).

2-Chloromethyl-3-(2-chlorophenyl)-5-methyl-3H-quinazolin-4-one (2g)

Prepared according to Procedure B with 1g (2.18 g, 8.36 mmol) and chloroacetyl chloride (2.0 mL, 25.1 mmol) in acetic acid (40 mL). Purified by two chromatographies in CH₂Cl₂ and EtOAc/hexanes, followed by recrystallization from isopropanol to afford 638 mg of an off-white crystalline solid (24%). ¹H NMR (DMSO-d₆) δ: 7.73–7.80 (m, 3H); 7.58–7.64 (m, 3H); 7.41 (d, J=7.4 Hz, 1H); 4.40 (d, J=12 Hz, 1H), 4.26 (d, J=12 Hz, 1H); 2.74 (s, 3H). MS (ES): m/z 319.0 (M+).

8-Chloro-2-chloromethyl-3-(2-chlorophenyl)-3H-quinazolin-4-one (2h)

Prepared according to Procedure B with 1h (500 mg, 1.78 mmol) and chloroacetyl chloride (0.49 mL, 6.13 mmol) in acetic acid (10 mL). Purified by extraction from aqueous $K_2CO_3$, followed by recrystallization from isopropanol to afford 448 mg of a yellow solid (74%). ¹H NMR (CDCl₃) δ: 8.23 (dd, J=1.4, 8.0 Hz, 1H); 7.90 (dd, J=1.4, 7.8 Hz, 1H); 7.61–7.66 (m, 1H); 7.51–7.55 (m, 3H); 7.47 (t, J=8.0 Hz, 1H); 4.48 (d, J=12 Hz, 1H), 4.12 (d, J=12 Hz, 1H). MS (ES): m/z 339.0 (M+)

3-Biphenyl-2-yl-5-chloro-2-chloromethyl-3H-quinazolin-4-one (2i)

Prepared according to Procedure B with 1i (2.0 g, 6.20 mmol) and chloroacetyl chloride (1.5 mL, 18.6 mmol) in acetic acid (30 mL). Purified by chromatography in CH₂Cl₂, followed by recrystallization from isopropanol to afford 1.44 g of an off-white solid (61%). ¹H NMR (CDCl₃) δ: 7.61–7.64 (m, 1H); 7.58–7.59 (m, 1H); 7.54–7.57 (m, 2H); 7.52–7.53 (m, 1H); 7.45–7.52 (m, 2H); 7.24 (s, 5H); 3.92–4.03 (m, 2H). MS (ES): m/z 381.0 (M+).

5-Chloro-2-chloromethyl-3-o-tolyl-3H-quinazolin-4-one (2j)

Prepared according to Procedure B with 1j (750 mg, 2.88 mmol) and chloroacetyl chloride (0.69 mL, 8.63 mmol) in acetic acid (15 mL). Purified by chromatography in CH₂Cl₂, followed by recrystallization from isopropanol to afford 340 mg of a white solid (37%). ¹H NMR (CDCl₃) δ: 7.69 (d, J=2.1 Hz, 1H); 7.68 (q, J=7.4 Hz, 1H); 7.54 (dd, J=2.2, 7.0 Hz, 1H); 7.35–7.47 (m, 3H); 7.21–7.25 (m, 1H); 4.27 (d, J=12 Hz, 1H); 4.11 (d, J=12 Hz, 1H); 2.18 (s, 3H). MS (ES): m/z 319.0 (M+).

5-Chloro-2-chloromethyl-3-(2-fluorophenyl)-3H-quinazolin-4-one (2k)

Prepared according to Procedure B with 1k (1.0 g, 3.78 mmol) and chloroacetyl chloride (0.90 mL, 11.3 mmol) in acetic acid (20 mL). Purified by chromatography in $CH_2Cl_2$ to afford 484 mg of a pale pink solid (40%). $^1$H NMR ($CDCl_3$) δ: 7.69 (s, 1H); 7.68 (d, J=3.2 Hz, 1H); 7.56 (d, J=3.0 Hz, 1H); 7.54 (d, J=3.0 Hz, 1H); 7.40–7.47 (m, 1H); 7.35–7.38 (m, 1H); 7.27–7.32 (m, 1H); 4.35 (d, J=12 Hz, 1H); 4.18 (d, J=12 Hz, 1H). MS (ES): m/z 323.0 (M+).

5-Chloro-2-chloromethyl-3-(2-methoxyphenyl)-3H-quinazolin-4-one (2l)

Prepared according to Procedure B with 1l (2.6 g, 9.41 mmol) and chloroacetyl chloride (2.2 mL, 28.2 mmol) in acetic acid (40 mL). Purified by chromatography in $CH_2Cl_2$, followed by recrystallization from isopropanol to afford 874 mg of a pale yellow solid (28%). $^1$H NMR ($CDCl_3$) δ: 7.55–7.74 (m, 2H); 7.47–7.54 (m, 2H); 7.34 (dd, J=1.7, 7.8 Hz, 1H); 7.13 (dt, J=1.2, 7.7 Hz, 1H); 7.08 (dd, J=1.0, 8.4 Hz, 1H); 4.29 (d, J=12 Hz, 1H); 4.11 (d, J=12 Hz, 1H); 3.80 (s, 3H). MS (ES): m/z 335.0 (M+).

2-Chloromethyl-3-(2-chlorophenyl)-8-trifluoromethyl-3H-quinazolin-4-one (2m)

Prepared according to Procedure B with 1m (500 mg, 1.59 mmol) and chloroacetyl chloride (0.38 mL, 4.77 mmol) in acetic acid (10 mL). Purified by recrystallization from isopropanol to afford 359 mg of a white crystalline solid (61%). $^1$H NMR ($CDCl_3$) δ: 8.51 (dd, J=1.0, 8.0 Hz, 1H); 8.14 (d, J=7.3 Hz, 1H); 7.65 (dd, J=2.5, 5.6 Hz, 1H); 7.62 (d, J=3.9 Hz, 1H); 7.48–7.60 (m, 3H); 4.44 (d, J=12 Hz, 1H); 4.12 (d, J=12 Hz, 1H). MS (ES): m/z 373.0 (M+).

2-Chloromethyl-3-(2-chlorophenyl)-3H-benzo[g]quinazolin-4-one (2n)

Prepared according to Procedure B with 1n (500 mg, 1.68 mmol) and chloroacetyl chloride (0.40 mL, 5.05 mmol) in acetic acid (10 mL). Purified by chromatography in $CH_2Cl_2$ followed by recrystallization from isopropanol to afford 232 mg of a light-brown solid (39%). $^1$H NMR ($CDCl_3$) δ: 8.92 (s, 1H); 8.29 (s, 1H); 8.81 (d, J=8.3 Hz, 1H); 8.32 (d, J=8.3 Hz, 1H); 7.51–7.69 (m, 4H); 7.55 (d, J=5.2 Hz, 1H); 7.53 (d, J=3.8 Hz, 1H); 4.43 (d, J=12 Hz, 1H), 4.12 (d, J=12 Hz, 1H). MS (ES): m/z 355.0 (M+).

2-Chloromethyl-3-(2-chlorophenyl)-7-nitro-3H-quinazolin-4-one (2o)

Prepared according to Procedure B with 1o (500 mg, 1.71 mmol) and chloroacetyl chloride (0.41 mL, 5.14 mmol) in acetic acid (10 mL). Purified by extraction from aqueous $K_2CO_3$, followed by two chromatographies in $CH_2Cl_2$ to afford 338 mg of a yellow oil (56%). $^1$H NMR ($CDCl_3$) δ: 8.64 (d, J=2.2 Hz, 1H); 8.48 (d, J=8.8 Hz, 1H); 8.32 (dd, J=2.2, 8.7 Hz, 1H); 7.66 (dd, J=2.5, 6.0 Hz, 1H); 7.52–7.59 (m, 3H); 4.41 (d, J=12 Hz, 1H), 4.10 (d, J=12 Hz, 1H). MS (ES): m/z 350.0 (M+)

Acetic acid 2-chloromethyl-3-(2-chlorophenyl)-4-oxo-3,4-dihydro-quinazolin-6-yl ester (2p)

Prepared according to Procedure B with 1p (670 mg, 2.55 mmol) and chloroacetyl chloride (0.61 mL, 7.65 mmol) in acetic acid (10 mL). Purified by chromatography in 0–3% MeOH/$CH_2Cl_2$, followed by recrystallization from isopropanol to afford 523 mg of the acetate as pale-peach crystals (57%). $^1$H NMR ($CDCl_3$) δ: 8.00 (d, J=2.7 Hz, 1H); 7.82 (d, J=8.8 Hz, 1H); 7.60–7.66 (m, 1H); 7.56 (dd, J=2.7, 8.8 Hz, 1H); 7.51 (t, J=4.7 Hz, 2H); 7.50 (s, 1H); 4.38 (d, J=12 Hz, 1H), 4.08 (d, J=12 Hz, 1H); 2.36 (s, 3H). MS (ES): m/z 363.0 (M+)

2-Chloromethyl-3-(2-chlorophenyl)-6,7-difluoro-3H-quinazolin-4-one (2q)

Prepared according to Procedure B with 1q (700 mg, 2.48 mmol) and chloroacetyl chloride (0.60 mL, 7.43 mmol) in acetic acid (12 mL). Purified by chromatography in $CH_2Cl_2$, followed by recrystallization from isopropanol to afford 219 mg of a yellow crystalline solid (26%). $^1$H NMR ($CDCl_3$) δ: 8.07 (dd, J=8.5, 9.7 Hz, 1H); 7.64 (dd, J=2.5, 5.6 Hz, 1H); 7.60 (dd, J=3.5, 11 Hz, 1H); 7.55 (q, J=2.9 Hz, 3H); 7.52 (d, J=1.9 Hz, 1H); 7.49–7.51 (m, 1H); 4.36 (d, J=12 Hz, 1H), 4.06 (d, J=12 Hz, 1H). MS (ES): m/z 341.0 (M+).

2-Chloromethyl-3-(2-chlorophenyl)-6-fluoro-3H-quinazolin-4-one (2r)

Prepared according to Procedure B with 1r (850 mg, 3.21 mmol) and chloroacetyl chloride (0.77 mL, 9.63 mmol) in acetic acid (15 mL). Purified by extraction from aqueous $K_2CO_3$, followed by chromatography in EtOAc/hexanes. A second chromatography in acetone/hexanes afforded 125 mg of a white solid (12%). $^1$H NMR ($CDCl_3$) δ: 7.95 (dd, J=2.9, 8.2 Hz, 1H); 7.81 (dd, J=4.8, 9.0 Hz, 1H); 7.61–7.66 (m, 1H); 7.57 (dd, J=2.7, 8.6 Hz, 1H); 7.57 (dd, J=2.7, 8.6 Hz, 1H); 7.52 (dd, J=3.2, 6.9 Hz, 1H); 7.52 (br s, 2H); 4.38 (d, J=12 Hz, 1H), 4.08 (d, J=12 Hz, 1H). MS (ES): m/z 323.0 (M+).

EXAMPLE 10

Preparation of PI3Kδ Inhibitor Compounds

Compound D-001

2-(6-Aminopurin-9-ylmethyl)-3-(2-chlorophenyl)-6,7-dimethoxy-3H-quinazolin-4-one Prepared according to Procedure C using Intermediate 2a (200 mg, 0.546 mmol), adenine (81 mg, 0.601 mmol), $K_2CO_3$ (83 mg, 0.601 mmol), and DMF (4 mL). The crude product was recrystallized from ethanol (EtOH) to provide 164 mg of a beige solid (65%), mp 281.5–282.7° C. (decomposes). $^1$H NMR (DMSO-$d_6$) δ: 8.06 (s, 1H); 8.04 (s, 1H); 7.76–7.81 (m, 1H); 7.70–7.76 (m, 1H); 7.60–7.67 (m, 2H); 7.45 (s, 1H); 7.22 (s, 2H); 6.90 (s, 1H); 5.08 (d, J=17 Hz, 1H); 4.91 (d, J=17 Hz, 1H); 3.87 (s, 3H); 3.87 (s, 3H). $^{13}$C NMR (DMSO-$d_6$) ppm: 159.9, 156.2, 155.4, 152.9, 150.0, 149.7, 149.4, 143.0, 141.9, 133.7, 132.1, 131.9, 131.2, 130.8, 129.3, 118.4, 113.6, 108.4, 105.8, 56.5, 56.1, 44.7. MS (ES): m/z 464.1 (M+). Anal. calcd. for $C_{22}H_{18}ClN_7O_3 \cdot 0.1C_2H_6O \cdot .05KCl$: C, 56.47; H, 3.97; Cl, 7.88; N, 20.76. Found: C, 56.54; H, 4.05; Cl, 7.77; N, 20.55.

Compound D-002

2-(6-Aminopurin-o-ylmethyl)-6-bromo-3-(2-chlorophenyl)-3H-quinazolin-4-one

Prepared according to Procedure C using Intermediate 2b (100 mg, 0.260 mmol), adenine (39 mg, 0.286 mmol), $K_2CO_3$ (40 mg, 0.286 mmol), and DMF (2 mL). The crude product was recrystallized from EtOH to provide 52 mg of an off-white solid (41%), mp 284.2–284.7° C. (decomposes). $^1$H NMR (DMSO-$d_6$) δ: 8.24 (d, J=2.0 Hz, 1H); 8.05 (s, 1H); 8.03 (s, 1H); 7.98 (dd, J=1.9, 8.6 Hz, 1H); 7.74–7.83 (m, 2H); 7.59–7.68 (m, 2H); 7.46 (d, J=8.7 Hz, 1H); 7.22 (s, 2H); 5.12 (d, J=17 Hz, 1H); 4.94 (d, J=17 Hz, 1H). $^{13}$C NMR (DMSO-$d_6$) ppm: 159.5, 156.2, 152.9, 152.0, 150.1, 145.8, 141.8, 138.4, 133.1, 132.2, 131.9, 131.1, 130.9, 130.1, 129.4, 128.9, 122.4, 120.4, 118.4, 45.0. MS (ES): m/z 482.0 (M+). Anal. calcd. for $C_{20}H_{13}ClBrN_7O \cdot 0.1KCl$: C, 49.01; H, 2.67; Cl, 7.96; N, 20.00. Found: C, 48.82; H, 2.82; Cl, 8.00; N, 19.79.

Compound D-003

2-(6-Aminopurin-o-ylmethyl)-3-(2-chlorophenyl)-7-fluoro-3H-quinazolin-4-one

Prepared according to Procedure C using Intermediate 2c (100 mg, 0.310 mmol), adenine (46 mg, 0.340 mmol), $K_2CO_3$ (47 mg, 0.340 mmol), and DMF (1 mL). The crude product was recrystallized from EtOH to provide 57 mg of a beige solid (44%), mp 216.8–217.2° C. $^1$H NMR (DMSO-$d_6$) δ: 8.22 (dd, J=6.3, 8.7 Hz, 1H); 8.05 (s, 1H); 8.03 (s, 1H); 7.78–7.80 (m, 2H); 7.61–7.64 (m, 2H); 7.46 (dt, J=2.1, 8.6 Hz, 1H); 7.32 (d, J=9.8 Hz, 1H); 7.22 (s, 2H); 5.13 (d, J=17 Hz, 1H); 4.95 (d, J=17 Hz, 1H). $^{13}$C NMR (DMSO-$d_6$) ppm: 166.1 (d, J=253 Hz), 159.6, 155.8, 152.5, 149.7, 148.6 (d, J=14 Hz), 141.4, 132.8, 131.8, 131.6, 130.8, 130.5, 129.8 (d, J=11 Hz), 129.0, 118.1, 117.4, 116.2 (d, J=24 Hz), 112.7 (d, J=22 Hz), 44.6. MS (ES): m/z 422.0 (M+). Anal. calcd. for $C_{20}H_{13}ClFN_7O.0.1H_2O(0.15KCl)$: C, 55.25; H, 3.06; Cl, 9.38; N, 22.55. Found: C, 55.13; H, 2.92; Cl, 9.12; N, 22.30.

Compound D-004
2-(6-Aminopurin-9-ylmethyl)-6-chloro-3-(2-chlorophenyl)-3H-quinazolin-4-one Prepared according to Procedure C using Intermediate 2d (100 mg, 0.294 mmol), adenine (44 mg, 0.323 mmol), $K_2CO_3$ (45 mg, 0.323 mmol), and DMF (1 mL). The crude product was recrystallized from EtOH to provide 50 mg of a yellow solid (39%), mp 294.5–294.8° C. (decomposes). $^1$H NMR (DMSO-$d_6$) δ: 8.10 (d, J=2.2 Hz, 1H); 8.05 (s, 1H); 8.03 (s, 1H); 7.86 (dd, J=2.4, 8.8 Hz, 1H); 7.75–7.82 (m, 2H); 7.59–7.67 (m, 2H); 7.53 (d, J=8.7 Hz, 1H); 7.22 (br s, 2H); 5.13 (d, J=17 Hz, 1H); 4.95 (d, J=17 Hz, 1H). $^{13}$C NMR (DMSO-$d_6$) ppm: 159.7, 156.2, 152.9, 151.9, 150.1, 145.5, 141.8, 135.7, 133.1, 132.3, 132.2, 131.9, 131.1, 130.9, 130.0, 129.4, 125.9, 122.0, 118.4, 44.9. MS (ES): m/z 438.0 (M+). Anal. calcd. for $C_{20}H_{13}Cl_2N_7O$: C, 54.81; H, 2.99; N, 22.37. Found: C, 54.72; H, 2.87; N, 22.18.

Compound D-005
2-(6-Aminopurin-9-ylmethyl)-3-(2-chlorophenyl)-5-fluoro-3H-quinazolin-4-one Prepared according to Procedure C using Intermediate 2e (200 mg, 0.619 mmol), adenine (92 mg, 0.681 mmol), $K_2CO_3$ (94 mg, 0.680 mmol), and DMF (4 mL). The crude product was chromatographed in MeOH/$CH_2Cl_2$ to provide 168 mg of an off-white solid (64%), mp 159–172° C. (gradually decomposes). $^1$H NMR (DMSO-$d_6$) δ: 8.10 (s, 1H); 8.08 (s, 1H); 7.73–7.89 (m, 3H); 7.57–7.71 (m, 2H); 7.37–7.48 (m, 2H); 7.34 (d, J=11 Hz, 1H); 7.30 (d, J=8.3 Hz, 1H); 5.14 (d, J=17 Hz, 1H); 4.94 (d, J=17 Hz, 1H). $^{13}$C NMR (DMSO-$d_6$) ppm: 160.8 (d, J=264 Hz), 157.5 (d, J=4.2 Hz), 155.8, 152.4, 152.4, 150.0, 148.7, 142.1, 136.4 (d, J=11 Hz), 133.0, 132.2, 132.1, 131.2, 130.9, 129.4, 123.8 (d, J=3.6 Hz), 118.4, 114.5 (d, J=20 Hz), 110.2 (d, J=6.0 Hz), 44.9. MS (ES): m/z 422.0 (M+). Anal. calcd. for $C_{20}H_{13}ClFN_7O$: C, 56.95; H, 3.11; Cl, 8.40; N, 23.24. Found: C, 54.62; H, 3.32; Cl, 9.40; N, 21.29.

Compound D-006
2-(6-Aminopurin-o-ylmethyl)-5-chloro-3-(2-chlorophenyl)-3H-quinazolin-4-one Prepared according to Procedure C using Intermediate 2f (300 mg, 0.883 mmol), adenine (131 mg, 0.972 mmol), $K_2CO_3$ (134 mg, 0.972 mmol), and DMF (4 mL). The crude product was chromatographed in MeOH/$CH_2Cl_2$ and recrystallized from EtOH to provide 188 mg of a pale orange crystalline solid (49%), mp 245.7–246.0© (starts to sweat at 220° C.). $^1$H NMR (DMSO-$d_6$) δ: 8.06 (s, 1H); 8.04 (s, 1H); 7.76–7.81 (m, 2H); 7.72 (d, J=8.0 Hz, 1H); 7.59–7.66 (m, 3H); 7.41 (d, J=8.1 Hz, 1H); 7.26 (br s, 2H); 5.11 (d, J=17 Hz, 1H); 4.93 (d, J=17 Hz, 1H). $^{13}$C NMR (DMSO-$d_6$) ppm: 158.5, 156.2, 152.9, 152.2, 150.1, 149.2, 141.8, 135.4, 133.3, 133.2, 132.1, 132.0, 131.2, 130.9, 130.4, 129.4, 127.3, 118.4, 117.7, 44.9. MS (ES): m/z 438.0 (M+). Anal. calcd. for $C_{20H13}Cl_2N_7O.0.1C_2H_6O.0.05H_2O$: C, 54.67; H, 3.11; Cl, 15.98; N, 22.09. Found: C, 54.35; H, 3.00; Cl, 15.82; N, 22.31.

Compound D-007
2-(6-Aminopurin-9-ylmethyl)-3-(2-chlorophenyl)-5-methyl-3H-quinazolin-4-one Prepared according to Procedure C using Intermediate 2g (250 mg, 0.783 mmol), adenine (116 mg, 0.862 mmol), $K_2CO_3$ (119 mg, 0.862 mmol), and DMF (4 mL). The crude product was recrystallized from EtOH to provide 93 mg of a pale yellow solid (28%), mp 190.7–190.9° C. $^1$H NMR (DMSO-$d_6$) δ: 8.05 (s, 1H); 8.03 (s, 1H); 7.76–7.79 (m, 1H); 7.71–7.74 (m, 1H); 7.59–7.67 (m, 1H); 7.34 (d, J=7.4 Hz, 1H); 7.28 (d, J=8.2 Hz, 1H); 7.24 (br s, 2H); 5.07 (d, J=17 Hz, 1H); 4.92 (d, J=17 Hz, 1H); 2.73 (s, 3H). $^{13}$C NMR (DMSO-$d_6$) ppm: 161.1, 156.2, 152.8, 150.9, 150.1, 148.3, 141.9, 141.0, 134.6, 133.6, 132.2, 131.9, 131.3, 130.8, 130.3, 129.3, 125.9, 119.1, 118.4, 44.8, 22.8. MS (ES): m/z 418.1 (M+). Anal. calcd. for $C_{21}H_{16}ClN_7O.H_2O$: C, 57.87; H, 4.16; Cl, 8.13; N, 22.49. Found: C, 57.78; H, 3.99; Cl, 8.38; N, 22.32.

Compound D-008
2-(6-Aminopurin-9-ylmethyl)-8-chloro-3-(2-chlorophenyl)-3H-quinazolin-4-one Prepared according to Procedure C using Intermediate 2h (100 mg, 0.294 mmol), adenine (44 mg, 0.324 mmol), $K_2CO_3$ (45 mg, 0.324 mmol), and DMF (1 mL). The crude product was chromatographed in MeOH/$CH_2Cl_2$ to provide 50 mg of a pale yellow solid (39%), mp 273.3–273.5° C. (discolors). $^1$H NMR (DMSO-$d_6$) δ: 8.11 (dd, J=1.3, 8.0 Hz, 1H); 8.08 (s, 1H); 8.05 (s, 1H); 8.00 (dd, J=1.3, 7.8 Hz, 1H); 7.79–7.83 (m, 2H); 7.63–7.66 (m, 2H); 7.56 (t, J=7.9 Hz, 1H); 7.21 (br s, 2H); 5.17 (d, J=17 Hz, 1H); 4.97 (d, J=17 Hz, 1H). $^{13}$C NMR (DMSO-$d_6$) ppm: 160.2, 156.1, 152.8, 152.2, 150.2, 143.3, 142.0, 135.6, 133.1, 132.3, 131.9, 131.1, 131.0, 130.9, 129.4, 128.4, 126.0, 122.5, 118.4, 45.0. MS (ES): m/z 438.0 (M+). Anal. calcd. for $C_{20}H_{13}Cl_2N_7O.0.1CH_4O.0.6H_2O(0.15KCl)$: C, 52.09; H, 3.18; N, 21.15. Found: C, 51.85; H, 2.93; N, 21.01.

Compound D-009
2-(6-Aminopurin-9-ylmethyl)-3-biphenyl-2-yl-5-chloro-3H-quinazolin-4-one Prepared according to Procedure C using Intermediate 2i (400 mg, 1.05 mmol), adenine (155 mg, 1.15 mmol), $K_2CO_3$ (159 mg, 1.15 mmol), and DMF (5 mL). The crude product was recrystallized from EtOH to provide 344 mg of a white solid (68%), mp 299.9–300.1° C. (discolors). $^1$H NMR (DMSO-$d_6$) δ: 8.08 (s, 1H); 7.89 (s, 1H); 7.58–7.73 (m, 5H); 7.51 (d, J=7.9 Hz, 1H); 7.46 (d, J=7.5 Hz, 2H); 7.27–7.41 (m, 3H); 7.14–7.27 (m, 3H); 5.14 (d, J=17 Hz, 1H); 4.82 (d, J=17 Hz, 1H). $^{13}$C NMR (DMSO-$d_6$) ppm: 159.6, 156.2, 152.8, 152.5, 150.0, 149.0, 141.7, 140.2, 137.7, 135.0, 133.3, 133.2, 131.8, 130.7, 130.1, 129.8, 129.5, 128.8, 128.6, 128.4, 127.1, 118.4, 117.6, 45.3. MS (ES): m/z 480.1 (M+). Anal. calcd. for $C_{26}H_{18}ClN_7O$: C, 65.07; H, 3.78; Cl, 7.39; N, 20.43. Found: C, 64.77; H, 3.75; Cl, 7.43; N, 20.35.

Compound D-010
5-Chloro-2-(9H-purin-6-ylsulfanylmethyl)-3-o-tolyl-3H-quinazolin-4-one Prepared according to Procedure C using Intermediate 2j (200 mg, 0.626 mmol), 6-kinases -mercaptopurine monohydrate (93 mg, 0.546 mmol), $K_2CO_3$ (95 mg, 0.689 mmol), and DMF (4 mL). The crude product was recrystallized from EtOH to provide 125 mg of an off-white solid (46%), mp 213.9° C. $^1$H NMR (DMSO-$d_6$) δ: 13.53 (br s, 1H); 8.49 (s, 1H); 8.44 (s, 1H); 7.78 (t, J=7.9 Hz, 1H); 7.63 (d, J=8.2 Hz, 1H); 7.59 (d, J=7.7 Hz, 1H); 7.49 (d, J=6.9 Hz, 1H); 7.24–7.41 (m, 3H); 4.32–4.45 (m, 2H); 2.14 (s, 3H). $^{13}$C NMR (DMSO-$d_6$) ppm: 158.9, 157.2, 154.2, 151.5, 149.7, 149.6, 143.5, 136.1, 135.9, 135.1, 133.2, 131.3, 130.3, 130.0, 129.9, 129.1, 127.6, 127.1, 117.8, 32.4, 17.5. MS (ES): m/z 438.0 (M+). Anal. calcd. for $C_{21}H_{15}ClN_6OS$: C, 58.00; H, 3.48; Cl, 8.15; N, 19.32; S, 7.37. Found: C, 58.05; H, 3.38; Cl, 8.89; N, 18.38; S, 7.00.

Compound D-011

5-Chloro-3-(2-fluorophenyl)-2-(9H-purin-6-ylsulfanylmethyl)-3H-quinazolin-4-one

Prepared according to Procedure C using Intermediate 2k (210 mg, 0.650 mmol), 6-mercaptopurine monohydrate (122 mg, 0.715 mmol), $K_2CO_3$ (99 mg, 0.715 mmol), and DMF (4 mL). The crude product was recrystallized from EtOH to provide 240 mg of an off-white solid (84%), mp 244.0° C. $^1$H NMR (DMSO-$d_6$) δ 13.56 (br s, 1H); 8.50 (s, 1H); 8.45 (s, 1H); 7.81 (t, J=8.0 Hz, 1H); 7.74 (t, J=7.7 Hz, 1H); 7.67 (d, J=8.1 Hz, 1H); 7.62 (d, J=7.7 Hz, 1H); 7.46–7.55 (m, 1H); 7.29–7.42 (m, 2H); 4.47–4.59 (m, 2H). $^{13}$C NMR (DMSO-$d_6$) ppm: 158.4, 157.3 (d, J=249 Hz), 156.4, 153.8, 151.0, 149.1, 143.2, 135.0, 132.9, 131.8 (d, J=8.0 Hz), 130.8, 129.9, 126.7, 125.3 (d, J=3.5 Hz), 123.6 (d, J=13 Hz), 117.0, 116.2 (d, J=19 Hz), 31.7. MS (ES): m/z 439.0 (M+). Anal. calcd. for $C_{20}H_{12}ClFN_6OS$: C, 54.74; H, 2.76; Cl, 8.08; N, 19.15; S, 7.31. Found: C, 54.42; H, 2.88; Cl, 8.08; N, 18.87; S, 7.08.

Compound D-012

2-(6-Aminopurin-9-ylmethyl)-5-chloro-3-(2-fluorophenyl)-3H-quinazolin-4-one

Prepared according to Procedure C using Intermediate 2k (210 mg, 0.650 mmol), adenine (97 mg, 0.715 mmol), $K_2CO_3$ (99 mg, 0.715 mmol), and DMF (4 mL). The crude product was recrystallized from EtOH to provide 137 mg of a tan solid (50%), mp 295.6–295.8° C. (decomposes). $^1$H NMR (DMSO-$d_6$) δ: 8.05 (s, 1H); 8.04 (s, 1H); 7.75 (t, J=7.6 Hz, 1H); 7.74 (t, J=7.9 Hz, 1H); 7.62–7.69 (m, 1H); 7.61 (d, J=7.6 Hz, 1H); 7.47–7.55 (m, 1H); 7.48 (d, J=7.8 Hz, 1H); 7.41 (d, J=8.0 Hz, 1H); 7.24 (br s, 2H); 5.19 (d, J=17 Hz, 1H); 5.03 (d, J=17 Hz, 1H). $^{13}$C NMR (DMSO-$d_6$) ppm: 158.7, 157.6 (d, J=250 Hz), 156.2, 152.8, 152.4, 150.0, 149.2, 141.8, 135.4, 133.3, 132.5 (d, J=8.0 Hz), 131.0, 130.4, 127.3, 126.2 (d, J=3.5 Hz), 123.1 (d, J=14 Hz), 118.4, 117.6, 117.2 (d, J=19 Hz), 45.1. MS (ES): m/z 422.0 (M+). Anal. calcd. for $C_{20}H_{13}ClFN_7O.0.05C_2H_6O$: C, 56.92; H, 3.16; Cl, 8.36; N, 23.12. Found: C, 56.79; H, 3.20; Cl, 8.46; N, 22.79.

Compound D-013

3-Biphenyl-2-yl-5-chloro-2-(9H-purin-6-ylsulfanylmethyl)-3H-quinazolin-4-one

Prepared according to Procedure C using Intermediate 2i (400 mg, 1.05 mmol), 6-mercaptopurine monohydrate (196 mg, 1.15 mmol), $K_2CO_3$ (159 mg, 1.15 mmol), and DMF (5 mL). The crude product was chromatographed in MeOH/$CH_2Cl_2$ and subsequently recrystallized from EtOH to provide 439 mg of a pale yellow crystalline solid (84%), mp 222.0–222.5° C. (dec). $^1$H NMR (DMSO-$d_6$) δ: 13.56 (br s, 1H); 8.55 (s, 1H); 8.45 (s, 1H); 7.73 (t, J=8.0 Hz, 1H); 7.64 (d, J=7.7 Hz, 1H); 7.50–7.59 (m, 4H); 7.41–7.48 (m, 1H); 7.25–7.38 (m, 5H); 4.41 (d, J=16 Hz, 1H); 4.16 (d, J=16 Hz, 1H). $^{13}$C NMR (DMSO-$d_6$) ppm: 160.2, 157.0, 153.7, 151.5, 149.7, 149.3, 143.5, 139.9, 137.8, 135.1, 134.1, 133.3, 131.5, 130.5, 130.3, 130.1, 129.1, 128.9, 128.4, 128.4, 126.9, 117.5, 32.3. MS (ES): m/z 497.0 (M+). Anal. calcd. for $C_{26}H_{17}ClN_6OS$: C, 62.84; H, 3.45; Cl, 7.13; N, 16.91; S, 6.45. Found: C, 62.60; H, 3.47; Cl, 7.15; N, 16.65; S, 6.41.

Compound D-014

5-Chloro-3-(2-methoxyphenyl)-2-(9H-purin-6-ylsulfanylmethyl)-3H-quinazolin-4-one Prepared according to Procedure C using Intermediate 2l (250 mg, 0.746 mmol), 6-mercaptopurine monohydrate (140 mg, 0.821 mmol), $K_2CO_3$ (113 mg, 0.821 mmol), and DMF (4 mL). The crude product was recrystallized from EtOH to provide 254 mg of an off-white solid (76%), mp 237.0° C. (dec; discolors at 154.6° C.). $^1$H NMR (DMSO-$d_6$) δ: 13.53 (br s, 1H); 8.52 (s, 1H); 8.45 (s, 1H); 7.78 (t, J=7.9 Hz, 1H); 7.64 (d, J=8.0 Hz, 1H); 7.59 (d, J=7.7 Hz, 1H); 7.48 (d, J=7.3 Hz, 1H); 7.42 (t, J=7.7 Hz, 1H); 7.15 (d, J=8.2 Hz, 1H); 7.03 (t, J=7.5 Hz, 1H); 4.45 (s, 2H); 3.76 (s, 3H). $^{13}$C NMR (DMSO-$d_6$) ppm: 158.9, 157.1, 154.8, 154.7, 151.5, 149.6, 143.6, 135.1, 133.2, 131.3, 130.4, 130.0, 127.0, 124.8, 121.2, 117.8, 112.7, 56.1, 32.0. MS (ES): m/z 451.0 (M+). Anal. calcd. for $C_{21}H_{15}ClN_6O_2S.0.15C_2H_6O.0.05KCl$: C, 55.43; H, 3.47; Cl, 8.07; N, 18.21; S, 6.95. Found: C, 55.49; H, 3.68; Cl, 7.95; N, 17.82; S, 6.82.

Compound D-015

3-(2-Chlorophenyl)-5-fluoro-2-(9H-purin-6-ylsulfanylmethyl)-3H-quinazolin-4-one

Prepared according to Procedure C using Intermediate 2e (200 mg, 0.619 mmol), 6-mercaptopurine monohydrate (116 mg, 0.681 mmol), $K_2CO_3$ (94 mg, 0.681 mmol), and DMF (5 mL). The crude product was recrystallized from EtOH to provide 152 mg of a white solid (56%), mp 222.7–223.8° C. (discolors). $^1$H NMR (DMSO-$d_6$) δ: 13.56 (br s, 1H); 8.48 (s, 1H); 8.44 (s, 1H); 7.89 (dt, J=5.6, 8.1 Hz, 1H); 7.76 (dd, J=1.6, 7.3 Hz, 1H); 7.67 (d, J=7.4 Hz, 1H); 7.56 (d, J=8.1 Hz, 1H); 7.47 (t, J=7.1 Hz, 1H), 7.41–7.53 (m, 2H); 7.37 (dd, J=8.7, 11 Hz, 1H); 4.38–4.52 (m, 2H). $^{13}$C NMR (DMSO-$d_6$) ppm: 160.9 (d, J=264 Hz), 157.6, 156.8, 154.1, 151.5, 149.6, 149.0, 143.6, 136.4 (d, J=11 Hz), 133.9, 132.2, 131.7, 131.6, 130.5, 130.2, 128.8, 123.6, 114.4 (d, J=20 Hz), 110.2, 32.0. MS (ES): m/z 439.0 (M+). Anal. calcd. for $C_{20}H_{12}ClFN_6OS.0.5C_2H_6O$: C, 54.61; H, 3.27; Cl, 7.68; N, 18.19; S, 6.94. Found: C, 54.37; H, 3.26; Cl, 7.89; N, 18.26; S, 6.55.

Compound D-016

3-(2-Chlorophenyl)-6,7-dimethoxy-2-(9H-purin-6-ylsulfanylmethyl)-3H-quinazolin-4-one Prepared according to Procedure C using Intermediate 2a (200 mg, 0.546 mmol), 6-mercaptopurine monohydrate (102 mg, 0.601 mmol), $K_2CO_3$ (83 mg, 0.601 mmol), and DMF (5 mL). The crude product was recrystallized from EtOH to provide 172 mg of an off-white solid (65%), mp 160–180° C. (gradually decomposes). $^1$H NMR (DMSO-$d_6$) δ: 13.55 (br s, 1H); 8.49 (s, 1H); 8.44 (s, 1H); 7.72 (d, J=6.9 Hz, 1H); 7.66 (d, J=6.9 Hz, 1H) 7.38–7.54 (m, 3H); 7.22 (s, 1H); 4.36–4.52 (m, 2H); 3.94 (s, 3H); 3.89 (s, 3H). $^{13}$C NMR (DMSO-$d_6$) ppm: 160.1, 155.4, 151.5, 151.1, 149.4, 143.2, 134.6, 132.3, 131.6, 131.5, 130.4, 128.7, 113.6, 108.4, 105.8, 56.5, 56.1, 32.0. MS (ES): m/z 481.1 (M+). Anal. calcd. for $C_{22}H_{17}ClN_6O_3S.0.5C_2H_6O.0.05KCl$: C, 54.41; H, 3.97; Cl, 7.33; N, 16.55; S, 6.32. Found: C, 54.43; H, 3.94; Cl, 7.69; N, 16.69; S, 6.52.

Compound D-017

6-Bromo-3-(2-chlorophenyl)-2-(9H-purin-6-ylsulfanylmethyl)-3H-quinazolin-4-one

Prepared according to Procedure C using Intermediate 2b (200 mg, 0.519 mmol), 6-mercaptopurine monohydrate (97 mg, 0.570 mmol), $K_2CO_3$ (79 mg, 0.572 mmol), and DMF (5 mL). The crude product was recrystallized from EtOH to provide 123 mg of an off-white solid (47%), mp 212–242° C. (gradually decomposes). $^1$H NMR (DMSO-$d_6$) δ: 13.07 (br s, 1H); 8.48 (s, 1H); 8.44. (s, 1H); 8.24 (d, J=2.3 Hz, 1H); 8.06 (dd, J=2.3, 8.7 Hz, 1H); 7.76 (dd, J=1.9, 7.4 Hz, 1H); 7.70 (d, J=8.7 Hz, 1H); 7.66 (d, J=8.1 Hz, 1H); 7.51 (dd, J=2.1, 7.9 Hz, 1H); 7.46 (dd, J=1.9, 7.9 Hz, 1H); 4.47 (s, 2H). $^{13}$C NMR (DMSO-$d_6$) ppm: 159.7, 156.8, 153.6, 151.5, 146.1, 143.6, 138.5, 134.0, 132.1, 131.8, 131.5, 130.5, 130.2, 129.9, 128.9, 128.8, 122.2, 120.3, 32.0. MS (ES): m/z 499.0 (M+). Anal. calcd. for $C_{20}H_{12}ClBrN_6OS.0.2C_2H_6O.0.05KCl$: C, 47.79; H, 2.59; N, 16.39; S, 6.25. Found: C, 47.56; H, 2.54; N, 16.25; S, 6.58.

Compound D-018
3-(2-Chlorophenyl)-(9H-purin-6-ylsulfanylmethyl)-trifluoromethyl-3H-quinazolin-4-one Prepared according to Procedure C using Intermediate 2m (200 mg, 0.536 mmol), 6-mercaptopurine monohydrate (100 mg, 0.588 mmol), $K_2CO_3$ (82 mg, 0.593 mmol), and DMF (4 mL). The crude product was recrystallized from EtOH to provide 148 mg of a white solid (56%), mp 218.5–219.4° C. $^1$H NMR (DMSO-$d_6$) δ: 13.52 (br s, 1H); 8.48 (s, 1H); 8.44 (s, 1H); 8.43 (d, J=6.0 Hz, 1H); 8.26 (d, J=7.5 Hz, 1H); 7.84 (dd, J=2.5, 6.7 Hz, 1H); 7.70–7.75 (m, 2H); 7.51–7.59 (m, 2H); 4.40–4.55 (m, 2H). $^{13}$C NMR (DMSO-$d_6$) ppm: 160.0, 157.2, 154.2, 151.4, 149.6, 144.4, 143.4, 133.8, 133.0 (q, J=5.1 Hz), 132.0, 131.9, 131.6, 131.4, 130.6, 129.0, 127.3, 125.2 (q, J=30 Hz), 123.6 (q, J=273 Hz), 121.8, 32.6. MS (ES): m/z 489.0 (M+). Anal. calcd. for $C_{21}H_{12}ClF_3N_6OS$: C, 51.59; H, 2.47; Cl, 7.25; N, 17.19; S, 6.56. Found: C, 51.51; H, 2.55; Cl, 7.37; N, 17.05; S, 6.38.

Compound D-019
3-(2-Chlorophenyl)-2-(9H-purin-6-ylsulfanylmethyl)-3H-benzo[g]quinazolin-4-one Prepared according to Procedure C using Intermediate 2n (200 mg, 0.563 mmol), 6-mercaptopurine monohydrate (105 mg, 0.619 mmol), $K_2CO_3$ (86 mg, 0.619 mmol), and DMF (4 mL). The crude product was recrystallized from EtOH to provide 128 mg of a dark yellow solid (48%), mp 247.8–254.4° C. (decomposes). $^1$H NMR (DMSO-$d_6$) δ: 13.56 (br s, 1H); 8.90 (s, 1H); 8.50 (s, 1H); 8.46 (s, 1H); 8.34 (s, 1H); 8.27 (d, J=8.2 Hz, 1H); 8.16 (d, J=8.2 Hz, 1H); 7.81 (dd, J=1.6, 7.3 Hz, 1H); 7.70 (t, J=7.5 Hz, 1H); 7.61–7.74 (m, 2H); 7.49 (t, J=7.5 Hz, 1H); 7.44–7.53 (m, 1H); 4.44–4.56 (m, 2H). $^{13}$C NMR (DMSO-$d_6$) ppm: 161.3, 151.6, 151.5, 143.9, 142.2, 136.7, 134.4, 132.5, 131.8, 131.6, 130.5, 129.7, 129.3, 128.8, 128.6, 128.3, 128.3, 127.1, 125.2, 119.5, 32.4. MS (ES): m/z 471.0 (M+). Anal. calcd. for $C_{24}H_{15}ClN_6OS.0.2C_2H_6O.0.05KCl$: C, 60.57; H, 3.37; Cl, 7.69; N, 17.37; S, 6.63. Found: C, 60.24; H, 3.46; Cl, 7.50; N, 17.34; S, 6.69.

Compound D-020
6-Chloro-3-(2-chlorophenyl)-2-(9H-purin-6-ylsulfanylmethyl)-3H-quinazolin-4-one Prepared according to Procedure C using Intermediate 2d (200 mg, 0.587 mmol), 6-mercaptopurine monohydrate (110 mg, 0.646 mmol), $K_2CO_3$ (90 mg, 0.651 mmol), and DMF (5 mL). The crude product was recrystallized from EtOH to provide 113 mg of a yellow crystalline solid (42%), mp 237.1–238.2° C. (decomposes). $^1$H NMR (DMSO-$d_6$) δ: 13.55 (br s, 1H); 8.48 (s, 1H); 8.44 (s, 1H); 8.11 (s, 1H); 7.94 (d, J=8.3 Hz, 1H); 7.78 (d, J=8.1 Hz, 2H); 7.66 (d, J=6.7 Hz, 1H); 7.48–7.56 (m, 2H); 4.48 (s, 2H). $^{13}$C NMR (DMSO-$d_6$) ppm: 159.8, 156.8, 153.5, 151.5, 149.6, 145.8, 143.6, 135.7, 134.0, 132.2, 132.1, 131.7, 131.5, 130.5, 130.2, 129.8, 128.8, 125.8, 121.9, 32.0. MS (ES): m/z 455.0 (M+). Anal. calcd. for $C_{20}H_{12}Cl_2N_6OS.0.1C_2H_6O.0.6H_2O(0.15KCl)$: C, 50.34; H, 2.89; Cl, 15.82; N, 17.44; S, 6.65. Found: C, 50.02; H, 2.63; Cl, 15.51; N, 17.39; S, 6.81.

Compound D-021
8-Chloro-3-(2-chlorophenyl)-2-(9H-purin-6-ylsulfanylmethyl)-3H-quinazolin-4-one Prepared according to Procedure C using Intermediate 2h (200 mg, 0.589 mmol), 6-mercaptopurine monohydrate (124 mg, 0.726 mmol), $K_2CO_3$ (100 mg, 0.726 mmol), and DMF (4 mL). The crude product was recrystallized from EtOH to provide 202 mg of a white solid (75%), mp 211.9–212.7© (decomposes). $^1$H NMR (DMSO-$d_6$) δ: 13.54 (br s, 1H); 8.47 (s, 1H); 8.44 (s, 1H); 8.12 (d, J=7.9 Hz, 1H); 8.07 (d, J=7.6 Hz, 1H); 7.78 (d, J=7.5 Hz, 1H); 7.67 (d, J=7.1 Hz, 1H); 7.58 (t, J=7.9 Hz, 1H); 7.42–7.54 (m, 2H); 4.52 (s, 2H). $^{13}$C NMR (DMSO-$d_6$) ppm: 160.3, 156.9, 153.9, 151.5, 149.7, 143.5, 135.7, 134.0, 132.1, 131.8, 131.4, 131.1, 130.5, 130.3, 128.9, 128.3, 126.1, 122.4, 32.5. MS (ES): m/z 455.0 (M+). Anal. calcd. for $C_{20}H_{12}Cl_2N_6OS$: C, 52.76; H, 2.66; Cl, 15.57; N, 18.46; S, 7.04. Found: C, 52.65; H, 2.79; Cl, 15.32; N, 18.47; S, 7.18.

Compound D-022
3-(2-Chlorophenyl)-7-fluoro-2-(9H-purin-6-ylsulfanylmethyl)-3H-quinazolin-4-one Prepared according to Procedure C using Intermediate 2c (200 mg, 0.619 mmol), 6-mercaptopurine monohydrate (116 mg, 0.681 mmol), $K_2CO_3$ (95 mg, 0.687 mmol), and DMF (4 mL). The crude product was recrystallized from EtOH to provide 143 mg of a white crystalline solid (53%), mp 151.4–154.2° C. (discolors). $^1$H NMR (DMSO-$d_6$) δ: 13.55 (br s, 1H); 8.48 (s, 1H); 8.44 (s, 1H); 8.23 (dd, J=6.3, 8.7 Hz, 1H); 7.77 (dd, J=1.7, 7.4 Hz, 1H); 7.64 (d, J=7.4 Hz, 1H); 7.57 (d, J=9.8 Hz, 1H); 7.45–7.52 (m, 3H); 4.48 (s, 2H). $^{13}$C NMR (DMSO-$d_6$) ppm: 169.0 (d, J=253 Hz), 162.6, 159.3, 157.0, 154.0, 152.2, 151.7 (d, J=13 Hz), 146.1, 136.5, 134.7, 134.2, 134.0, 133.0, 132.6 (d, J=11 Hz), 131.3, 120.2, 118.9 (d, J=24 Hz), 115.3 (d, J=22 Hz), 34.6. MS (ES): m/z 439.0 (M+). Anal. calcd. for $C_{20}H_{12}ClFN_6OS.0.4C_2H_6O.0.4H_2O$ (0.15KCl: C, 52.52; H, 3.22; Cl, 8.57; N, 17.67. Found: C, 52.25; H, 3.11; Cl, 8.20; N, 17.69.

Compound D-023
3-(2-Chlorophenyl)-7-nitro-2-(9H-purin-6-ylsulfanylmethyl)-3H-quinazolin-4-one Prepared according to Procedure C using Intermediate 2o (216 mg, 0.617 mmol), 6-mercaptopurine monohydrate (116 mg, 0.681 mmol), $K_2CO_3$ (94 mg, 0.680 mmol), and DMF (4 mL). The crude product was recrystallized from EtOH to provide 212 mg of a yellow crystalline solid (74%), mp 218.0–218.3° C. (decomposes). $^1$H NMR (DMSO-$d_6$) δ: 13.56 (br s, 1H); 8.49 (s, 1H); 8.42 (s, 1H); 8.38–8.45 (m, 2H); 8.31 (d, J=8.4 Hz, 1H); 7.81 (d, J=6.5 Hz, 1H); 7.68 (d, J=6.7 Hz, 1H); 7.43–7.58 (m, 2H); 4.53 (s, 2H). $^{13}$C NMR (DMSO-$d_6$) ppm: 157.7, 154.4, 153.3, 149.8, 149.3, 147.6, 145.2, 141.4, 131.5, 129.8, 129.7, 129.2, 128.4, 127.1, 126.7, 122.7, 120.3, 119.4, 29.9. MS (ES): m/z 466.0 (M+). Anal. calcd. for $C_{20}H_{12}ClN_7O_3S.0.4C_2H_6O.0.05KCl$: C, 51.19; H, 2.97; Cl, 7.63; N, 20.09; S, 6.57. Found: C, 51.27; H, 2.88; Cl, 7.40; N, 20.04; S, 6.52.

Compound D-024
3-(2-Chlorophenyl)-6-hydroxy-2-(9H-purin-6-ylsulfanylmethyl)-3H-quinazolin-4-one Prepared according to Procedure C using Intermediate 2p (200 mg, 0.552 mmol), 6-mercaptopurine monohydrate (117 mg, 0.685 mmol), $K_2CO_3$ (95 mg, 0.687 mmol), and DMF (4 mL). The crude product was recrystallized from EtOH to provide 182 mg of a white solid, a mixture of the desired product and the acetyl derivative. A portion of this material (120 mg) was suspended in a mixture of MeOH (2 mL) and aqueous $NaHCO_3$ (satd., 1 mL) and stirred rapidly for 4 hours. The mixture was concentrated in vacuo, suspended in $H_2O$ (10 mL), and stored at 4° C. overnight. The white solid was collected and dried to 103 mg (66%), mp 186–214° C. (gradually decomposes). $^1$H NMR (DMSO-$d_6$) δ: 8.48 (s, 1H); 8.45 (s, 1H); 7.71 (d, J=6.8 Hz, 1H); 7.62–7.64 (m, 2H); 7.43–7.51 (m, 2H); 7.40–7.43 (m, 1H); 7.35 (d, J=8.8 Hz, 1H); 4.39–4.52 (m, 2H). $^{13}$C NMR (DMSO-$d_6$) ppm:

160.6, 157.1, 156.2, 151.4, 150.8, 149.3, 144.1, 140.2, 134.5, 132.2, 131.6, 131.4, 130.4, 129.3, 128.7, 124.8, 121.7, 109.8, 32.0. MS (ES): m/z 437.0 (M+). Anal. calcd. for (2 $C_{20}H_{13}ClN_6O_2S \cdot 0.1C_2H_6O \cdot 0.6H_2O$: C, 49.68; H, 3.88; Cl, 7.26; N, 17.21; S, 6.57. Found: C, 49.43; H, 3.62; Cl, 7.32; N, 17.07; S, 6.58.

Compound D-025

5-Chloro-3-(2-chlorophenyl)-2-(9H-purin-6-ylsulfanylmethyl)-3H-quinazolin-4-one

Prepared according to Procedure C using Intermediate 2f (300 mg, 0.883 mmol), 6-mercaptopurine monohydrate (165 mg, 0.972 mmol), $K_2CO_3$ (134 mg, 0.972 mmol), and DMF (4 mL). The crude product was recrystallized from EtOH to provide 341 mg of a pale orange crystalline solid (85%), mp 233.7–234.4° C. (decomposes). $^1$H NMR (DMSO-$d_6$) δ: 13.58 (br s, 1H); 8.50 (s, 1H); 8.47 (s, 1H); 7.77–7.85 (m, 2H); 7.68 (d, J=8.1 Hz, 2H); 7.65 (d, J=7.7 Hz, 1H); 7.41–7.56 (m, 2H); 4.45 (d, J=1.2 Hz, 2H). $^{13}$C NMR (DMSO-$d_6$) ppm: 158.7, 156.8, 153.8, 151.5, 149.6, 149.5, 143.5, 135.4, 134.1, 133.3, 132.2, 131.6, 131.6, 130.5, 130.2, 128.8, 127.1, 117.6, 32.0. MS (ES): m/z 455.0 (M+). Anal. calcd. for $C_{20}H_{12}Cl_2N_6OS \cdot C_2H_6O \cdot 0.3H_2$: C, 52.14; H, 3.70; Cl, 13.99; N, 16.58; S, 6.33. Found: C, 52.07; H, 3.37; Cl, 13.40; N, 16.65; S, 6.42.

Compound D-026

3-(2-Chlorophenyl)-5-methyl-2-(9H-purin-6-ylsulfanylmethyl)-3H-quinazolin-4-one

Prepared according to Procedure C using Intermediate 2g (300 mg, 0.940 mmol), 6-mercaptopurine monohydrate (176 mg, 1.03 mmol), $K_2CO_3$ (142 mg, 1.03 mmol), and DMF (5 mL). The crude product was recrystallized from EtOH to provide 324 mg of a white crystalline solid (79%), mp 227.8–230.1° C. (decomposes). $^1$H NMR (DMSO-$d_6$) δ: 13.57 (br s, 1H); 8.49 (s, 1H); 8.47 (s, 1H); 7.69–7.78 (m, 2H); 7.66 (d, J=7.3 Hz, 1H); 7.55 (d, J=7.9 Hz, 1H); 7.39–7.52 (m, 2H); 7.36 (d, J=6.9 Hz, 1H); 4.38–4.50 (m, 2H); 2.74 (s, 3H). $^{13}$C NMR (DMSO-$d_6$) ppm: 161.2, 156.3, 152.4, 151.5, 148.6, 143.9, 141.0, 134.6, 134.5, 132.3, 131.7, 131.4, 130.4, 130.2, 128.7, 125.7, 119.0, 32.0, 22.8. MS (ES): m/z 435.0 (M+). Anal. calcd. for $C_{21}H_{15}ClN_6OS \cdot 0.65C_2H_6O \cdot 0.1H_2O$: C, 57.40; H, 4.13; Cl, 7.60; N, 18.01; S, 6.87. Found: C, 57.11; H, 3.96; Cl, 7.45; N, 17.79; S, 6.90.

Compound D-027

3-(2-Chlorophenyl)-6,7-difluoro-2-(9H-purin-6-ylsulfanylmethyl)-3H-quinazolin-4-one Prepared according to Procedure C using Intermediate 2q (200 mg, 0.586 mmol), 6-mercaptopurine monohydrate (110 mg, 0.645 mmol), $K_2CO_3$ (89 mg, 0.645 mmol), and DMF (4 mL). The crude product was recrystallized from EtOH to provide 143 mg of a pale yellow crystalline solid (53%), mp 207.8° C. (discolors; sweats at 136(C). $^1$H NMR (DMSO-$d_6$) δ: 13.57 (br s, 1H); 8.49 (s, 1H); 8.46 (s, 1H); 8.11 (t, J=9.4 Hz, 1H); 7.88 (dd, J=7.3, 11 Hz, 1H); 7.77 (dd, J=1.7, 7.3 Hz, 1H); 7.67 (d, J=7.4 Hz, 1H); 7.42–7.55 (m, 2H); 4.48 (s, 2H). $^{13}$C NMR (DMSO-$d_6$) ppm: 159.5 (d, J=2.5 Hz), 154.6 (dd, J=14, 255 Hz), 154.0 (d, J=1.5 Hz), 151.5, 149.3 (dd, J=14, 250 Hz), 145.1 (d, J=12 Hz), 143.9, 133.9, 132.1, 131.8, 131.4, 130.5, 128.9, 118.0 (d, J=4.9 Hz), 115.8 (d, J=18 Hz), 114.6 (d, J=20 Hz), 32.0. MS (ES): m/z 457.0 (M+). Anal. calcd. for $C_{20}H_{11}ClF_2N_6OS$: C, 52.58; H, 2.43; Cl, 7.76; N, 18.40; S, 7.02. Found: C, 51.81; H, 2.37; Cl, 7.49; N, 18.04; S, 7.55.

Compound D-028

3-(2-Chlorophenyl)-6-fluoro-2-(9H-purin-6-ylsulfanylmethyl)-3H-quinazolin-4-one

Prepared according to Procedure C using Intermediate 2r (118 mg, 0.365 mmol), 6-mercaptopurine monohydrate (68 mg, 0.402 mmol), $K_2CO_3$ (56 mg, 0.402 mmol), and DMF (2 mL). The crude product was recrystallized from EtOH to provide 103 mg of an off-white crystalline solid (64%), mp 232.8–233.0° C. (discolors). $^1$H NMR (DMSO-$d_6$) δ: 13.56 (br s, 1H); 8.48 (s, 1H); 8.44 (s, 1H); 7.81–7.86 (m, 3H); 7.76 (d, J=7.5 Hz, 1H); 7.67 (d, J=7.5 Hz, 1H); 7.40–7.54 (m, 2H); 4.48 (br s, 2H). $^{13}$C NMR (DMSO-$d_6$) ppm: 160.8 (d, J=247 Hz), 160.2 (d, J=3.3 Hz), 156.9, 152.3 (d, J=1.9 Hz), 151.5, 149.7, 144.0, 143.6, 134.1, 132.1, 131.7, 131.5, 130.5, 130.4, 130.2, 128.8, 124.0 (d, J=24 Hz), 122.0 (d, J=8.7 Hz), 111.7 (d, J=24 Hz), 32.0. MS (ES): m/z 439.0 (M+). Anal. calcd. for $C_{20}H_{12}ClFN_6OS \cdot 0.2C_2H_6O \cdot 0.1H_2O$: C, 54.46; H, 3.00; Cl, 7.88; N, 18.68. Found: C, 54.09; H, 2.73; Cl, 7.80; N, 18.77.

Compound D-029

2-(6-Aminopurin-9-ylmethyl)-3-(2-isopropylphenyl)-5-methyl-3H-quinazolin-4-one

Thionyl chloride (2.2 mL, 30 mmol) was added to a stirred solution of 2-amino-6-methylbenzoic acid (1.51 g, 10 mmol) in benzene (50 mL) and the mixture was heated at reflux for 18 h. Once cooled, the solvent was removed in vacuo and stripped down twice with benzene (25 mL). The residue was dissolved in $CHCl_3$ (50 mL) and treated with 2-isopropylaniline (2.83 mL, 20 mmol). The slurry was then heated at reflux for 3 h. At that time TLC (50% EtOAc/hexane) indicated that the reaction was complete. After cooling to room temperature, the reaction mixture was poured atop a 4 cm plug of silica gel and flushed through with 20% EtOAc/hexane. The product containing fractions were combined and concentrated in vacuo. The residue was dissolved in HOAC (50 mL) and treated with chloro-actyl chloride (1.6 mL, 20 mmol) and the mixture was heated at reflux for 18 h. The reaction was cooled and concentrated in vacuo. The remaining HOAc was removed by azeotroping with toluene (25 mL) three times. The residue was dissolved in toluene (10 mL) and poured through a 4 cm plug of silica gel, flushing through with 20% EtOAc/hexane. The product containing fractions were identified by LCMS (MS (ES): m/z 327 (M+)), and concentrated in vacuo to afford 975 mg (30%) as a white foam. The white foam chloride (450 mg, 1.36 mmol) was dissolved in DMF (10 mL) and treated with adenine (275 mg, 2.04 mmol) and $K_2CO_3$ (281 mg, 2.04 mmol) and the mixture was stirred overnight at room temperature. The suspension was then poured into 200 mL of water, stirred at room temperature for 30 min then chilled in the refrigerator for 30 min. The resultant solid was collected by vacuum filtration and recrystallized from EtOH to afford 285 mg (49%) of an off white solid. mp 258.0–258.2° C. $^1$H NMR (DMSO-$d_6$) δ: 8.19 (s, 1H), 8.09 (s, 1H), 7.60 (m, 3H), 7.45 (m, 2H), 7.23 (m, 3H), 5.11 (d, J=17.5 Hz, 1H), 4.71 (d, J=17.5 Hz, 1H), 2.68 (s, 3H), 2.73 (q, J=6.9 Hz, 1H), 1.34 (d, J=6.8 Hz, 3H), 1.13 (d, J=6.8 Hz, 3H). $^{13}$C NMR (DMSO-$d_6$) ppm: 161.9, 156.2, 152.8, 151.6, 150.1, 148.4, 146.1, 142.2, 140.8, 134.3, 133.7, 130.6, 130.0, 129.0, 127.7, 127.6, 125.8, 119.2, 118.4, 44.8, 28.3, 24.4, 23.3, 22.9. MS (ES): m/z 426.4 (M+). Anal. calcd. for $C_{24}H_{23}N_7O$: C, 67.75; H, 5.45; N, 23.04. Found: C, 67.60; H, 5.45; N, 22.82.

Compound D-030

2-(6-Aminopurin-9-ylmethyl)-5-methyl-3-o-tolyl-3H-quinazolin-4-one

Thionyl chloride (2.2 mL, 30 mmol) was added to a stirred solution of 2-amino-6-methylbenzoic acid (1.51 g, 10 mmol) in benzene (50 mL) and the mixture was heated at reflux for 18 h. Once cooled, the solvent was removed in vacuo and stripped down twice with benzene (25 mL). The residue was dissolved in $CHCl_3$ (50 mL) and treated with o-toluidine (2.13 mL, 20 mmol). The slurry was then heated at reflux for 3 h. At that time TLC (50% EtOAc/hexane) indicated that the reaction was complete. After cooling to room temperature, the reaction mixture was poured atop a 4 cm plug of silica gel and flushed through with 20% EtOAc/hexane. The product containing fractions were combined and concentrated in vacuo. The residue was dissolved in HOAc (50 mL) and treated with chloroactyl chloride (1.6 mL, 20 mmol) and the mixture was heated at reflux for 18 h. The reaction was cooled and concentrated in vacuo. The remaining HOAc was removed by azeotroping with toluene (25 mL) three times. The residue was dissolved in toluene (10 mL) and poured through a 4 cm plug of silica gel, flushing through with 20% EtOAc/hexane. The product containing fractions were identified by LCMS [MS (ES): m/z 299 (M+)), and concentrated in vacuo to afford 476 mg (16%) as a white foam. The white foam chloride (470 mg, 1.57 mmol) was dissolved in DMF (10 mL) and treated with adenine (423 mg, 3.14 mmol) and $K_2CO_3$ (433 mg, 3.14 mmol) and the mixture was stirred overnight at room temperature. The suspension was then poured into 200 mL of $H_2O$, stirred at room temperature for 30 min then chilled in the refrigerator for 30 min. The resultant solid was collected by vacuum filtration and recrystallized from EtOH to afford 123 mg (20%) of an off white solid. mp 281.5–282.7° C. (decomposes). $^1H$ NMR (DMSO-$d_6$) δ: 8.07 (s, 1H); 8.05 (s, 1H); 7.61 (t, J=7.8 Hz, 1H), 7.48 (m, 4H), 7.25 (m, 3H), 5.09 (d, J=17.4 Hz, 1H), 4.76 (d, J=17.4 Hz, 1H), 2.73 (s, 3H), 2.18 (s, 3H). $^{13}C$ NMR (DMSO-$d_6$) ppm: 161.3, 156.2, 152.8, 151.4, 150.0, 148.5, 142.2, 140.9, 136.1, 135.4, 134.3, 131.7, 130.1, 130.0, 129.0, 128.0, 125.8, 119.2, 118.5, 44.8, 22.9, 17.4. MS (ES): m/z 398.2 (M+). Anal. calcd. for $C_{22}H_{19}N_7O$: C, 66.49; H, 4.82; N, 24.67. Found: C, 66.29; H, 4.78; N, 24.72.

Compound D-031

3-(2-Fluorophenyl)-5-methyl-2-(9H-purin-6-ylsulfanylmethyl)-3H-quinazolin-4-one

Thionyl chloride (2.2 mL, 30 mmol) was added to a stirred solution of 2-amino-6-methylbenzoic acid (1.51 g, 10 mmol) in benzene (50 mL) and the mixture was heated at reflux for 18 h. Once cooled, the solvent was removed in vacuo and stripped down twice with benzene (25 mL). The residue was dissolved in $CHCl_3$ (50 mL) and treated with 2-fluoroaniline (1.93 mL, 20 mmol). The slurry was then heated at reflux for 3 h. At that time TLC (50% EtOAc/hexane) indicated that the reaction was complete. After cooling to room temperature, the reaction mixture was poured atop a 4 cm plug of silica gel and flushed through with 20% EtOAc/hexane. The product containing fractions were combined and concentrated in vacuo. The residue was dissolved in HOAc (50 mL) and treated with chloroactyl chloride (1.6 mL, 20 mmol) and the mixture was heated at reflux for 18 h. The reaction was cooled and concentrated in vacuo. The remaining HOAc was removed by azeotroping with toluene (25 mL) three times. The residue was dissolved in toluene (10 mL) and poured through a 4 cm plug of silica gel, flushing through with 20% EtOAc/hexane. The product containing fractions were identified by LCMS [MS (ES): m/z 303 (M+)), and concentrated in vacuo to afford 1.12 g (37%) as a white foam. The white foam chloride (455 mg, 1.50 mmol) was dissolved in DMF (10 mL) and treated with 6-mercaptopurine monohydrate (510 mg, 3.0 mmol) and $K_2CO_3$ (414 mg, 3.0 mmol) and the mixture was stirred overnight at room temperature. The suspension was then poured into 200 mL of water, stirred at room temperature for 30 min then chilled in the refrigerator for 30 min. The resultant solid was collected by vacuum filtration and recrystallized from EtOH to afford 487 mg (77%) of an off white solid. mp 151.9–152.2° C. $^1H$ NMR (DMSO-$d_6$) δ: 8.48 (s, 1H0, 8.44 (s, 1H), 7.70 (m, 2H), 7.48 (m, 2H), 7.33 (m, 3H), 4.55 (d, J=15.1 Hz, 1H), 4.48 (d, J=15.1 Hz, 1H), 2.73 (s, 3H). $^{13}C$ NMR (DMSO-$d_6$) ppm: 161.3, 157.8 (d, J=249.1 Hz), 156.9, 152.8, 151.5, 149.6, 148.6, 143.6, 140.9, 134.7, 131.9 (d, J=8.0 Hz), 131.4, 130.2, 125.6 (d, J=3.6 Hz), 125.5, 124.4 (d, J=13.5 Hz), 118.8, 116.6 (d, J=19.6 Hz), 56.4, 22.9. MS (ES): m/z 419.5 (M+). Anal. calcd. for $C_{21}H_{15}FN_6OS\cdot0.15C_2H_6O$: C, 60.14; H, 3.77; F, 4.47; N, 19.76; S, 7.54. Found: C, 59.89; H, 3.88; F, 4.42; N, 19.42; S, 7.23.

Compound D-032

2-(6-Aminopurin-9-ylmethyl)-5-chloro-3-o-tolyl-3H-quinazolin-4-one

Prepared according to Procedure C using 2j. (200 mg, 0.626 mmol), adenine (93 mg, 0.689 mmol), $K_2CO_3$ (95 mg, 0.689 mmol), and DMF (3 mL). The crude product was chromatographed in MeOH/$CH_2Cl_2$ to provide 101 mg of an off-white solid (39%), mp 262.0–266.5° C. $^1H$ NMR (DMSO-$d_6$) δ: 8.08 (s, 1H); 8.07 (s, 1H); 7.70 (t, J=8.0 Hz, 1H); 7.58 (dd, J=0.6, 7.9 Hz, 1H); 7.43–7.57 (m, 4H); 7.36 (dd, J=0.7, 8.0 Hz, 1H); 7.26 (br s, 2H); 5.12 (d, J=18 Hz, 1H); 4.78 (d, J=18 Hz, 1H); 2.20 (s, 3H). $^{13}C$ NMR (DMSO-$d_6$) ppm: 158.7, 156.2, 152.9, 152.7, 150.0, 149.4, 142.1, 136.1, 135.1, 135.0, 133.2, 131.8, 130.3, 130.1, 128.9, 128.1, 127.2, 118.5, 117.9, 44.9, 17.4. MS (ES): m/z 418.1 (M+). Anal. calcd. for $C_{21}H_{16}ClN_7O\cdot0.1H_2O\cdot0.05KCl$: C, 59.57; H, 3.86; Cl, 8.79; N, 23.16. Found: C, 59.65; H, 3.80; Cl, 8.70; N, 22.80.

Compound D-033

2-(6-Aminopurin-9-ylmethyl)-5-chloro-3-(2-methoxyphenyl)-3H-quinazolin-4-one

Prepared according to Procedure C using 2l (250 mg, 0.746 mmol), adenine (111 mg, 0.821 mmol), $K_2CO_3$ (113 mg, 0.821 mmol), and DMF (4 mL). The crude product was chromatographed in MeOH/$CH_2Cl_2$ and recrystallized from EtOH to provide 124 mg of a brown solid (38%), mp 257.0–257.1° C. $^1H$ NMR (DMSO-$d_6$) δ: 8.06 (s, 1H); 8.01 (s, 1H); 7.71 (t, J=8.0 Hz, 1H); 7.57 (dd, J=0.9, 7.9 Hz, 1H); 7.52–7.59 (m, 1H); 7.50 (dd, J=1.6, 7.8 Hz, 1H); 7.38 (dd, J=1.1, 8.2 Hz, 1H); 7.27 (dd, J=0.6, 8.3 Hz, 1H); 7.24 (br s, 2H); 7.17 (dt, J=0.9, 7.6 Hz, 1H); 5.07 (d, J=17 Hz, 1H); 4.97 (d, J=17 Hz, 1H); 3.79 (s, 3H). $^{13}C$ NMR (DMSO-$d_6$) ppm: 158.8, 156.2, 154.7, 153.2, 152.8, 150.1, 149.3, 142.0, 135.1, 133.2, 131.8, 130.1, 130.1, 127.2, 123.8, 121.6, 118.4, 117.9, 113.1, 56.2, 44.8. MS (ES): m/z 434.0 (M+). Anal. calcd. for $C_{21}H_{16}ClN_7O_2\cdot0.5H_2O\cdot0.04KCl$: C, 56.57; H, 3.84; Cl, 8.27; N, 21.99. Found: C, 56.29; H, 3.75; Cl, 8.21; N, 21.61.

The following compounds were made generally in accordance with the above-described methods and serve to further illustrate specific embodiments of the compounds of the invention:

3-(2,6-dichlorophenyl)-5-methyl-2-(9H-purin-6-ylsulfanylmethyl)-3H-quinazolin-4-one (D-034)
3-(2-isopropylphenyl)-5-methyl-2-(9H-purin-6-ylsulfanylmethyl)-3H-quinazolin-4-one (D-035)
3-(2-methoxyphenyl)-2-(9H-purin-6-ylsulfanylmethyl)-3H-quinazolin-4-one (D-036)
3-benzyl-2-(9H-purin-6-ylsulfanylmethyl)-3H-quinazolin-4-one (D-037)
3-butyl-2-(9H-purin-6-ylsulfanylmethyl)-3H-quinazolin-4-one (D-038)

3-morpholin-4-yl-2-(9H-purin-6-ylsulfanylmethyl)-3H-quinazolin-4-one, acetate salt (D-039)

3-(3-methoxyphenyl)-2-(9H-purin-6-ylsulfanylmethyl)-3H-quinazolin-4-one (D-040)

3-(3-chlorophenyl)-2-(9H-purin-6-ylsulfanylmethyl)-3H-quinazolin-4-one (D-041)

2-(9H-purin-6-ylsulfanylmethyl)-3-pyridin-4-yl-3H-quinazolin-4-one (D-042)

3-benzyl-5-fluoro-2-(9H-purin-6-ylsulfanylmethyl)-3H-quinazolin-4-one (D-043)

3-(4-methylpiperazin-1-yl)-2-(9H-purin-6-ylsulfanylmethyl)-3H-quinazolin-4-one, acetate salt (D-044)

[5-fluoro-4-oxo-2-(9H-purin-6-ylsulfanylmethyl)-4H-quinazolin-3-yl]acetic acid ethyl ester (D-045)

3-(2-methoxyphenyl)-2-(9H-purin-6-ylsulfanylmethyl)-3H-quinazolin-4-one (D-046)

3-(2-methoxyphenyl)-5-methyl-2-(9H-purin-6-ylsulfanylmethyl)-3H-quinazolin-4-one (D-047)

2-(6-aminopurin-9-ylmethyl)-3-(2-fluorophenyl)-5-methyl-3H-quinazolin-4-one (D-048)

2-(6-aminopurin-9-ylmethyl)-3-benzyl-5-fluoro-3H-quinazolin-4-one (D-049)

2-(6-aminopurin-9-ylmethyl)-3-butyl-3H-quinazolin-4-one (D-050)

2-(6-aminopurin-9-ylmethyl)-3-morpholin-4-yl-3H-quinazolin-4-one, acetate salt (D-051)

3-(4-chlorophenyl)-2-(9H-purin-6-ylsulfanylmethyl)-3H-quinazolin-4-one (D-052).

Additional compounds of the present invention were prepared by the following synthetic procedures.

The following intermediates were prepared by the above-described Procedure A.

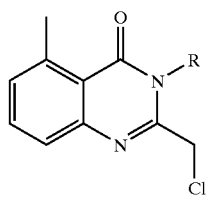

3a R=cyclopropyl
3b R=cyclopropylmethyl
3c R=phenethyl
3d R=cyclopentyl
3e R=3-(2-chloro)pyridyl
3f R=4-(2-methyl)benzoic acid
3g R=4-nitrobenzyl
3h R=cyclohexyl
3i R=E-(2-phenyl)cyclopropyl Additional compounds of the present invention (D-053 through D-070) having the following core structure are discussed in the following Experimental Section. All were prepared following Procedure C.

Core Structure:

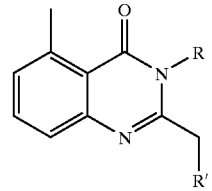

| Compound No. | R | R' |
|---|---|---|
| D-053 | cyclopropyl | C |
| D-054 | cyclopropylmethyl | B |
| D-055 | cyclopropylmethyl | A |
| D-056 | cyclopropylmethyl | C |
| D-057 | phenethyl | B |
| D-058 | phenethyl | C |
| D-059 | cyclopentyl | B |
| D-060 | cyclopentyl | A |
| D-061 | 3-(2-chloro)pyridyl | B |
| D-062 | 3-(2-chloro)pyridyl | A |
| D-063 | 4-(2-methyl)benzoic acid | B |
| D-064 | cyclopropyl | B |
| D-065 | cyclopropyl | A |
| D-066 | 4-nitrobenzyl | B |
| D-067 | cyclohexyl | B |
| D-068 | cyclohexyl | A |
| D-069 | cyclohexyl | C |
| D-070 | E-(2-phenyl)cyclopropyl | B |

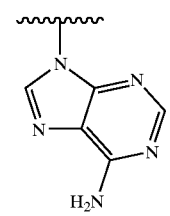

A

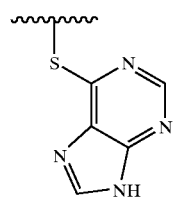

B

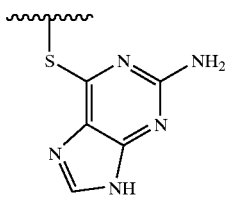

C 2-(2-Amino-9H-purin-6-ylsulfanylmethyl)-3-cyclopropyl-5-methyl-3H-quinazolin-4-one (D-053)

Prepared according to procedure C using 3a (100 mg, 0.4 mmol), 2-amino-6-mercaptopurine (80 mg, 0.48 mmol), and $K_2CO_3$ (77 mg, 0.56 mmol). The product was purified by trituration from $H_2O$. $^1H$ NMR (DMSO-$d_6$) δ: 7.89 (d, J=0.9 Hz, 1H); 7.54 (t, J=7.4 Hz, 1H); 7.34 (d, J=8.1 Hz, 1H); 7.19 (d, J=7.2 Hz, 1H); 6.28 (s, 2H); 4.94 (s, 2H); 2.70 (s, 3H); 1.24 (d, J=6.5 Hz, 2H); 0.91 (s, 2H). MS (ES): m/z 380 (M+H), 190.

3-Cyclopropylmethyl-5-methyl-2-(9H-purin-6-ylsulfanylmethyl)-3H-quinazolin-4-one (D-054)

Prepared according to procedure C using 3b (300 mg, 1.14 mmol), 6-mercaptopurine monohydrate (214 mg, 1.26 mmol), and $K_2CO_3$ (189 mg, 1.37 mmol) The product was purified by trituration from $H_2O$, followed by recrystallization from MeOH. $^1$H NMR (DMSO-$d_6$) δ: 13.60 (br s, 1H); 8.72 (s, 1H); 8.48 (s, 1H); 7.63 (t, J=7.8 Hz, 1H); 7.42 (d, J=8.0 Hz, 1H); 7.28 (d, J=7.3 Hz, 1H); 5.01 (s, 2H); 4.11 (d, J=6.8 Hz, 2H); 2.78 (s, 3H); 1.35 (quint, J=6.2 Hz, 1H); 0.44–0.59 (m, 4H). MS (ES): m/z 379 (M+H), 325.

2-(6-Aminopurin-9-ylmethyl)-3-cyclopropylmethyl-5-methyl-3H-quinazolin-4-one (D-055)

Prepared according to procedure C using 3b (300 mg, 1.14 mmol), adenine (170 mg, 1.26 mmol), and $K_2CO_3$ (189 mg, 1.37 mmol). The product was purified by trituration from $H_2O$, followed by recrystallization from MeOH. $^1$H NMR (DMSO-$d_6$) δ: 8.21 (s, 1H); 8.10 (s, 1H); 7.52 (t, J=7.7 Hz, 1H); 7.18–7.31 (m, 3H); 7.06 (d, J=8.1 Hz, 1H); 5.68 (s, 2H); 4.14 (d, J=6.8 Hz, 2H); 2.77 (s, 3H); 1.34 (quint, J=6.4 Hz, 1H); 0.45–0.60 (m, 4H). MS (ES): m/z 362 (M+H), 308.

2-(2-Amino-9H-purin-6-ylsulfanylmethyl)-3-cyclopropylmethyl-5-methyl-3H-quinazolin-4-one (D-056)

Prepared according to procedure C using 3b (280 mg, 1.1 mmol), 2-amino-6-mercaptopurine (200 mg, 1.2 mmol), and $K_2CO_3$ (180 mg, 1.3 mmol). The product was purified by trituration from MeOH. $^1$H NMR (DMSO-$d_6$) δ: 12.70 (br s, 1H); 7.95 (s, 1H); 7.64 (t, J=7.8 Hz, 1H); 7.44 (d, J=7.9 Hz, 1H); 7.28 (d, J=7.4 Hz, 1H); 6.41 (s, 2H); 4.91 (s, 2H); 4.05 (d, J=6.8 Hz, 2H); 2.78 (s, 3H); 1.26–1.43 (m, 1H); 0.36–0.56 (m, 4H). MS (ES): m/z 394 (M+H), 340.

5-Methyl-3-phenethyl-2-(9H-purin-6-ylsulfanylmethyl)-3H-quinazolin-4-one (D-057)

Prepared according to procedure C using 3c (750 mg, 2.4 mmol), 6-mercaptopurine monohydrate (442 mg, 2.6 mmol), and $K_2CO_3$ (398 mg, 2.9 mmol). The product was purified by trituration from $H_2O$. $^1$H NMR (DMSO-$d_6$) δ: 13.61 (s, 1H); 8.71 (s, 1H); 8.48 (s, 1H); 7.65 (t, J=7.7 Hz, 1H); 7.44 (d, J=7.9 Hz, 1H); 7.16–7.35 (m, 6H); 4.89 (s, 2H); 4.29 (br t, J=7.9 Hz, 2H); 3.08 (br t, J=7.8 Hz, 2H); 2.81 (s, 3H). MS (ES): m/z 429 (M+H), 105.

2-(2-Amino-9H-purin-6-ylsulfanylmethyl)-5-methyl-3-phenethyl-3H-quinazolin-4-one (D-058)

Prepared according to procedure C using 3c (750 mg, 2.4 mmol), 2-amino-6-mercaptopurine (435 mg, 2.6 mmol), and $K_2CO_3$ (398 mg, 2.9 mmol). The product was purified by trituration from $H_2O$. $^1$H NMR (DMSO-$d_6$) δ: 12.61 (s, 1H); 7.95 (s, 1H); 7.65 (t, J=7.7 Hz, 1H); 7.45 (d, J=7.9 Hz, 1H); 7.14–7.32 (m, 6H); 6.44 (s, 2H); 4.81 (s, 2H); 4.24 (br t, J=7.9 Hz, 2H); 3.04 (br t, J=7.8 Hz, 2H); 2.81 (s, 3H). MS (ES): m/z 444 (M+H), 340.

3-Cyclopentyl-5-methyl-2-(9H-purin-6-ylsulfanylmethyl)-3H-quinazolin-4-one (D-059)

Prepared according to procedure C using 3d (100 mg, 0.36 mmol), 6-mercaptopurine monohydrate (73 mg, 0.43 mmol), and $K_2CO_3$ (100 mg, 0.72 mmol). The product was purified by recrystallization from MeOH.

$^1$H NMR (DMSO-$d_6$) δ: 13.62 (br s, 1H); 8.77 (s, 1H); 8.48 (s, 1H); 7.62 (t, J=7.7 Hz, 1H); 7.42 (d, J=7.8 Hz, 2H); 7.26 (d, J=7.4 Hz, 1H); 5.03 (s, 2H); 4.80 (quint, J=8.0 Hz, 1H); 2.76 (s, 3H); 2.12–2.31 (m, 2H); 1.79–2.04 (m, 4H); 1.44–1.58 (m, 2H). MS (ES): m/z 393 (M+H), 325.

2-(6-Aminopurin-9-ylmethyl)-3-cyclopentyl-5-methyl-3H-quinazolin-4-one (D-060)

Prepared according to procedure C using 3d (10 mg, 0.36 mmol), adenine (58 mg, 0.43 mmol), and $K_2CO_3$ (100 mg, 0.72 mmol). The product was purified by recrystallization from MeOH. $^1$H NMR (DMSO-$d_6$) δ: 8.15 (s, 1H); 8.11 (s, 1H); 7.52 (t, J=7.7 Hz, 1H); 7.16–7.31 (m, 3H); 7.10 (d, J=8.0 Hz, 2H); 5.68 (s, 2H); 4.78 (quint, J=8.3 Hz, 1H); 2.74 (s, 3H); 2.09–2.32 (m, 2H); 1.86–2.04 (m, 2H); 1.68–1.86 (m, 2H); 1.43–1.67 (m, 2H). MS (ES): m/z 376 (M+H), 308, 154.

3-(2-Chloro-pyridin-3-yl)-5-methyl-2-(9H-purin-6-ylsulfanylmethyl)-3H-quinazolin-4-one (D-061)

Prepared according to procedure C using 3e (500 mg, 1.6 mmol), 6-mercaptopurine monohydrate (289 mg, 1.7 mmol), and $K_2CO_3$ (262 mg, 1.9 mmol). The product was purified by trituration from $H_2O$. MS (ES): m/z 436 (M+H), 200.

2-(6-Aminopurin-9-ylmethyl)-3-(2-chloro-pyridin-3-yl)-5-methyl-3H-quinazolin-4-one (D-062)

Prepared according to procedure C using 3e (500 mg, 1.6 mmol), adenine (230 mg, 1.7 mmol), and $K_2CO_3$ (262 mg, 1.9 mmol). The product was purified by trituration from $H_2O$. $^1$H NMR (DMSO-$d_6$) δ: 8.59 (dd, J=1.7, 4.8 Hz, 1H); 8.22 (dd, J=1.7, 7.8 Hz, 1H): 8.025 (s, 1H); 8.017 (s, 1H); 7.60–7.72 (m, 2H); 7.35 (t, J=8.2 Hz, 2H); 7.22 (s, 2H); 5.12 (d, J=17.0 Hz, 1H); 5.02 (d, J=17.0 Hz, 1H); 2.72 (s, 3H). MS (ES): m/z 419 (M+H).

3-Methyl-4-[5-methyl-4-oxo-2-(9H-purin-6-ylsulfanylmethyl)-4H-quinazolin-3-yl]-benzoic acid (D-063)

Prepared according to procedure C using 3f (400 mg, 1.17 mmol), 6-mercaptopurine monohydrate (219 mg, 1.29 mmol), and $K_2CO_3$ (226 mg, 1.64 mmol) The product was purified by recrystallization from MeOH. $^1$H NMR (DMSO-$d_6$) δ: 13.54 (br s, 1H); 8.44 (s, 1H); 8.42 (s, 1H); 7.80 (s, 2H); 7.71 (t, J=7.7 Hz, 1H); 7.59 (d, J=8.6 Hz, 1H); 7.52 (d, J=7.9 Hz, 1H); 7.34 (d, J=7.4 Hz, 1H); 4.46 (d, J=15.4 Hz, 1H); 4.34 (d, J=15.7 Hz, 1H); 3.17 (d, J=4.4 Hz, 1H); 2.73 (s, 3H); 2.17 (s, 3H). MS (ES): m/z 459 (M+H).

3-Cyclopropyl-5-methyl-2-(9H-purin-6-ylsulfanylmethyl)-3H-quinazolin-4-one (D-064)

Prepared according to procedure C using 3a (100 mg, 0.40 mmol), 6-mercaptopurine monohydrate (90 mg, 0.53 mmol), and $K_2CO_3$ (97 mg, 0.7 mmol). The product was purified by trituration from $H_2O$. $^1$H NMR (DMSO-$d_6$) δ: 8.69 (d, J=0.8 Hz, 1H); 8.47 (s, 1H); 7.57 (d, J=7.9 Hz, 1H); 7.37 (d, J=8.1 Hz, 1H); 7.23 (d, J=7.3 Hz, 1H); 5.08 (s, 2H); 3.06–3.18 (m, 1H); 2.74 (s, 3H); 1.14–1.36 (m, 2H); 0.92–1.06 (m, 2H).

2-(6-Aminopurin-9-ylmethyl)-3-cyclopropyl-5-methyl-3H-quinazolin-4-one (D-065)

Prepared according to procedure C using 3a (100 mg, 0.40 mmol), adenine (94 mg, 0.7 mmol), and $K_2CO_3$ (121 mg, 0.88 mmol). The product was purified by trituration from $H_2O$. $^1$H NMR (DMSO-$d_6$) δ: 8.19 (d, J=0.9 Hz, 1H); 8.09 (d, J=1.0 Hz, 1H); 7.48 (t, J=7.8 Hz, 1H); 7.13–7.29 (m, 3H); 7.04 (d, J=8.1 Hz, 1H); 5.74 (s, 2H); 3.00–3.13 (m, 1H); 2.73 (s, 3H); 1.18–1.38 (m, 2H); 0.94–1.09 (m, 2H).

5-Methyl-3-(4-nitro-benzyl)-2-(9H-purin-6-ylsulfanylmethyl)-3H-quinazolin-4-one (D-066)

Prepared according to procedure C using 3g (200 mg, 0.58 mmol), 6-mercaptopurine monohydrate (148 mg, 0.87 mmol), and $K_2CO_3$ (160 mg, 1.16 mmol) The product was purified by trituration from MeOH. $^1$H NMR (DMSO-$d_6$) δ: 13.44 (br s, 1H); 8.50 (s, 1H); 8.31 (s, 1H); 8.03 (d, J=8.6 Hz, 2H); 7.58 (t, J=7.9 Hz, 1H); 7.37 (d, J=8.3 Hz, 3H); 7.22 (d, J=7.5 Hz, 1H); 5.44 (s, 2H); 4.70 (s, 2H); 2.66 (s, 3H). MS (ES): m/z 460 (M+H)

3-Cyclohexyl-5-methyl-2-(9H-purin-6-ylsulfanylmethyl)-3H-quinazolin-4-one (D-067)

Prepared according to procedure C using 3h (150 mg, 0.52 mmol), 6-mercaptopurine monohydrate (97 mg, 0.57 mmol), and $K_2CO_3$ (86 mg, 0.62 mmol). The product was purified by trituration from MeOH. $^1$H NMR (DMSO-$d_6$) δ: 13.66 (br s, 1H); 8.82 (s, 1H); 8.50 (s, 1H); 7.62 (t, J=7.7 Hz, 1H); 7.42 (d, J=8.0 Hz, 1H); 7.26 (d, J=7.3 Hz, 1H); 5.01 (s, 2H); 4.11 (br s, 1H); 2.75 (s, 3H); 2.38–2.65 (m, 2H); 1.58–1.90 (m, 4H); 1.37–1.57 (m, 1H); 0.71–1.26 (m, 3H). MS (ES): m/z 407 (M+H), 325.

2-(6-Aminopurin-9-ylmethyl)-3-cyclohexyl-5-methyl-3H-quinazolin-4-one (D-068)

Prepared according to procedure C using 3h (150 mg, 0.52 mmol), adenine (77 mg, 0.57 mmol), and $K_2CO_3$ (86 mg, 0.62 mmol). The product was purified by trituration from MeOH. $^1$H NMR (DMSO-$d_6$) δ: 8.15 (s, 2H); 7.54 (t, J=7.9 Hz, 1H); 7.06–7.35 (m, 4H); 5.65 (s, 2H); 4.09 (br s, 1H); 2.73 (s, 3H); 1.41–1.90 (m, 6H); 0.99–1.34 (m, 4H). MS (ES): m/z 390 (M+H), 308.

2-(2-Amino-9H-purin-6-ylsulfanylmethyl)-3-cyclohexyl-5-methyl-3H-quinazolin-4-one (D-069)

Prepared according to procedure C using 3h (150 mg, 0.52 mmol), 2-amino-6-mercaptopurine (95 mg, 0.57 mmol), and $K_2CO_3$ (86 mg, 0.62 mmol). The product was purified by reversed-phase HPLC (C18 Luna column, 4.6× 250 mm, 4.7 mL/min, 10–75% acetonitrile/water over 15 min, 100% acetonitrile at 18 min, detector at 220). MS (ES): m/z 422 (M+H), 340, 170.

5-Methyl-3-(E-2-phenyl-cyclopropyl)-2-(9H-purin-6-ylsulfanylmethyl)-3H-quinazolin-4-one (D-070)

Prepared according to procedure C using 3i and 6-mercaptopurine monohydrate). The product was purified by reversed-phase HPLC (C18 Luna column, 4.6×250 mm, 4.7 mL/min, 10–75% acetonitrile/water over 15 min, 100% acetonitrile at 18 min, detector at 220). MS (ES): m/z 441.

The following Methods 1 and 2 were used as the HPLC analyses for the following compounds:

HPLC Method 1. Column: 2×50 mm C18 Luna column (from Phenomenex), flow rate: 0.3 mL/min, UV detection at 214 and 254 nm. Initial conditions: 2% solvent B in solvent A; t=3 min, 20% Solvent B; t=6 min, 80% Solvent B, where Solvent A=water with 0.05% formic acid and Solvent B=acetonitrile with 0.05% formic acid.

HPLC Method 2. Column: 2×50 mm C18 Luna column (from Phenomenex), flow rate: 0.3 mL/min, UV detection at 214 and 254 nm. Initial conditions: 10–100% solvent B in solvent A over 6 min, where Solvent A=water and Solvent B=acetonitrile.

Compounds D-070A and D-070B were prepared as follows:

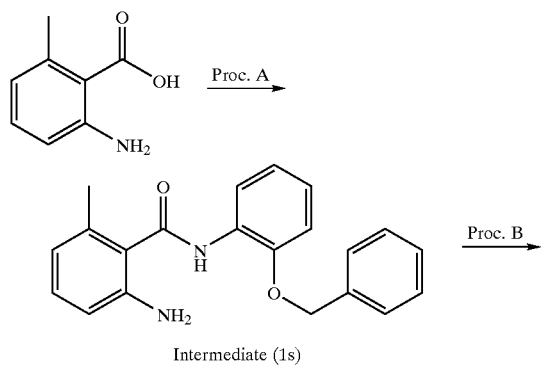

Intermediate (1s)

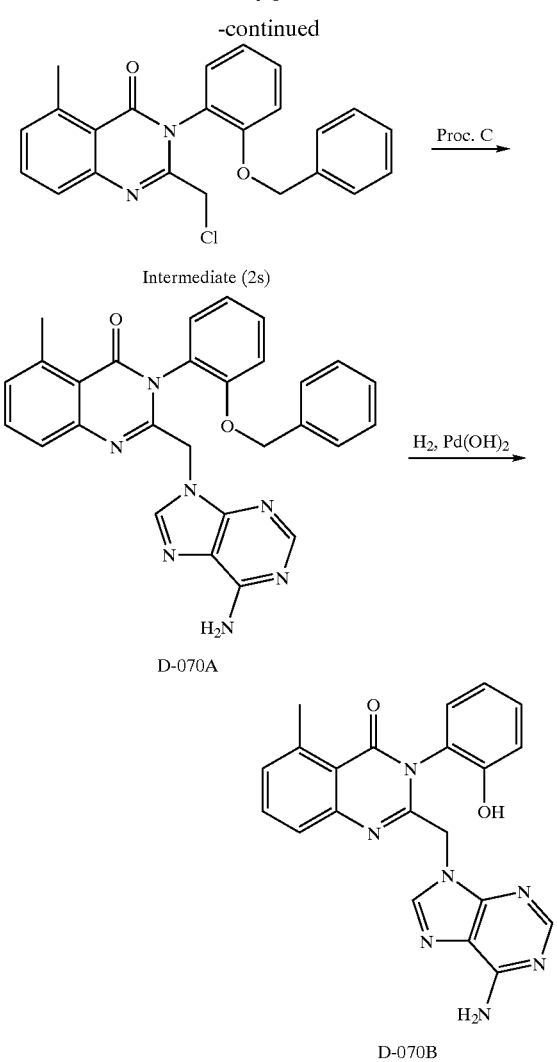

2-(6-Aminopurin-9-ylmethyl)-3-(2-benzyloxyphenyl)-5-methyl-3H-quinazolin-4-one (D-070A)

Using procedure A, 6-methylanthranilic acid and 2-benzyloxyaniline were converted to Intermediate (1s). Using procedure B, Intermediate (1s) was converted to Intermediate (2s). Using procedure C, Intermediate (2s) was converted to D-070A. Retention time using HPLC Method 2: 4.7 min. LRMS (ES pos.) m/z=490 (M+1).

2-(6-Aminopurin-9-ylmethyl)-3-(2-hydroxyphenyl)-5-methyl-3H-quinazolin-4-one (D-070B)

A mixture of D-070A (35 mg, 0.07 mmol) and Pd(OH)$_2$ (20% by wt. on C, 50 mg) in ethanol (5 mL) was shaken 24 hours under 40 psi of hydrogen gas. The catalyst was removed by filtration through a 0.22 um cellulose acetate membrane (Corning), and the filtrate was concentrated in vacuo to afford the solid product (10 mg). Retention time using HPLC Method 2: 3.6 min. LRMS (ES pos.) m/z=400 (M+1).

Compounds D-070C through D-070F were prepared according to the following scheme.

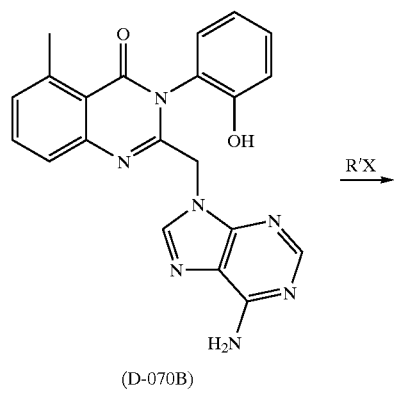

(D-070B)

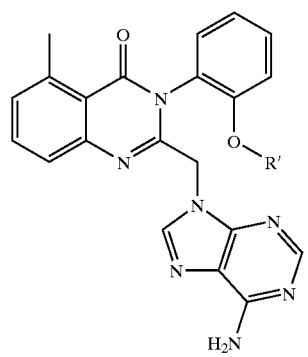

2-(6-Aminopurin-9-ylmethyl)-5-methyl-3-{2-(2-(1-methylpyrrolidin-2-yl)-ethoxy)-phenyl}-3H-quinazolin-4-one (D-070C)

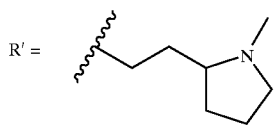

A mixture of D-070B (30 mg, 0.075 mmol), 2-(2-chloroethyl)-1-methylpyrrolidine hydrochloride (28 mg, 0.15 mmol), and potassium carbonate (50 mg, 0.36 mmol) in DMF (0.3 mL) was stirred at 80° C. for 16 hours. The solvent was removed in vacuo, then the residue was dissolved in DMSO/water (1 mL) and purified by HPLC in two portions (C18 Luna column, 4.6×250 mm, 4.7 mL/min, 2–50% acetonitrile/water over 15 min, 100% acetonitrile at 18 min, 0.05% TFA in all solvents, detector at 2201). Appropriate fractions were concentrated in vacuo, then concentrated twice from 1 N HCl (1 mL) to yield the final product as the HCl salt (10 mg). Retention time using HPLC method 1: 4.7 min. LRMS (ES pos.) m/z=511 (M+1).

2-(6-Aminopurin-9-ylmethyl)-3-(2-(3-dimethylaminopropoxy)-phenyl)-5-methyl-3H-quinazolin-4-one (D-070D)

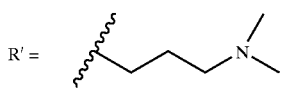

A mixture of D-070B (30 mg, 0.075 mmol), 2-chloroethyl)-1-methylpyrrolidine hydrochloride (28 mg, 0.15 mmol), and potassium carbonate (50 mg, 0.36 mmol) in DMF (0.3 mL)-was stirred at 80° C. for 16 h. The solvent was removed in vacuo, then the residue was dissolved in DMSO/water (1 mL) and purified by HPLC in two portions (C18 Luna column, 4.6×250 mm, 4.7 mL/min, 2–50% acetonitrile/water over 15 min, 100% acetonitrile at 18 min, 0.05% TFA in all solvents, detector at 2201). Appropriate fractions were concentrated in vacuo, then concentrated twice from 1 N HCl (1 mL) to yield the final product as the HCl salt (14 mg). Retention time using HPLC Method 1: 4.5 min. LRMS (ES pos.) m/z=485 (M+1).

2-(6-Aminopurin-9-ylmethyl)-5-methyl-3-(2-prop-2-ynyloxyphenyl)-3H-quinazolin-4-one (D-070E)

A mixture of D-070B (20 mg, 0.05 mmol), propargyl chloride (0.025 mL, 0.33 mmol), and potassium carbonate (14 mg, 0.1 mmol) in DMF (0.3 mL) was stirred at 80° C. for 16 hours. The reaction mixture was cooled to room temperature, treated with water (5 mL), and the resulting dark brown precipitate was collected by filtration. The crude solid was dissolved in 0.6 mL DMSO and purified by HPLC (C18 Luna column, 4.6×250 mm, 4.7 mL/min, 10–75% acetonitrile/water over 15 min, 100% acetonitrile at 18 min, detector at 2201). Appropriate fractions were concentrated in vacuo to yield the final product as a white solid (4 mg.). Retention time using HPLC Method 2: 4.1 min. LRMS (ES pos.) m/z=438 (M+1).

2-{2-(2-(6-Aminopurin-9-ylmethyl)-5-methyl-4-oxo-4H-quinazolin-3-yl)-phenoxy}-acetamide (D-070F)

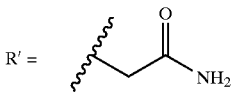

A mixture of D-070B (20 mg, 0.05 mmol), 2-chloroacetamide (14 mg, 0.15 mmol), and potassium carbonate (21 mg, 0.15 mmol) in DMF (0.3 mL) was stirred at 80° C. for 16 hours. The reaction mixture was cooled to room temperature, treated with water (5 mL), and the resulting precipitate was collected by filtration. Retention time using HPLC Method 2: 3.4 min. LRMS (ES pos.) m/z=457 (M+1).

Additional compounds of the present invention were prepared by the following synthetic procedures.

Additional compounds of the invention follow, together with the synthetic route to compounds D-071 to D-118.

Procedure D

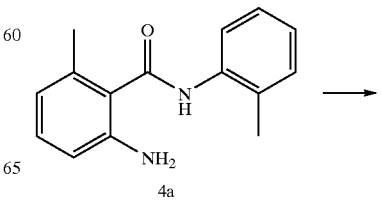

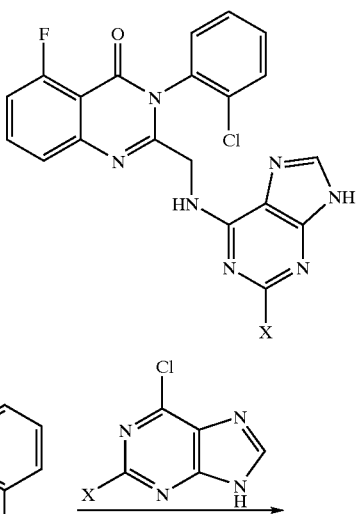
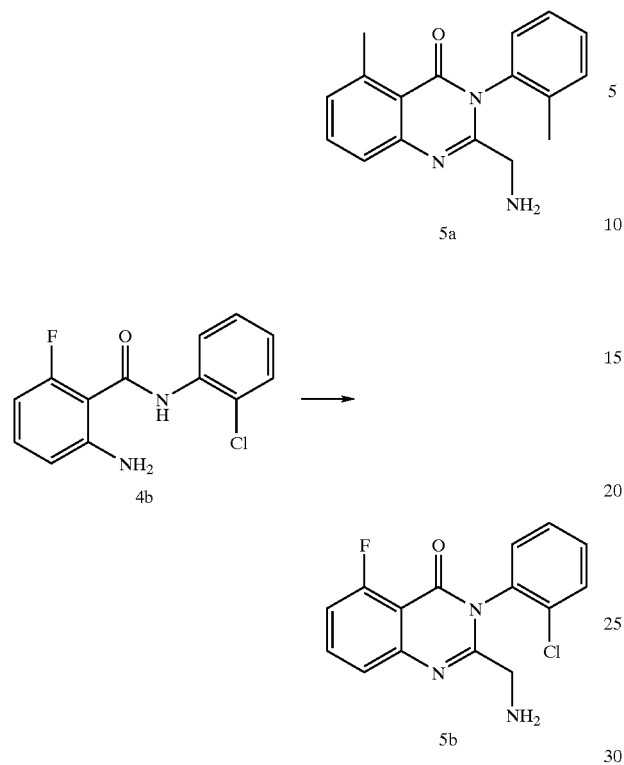
Procedure E
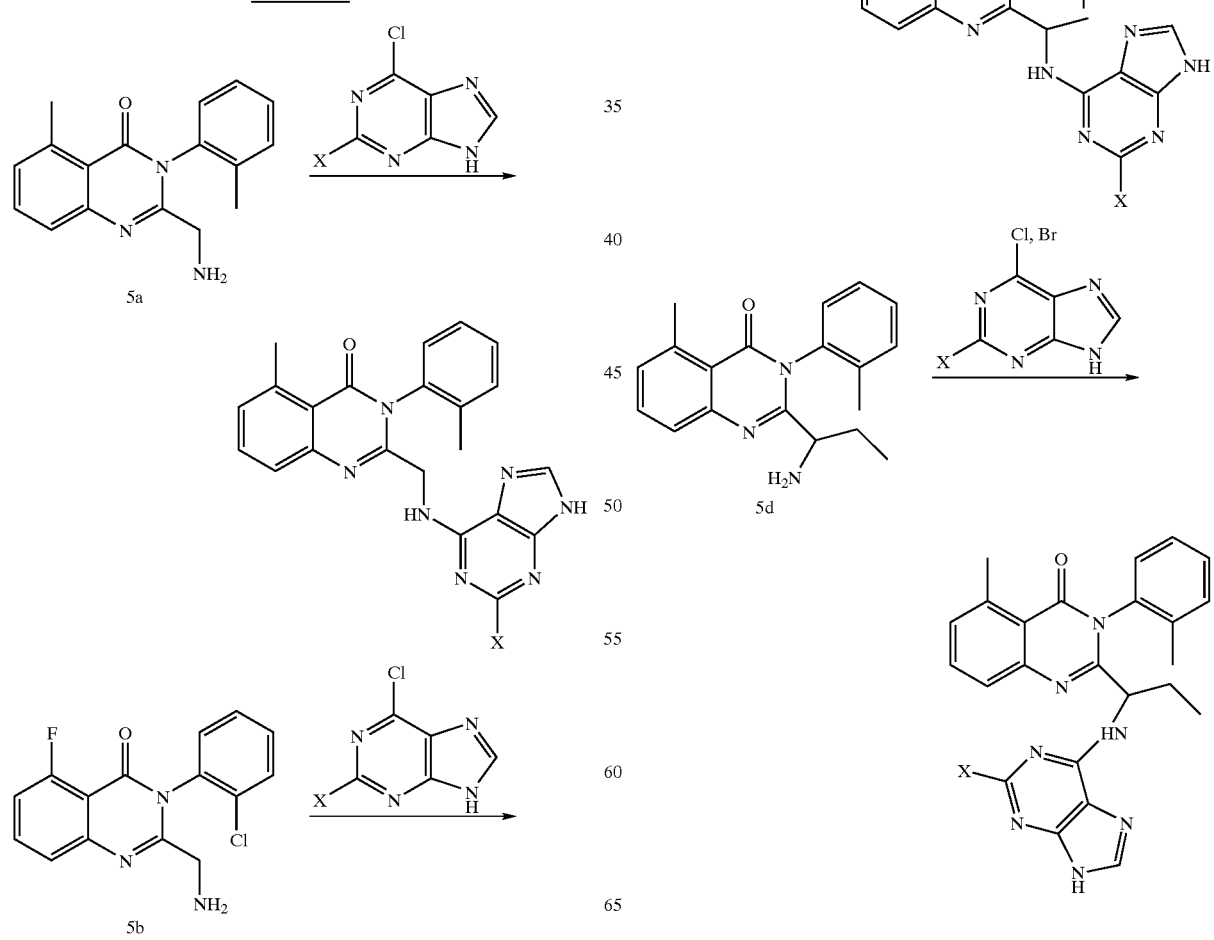

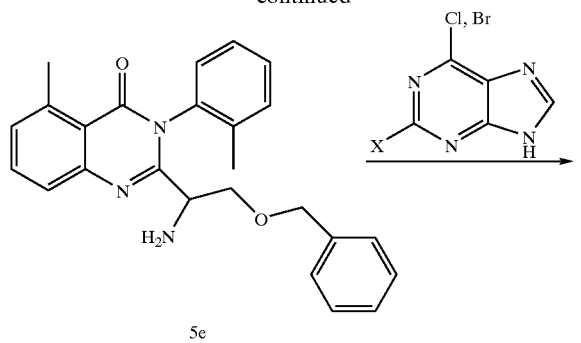

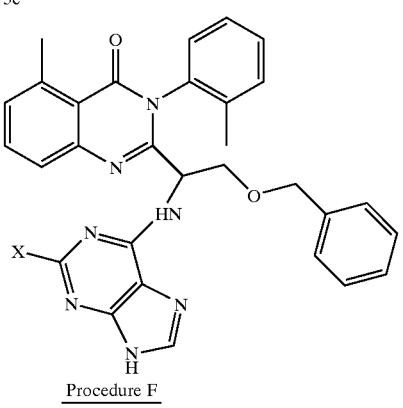

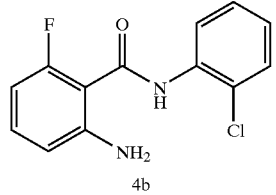

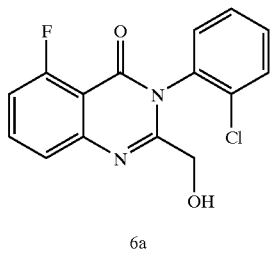

Procedure D: A mixture of amide 4a or 4b, FMOC-glycyl-chloride, and glacial acetic acid was heated to 120° C. for 1 to 4 hours. The resulting mixture was concentrated in vacuo and purified by flash chromatography to provide the protected, cyclized amine. This material was combined with 10 equivalents octanethiol and a catalytic amount of DBU in THF and stirred at ambient temp until consumption of starting material was indicated by LCMS. The reaction was poured directly onto a flash column (equilibrated in $CH_2Cl_2$) and eluted with 0–5% $MeOH/CH_2Cl_2$ to provide the free amine, 5a or 5b. Compound 5c was prepared in an analogous manner using (±) FMOC-alanyl-chloride in place of FMOC-glycyl chloride.

Procedure D1: Amide 4a was admixed with Cbz-α-aminobutyric acid OSu, DIEA, DMAP (cat.), and toluene, then stirred at reflux for 3 days. The resulting mixture was purified by flash chromatography (EtOAc/hexanes) to provide the protected, cyclized amine. The amine was dissolved in EtOH with a catalytic amount of Pd/C, and allowed to stir at ambient temperature under $H_2$ until a complete reaction was indicated by LCMS. The reaction mixture was filtered, and the filtrate concentrated in vacuo. Purification by flash chromatography ($MeOH/CH_2Cl_2$) provided the free amine 5d.

Procedure D2: Amide 4a was combined with Boc-Serine (OBn)-OSu, DIEA, DMAP (cat.), and toluene, then stirred at reflux for 4 days. The resulting mixture was purified by flash chromatography (EtOAc/hexanes) to provide the protected, cyclized amine. The product was dissolved in a mixture of TFA and $CH_2Cl_2$, and allowed to stir at ambient temperature until a complete reaction was indicated by LCMS. The reaction was concentrated in vacuo and purified by flash chromatography ($MeOH/CH_2Cl_2$) to provide free amine 5e.

Procedure E: Compounds 5(a–e), the appropriate 6-chloropurine or 6-bromopurine, and DIEA were combined with EtOH or DMF in a small vial and heated to 80° C. The reaction was monitored regularly by LCMS and purified as stated.

Procedure F: A mixture of amide 4b, acetoxyacetyl chloride, and glacial acetic acid was heated to 120° C. and stirred for 2 hours. The cooled reaction was filtered and the solids washed with $CH_2Cl_2$ to provide the cyclized acetate as a white solid. This material was combined with $K_2CO_3$ in aqueous methanol and stirred for one hour, then concentrated in vacuo. The resulting solids were triturated from $H_2O$ to provide 6a as a white solid.

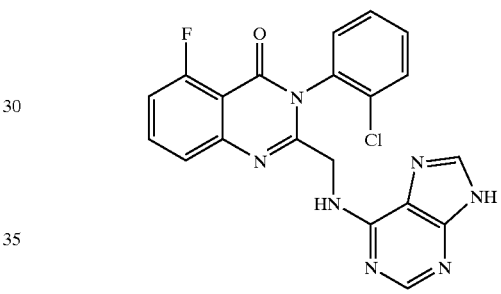

3-(2-Chlorophenyl)-5-fluoro-2-[(9H-purin-6-ylamino)-methyl]-3H-quinazolin-4-one (D-072)

Prepared according to procedure E using 5b (50 mg, 0.165 mmol) and 6-chloropurine (26 mg, 0.165 mmol) in 1 mL EtOH. After 5 days, reaction purified by HPLC (C18 Luna column, 4.6×250 mm, 4.7 mL/min, 10–75% acetonitrile/water over 15 min, 100% acetonitrile at 18 min, detector at 220λ). $^1$H NMR (DMSO-$d_6$) δ: 12.99 (br s, 1H); 8.14 (br s, 1H); 8.12 (s, 1H); 7.85 (dt, J=5.7, 8.1 Hz., 1H); 7.68–7.79 (m, 3H); 7.57 (t, J=6.2 Hz., 1H); 7.57 (d, J=7.7 Hz., 1H); 7.50 (d, J=8.1 Hz., 1H); 7.35 (dd, J=8.4, 10.7 Hz., 1H); 4.15–4.55 (m, 2H). MS (ES): m/z 422 (M+H), 211.

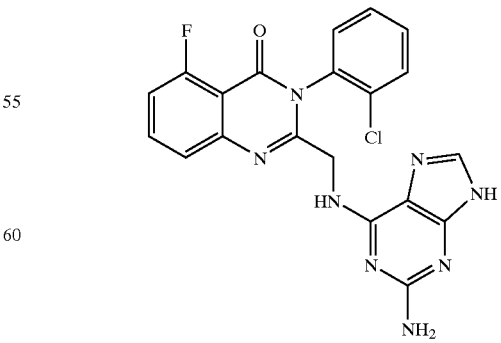

2-[(2-Amino-9H-purin-6-ylamino)methyl]-3-(2-chlorophenyl)-5-fluoro-3H-quinazolin-4-one (D-074)

Prepared according to procedure E using 5b (50 mg, 0.165 mmol) and 2-amino-6-chloropurine (28 mg, 0.165 mmol) in 1 mL EtOH. After 5 days, reaction purified by HPLC (C18 Luna column, 4.6×250 mm, 4.7 mL/min, 10–75% acetonitrile/water over 15 min, 100% acetonitrile at 18 min, detector at 220λ). $^1$H NMR (DMSO-d$_6$) δ: 12.13 (br s, 1H); 7.86 (dt, J=5.6, 8.2 Hz., 1H); 7.76–7.83 (m, 2H); 7.68 (br s, 1H); 7.61 (t, J=5.7 Hz., 1H); 7.61 (d, J=7.2 Hz., 1H); 7.53 (d, J=8.2 Hz., 1H); 7.35 (dd, J=8.2, 10.9 Hz., 1H); 5.66 (br s, 2H); 4.16–4.50 (m, 1H); 4.09 (q, J=5.3 Hz., 2H). MS (ES): m/z 437 (M+H), 219.

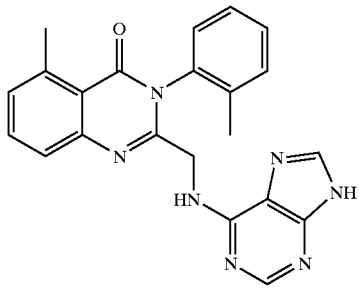

5-Methyl-2-[(9H-purin-6-ylamino)methyl]-3-o-tolyl-3H-quinazolin-4-one (D-071)

Prepared according to procedure E-using 6-chloropurine (11 mg, 0.072 mmol) and 5a (20 mg, 0.072 mmol). After 5 days, the reaction was quenched with water and the resulting suspension filtered. The solids were purified by HPLC (C18 Luna column, 4.6×250 mm, 4.7 mL/min, 10–75% acetonitrile/water over 15 min, 100% acetonitrile at 18 min, detector at 220λ). $^1$H NMR (DMSO-d$_6$) δ: 12.98 (br s, 1H); 8.14 (br s, 1H); 8.10 (s, 1H); 7.58–7.79 (m, 2H); 7.37–7.48 (m, 4H); 7.26–7.36 (m, 2H); 3.93–4.39 (m, 2H); 2.75 (s, 3H); 2.18 (s, 3H). MS (ES): m/z 398 (M+H), 199.

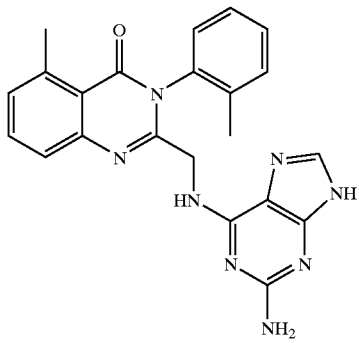

2-[(2-Amino-9H-purin-6-ylamino)methyl]-5-methyl-3-o-tolyl-3H-quinazolin-4-one (D-073)

Prepared according to procedure E using 5a (189 mg, 0.677 mmol) and 2-amino-6-chloropurine (115 mg, 0.677) in 3 mL EtOH. After 3 days, the reaction was filtered to remove excess purine and the filtrate purified by HPLC (C18 Luna column, 4.6×250 mm, 4.7 mL/min, 10–75% acetonitrile/water over 15 min, 100% acetonitrile at 18 min, detector at 220λ) to provide 7 mg of the product as the TFA salt. $^1$H NMR (DMSO-d$_6$) δ: 8.88 (br s, 1H); 8.21 (s, 1H); 7.71 (t, J=7.7 Hz, 1H); 7.45–7.56 (m, 2H); 7.38–7.44 (m, 3H); 7.35 (d, J=7.5 Hz., 1H); 7.30 (br s, 1H); 4.40 (dd, J=4.5, 17.5 Hz., 1H); 4.27 (dd, J=5.3, 17.4 Hz., 1H); 2.75 (s, 3H); 2.09 (s, 3H). MS (ES): m/z 413 (M+H), 207, 163.

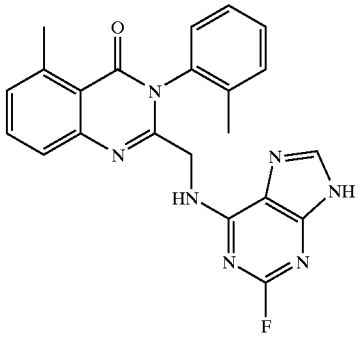

2-[(2-Fluoro-9H-purin-6-ylamino)methyl]-5-methyl-3-o-tolyl-3H-quinazolin-4-one (D-076)

Prepared according to procedure E using 5a (20 mg, 0.072 mmol) and 2-fluoro-6-chloropurine (16 mg, 0.094 mmol) in 1 mL EtOH. After 18 hours, the reaction was purified by HPLC (C18 Luna column, 4.6×250 mm, 4.7 mL/min, 10–75% acetonitrile/water over 15 min, 100% acetonitrile at 18 min, detector at 220λ) and subsequently recrystallized from EtOH to provide 14 mg of the product as a yellow solid. $^1$H NMR (DMSO-d$_6$) δ: 13.12 (br s, 1H); 8.40 (br s, 1H); 8.15 (s, 1H); 7.66 (t, J=7.7 Hz, 1H); 7.35–7.49 (m, 4H); 7.31 (d, J=7.2 Hz., 1H); 4.00–4.22 (m, 2H); 3.17 (s, 1H); 2.74 (s, 3H); 2.18 (s, 3H). MS (ES): m/z 416 (M+H), 208.

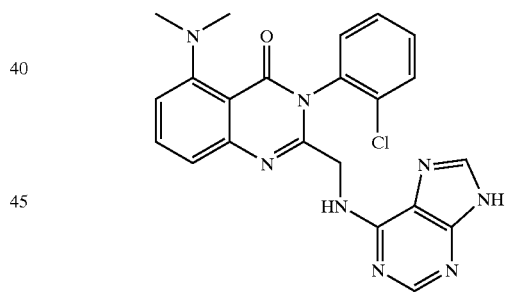

(2-Chlorophenyl)-dimethylamino-(9H-purin-6-ylsulfanylmethyl)-3H-quinazolin-4-one (D-075)

D-015 (100 mg, 0.228 mmol) was combined with ammonium hydroxide (28–30%, 1 mL) in DMF (2 mL) and heated to 80° C. After 2 days, the reaction was purified by HPLC (C18 Luna column, 4.6×250 mm, 4.7 mL/min, 10–75% acetonitrile/water over 15 min, 100% acetonitrile at 18 min, detector at 220λ) to provide the product as a yellow solid, ~2 mg. $^1$H NMR (DMSO-d$_6$) δ: 13.52 (br s, 1H); 8.46 (s, 1H); 8.42 (s, 1H); 7.69 (dd, J=2.1, 7.3 Hz, 1H); 7.62 (dd, J=1.6, 7.6 Hz., 1H); 7.61 (t, J=8.0 Hz., 1H); 7.37–7.48 (m, 2H); 7.05 (d, J=7.9 Hz., 1H); 6.96 (d, J=7.8 Hz., 1H); 4.32–4.45 (m, 2H); 2.80 (s, 6H). MS (ES): m/z 464 (M+H), 232.

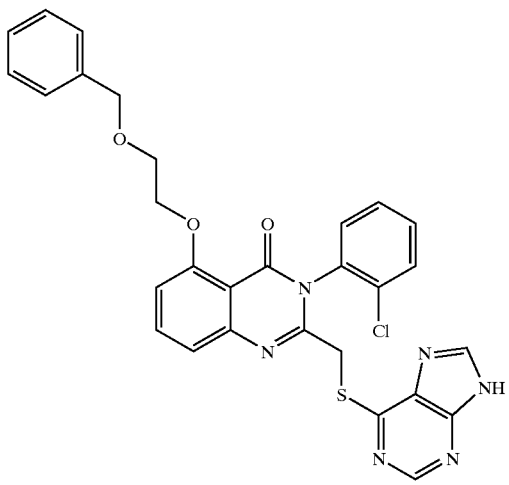

5-(2-Benzyloxyethoxy)-3-(2-chlorophenyl)-2-(9H-purin-6-ylsulfanylmethyl)-3H-quinazolin-4-one (D-078)

To a solution of 2-benzyloxyethanol (0.3 mL) in DMF (1.0 mL) was added NaH (50 mg, 2.08 mmol). After stirring for 5 minutes, 0.5 mL was added to a solution of D-015 (50 mg, 0.114 mmol) in anhydrous DMF (0.75 mL). The reaction was heated to 500° C. and stirred for 3 days. Purification by HPLC (C18 Luna column, 4.6×250 mm, 4.7 mL/min, 10–75% acetonitrile/water over 15 min, 100% acetonitrile at 18 min, detector at 220λ) provided the product as a heterogenous solid, 150 μg. MS (ES): m/z 571 (M+H), 481.

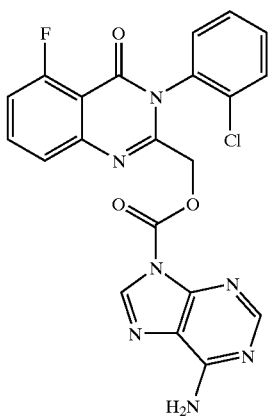

6-Aminopurine-9-carboxylic acid 3-(2-chlorophenyl)-5-fluoro-4-oxo-3,4-dihydro-quinazolin-2-ylmethyl ester (D-079)

To a solution of 3b (20 mg, 0.066 mmol) in CH$_2$Cl$_2$ (500 μL) at 0° C. was added phosgene (2M/toluene, 36 μL, 0.072 mmol), followed by adenine (10 mg, 0.072 mmol), and DIEA (25 μL, 0.145 mmol). The reaction was allowed to attain ambient temperature and stir for 8 days. Purification by HPLC (C18 Luna column, 4.6×250 mm, 4.7 mL/min, 10–75% acetonitrile/water over 15 min, 100% acetonitrile at 18 min, detector at 220λ) provided the product as a mixture. $^1$H NMR (DMSO-d$_6$) δ: 11.04 (br s, 1H); 8.61 (s, 1H); 8.40 (s, 1H); 7.85–7.95 (m, 1H); 7.76 (dd, J=5.4, 9.6 Hz, 1H); 7.70–7.78 (m, 1H); 7.52–7.63 (m, 3H); 7.38 (dt, J=8.3, 10.6 Hz., 1H); 4.76–4.89 (m, 2H). MS (ES): m/z 466 (M+H), 331, 305.

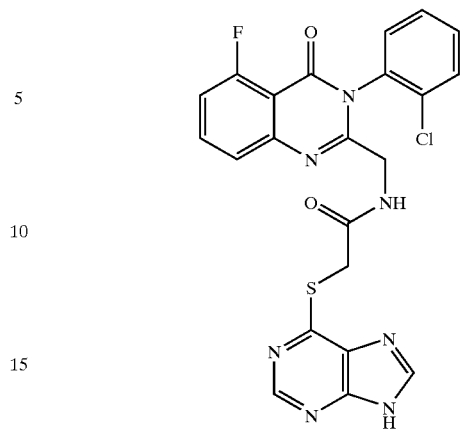

N-[3-(2-Chlorophenyl)-5-fluoro-4-oxo-3,4-dihydro-quinazolin-2-ylmethyl]-2-(9H-purin-6-ylsulfanyl)-acetamide (D-077)

(9H-Purin-6-ylsulfanyl)-acetic acid (63 mg, 0.296 mmol), 5b (108 mg, 0.355 mmol), EDC (68 mg, 0.355 mmol), HOBT (48 mg, 0.355 mmol), DIEA (62 μL, 0.355 mmol), and DMF (1 mL) were combined in a flask and stirred at ambient temperature for one hour. The reaction was diluted with EtOAc (20 mL) and washed with dilute brine (2×13 mL). The organic phase was concentrated in vacuo and chromatographed in 5% MeOH/CH$_2$Cl$_2$ to provide the 91 mg of the product as a viscous, peach foam. $^1$H NMR (DMSO-d$_6$) δ: 12.88 (br s, 1H); 8.72 (s, 1H); 8.62 (t, J=5.0 Hz, 1H); 8.49 (s, 1H); 7.88 (dt, J=5.6, 8.2 Hz, 1H); 7.73–7.78 (m, 1H); 7.67–7.72 (m, 1H); 7.57–7.65 (m, 2H); 7.38 (d, J=8.1 Hz., 1H); 7.36 (dd, J=8.3, 11.1 Hz., 1H); 4.11–4.24 (m, 2H); 3.96 (dd, J=5.0, 17.4 Hz, 1H); 3.78 (dd, J=5.2, 17.4 Hz, 1H). MS (ES): m/z 496 (M+H), 248.

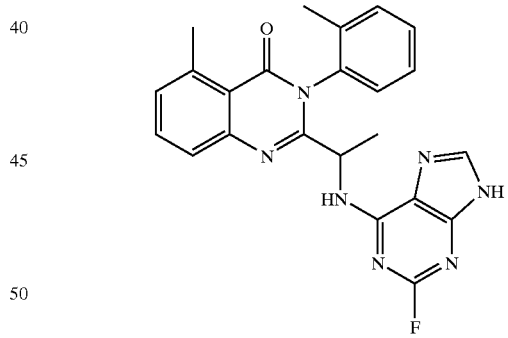

2-[1-(2-Fluoro-9H-purin-6-ylamino)ethyl]-5-methyl-3-o-tolyl-3H-quinazolin-4-one (D-080)

Prepared according to procedure E using 5c (50 mg, 0.17 mmol) and 2-fluoro-6-chloropurine (35 mg, 0.204 mmol) in 1.2 mL EtOH. Purification by HPLC (C18 Luna column, 4.6×250 mm, 4.7 mL/min, 10–75% acetonitrile/water over 15 min, 100% acetonitrile at 18 min, detector at 220λ) provided two atropisomers as white solids. Data for one of these follows: $^1$H NMR (DMSO-d$_6$) δ: 8.48 (br d, J=6.4 Hz, 1H); 8.17 (s, 1H); 7.69 (t, J=7.8 Hz, 1H); 7.53 (d, J=7.8 Hz, 1H); 7.44 (d, J=7.8 Hz, 2H); 7.33 (d, J=7.2 Hz, 2H); 7.07 (br t, J=7.2 Hz, 1H); 4.80 (br t, J=6.8 Hz, 1H); 2.74 (s, 3H); 2.09 (s, 3H); 1.38 (d, J=6.7 Hz, 3H). MS (ES): m/z 430 (M+H), 215.

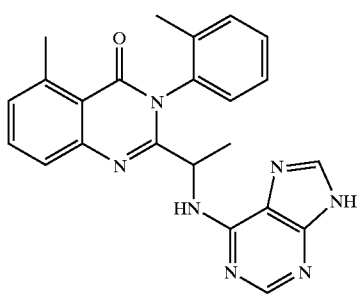

5-Methyl-2-[1-(9H-purin-6-ylamino)ethyl]-3-o-tolyl-3H-quinazolin-4-one (D-081)

Prepared according to procedure E using 5c (50 mg, 0.17 mmol) and 6-chloropurine (32 mg, 0.204 mmol) in 1.2 mL EtOH. Purification by HPLC (C18 Luna column, 4.6×250 mm, 4.7 mL/min, 10–75% acetonitrile/water over 15 min, 100% acetonitrile at 18 min, detector at 220λ) provided two atropisomers as yellow solids. Data for one of these follows: $^1$H NMR (DMSO-$d_6$) δ: 8.39 (br s, 1H); 8.34 (s, 1H); 8.18 (s, 1H); 7.71 (t, J=7.7 Hz, 1H); 7.56 (d, J=7.9 Hz, 1H); 7.49 (d, J=6.9 Hz, 1H); 7.28–7.43 (m, 3H); 7.20 (br s, 1H); 5.06 (br s, 1H); 2.73 (s, 3H); 2.04 (s, 3H); 1.51 (d, J=6.6 Hz, 3H). MS (ES): m/z 412 (M+H), 206.

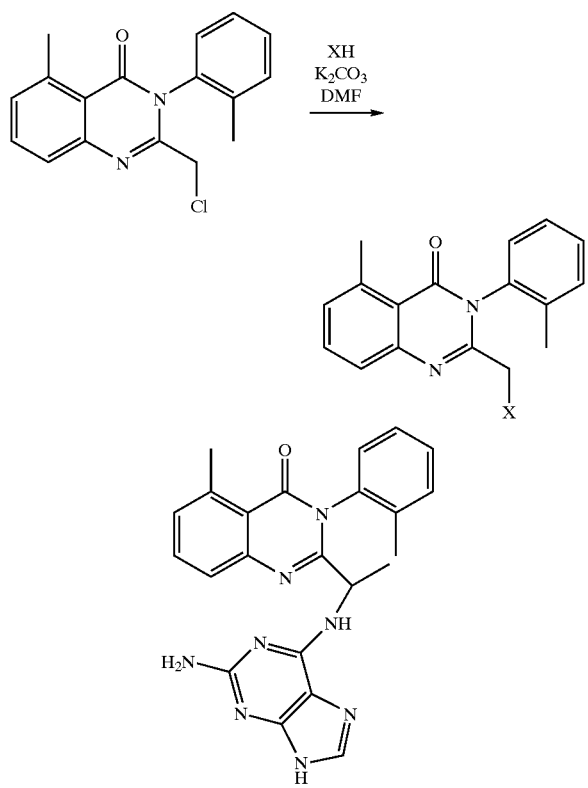

2-(1-(2-Amino-9H-purin-6-ylamino)ethyl)-5-methyl-3-o-tolyl-3H-quinazolin-4-one (D-081a)

Synthesized according to procedure E using compound 5c (61 mg, 0.209 mmol) and 2-amino-6-chloropurine (43 mg, 0.251 mmol) in 1 mL EtOH. Purification by HPLC (C18 Luna column, 4.6×250 mm, 4.7 mL/min, 10–75% acetonitrile/water over 15 min, 100% acetonitrile at 18 min, detector at 220λ) provided a white solid consisting of a mixture of two atropisomers (in brackets in nmr). $^1$H NMR (DMSO-$d_6$) δ: 8.93–9.02 (m, 1H); [8.19 (s), 8.15 (s), 1H]; [7.76 (t, J=8.1 Hz), 7.73 (t, J=7.8 Hz), 1H]; [7.64 (d, J=7.9 Hz), 7.57 (d, J=8.0 Hz), 1H]; [7.50 (d, J=7.7 Hz), 7.45 (d, J=7.8 Hz), 1H]; 7.29–7.40 (m, 3H); [7.23 (t, J=7.5 Hz), 7.15–7.22 (m), 1H]; [7.09 (t, J=7.5 Hz), 6.98 (d, J=7.3 Hz), 1H]; [5.28 (dd, J=7.2, 8.0 Hz), 4.96 (pent, J=7.0 Hz), 1H]; 2.75 (s, 3H); [2.10 (s), 1.84 (s), 3H]; [1.51 (d, J=6.6 Hz), 1.39 (d, J=6.7 Hz), 3H]. MS (ES): m/z 427 (M+H), 214.

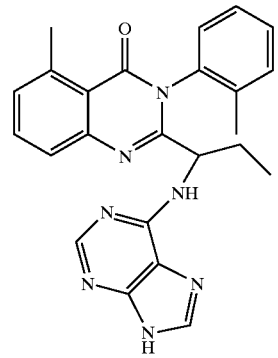

5-Methyl-2-(1-(9H-purin-6-ylamino)propyl)-3-o-tolyl-3H-quinazolin-4-one (D-081b)

Synthesized according to procedure E using compound 5d (100 mg, 0.325 mmol) and 6-bromopurine (78 mg, 0.390 mmol) in 2 mL EtOH. Purification by HPLC (C18 Luna column, 4.6×250 mm, 4.7 mL/min, 10–75% acetonitrile/water over 15 min, 100% acetonitrile at 18 min, detector at 220λ) provided two atropisomers as yellow solids. Data for one isomer follows: $^1$H NMR (DMSO-$d_6$) δ: 8.64 (br s, 1H); 8.44 (s, 1H); 8.27 (s, 1H); 7.72 (t, J=7.7 Hz, 1H); 7.56 (d, J=8.0 Hz, 1H); 7.50 (d, J=6.6 Hz, 1H); 7.34–7.44 (m, 2H); 7.35 (d, J=7.4 Hz, 1H); 7.18–7.27 (m, 1H); 4.85–5.01 (m, 1H); 2.73 (s, 3H); 2.04–2.19 (m, 1H); 1.99 (s, 3H); 1.78–1.91 (m, 1H); 0.79 (t, J=7.0 Hz, 3H). MS (ES): m/z 426 (M+H), 213.

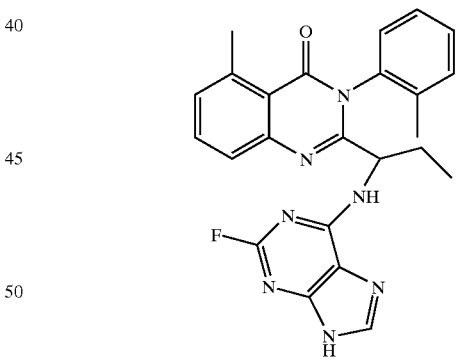

2-(1-(2-Fluoro-9H-purin-6-ylamino)propyl)-5-methyl-3-o-tolyl-3H-quinazolin-4-one (D-081c)

Synthesized according to procedure E using compound 5d (100 mg, 0.325 mmol) and 2-fluoro-6-chloropurine (78 mg, 0.455 mmol) in 2 mL EtOH. Purification by HPLC (C18 Luna column, 4.6×250 mm, 4.7 mL/min, 10–75% acetonitrile/water over 15 min, 100% acetonitrile at 18 min, detector at 220λ) provided two atropisomers as off-white solids. Data for one isomer: $^1$H NMR (DMSO-$d_6$) δ: 8.46 (br d, J=7.1 Hz, 1H); 8.20 (s, 1H); 7.71 (t, J=7.7 Hz, 1H); 7.55 (d, J=7.9 Hz, 1H); 7.45 (d, J=7.3 Hz, 1H); 7.28–7.37 (m, 3H); 7.00 (t, J=7.3 Hz, 1H); 4.66 (q, J=6.7 Hz, 1H); 2.74 (s, 3H); 2.10 (s, 3H); 1.65–1.95 (m, 2H); 0.80 (t, J=7.1 Hz, 3H). MS (ES): m/z 444 (M+H), 222.

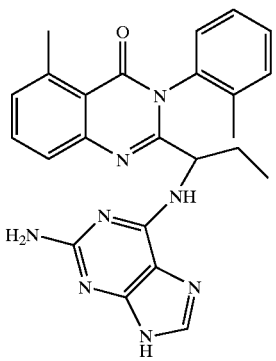

2-[1-(2-Amino-9H-purin-6-ylamino)propyl]-5-methyl-3-o-tolyl-3H-quinazolin-4-one (Compound 081d)

Synthesized according to procedure E using compound 5d (100 mg, 0.325 mmol) and 2-amino-6-bromopurine (104 mg, 0.488 mmol) in 2 mL EtOH. Purification by HPLC (C18 Luna column, 4.6×250 mm, 4.7 mL/min, 10–75% acetonitrile/water over 15 min, 100% acetonitrile at 18 min, detector at 220l) provided an off-white solid consisting of a mixture of two atropisomers (in brackets in nmr). $^1$H NMR (DMSO-d$_6$) δ: 8.89 (br d, J=7.8 Hz, 1H); [8.20 (s), 8.17 (s), 1H]; 7.75 (q, J=7.6 Hz, 1H); [7.62 (d, J=7.9 Hz); 7.57 (d, J=7.8 Hz), 1H]; 7.48 (t, J=7.3 Hz, 1H); 7.25–7.43 (m, 4H); 7.15 (br s, 1H); 7.02–7.12 (m, 1H); [5.03–5.15 (m), 4.77–4.87 (m), 1H]; 2.74 (s, 3H); [2.11 (s), 1.83 (s), 3H]; 1.65–2.19 (m, 2H); [0.83 (t, J=7.3 Hz), 0.80 (t, J=7.5 Hz), 3H]. MS (ES): m/z 441 (M+H), 221.

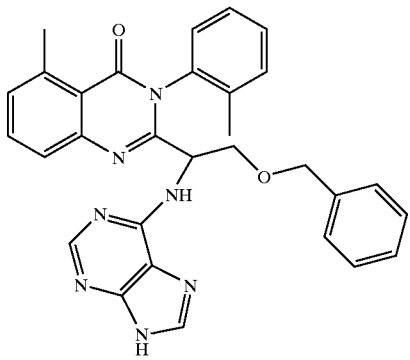

2-[2-Benzyloxy-1-(9H-purin-6-ylamino)ethyl]-5-methyl-3-o-tolyl-3H-quinazolin-4-one (D-081e)

Synthesized according to procedure E using compound 5e (212 mg, 0.413 mmol) and 6-bromopurine (107 mg, 0.537 mmol) in 2 mL EtOH. Purification by HPLC (C18 Luna column, 4.6×250 mm, 4.7 mL/min, 10–75% acetonitrile/water over 15 min, 100% acetonitrile at 18 min, detector at 220l) provided two atropisomers as brown solids. Data for one isomer: $^1$H NMR (DMSO-d$_6$) δ: 8.45–8.63 (m, 1H); 8.35–8.44 (m, 1H); 8.27 (s, 1H); 7.75 (t, J=7.7 Hz, 1H); 7.59 (d, J=7.8 Hz, 1H); 7.30–7.44 (m, 3H); 7.21–7.30 (m, 4H); 7.13–7.19 (m, 2H); 6.95–7.07 (m 1H); 5.35–5.45 (m, 1H); 5.14–5.26 (m, 1H); 4.43 (s, 2H); 3.94–4.04 (m, 1H); 3.67 (dd, J=6.0, 9.4 Hz, 1H); 2.74 (s, 3H); 2.01 (s, 3H). MS (ES): m/z 518 (M+H), 410.

The following compounds of the present invention (D-082 through D-109) were prepared as outlined in Procedure C, using 2-chloromethyl-5-methyl-3-o-tolyl-3H-quinazolin-4-one (10 mg), the appropriate nucleophile XH (20 mg, excess), and potassium carbonate (10 mg) in DMF (0.25 mL). The reaction mixture was stirred 16 h at room temperature, quenched with water, and the crude solid product was collected by filtration and air dried. The crude material was dissolved in 0.5 mL of DMSO and purified by reversed-phase HPLC (C18 Luna column, 4.6×250 mm, 4.7 mL/min, 10–75% acetonitrile/water over 15 min, 100% acetonitrile at 18 min, detector at 220λ). Appropriate fractions were concentrated in vacuo to yield the final products.

2-(6-Dimethylaminopurin-9-ylmethyl)-5-methyl-3-o-tolyl-3H-quinazolin-4-one (D-082)

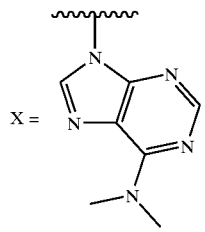

Yield: 8.1 mg. $^1$H NMR (300 MHz, d$_6$-DMSO) δ: 8.13 (s, 1H), 8.11 (s, 1H), 7.60 (t, J=7.8 Hz, 1H), 7.54–7.38 (m, 4H), 7.30 (d, J=7.4 Hz, 1H), 7.20 (d, J=8.1 Hz, 1H), 5.11 (d, J=17.4 Hz, 1H), 4.76 (d, J=17.4 Hz, 1H), 3.33 (s, 6H), 2.73 (s, 3H), 2.20 (s, 3H). LRMS (ES pos.) m/z=426 (M+1).

5-Methyl-2-(2-methyl-6-oxo-1,6-dihydro-purin-7-ylmethyl)-3-o-tolyl-3H-quinazolin-4-one (D-083)

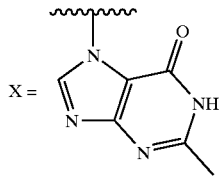

Yield: 3.3 mg. $^1$H NMR (300 MHz, d$_6$-DMSO) δ: 12.06 (s, 1H), 8.12 (s, 1H), 7.60 (t, J=7.8 Hz, 1H), 7.55–7.38 (m, 4H), 7.30 (d, J=7.4 Hz, 1H), 7.15 (d, J=7.9 Hz, 1H), 5.26 (d, J=17.4 Hz, 1H), 4.94 (d, J=17.4 Hz, 1H), 2.73 (s, 3H), 2.32 (S, 3H), 2.24 (S, 3H) Alkylation at purine N$_7$ assigned arbitrarily based on downfield shift of methylene protons due to the carbonyl group. LRMS (ES pos.) m/z=413 (M+1).

5-Methyl-2-(2-methyl-6-oxo-1,6-dihydro-purin-9-ylmethyl)-3-o-tolyl-3H-quinazolin-4-one (D-084)

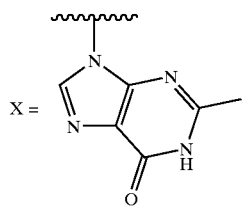

Purified from same reaction mixture as D-083. Yield: 3.6 mg. $^1$H NMR (300 MHz, d$_6$-DMSO) 12.17 (s, 1H), 7.96 (s, 1H), 7.63 (t, J=7.8 Hz, 1H), 7.57–7.39 (m, 4H), 7.32 (d, J=7.4 Hz, 1H), 7.26 (d, J=8.1 Hz, 1H), 5.08 (d, J=17.2 Hz, 1H), 4.70 (d, J=17.2 Hz, 1H), 2.73 (5, 3H), 2.27 (s, 3H), 2.17 (s, 3H). LRMS (ES pos.) m/z=413 (M+1).

2-(Amino-dimethylaminopurin-9-ylmethyl)-5-methyl-3-o-tolyl-3H-quinazolin-4-one (D-085)

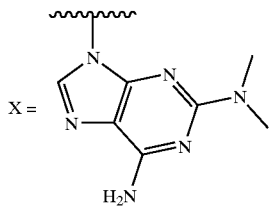

Yield: 6.7 mg. $^1$H NMR (300 MHz, d$_6$-DMSO) δ: 7.66 (s, 1H0, 7.61 (d, J=7.8 Hz, 1H), 7.55–7.40 (m, 4H), 7.32–7.26 (m, 2H), 6.74 (s, 2H), 4.94 (d, J=17.2 Hz, 1H), 4.63 (d, J=17.2 Hz, 1H), 4.63 (d, J=17.2 Hz, 1H), 2.97 (s, 6H), 2.73 (s, 3H), 2.17 (s, 3H), 2.08 (s, 3H). LRMS (ES pos.) m/z=441 (M+1).

2-(2-Amino-9H-purin-6-ylsulfanylmethyl)-5-methyl-3-o-tolyl-3H-quinazolin-4-one (D-086)

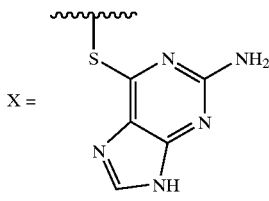

Yield: 9.5 mg. $^1$H NMR (300 MHz, d$_6$-DMSO) δ: 12.54 (s, 1H), 7.89 (s, 1H), 7.69 (t, J=7.8 Hz, 1H), 7.51 (d, J=8.0 Hz, 1H), 7.51 (d, J=8.0 Hz, 1H), 7.43 (t, J=3.9 Hz, 1H), 7.34–7.26 (m, 4H), 6.16 (s, 2H), 4.32 (AB quartet, J$_{AB}$=14.8 Hz, Δn=23.7), 2.74 (s, 3H), 2.09 (s, 3H). LRMS (ES pos.) m/z=430 (M+1).

2-(4-Amino-1,3,5-triazin-2-ylsulfanylmethyl)-5-methyl-3-o-tolyl-3H-quinazolin-4-one (D-087)

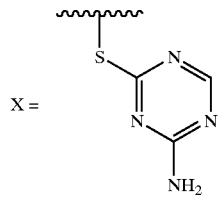

Yield: 5.8 mg. $^1$H NMR (300 MHz, d$_6$-DMSO) δ: 8.10 (s, 1H), 7.70 (t, J=7.8 Hz, 1H), 7.58 (s, 1H), 7.52 (d, J=8.0 Hz, 1H), 7.48–7.26 (m, 6H), 4.08 (s, 2H), 2.73 (s, 3H), 2.09 (s, 3H). LRMS (ES pos.) m/z=391 (M+1).

5-Methyl-2-(7-methyl-7H-purin-6-ylsulfanylmethyl)-3-o-tolyl-3H-quinazolin-4-one (D-088)

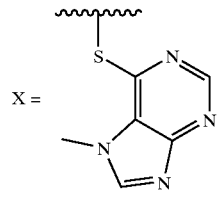

Yield: 3.1 mg. $^1$H NMR (300 MHz, d$_6$-DMSO) δ: 8.52 (s, 1H), 8.49 (s, 1H), 7.70 (t, J=7.8 Hz, 1H), 7.50 (d, J=7.8 Hz, 1H), 7.45 (d, J=7.1 Hz, 1H), 7.35–7.20 (m, 4H), 4.41 (AB quartet, J$_{AB}$=15.3 Hz, Δv=19.2 Hz), 4.08 (s, 3H), 2.73 (s, 3H), 2.12 (s, 3H). LRMS (ES pos.) m/z=406 (M+1).

5-Methyl-2-(2-oxo-1,2-dihydro-pyrimidin-4-ylsulfanylmethyl)-3-o-tolyl-3H-quinazolin-4-one (D-089)

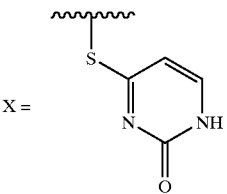

Yield: 2.4 mg. $^1$H NMR (300 MHz, d$_6$-DMSO) δ: 11.49 (s, 1H), 7.70 (t, J=7.8 Hz, 1H), 7.60 (brt, J=6.0 Hz, 1H), 7.53–7.48 (m, 2H), 7.46–7.28 (m, 4H), 6.31 (d, J=6.7 Hz, 1H), 4.05 (s, 2H), 2.73 (s, 3H), 2.12 (s, 3H). LRMS (ES pos.) m/z=391 (M+1).

5-Methyl-2-purin-7-ylmethyl-3-o-tolyl-3H-quinazolin-4-one (D-090)

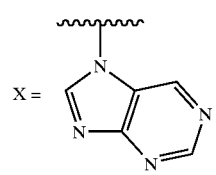

$^1$H NMR (300 MHz, d$_6$-DMSO) δ: 9.04 (s, 1H), 8.97 (s, 1H), 8.48 (s, 1H), 7.65–7.54 (m, 2H), 7.53–7.39 (m, 3H), 7.31 (d, J=7.4 Hz, 1H), 7.13 (d, J=8.0 Hz, 1H), 5.31 (d, J=17.6 Hz, 1H), 5.16 (d, J=17.6 Hz, 1H), 2.73 (s, 3H), 2.09 (s, 3H). Alkylation at purine N7 was determined by NOE enhancement between the purine 6-position proton and methylene protons on the linker between the purine and quinazolinone groups. LRMS (ES pos.) m/z=383 (M+1).

5-Methyl-2-purin-9-ylmethyl-3-o-tolyl-3H-quinazolin-4-one (D-091)

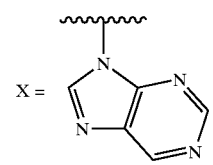

From same reaction that produced D-090. $^1$H NMR (300 MHz, d$_6$-DMSO) δ: 9.17 (s, 1H), 8.86 (s, 1H), 8.55 (s, 1H), 7.59 (t, J=7.8 Hz, 1H), 7.55–7.42 (m, 4H), 7.30 (d, J=7.4 Hz, 1H), 7.13 (d, J=8.0 Hz, 1H), 5.26 (d, J=17.5 Hz, 1H), 4.92 (d, J=17.5 Hz, 1H), 2.73 (s, 3H), 2.19 (s, 3H). Alkylation at purine N9 suggested by the lack of NOE enhancement between purine 6-position protons and the linker methylene protons. LRMS (ES pos.) m/z=383 (M+1).

5-Methyl-2-(9-methyl-9H-purin-6-ylsulfanylmethyl)-3-o-tolyl-3H-quinazolin-4-one (D-092)

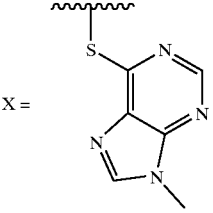

$^1$H NMR (300 MHz, d$_6$-DMSO) δ: 8.52 (s, 1H), 8.42 (s, 1H), 7.69 (t, J=7.7 Hz, 1H), 7.50 (d, J=8.0 Hz, 1H), 7.44 (d,

J=7.6 Hz, 1H), 7.36–7.27 (m, 4H), 4.38 (AB quartet, $J_{AB}$=15.5 Hz, Δv=21.0 Hz), 3.80 (s, 3H), 2.73 (s, 3H), 2.12 (s, 3H). LRMS (ES pos.) m/z=429 (M+1).

2-(2,6-Diamino-pyrimidin-4-ylsulfanylmethyl)-5-methyl-3-o-tolyl-3H-quinazolin-4-one (D-093)

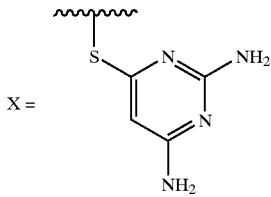

¹H NMR (300 MHz, d₆-DMSO) δ: 7.70 (t, J=7.7 Hz, 1H), 7.54 (d, J=8.0 Hz, 1H), 7.45–7.27 (m, 5H), 6.22 (br s, 1H), 5.80 (br s, 1H), 3.99 (AB quartet, $J_{AB}$=14.6 Hz, Δv=26.9 Hz, 2H), 2.73 (s, 3H), 2.08 (s, 3H). LRMS (ES pos.) m/z=405 (M+1).

5-Methyl-2-(5-methyl-[1,2,4]triazolo[1,5-a]pyrimidin-7-ylsulfanylmethyl)-3-o-tolyl-3H-quinazolin-4-one (D-094)

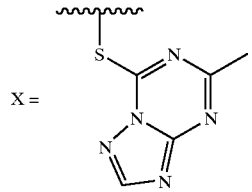

¹H NMR (300 MHz, d₆-DMSO) δ: 8.57 (s, 1H), 7.73 (t, J=7.8 Hz, 1H), 7.55–7.35 (m, 4H), 7.18 (s, 1H), 4.27 (s, 2H), 2.74 (s, 3H0, 2.55 (s, 3H), 2.08 (s, 3H). LRMS (ES pos.) m/z=429 (M+1).

5-Methyl-2-(2-methylsulfanyl-9H-purin-6-ylsulfanylmethyl)-3-o-tolyl-3H-quinazolin-4-one (D-095)

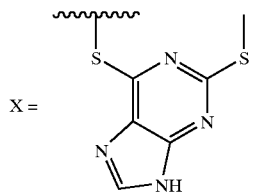

¹H NMR (300 MHz, d₆-DMSO) δ: 13.30 (s, 1H), 8.29 (s, 1H), 7.72 (t, J=7.8 Hz, 1H), 7.54 (d, J=7.8 Hz, 1H), 7.47 9d, J=6.3 Hz, 1H), 7.38–7.26 (m, 4H), 4.34 (AB quartet, $J_{AB}$=16.1 Hz, Δv=23.6 Hz, 2H), 2.74 (s, 3H), 2.32 (s, 3H), 2.10 (s, 3H). LRMS (ES pos.) m/z=461 (M+1).

2-(2-Hydroxy-9H-purin-6-ylsulfanylmethyl)-5-methyl-3-o-tolyl-3H-quinazolin-4-one (D-096)

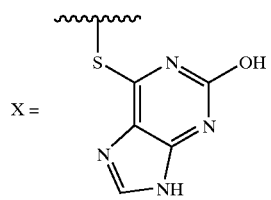

¹H NMR (300 MHz, d₆-DMSO) δ: 8.08 (s, 1H), 7.69 (t, J=7.8 Hz, 1H), 7.50 (brd, J=t.8 Hz, 2H), 7.33–7.50 (m, 4H), 4.28 (AB quartet, $J_{AB}$=15.5 Hz, Δv=21.3 Hz, 2H), 2.74 (s, 3H), 2.12 (s, 3H). LRMS (ES pos.) m/z=431 (M+1).

5-Methyl-2-(1-methyl-1H-imidazol-2-ylsulfanylmethyl)-3-o-tolyl-3H-quinazolin-4-one (D-097)

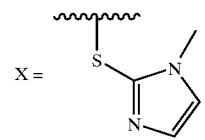

¹H NMR (300 MHz, d₆-DMSO) δ: 7.69 t, J=7.8 Hz, 1H), 7.46–7.37 (m, 5H), 7.32 (d, J=7.3 Hz, 1H), 7.20 (d, J=1.0 Hz, 1H), 6.48 (d, J=1.0 Hz), 3.83 (AB quartet, $J_{AB}$=15.0 Hz, Δv=18.8 Hz, 1H), 3.55 (s, 3H), 2.73 (s, 3H), 2.09 (s, 3H). LRMS (ES pos.) m/z=364 (M+1).

5-Methyl-3-o-tolyl-2-(1H-[1,2,4]triazol-3-ylsulfanylmethyl)-3H-quinazolin-4-one (D-098)

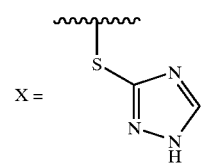

¹H NMR (300 MHz, d₆-DMSO) δ: 13.98 (s, 1H), 8.47 (s, 1H), 7.70 (t, J=7.8 Hz, 1H), 7.49 (d, J=7.9 Hz, 1H), 7.44–7.31 (m, 5H), 4.04 (AB quartet, $J_{AB}$=15.5 Hz, Δv=19.1 Hz, 1H), 2.74 (s, 3H), 2.10 (s, 3H). LRMS (ES pos.) m/z=364 (M+1).

2-(2-Amino-6-chloro-purin-9-ylmethyl)-5-methyl-3-o-tolyl-3H-quinazolin-4-one (D-099)

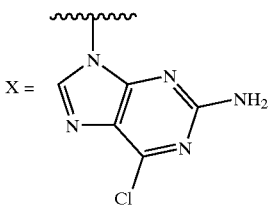

LRMS (ES pos.) 432 (M+1).

2-(6-Aminopurin-7-ylmethyl)-5-methyl-3-o-tolyl-3H-quinazolin-4-one (D-100)

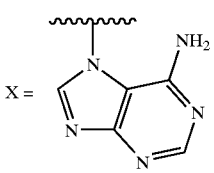

¹H NMR (300 MHz, d₆-DMSO) δ: 8.19 (s, 3H), 7.66 (t, J=7.8 Hz, 1H), 7.59–7.43 (m, 5H), 7.34 9d, J=7.4 Hz, 1H), 7.23 (d, J=8.0 Hz, 1H), 6.90 (s, 2H), 5.21 (AB quartet, $J_{AB}$=17.4 Hz, Δv=22.1 Hz, 2H), 2.72 (s, 3H), 1.93 (s, 3H). Alkylation at purine N7 was confirmed by NOE enhancements between the following protons: 1) Exocyclic amine and methylene protons; 2) Exocyclic amine and toluyl methyl protons. LRMS (ES pos.) m/z=398 (M+1)

2-(7-Amino-1,2,3-triazolo[4,5-d]pyrimidin-3-ylmethyl)-5-methyl-3-o-tolyl-3H-quinazolin-4-one (D-101)

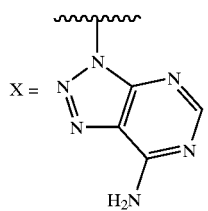

$^1$H NMR (300 MHz, d$_6$-DMSO) δ: 8.43 (br s, 1H), 8.19 (s, 1H), 8.10 (br s, 1H), 7.62 (t, J=7.8 Hz, 1H), 7.49–7.28 (m, 5H), 7.22 (d, J=8.1 Hz, 1H), 5.49 (d, J=17.0 Hz, 1H), 5.19 (d, J=17.0 Hz, 1H), 2.73 (s, 3H), 2.11 (s, 3H). Alkylation at purine N7 determined by similarity to nmr spectrum of D-030. LRMS (ES pos.) m/z=399 (M+1).

2-(7-Amino-1,2,3-triazolo[4,5-d]pyrimidin-1-ylmethyl)-5-methyl-3-o-tolyl-3H-quinazolin-4-one (D-102)

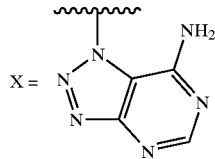

From same reaction mixture as D-101. $^1$H NMR (300 MHz, d$_6$-DMSO) δ: 8.27 (s, 1H), 8.20 (br s, 1H), 8.05 (br s, 1H), 7.70 (t, J=7.8 Hz, 1H), 7.47–7.26 (m, 6H), 5.61 (AB quartet, J$_{AB}$=16.0 Hz, Δν=20.7 Hz, 2H), 2.75 (s, 3H), 1.98 (s, 3H)). Alkylation at purine N7 determined by similarity to nmr spectrum of D-100. LRMS (ES pos.) m/z=399 (M+1).

2-(6-Amino-9H-purin-2-ylsulfanylmethyl)-5-methyl-3-o-tolyl-3H-quinazolin-4-one (D-103)

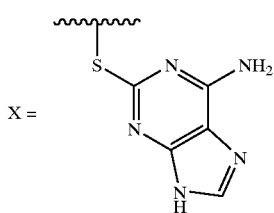

$^1$H NMR (300 MHz, d$_6$-DMSO) δ: 12.62 (s, 1H), 7.93 (s, 1H), 7.69 (t, J=7.7 Hz, 1H), 7.51 (d, J=8.1 Hz, 1H), 7.42 (dd, J=7.6, 1.7 Hz, 1H), 7.35–7.15 (m, 6H), 4.12 (AB quartet, J$_{AB}$=14.5 Hz, Δν=18.2 Hz, 2H), 2.73 (s, 3H), 2.10 (s, 3H). LRMS (ES pos.) m/z=430 (M+1).

2-(2-Amino-6-ethylamino-pyrimidin-4-ylsulfanylmethyl)-5-methyl-3-o-tolyl-3H-quinazolin-4-one (D-104)

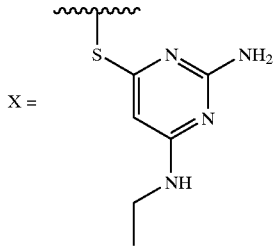

$^1$H NMR (300 MHz, d$_6$-DMSO) δ: 7.70 (T, J=7.8 Hz, 1H), 7.53 (d, J=8.0 Hz, 1H), 7.44–7.31 (m, 5H), 6.69 (br s, 1H), 5.83, (br s, 2H), 5.61 (s, 1H), 4.03 (d, J=14.6 Hz, 1H), 3.95 (d, J=14.6 Hz, 1H), 3.22–3.11 (m, 2H), 2.73 (s, 3H), 2.08 (s, 3H), 1.06 (t, J=7.1 Hz, 3H). LRMS (ES pos.) m/z=433 (M+1).

2-(3-Amino-5-methylsulfanyl-1,2,4-triazol-1-ylmethyl)-5-methyl-3-o-tolyl-3H-quinazolin-4-one (D-105)

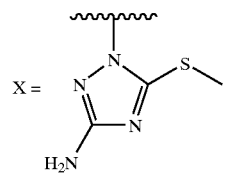

Yield: 5.0 mg. $^1$H NMR (300 MHz, d$_4$-MeOH) δ: 7.67 (t, J=7.8 Hz, 1H), 7.55–7.37 (m, 4H), 7.35–7.27 (m, 2H), 4.77 (d, J=17.1 Hz, 1H), 4.60 (d, J=17.1 Hz, 1H), 2.80 (s, 3H), 2.43 (s, 3H), 2.14 (s, 3H). LRMS (ES pos.) m/z=393 (M+1).

2-(5-Amino-3-methylsulfanyl-1,2,4-triazol-1-ylmethyl)-5-methyl-3-o-tolyl-3H-quinazolin-4-one (D-106)

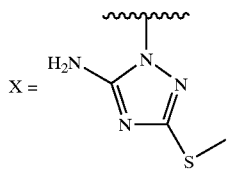

Yield: 0.6 mg. Purified from same reaction mixture as D-105. $^1$H NMR (300 MHz, d$_4$-MeOH) δ: 7.67 (t, J=7.8 Hz, 1H), 7.50–7.24 (m, 6H), 4.83 (d, J=16.5 Hz, 1H), 4.70 (d, J=16.5 Hz, 1H), 2.79 (s, 3H), 2.47 (s, 3H), 2.14 (s, 3H). LRMS (ES pos.) m/z=393 (M+1).

5-Methyl-2-(6-methylaminopurin-9-ylmethyl)-3-o-tolyl-3H-quinazolin-4-one (D-107)

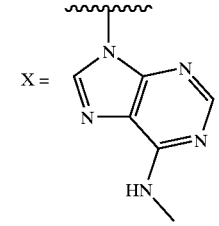

Yield: 5.0 mg $^1$H NMR (300 MHz, d$_4$-MeOH) δ: 8.17 (s, 1H), 8.03 (s, 1H), 7.54–7.43 (m 4H), 7.31–7.23 (m, 2H), 5.14 (d, J=17.5 Hz, 1H), 4.90 (d, J=17.5 Hz, 1H), 3.14 (br s, 3H), 2.79 (s, 3H), 2.22 (s, 3H). LRMS (ES pos.) m/z=412 (M+1).

2-(6-Benzylaminopurin-9-ylmethyl)-5-methyl-3-o-tolyl-3H-quinazolin-4-one (D-108)

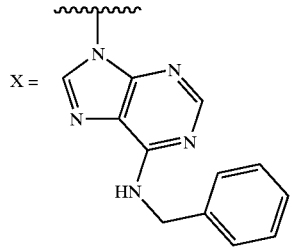

Yield: 6.7 mg. $^1$H NMR (300 MHz, d$_4$-MeOH) δ: 8.13 (s, 1H), 8.04 (s, 1H), 7.58 (t, J=7.8 Hz, 1H), 7.51–7.21 (m, 11H), 5.15 (d, J=17.5 Hz, 1H), 4.91 (d, J=17.5 Hz, 1H), 4.83 (s, 2H, under H₂O Peak), 2.79 (s, 3H), 2.22 (s, 3H). LRMS (ES pos.) m/z=488 (M+1).

2-(2,6-Diaminopurin-9-ylmethyl)-5-methyl-3-o-tolyl-3H-quinazolin-4-one (D-109)

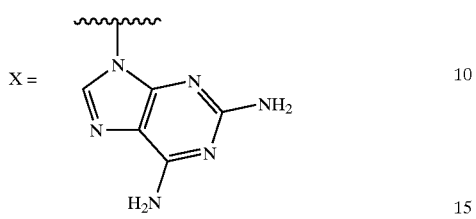

Doubled the amounts of all reactants. Yield: 14 mg. ¹H NMR (300 MHz, d₆-DMSO) δ: 8.53 (br s, 2H), 8.01 (s, 1H), 7.64 (t, J=7.8 Hz, 1H), 7.53–7.40 (m, 4H), 7.33 (d, J=7.4 Hz, 1H), 7.27 9d, J=7.9 Hz, 1H), 4.96 (d, J=17.5 Hz, 1H), 4.64 (d, J=17.5 Hz, 1H), 2.74 (s, 3H), 2.17. (s, 3H). LRMS (ES pos.) m/z=413 (M+1).

Compounds D-110 through D-115 of the following general structure were prepared from the following Intermediates E-1 through E-3.

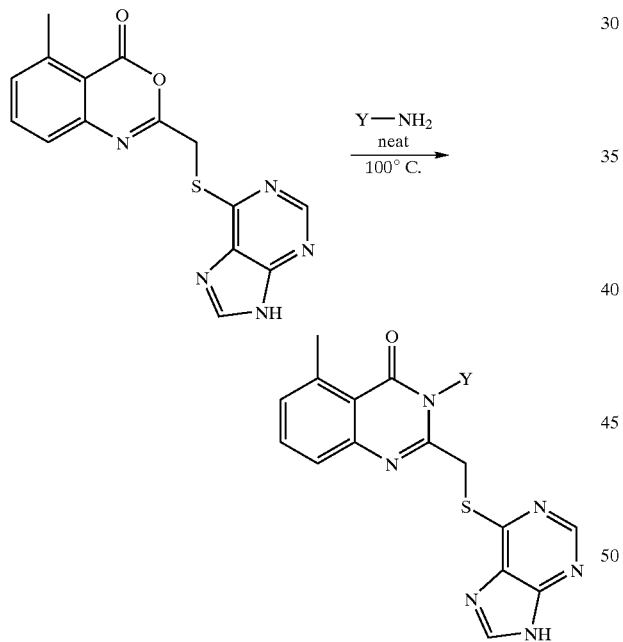

Intermediate E-1.

5-Methyl-2-(9H-purin-6-ylsulfanylmethyl)-3,1-benzoxazin-4-one

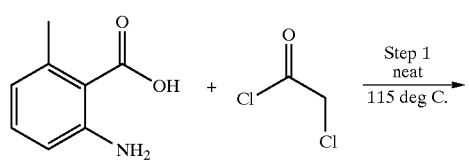

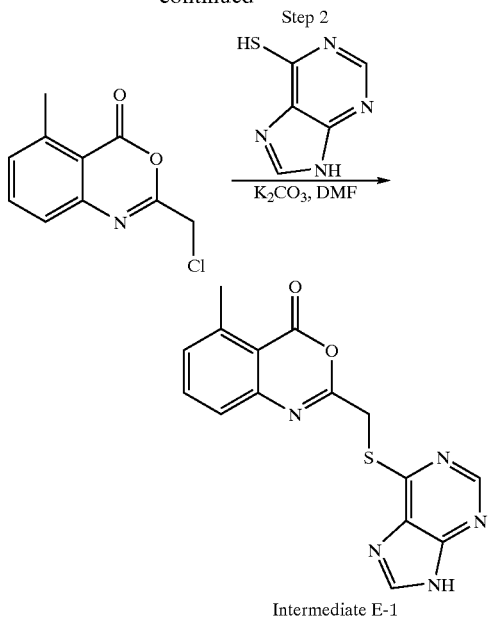

Intermediate E-1

Step 1. A suspension of 6-methylanthranilic acid (2 g, 13.2 mmol) in chloroacetyl chloride (12 mL, large excess) was stirred at 115° C. in a sealed vial for 30 min. The resulting solution was cooled to room temperature and treated with ether (~5 mL). After cooling at 4° C. overnight, the resulting tan precipitate was collected by filtration, washed with ether, and dried in vacuo to yield the chloro intermediate (1.39 g, 50%). ¹H NMR (300 MHz, CDCl₃) δ: 7.67 (t, J=7.8 Hz, 1H), 7.46 (d, J=7.9 Hz, 1H), 7.35 (d, J=7.6 Hz, 1H), 4.39 (s, 2H), 2.81 (s, 3H). LRMS (ES pos.) m/z=210, (M+1).

Step 2. A mixture of the chloro intermediate (50 mg, 0.25 mmol), 6-mercaptopurine monohydrate (43 mg, 0.25 mmol), and potassium carbonate (25 mg, 0.25 mmol) in dry DMF (0.5 mL) was stirred at room temperature for 30 min. The mixture was poured into ethyl acetate (20 mL) and all insoluble material was filtered off and discarded. The filtrate was concentrated in vacuo to remove all ethyl acetate, and the residue was treated with ether, resulting in a light orange precipitate. The precipitate was collected by filtration, washed with ether, and dried in vacuo to afford Intermediate E-1 (41 mg, 51%). ¹H NMR (300 MHz, d₆-DMSO) δ: 8.64 (s, 1H), 8.39 (s, 1H), 7.73 (t, J=7.8 Hz, 1H), 7.44–7.37 (m, 2H), 4.69 (s, 2H), 2.69 (s, 3H). LRMS (ES pos.) m/z=326 (M+1).

Intermediate E-2

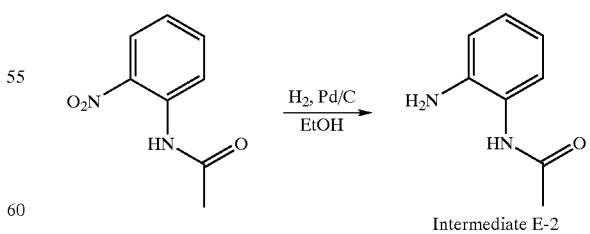

Intermediate E-2

A solution of 2-nitroacetanilide (1.0 g, 5.6 mmol) in EtOH was purged with nitrogen, treated with Pd(OH)₂ (20% by wt. on C, 200 mg, cat.), and shaken for 2 h under H₂ (20 psi). The catalyst was removed by filtration through a 0.22 um cellulose acetate membrane (Corning), and the filtrate was concentrated in vacuo to afford the white crystalline solid product (800 mg, 96%). ¹H NMR (300 MHz, d₆-DMSO) δ: 9.12 (s, 1H), 7.14 (dd, J=7.8, 1.3 Hz, 1H), 6.88 (dt, J=7.6, 1.5 Hz, 1H), 6.70 (dd, J=8.0, 1.3 Hz, 1H), 6.52 (dt, J=7.5, 1.4 Hz, 1H), 4.85 (br s, 2H), 2.03 (s, 3H). LRMS (ES pos.) m/z=151 (M+1).

Intermediate E-3

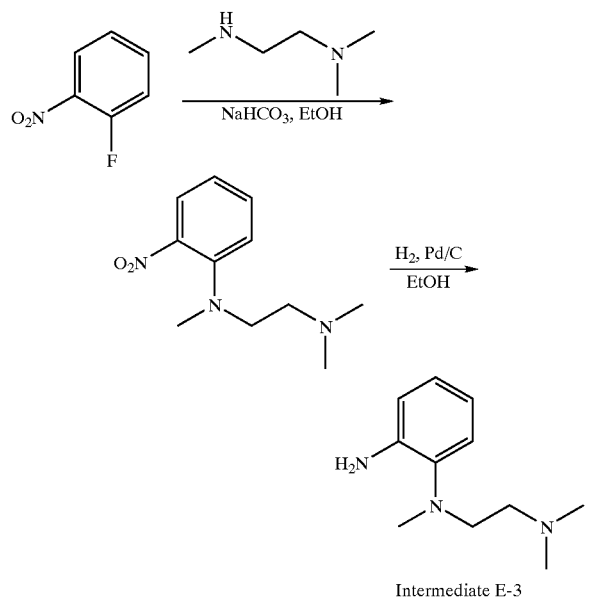

Intermediate E-3

A mixture of 2-fluoro-nitrobenzene (1.41 g, 10 mmol) and NaHCO₃ in EtOH (20 mL) was treated with (N,N,N'-trimethyl)-1,2-diaminoethane (1.1 g, 11 mmol) and was stirred 16 h at 80° C. Solvent was removed in vacuo, residue was treated with 0.1 M NaOH (120 mL), and the mixture was extracted with ethyl acetate (2×50 mL). The organic layers were combined and washed with 20 mL of water (1×) and brine (2×), dried with sodium sulfate, and concentrated in vacuo to an orange liquid (2.2 g, 100%; ESMS: m/z=224, M+1).

This intermediate was dissolved in EtOH, the solution was purged with nitrogen, treated with Pd(OH)₂ (20% by wt. on C, 180 mg, cat.), and shaken for 2 h under H₂ (50 psi). The catalyst was removed by filtration through a 0.22 um cellulose acetate membrane (Corning), and the filtrate was concentrated in vacuo to afford the red liquid product E-3 (1.8 g, 95%). ¹H NMR (300 MHz, CDCl₃) δ: 8.64 (s, 1H), 7.03 (dd, J=8.3, 1.4 Hz, 1H), 6.91 (ddd, J=7.6, 7.2, 1.4 Hz, 1H), 6.73–6.67 (m, 2H), 4.20 (br s, 2H), 2.95 (t, J=6.7 Hz, 2H), 2.68 (s, 3H), 2.41 (t, J=6.7 Hz, 1H), 2.26 (s, 6H). LRMS (ES pos.) m/z=194 (M+1).

Compounds D-110 through D-115 were prepared as follows:

5-Methyl-2-(9H-purin-6-ylsulfanylmethyl)-3-o-tolyl-3H-quinazolin-4-one (D-110)

Y = 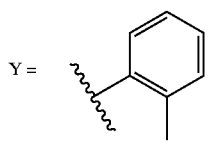

A mixture of Intermediate E-1 (40 mg) and o-toluidine (0.3 mL, large excess) was warmed at 100° C. in a sealed vial for 16 h. The reaction mixture was cooled, treated with 1N HCl (2 mL) and ether (2 mL), and the resulting gray precipitate was collected by filtration, washed with ether, and air dried (19 mg crude). The crude solid was dissolved in 0.5 mL DMSO and purified by HPLC (C18 Luna column, 4.6×250 mm, 4.7 mL/min, 10–75% acetonitrile/water over 15 min, 100% acetonitrile at 18 min, detector at 220×). Appropriate fractions were concentrated in vacuo to yield the final product as a white solid (4 mg). ¹H NMR (300 MHz, d₆-DMSO) δ: 13.52 (s, 1H), 8.47 (s, 1H), 8.43 (s, 1H), 7.69 (t, J=7.8 Hz, 1H), 7.50 (d, J=7.9 Hz, 1H), 7.46–7/43 (m, 1H), 7.37–7.25 (m, 4H), 4.37 (AB quartet, J_{AB}=15.4 Hz, Δv=22.4 Hz, 2H), 2.74 (5, 3H), 2.12 (5, 3H). LRMS (ES pos.) m/z=415 (M+1).

3-Isobutyl-5-methyl-2-(9H-purin-6-ylsulfanylmethyl)-3H-quinazolin-4-one (D-111)

Y = 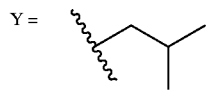

A mixture of Intermediate E-1 (40 mg) and isobutylamine (0.4 mL, large excess) was warmed at 120° C. in a sealed vial for 16 h. Excess isobutylamine was allowed to evaporate, residue was dissolved in 1 mL DMSO and purified in two portions by HPLC (C18 Luna column, 4.6×250 mm, 4.7 mL/min, 10–75% acetonitrile/water over 15 min, 100% acetonitrile at 18 min, detector at 220λ). Appropriate fractions were concentrated in vacuo to yield the final product as a white solid (4 mg). ¹H NMR (300 MHz, d₆-DMSO) δ: 13.75 (br s, 1H), 8.73 (s, 1H), 8.50 (s, 1H), 7.63 (t, J=7.7 Hz, 1H), 7.42 (d, J=8.0 Hz, 1H), 7.28 (d, J=7.3 Hz, 1H), 4.96 (s, 2H), 4.00 (d, J=7.5 Hz, 2H), 2.77 (s, 3H), 2.30–2.15 (m, 1H), 0.98 (d, J=6.7 Hz, 1H). LRMS (ES pos.) m/z=381 (M+1).

N-{2-[5-Methyl-4-oxo-2-(9H-purin-6-ylsulfanylmethyl)-4H-quinazolin-3-yl]-phenyl}-acetamide (D-112)

Y = 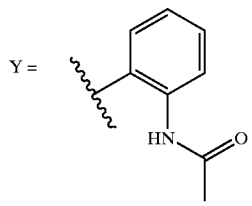

A mixture of Intermediate E-1 (80 mg, 0.25 mmol) and Intermediate E-2 (75 mg, 0.5 mmol, 2 eq) was warmed until melted in a sealed vial using a heat gun. The reaction mixture was triturated with ether and the solids were collected by filtration. The crude material was dissolved in 1 mL DMSO and purified in two portions by HPLC (C18 Luna column, 4.6×250 mm, 4.7 mL/min, 10–75% acetonitrile/ water over 15 min, 100% acetonitrile at 18 min, detector at 220λ). Appropriate fractions were concentrated in vacuo to yield the final product as a white solid. ¹H NMR (300 MHz, d₆-DMSO) δ: 13.52 (s, 1H), 9.52 (s, 1H), 8.48 (s, 3H), 8.42 (s, 3H), 8.02 (d, J=8.0 Hz, 1H), 7.69 (t, J=7.8 Hz, 1H), 7.51 (d, J=7.9 Hz, 1H), 7.45–7.37 (m, 2H), 7.31 (d, J=7.3 Hz, 1H), 7.19 (t, J=7.5 Hz, 1H), 4.38 (s, 2H), 2.74 (s, 3H), 1.93 (s, 3H). LRMS (ES pos.) m/z=458 (M+1).

5-Methyl-3-(E-2-methyl-cyclohexyl)-2-(9H-purin-6-ylsulfanylmethyl)-3H-quinazolin-4-one (D-113)

Y = 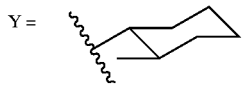

A mixture of Intermediate E-1 (80 mg, 0.25 mmol) and trans-2-methyl-1-aminocyclohexane (0.25 mL, large excess) was warmed in a sealed vial at 100° C. for 16 h. The reaction mixture was triturated with ether and the solids were collected by filtration. The crude material was dissolved in 0.5 mL DMSO and purified by HPLC (C18 Luna column, 4.6×250 mm, 4.7 mL/min, 10–75% acetonitrile/water over 15 min, 100% acetonitrile at 18 min, detector at 220λ). Appropriate fractions were concentrated in vacuo to yield the final product as a white solid (1.5 mg). $^1$H NMR (300 MHz, $d_6$-DMSO) δ: 13.5 (br s, 1H), 8.82 (s, 1H), 8.51 (s, 1H), 7.63 (t, J=7.7 Hz, 1H), 7.43 (d, J=7.9 Hz, 1H), 7.27 (d, J=7.4 Hz, 1H), 5.11 (d, J=14.5 Hz, 1H), 3.78–3.69 (m, 1H), 2.73 (s, 3H), 2.55–2.40 (m, 3H), 1.88–1.46 (m, 4H), 1.31–1.11 (m, 1H), 0.90–0.65 (m, 1H), 0.74 (d, J=6.7 Hz, 3H). LRMS (ES pos.) m/z=421 (M+1).

2-[5-Methyl-4-oxo-2-(9H-purin-6-ylsulfanylmethyl)-4H-quinazolin-3-yl]-benzoic acid (D-114)

Y = 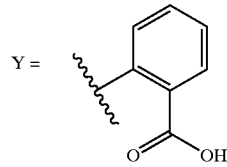

A mixture of Intermediate E-1 (80 mg, 0.25 mmol) methyl anthranilate (0.25 mL, large excess) was warmed in a sealed vial at 100° C. for 16 h. The reaction mixture was triturated with ether and the solids were collected by filtration. The crude material was dissolved in 0.5 mL DMSO and purified by HPLC (C18 Luna column, 4.6×250 mm, 4.7 mL/min, 10–75% acetonitrile/water over 15 min, 100% acetonitrile at 18 min, detector at 220λ). Appropriate fractions were concentrated in vacuo to yield the final product as a white solid (8 mg). $^1$H NMR (300 MHz, $d_6$-DMSO) δ: 13.51 (s, 1H), 8.51 (s, 1H), 8.42 (s, 1H), 8.11 (dd, J=7.4, 1.1 Hz, 1H), 7.88 (dt, J=7.7, 1.4 Hz, 1H), 7.70 (d, J=8.0 Hz, 1H), 7.57 (t, J=7.2 Hz, 1H), 7.49–7.35 (m, 3H), 4.58 (d, J=15.5 Hz, 1H), 4.35 (d, J=15.5 Hz, 1H), 2.44 (s, 3H). LRMS (ES pos.) m/z=445 (M+1).

3-{2-[(2-Dimethylamino-ethyl)-methyl-amino]-phenyl}-5-methyl-2-(9H-purin-6-ylsulfanylmethyl)-3H-quinazolin-4-one (D-115)

Y = 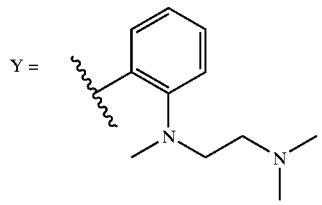

A mixture of Intermediate E-1 (40 mg, 0.25 mmol) Intermediate E-3 (0.2 mL, large excess) was warmed in a sealed vial at 100° C. for 16 h. The reaction mixture was triturated with ether and the solids were collected by filtration. The crude material was dissolved in 1 mL DMSO and purified by HPLC in two portions (C18 Luna column, 4.6×250 mm, 4.7 mL/min, 10–75% acetonitrile/water over 15 min, 100% acetonitrile at 18 min, 0.05% TFA in all solvents, detector at 220λ). Appropriate fractions were concentrated in vacuo to yield the final product as the TFA salt (11 mg). $^1$H NMR (300 MHz, $d_6$-DMSO) δ: 13.4 (br s, 1H), 9.27 (s, 1H), 8.52 (s, 1H), 8.44 (s, 1H), 7.72 (t, J=7.8 Hz, 1H), 7.53 (d, J=7.9 Hz, 1H), 7.40–7.33 (m, 4H), 7.10–7.04 (m, 1H), 4.42 (s, 3H), 3.5 (m, 2H), 3.23–3.03 (m, 3H), 2.75 (s, 3H), 2.68–2.56 (m, 8H). LRMS (ES pos.) m/z=501 (M+1).

Compounds D-116 through D-118 were prepared as follows:

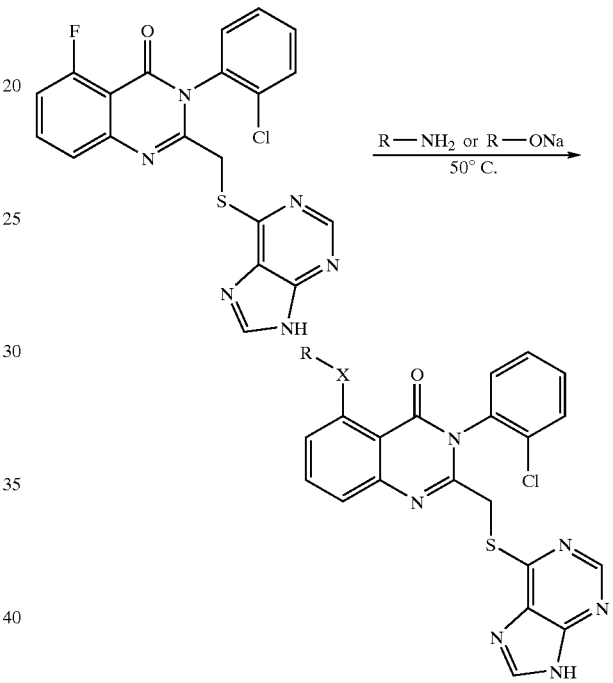

3-(2-Chlorophenyl)-5-methoxy-2-(9H-purin-6-ylsulfanylmethyl)-3H-quinazolin-4-one (D-116)

(R=Me, X=O)

A mixture of D-015 (25 mg) in 0.5 M NaOMe (2 mL in MeOH; large excess) was stirred at 50° C. for 16 h in a sealed vial. The reaction mixture was cooled to room temperature, treated with water (5 mL), and the resulting precipitate was collected by filtration, washed with water, and air dried. The crude material was dissolved in 0.5 mL DMSO and purified by HPLC (C18 Luna column, 4.6×250 mm, 4.6×250 mm, 4.7 mL/min, 10–75% acetonitrile/water over 15 min, 100% acetonitrile at 18 min, detector at 220λ). Appropriate fractions were concentrated in vacuo to yield the final product as a white solid (5.3 mg). $^1$H NMR (300 MHz, $d_6$-DMSO) δ: 13.52 (s, 1H), 8.48 (s, 1H), 8.44 (br s, 1H), 7.77 (t, J=8.2 Hz, 1H), 7.71–7.60 (m, 2H), 7.51–7.34 (m, 2H), 7.23 (d, J=8.2 Hz, 1H), 7.10 (d, J=8.4 Hz, 1H), 4.39 (AB quartet, $J_{AB}$=5.2 Hz, Δν=23.2 Hz, 2H), 3.85 (s, 3H). LRMS (ES positive) m/z=451 (M+1).

3-(2-Chlorophenyl)-5-(2-morpholin-4-yl-ethylamino)-2-(9H-purin-6-ylsulfanylmethyl)-3H-quinazolin-4-one (D-117)

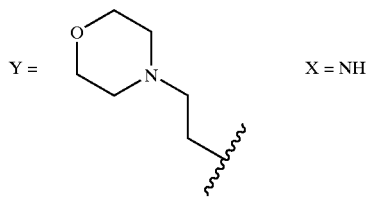

A mixture of D-015 (25 mg) and 4-(aminoeth-2-yl)-morpholine (650 mg, large excess) was stirred at 50° C. for 16 h. The crude reaction mixture was purified by HPLC (C18 Luna column, 4.6×250 mm, 4.7 mL/min, 10–75% acetonitrile/water over 15 min, 100% acetonitrile at 18 min, detector at 220×). Appropriate fractions were concentrated in vacuo to yield the final product. $^1$H NMR (300 MHz, d$_6$-acetone) δ: 8.57 (br s, 1H), 8.47 (s, 1H), 8.37 (s, 1H), 7.72 (dd, J=7.7, 1.6 Hz, 1H), 7.65 (dd, J=8.0, 1.2 Hz, 1H), 7.57 (t, J=8.1 Hz, 1H), 7.49 (dt, J=7.7, 1.6 Hz, 1H), 7.40 (dt, J=7.7, 1.5 Hz, 1H), 6.86 (d, J=7.4 Hz, 1H), 6.82 (d, J=8.3 Hz, 1H), 4.55 (d, J=15.0 Hz, 1H), 4.42 (d, J=15.1 Hz, 1H), 4.05–3.90 (m, 4H), 3.90 (t, J=6.9 Hz, 2H), 3.75–3.4 (m, 4H), 3.54 (t, J=6.9 Hz, 2H). LRMS (ES positive) m/z=549 (M+1).

3-Benzyl-5-methoxy-2-(9H-purin-6-ylsulfanylmethyl)-3H-quinazolin-4-one (D-118)

Scheme H

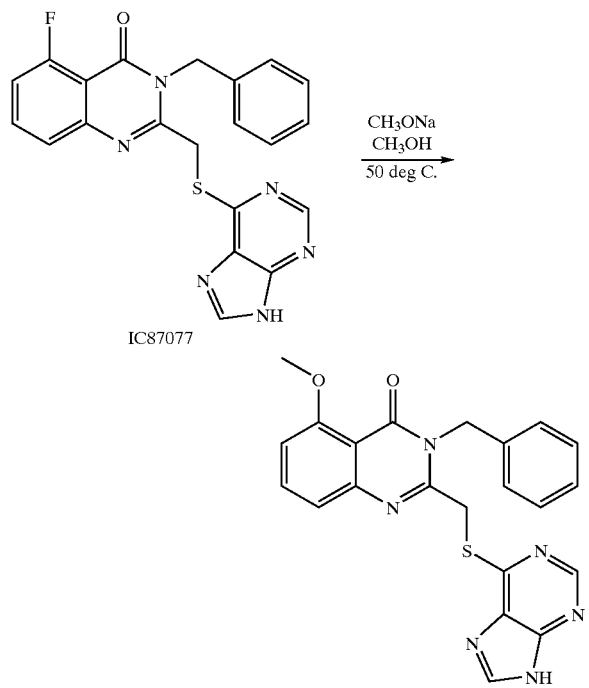

A mixture of D-043 (25 mg) in 0.5 M NaOMe (2 mL in MeOH; large excess) was stirred at 50° C. for 16 h in a sealed vial. The reaction mixture was treated with 1 N HCl (1 mL) and aliquots of this solution (0.5 mL each) were purified by HPLC (C18 Luna column, 4.6×250 mm, 4.7 mL/min, 10–75% acetonitrile/water over 15 min, 100% acetonitrile at 18 min, detector at 220λ). Appropriate fractions were concentrated in vacuo to yield the final product as a white solid (6.6 mg). $^1$H NMR (300 MHz, d$_6$-DMSO) δ: 13.57 (s, 1H), 8.60 (S, 1H), 8.45 (s, 1H), 7.72 (t, J=8.1 Hz, 1H), 7.42–7.30 (m, 2H), 7.30–7.19 (m, 3H), 7.15 (d, J=8.0 Hz, 1H), 7.06 (d, J=8.3 Hz, 1H), 5.43 (s, 2H), 4.80 (s, 2H), 3.87 (s, 3H). LRMS (ES positive) m/z=431 (M+1).

Compound D-999 (Comparative)

3-(2-Chlorophenyl)-2-(1H-pyrazolo[3,4-d]pyrimidin-4-ylsulfanylmethyl)-3H-quinazolin-4-one An analog compound, 3-(2-chlorophenyl)-2-(1H-pyrazolo[3,4-d]pyrimidin-4-ylsulfanylmethyl)-3H-quinazolin-4-one, also was synthesized generally in accordance with the described methods, except that a 4-mercapto-1H-pyrazolo[3,4-d]pyrimidine was substituted for the mercaptopurine in the final step.

EXAMPLE 11

Biochemical Assays of PI3K Potency and Selectivity

A. Biochemical Assay Using 20 μM ATP

Using the method described in Example 2, above, compounds of the invention were tested for inhibitory activity and potency against PI3Kδ, and for selectivity for PI3Kδ versus other Class I PI3K isozymes. In Table 2, IC$_{50}$ values (μM) are given for PI3Kα ("Alpha"), PI3Kβ ("Beta"), PI3γ ("Gamma"), and PI3Kδ ("Delta"). To illustrate selectivity of the compounds, the ratios of the IC$_{50}$ values of the compounds for PI3Kα, PI3Kβ, and PI3Kγ relative to PI3Kδ are given, respectively, as "Alpha/Delta Ratio," "Beta/Delta Ratio," and "Gamma/Delta Ratio."

The initial selectivity assays were done identically to the selectivity assay protocol in Example 2, except using 100 μL Ecoscint for radio-label detection. Subsequent selectivity assays were done similarly using the same 3× substrate stocks except they contained 0.05 mCi/mL γ[$^{32}$P]ATP and 3 mM PIP$_2$. Subsequent selectivity assays also used the same 3X enzyme stocks, except they now contained 3 nM of any given PI3K isoform.

For all selectivity assays, the test compounds were weighed out and dissolved into 10–50 mM stocks in 100% DMSO (depending on their respective solubilities) and stored at −20° C. Compounds were thawed (to room temperature or 37° C.), diluted to 300 μM in water from which a 3-fold dilution series into water was done. From these dilutions, 20 μL was added into the assay wells alongside water blanks used for the enzyme (positive) control and the no enzyme (background) control. The rest of the assay was essentially done according to the selectivity assay protocol in Example 2.

For those cases in which the greatest concentration used in the assay, i.e., 100 μM, did not inhibit activity of the enzyme by at least 50%, the table recites the percent activity remaining at that concentration (i.e., at 100 μM). In these cases, the true activity ratio(s) for the compounds cannot be calculated, since one of the required IC$_{50}$ values is missing. However, to provide some insight into the characteristics of these compounds, a hypothetical activity ratio is calculated using 100 μM substituted for the missing value. In such cases, the selectivity ratio must in fact be greater than the hypothetical value, and this is indicated by use of a greater than (>) symbol.

TABLE 2
| Compound | Alpha IC$_{50}$ | Beta IC$_{50}$ | Delta IC$_{50}$ | Gamma IC$_{50}$ | Alpha/Delta Ratio | Beta/Delta Ratio | Gamma/Delta Ratio |
|---|---|---|---|---|---|---|---|
| D-000 | 86% | 74% | 0.33 | 7.7 | >302 | >302 | 23 |
| D-001 | 83% | 45 | 68 | | >1.5 | 0.66 | |
| D-002 | 88% | 78% | 44 | | >2.3 | >2.3 | |
| D-003 | 92 | 53% | 4 | | 22 | >24 | |
| D-004 | 93% | 89% | 64 | | >2 | >1.6 | |
| D-005 | 89% | 46 | 0.8 | | >121 | 56 | |
| D-006 | 78% | 6 | 0.15 | | >652 | 38 | |
| D-007 | 82% | 30 | 0.16 | | >619 | 188 | |
| D-008 | 82% | 68 | 1.2 | | >85 | 57 | |
| D-009 | 82 | 6 | 0.12 | | 683 | 50 | |
| D-010 | 48 | 11 | 0.06 | 0.70 | 800 | 183 | 12 |
| D-011 | 72% | 55 | 0.10 | 1.0 | >1,000 | 550 | 10 |
| D-012 | 69% | 11 | 0.17 | | >588 | 65 | |
| D-013 | 71% | 13 | 0.05 | 2.1 | >2,000 | 260 | 42 |
| D-014 | 63% | 3.6 | 0.06 | 0.56 | >1,667 | 60 | 9.3 |
| D-015 | 65% | 69% | 0.21 | 3.6 | >480 | >480 | 17 |
| D-016 | 91% | 81% | 40 | | >2.5 | >3 | |
| D-017 | 89% | 108% | 12 | | >8 | >8 | |
| D-018 | 88% | 93% | 4.2 | | >24 | >24 | |
| D-019 | 67 | 105 | 7 | | 10 | 15 | |
| D-020 | 69% | 69% | 1.9 | | >53 | >53 | |
| D-021 | 100 | 110 | 1.6 | | 62 | 68 | |
| D-022 | 81% | 110 | 0.8 | 40 | >125 | 137.50 | 50 |
| D-023 | 83% | 91% | 26 | | >4 | >3.9 | |
| D-024 | 100 | 76% | 2.6 | | 38 | >38 | |
| D-025 | 73% | 61% | 0.11 | 1.5 | >909 | >909 | 14 |
| D-026 | 68% | 54% | 0.08 | 1.7 | >1,250 | >1,250 | 21 |
| D-027 | 59% | 58 | 0.6 | | >169 | 97 | |
| D-028 | 67% | 13 | 0.18 | | >556 | 69 | |
| D-029 | 49 | 3.0 | 0.06 | | 882 | 54 | |
| D-030 | 50 | 5 | 0.07 | | 758 | 70 | |
| D-031 | 74 | 10 | 0.12 | | >833 | 83 | |
| D-034 | 19 | 11 | 0.15 | | 131 | 74 | |
| D-035 | 9 | 3 | 0.05 | | 199 | 65 | |
| D-036 | 63% | 31 | 0.4 | | >226 | 69 | |
| D-037 | 64% | 80 | 0.8 | | >125 | 100 | |
| D-039 | 77% | 66% | 0.9 | 38 | >111 | >111 | 42 |
| D-038 | 77% | 63% | 0.6 | 60 | >167 | >170 | 100 |
| D-040 | 77% | 64% | 1.7 | | >61 | >61 | |
| D-041 | 67% | 65% | 4 | | >25 | >25 | |
| D-042 | 70% | 25 | 3 | | >32 | 8 | |
| D-043 | 83% | 77% | 2.1 | | >47 | >47 | |
| D-044 | 105 | 61 | 4.2 | | 25 | 15 | |
| D-045 | 98% | 74% | 7.6 | | >13 | >13 | |
| D-046 | 64% | 95 | 9 | | >11 | 11 | |
| D-047 | 30 | 9 | 0.09 | 0.5 | 333 | 100 | 5.6 |
| D-048 | 70 | 14 | 0.16 | | 449 | 90 | |
| D-049 | 110% | 30 | 1.0 | | >100 | 30 | |
| D-050 | 99% | 41 | 1.6 | | >63 | 26 | |
| D-051 | 89% | 57% | 3.3 | | >31 | >31 | |
| D-052 | 0.7 | 69% | 8 | | 0.09 | >13 | |
| D-121 | 69% | 70% | 0.48 | | >211 | >211 | |
| D-999 | 105 | 71% | 47 | 60 | 2.2 | 2.1 | 1.3 |
| LY294002 | 1.2 | 0.4 | 0.23 | | 5.3 | 1.7 | |
[1])Compound D-121 is 3-phenyl-2-(9H-purin-6-ylsulfanylmethyl)-3H-quinazolin-4-one
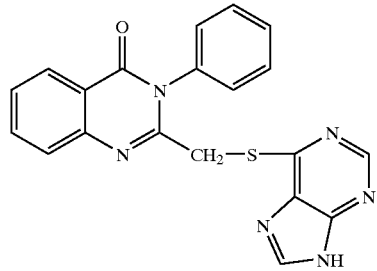

B. Biochemical Assay Using 200 μM ATP

In Part A, above, compounds of the invention were tested to establish their $IC_{50}$ for inhibition of the alpha, beta, delta, and gamma isoforms of PI3K using 20 μM ATP. A further screen was performed to establish the $IC_{50}$ for inhibition of the four PI3K isoforms at a final concentration of 200 μM ATP, 10-fold greater, and substantially closer to the normal physiological concentration of ATP in cells. This selectivity protocol is identical to that described above, except the 3X stock ATP concentration was 600 μM. Data from this assay are summarized in Table 3, below. The observed sensitivity to ATP concentration suggests that these PI3Kδ inhibitor compounds act as ATP competitors.

TABLE 3

| Compound | Alpha $IC_{50}$ | Beta $IC_{50}$ | Delta $IC_{50}$ | Gamma $IC_{50}$ | Alpha/Delta Ratio | Beta/Delta Ratio | Gamma/Delta Ratio |
|---|---|---|---|---|---|---|---|
| D-000 | 91 ± 1% | 84 ± 2% | 2 ± 1 | 35 ± 35 | 91 | 84 | 18 |
| D-005 | 104% | 82% | 11 | 91% | 20 | 16 | 17 |
| D-006 | 104 ± 1% | 44 ± 5 | 0.92 ± 0.1 | 87 ± 33 | 226 | 48 | 95 |
| D-007 | 92 ± 11% | 72 ± 12 | 0.73 ± 0.2 | 88 ± 4 | 252 | 99 | 121 |
| D-009 | 70% | 18 | 0.7 | 53 | 200 | 26 | 76 |
| D-010 | 74 ± 18% | 33 ± 4 | 0.23 ± 0.2 | 6 ± 3 | 658 | 144 | 27 |
| D-011 | 88 ± 4% | 105 ± 35 | 0.25 ± 0.2 | 61 ± 70 | 700 | 420 | 244 |
| D-012 | 70 ± 4% | 108 ± 4 | 1.3 ± 0.4 | 50 ± 0 | 107 | 83 | 38 |
| D-013 | 117 ± 8% | 73 ± 24% | 0.51 ± 0.6 | 12 ± 1 | 461 | 289 | 24 |
| D-014 | 100 ± 6% | 13 ± 0 | 0.5 ± 0.4 | 5 ± 3 | 398 | 26 | 10 |
| D-015 | 95 ± 22% | 81 ± 3% | 1.1 ± 0.5 | 83 ± 37% | 180 | 154 | 160 |
| D-019 | 100% | 100 | 30 | 33 | 7 | 3 | 1 |
| D-022 | 88% | 101% | 4.2 | 60% | 42 | 48 | 29 |
| D-025 | 89 ± 11% | 77 ± 6% | 0.32 ± 0.3 | 7.8 ± 3 | 556 | 478 | 24 |
| D-026 | 83 ± 1% | 77 ± 8% | 0.38 ± 0.2 | 13 ± 10 | 443 | 411 | 34 |
| D-027 | 74% | 110 | 4 | 60 | 37 | 28 | 15 |
| D-028 | 100% | 81% | 1.6 | 29 | 125 | 101 | 18 |
| D-029 | 110 ± 12% | 34 ± 4 | 0.34 ± 0.08 | 13 ± 0.7 | 653 | 101 | 37 |
| D-030 | 95 ± 11% | 80 ± 14 | 0.53 ± 0.05 | 31 ± 10 | 362 | 152 | 59 |
| D-031 | 87 ± 10% | 137 ± 23 | 0.2 ± 0.01 | 155 ± 60 | 903 | 707 | 802 |
| D-034 | 92 ± 11% | 103 ± 4 | 1.2 ± 0.3 | 34 ± 1 | 153 | 85 | 28 |
| D-035 | 95 ± 6 | 34 ± 6 | 0.49 ± 0.1 | 6.8 ± 1 | 193 | 69 | 14 |
| D-036 | 99% | 73% | 4.1 | 72 | 48 | 36 | 18 |
| D-037 | 112% | 58% | 3.5 | 45 | 64 | 33 | 13 |
| D-038 | 69% | 74% | 1.8 | 55 | 77 | 82 | 31 |
| D-039 | 85% | 65% | 2.6 | 57% | 65 | 50 | 44 |
| D-047 | 81% | 30 | 0.2 | 4.5 | 810 | 150 | 23 |
| D-048 | 90 ± 57 | 95 ± 7 | 1.4 ± 0.9 | 123 ± 40 | 67 | 70 | 91 |
| D-121 | 71% | 62% | 0.9 | 61% | 158 | 138 | 136 |
| D-999 | 62% | 71% | 75 | 90 | 2 | 2 | 1 |
| LY294002 | 23 ± 5 | 3.7 ± 2 | 2.1 ± 1.5 | 29 ± 13 | 11 | 2 | 13 |

EXAMPLE 12
Cell-Based Assay Data for Inhibitors of PI3Kδ Activity

Using the methods described in Examples 3–5, above, compounds of the invention were tested for inhibitory activity and potency in assays of stimulated B and T cell proliferation, neutrophil (PMN) migration, and neutrophil (PMN) elastase release. Data from these assays are set forth in Table 4, below. In Table 4, the values shown are effective concentrations of the compound ($EC_{50}$; μM). Where no value is given, no assay was performed.

TABLE 4

| Compound | Mouse BCR Stim ($EC_{50}$) | Mouse TCE Stim ($EC_{50}$) | Human PMN Elastase ($EC_{50}$) | Human PMN Migration ($EC_{50}$) |
|---|---|---|---|---|
| D-000 | 0.9 ± 0.4 | 5.5 ± 4 | 2.2 ± 2 | 1–5 |
| D-003 | 3.9 | 5.7 | | |
| D-005 | 0.7 ± 0.1 | 3.9 | 4.3 ± 1 | |
| D-006 | 0.2 ± 0.1 | 5.3 | 0.3 ± 0.1 | |
| D-007 | 0.3 ± 0.1 | 4.2 | 0.4 | |
| D-008 | 1.0 | | | |
| D-009 | 0.3 ± 0.2 | | 10.5 | |
| D-010 | 0.2 ± 0.1 | | 0.3 ± 0.3 | |
| D-011 | 0.3 ± 0.1 | | 0.9 ± 0.7 | |
| D-012 | 0.3 ± 0.2 | | 0.3 | |
| D-013 | 1.4 | | | |
| D-014 | 0.2 ± 0.1 | 4.3 | | |
| D-015 | 1.2 ± 0.2 | 1.8 | 1.3 ± 0.4 | 2.0 |
| D-019 | 0.9 ± 0.01 | 0.9 | | |
| D-021 | 1.8 | 3.5 | | |
| D-022 | 1.8 | 2.3 | | |
| D-024 | | | 2.9 | |
| D-025 | 0.3 ± 0.1 | 4.4 ± 0.6 | 0.2 ± 0.2 | 0.3 ± 0.3 |
| D-026 | 0.3 ± 0.1 | 3.5 | 0.2 ± 0.2 | 0.3 ± 0.3 |
| D-027 | >2 | | 2 | |
| D-028 | 0.4 ± 0.2 | | 1 | |
| D-029 | 0.1 ± 0.03 | 3.4 ± 2 | 0.5 ± 0.6 | 0.3 |
| D-030 | 0.1 ± 0.1 | 6 | 0.4 ± 0.5 | 0.2 |
| D-031 | 0.2 ± 0.1 | | 0.7 ± 0.1 | |
| D-034 | 0.6 ± 0.4 | | | |
| D-035 | 0.2 ± 0.1 | 2.9 ± 0.7 | 0.3 ± 0.1 | |
| D-036 | 0.9 ± 0.04 | 4.1 | 5.5 ± 5 | 0.2 |
| D-037 | 1.2 ± 0.4 | | 1.3 ± 0.4 | 2.0 |
| D-038 | 1.4 ± 0.1 | 2.9 | 5 | |

TABLE 4-continued

| Compound | Mouse BCR Stim (EC$_{50}$) | Mouse TCE Stim (EC$_{50}$) | Human PMN Elastase (EC$_{50}$) | Human PMN Migration (EC$_{50}$) |
|---|---|---|---|---|
| D-039 | 0.9 ± 0.1 | | 5 | |
| D-043 | 1.4 | 2.6 | | |
| D-045 | | | 9.0 | |
| D-047 | 0.3 ± 01. | | 0.5 ± 0.2 | |
| D-048 | 0.4 ± 0.2 | 5 | 0.9 ± 0.2 | |
| D-049 | 2.0 | 6.3 | 5.0 | |
| D-121 | 1.4 | | | |
| D-999 | 3.1 ± 0.7 | 5.9 | >20 | 1 |
| LY294002 | 0.9 ± 0.5 | | | |

EXAMPLE 13
Assay of Inhibitors of PI3Kδ Activity in Cancer Cells

The effect of compounds of the invention on cancer cell proliferation was evaluated by testing one of the compounds against a panel of Chronic Myeloid Leukemia (CML) cell lines, including KU812, RWLeu4, K562, and MEG-01.

The inhibitory activity of the compound (D-000, dissolved in DMSO) was determined as follows. The tested compound was added in a series of concentrations (0.001 µM to 20 µM) to 96-well microtiter plates with cells (1000 to 5000 cells/well). Plates were incubated for five days at 37° C. during which the control cultures without test compound were able to undergo at least two cell-division cycles. Cell growth was measured by incorporation of [$^3$H]-thymidine for eighteen hours added at days three, four, and five. Cells were transferred to a filter, washed and the radioactivity counted using a Matrix 96 beta counter (Packard). The percentage of cell growth was measured as follows:

$$\% \text{ Cell growth} = \frac{\text{(average counts of cells incubated with a given inhibitor concentration)} \times 100}{\text{(average counts of the cells without inhibitor)}}$$

The EC$_{50}$ value in these experiments was determined by the concentration of the test compound that resulted in a radioactivity count 50% lower than that obtained using the control without inhibitor. The D-000 compound exhibited inhibitory activity with an EC$_{50}$ of approximately 2 µM for the KU812 and RWLeu4 lines. The compound was not found to exhibit an effect in the K562 and MEG-01 lines.

PI3Kδ inhibitors of the invention appear to inhibit CML cell growth and therefore could be useful in the treatment of benign or malignant tumors. PI3Kδ expression has been demonstrated so far mostly in cells of hematopoietic origin. However, it could be present in a broader variety of proliferating cells. Therefore, the compounds of the invention could be used to induce tumor regression and to prevent the formation of tumor metastasis in both leukemia and solid tumor or in proliferation of nontumoral origin. In addition, the compounds could be used both alone and in combination with other pharmacologically active compounds or in combination with radiation as a sensitizing agent.

EXAMPLE 14
Measurement of Elastase Exocytosis in Mouse Air Pouch Lavage

The effect of D-030 on leukocyte influx and neutrophil elastase exocytosis in animal models was tested. The six-day air pouch model is an in vivo inflammation model that histologically resembles a joint synovium. A lining of organized mononuclear cells and fibroblasts develops that closely resembles a synovial cavity. The model represents an "acute" model of a chronic disease (e.g., rheumatoid arthritis). This model allows for the in vivo evaluation of agents to block cellular influx into the air pouch under the influence of an inflammatory stimulus.

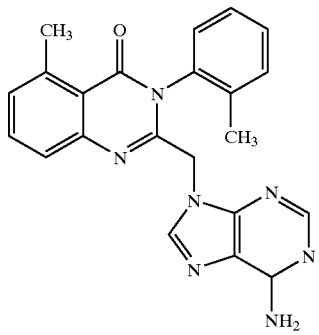

D-030

The test was performed as follows: on day zero, groups of rats were shaved and 10 ml of air was injected subcutaneously on the back of each, forming a pouch. On day three, 10 ml of air was reinjected. Six hours prior to TNF challenge on day six, one group of rats (n=6) received D-030 (100 mg/kg in PEG 400 vehicle) orally, and another group (n=12) received vehicle alone orally. Six hours following dosing, the air pouches of both groups received 2.5 ng of TNF. Twelve hours following dosing, the pouches were washed with saline, and the resulting lavage fluid was analyzed for leukocyte counts and neutrophil elastase activity. In addition, blood was drawn to determine the levels of D-030 in circulation. The results were as follows: rats that received D-030 for twelve hours had an average of 8.7 µM of compound in circulation and had an 82% reduction in total leukocytes in the lavage fluid compared to vehicle controls. Reductions in specific leukocyte counts were as follows: neutrophils (90%), eosinophils (66%), and lymphocytes (70%). Quantitation of neutrophil elastase showed that D-030-treated rats had elastase levels that were somewhat reduced (15%) versus vehicle controls.

In another test, an area of the mouse back was shaved using clippers, and an air pouch was created by injecting 3 ml air subcutaneously. On day three, the air injection was repeated. On day six, the animals were dosed with either D-030 (32 mg/kg in LABRAFIL®) or LABRAFIL® only one hour before and two hours after challenge with TNF-α (0.5 ng in 1 ml PBS), or PBS only. PBS is phosphate buffered saline. Four hours after TNF challenge, the animals were anesthetized and the pouches were lavaged with 2 mL of 0.9% saline with 2 mM EDTA. The lavages were centrifuged at 14,000 rpm in a microcentrifuge. Fifty microliters of the supernatant was used to measure elastase exocytosis according to the procedure described above.

Figure 9:
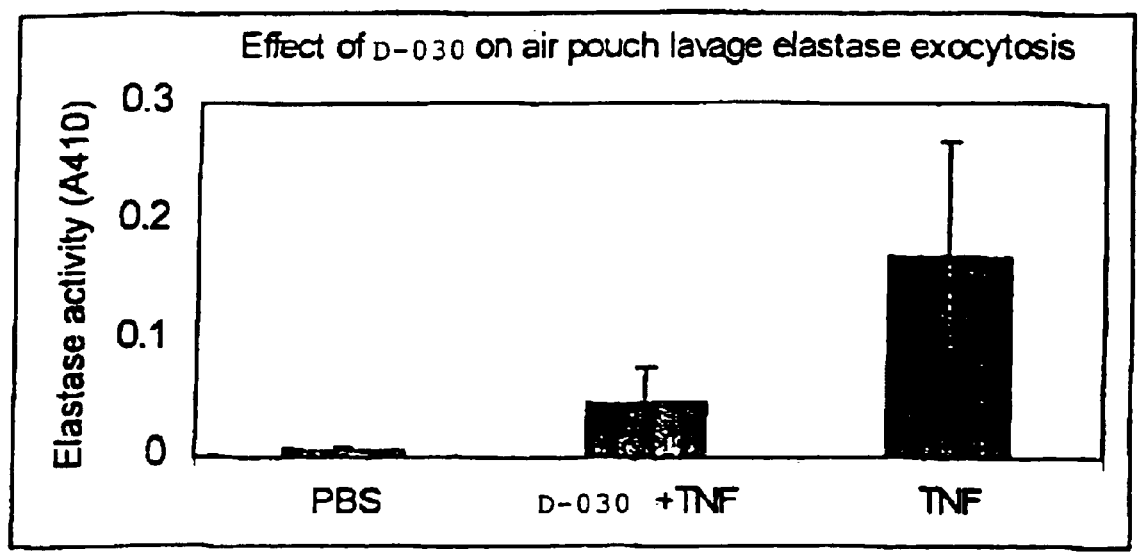
FIG. 9 shows the effect of a selective PI3Kδ inhibitor on elastase exocytosis in an animal model.

As shown in FIG. 9, TNF challenge induced a high level of elastase exocytosis compared to PBS challenged animals. However, when the TNF challenged animals were treated with D-030, a significant decrease in the elastase activity in the air pouch lavages was observed.

All publications and patent documents cited in this specification are incorporated herein by reference for all that they disclose.

While the present invention has been described with specific reference to certain preferred embodiments for purposes of clarity and understanding, it will be apparent to the skilled artisan that further changes and modifications can be practiced within the scope of the invention as it is defined in the claims set forth below. Accordingly, no limitations should be placed on the invention other than those specifically recited in the claims.

---

What is claimed is:

1. A method of disrupting leukocyte function comprising a step of contacting leukocytes with a compound having a structure

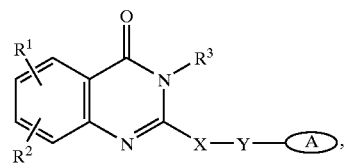

wherein A is an optionally substituted monocyclic 5-membered heterocyclic ring system containing two or three nitrogen atoms or a bicyclic ring system containing at least two nitrogen atoms, and at least one ring of the bicyclic system is aromatic;

X is selected from the group consisting of $C(R^b)_2$, $CH_2CHR^b$, and $CH=C(R^b)$;

Y is selected from the group consisting of null, S, SO, and $SO_2$, NH, O, C(=O), OC(=O), C(=O)O, and NHC(=O)$CH_2$S;

$R^1$ and $R^2$, independently, are selected from the group consisting of hydrogen, $C_{1-6}$alkyl, aryl, heteroaryl, halo, NHC(=O)$C_{1-3}$alkyleneN($R^a$)$_2$, $NO_2$, $OR^a$, $CF_3$, $OCF_3$, N($R^a$)$_2$, CN, OC(=O)$R^a$, C(=O)$R^a$, C(=O)$OR^a$, arylOR$^b$, Het, $NR^aC(=O)C_{1-3}$alkyleneC(=O)$OR^a$, arylOC$_{1-3}$alkyleneN($R^a$)$_2$, arylOC(=O)$R^a$, $C_{1-4}$alkyleneC(=O)$OR^a$, OC$_{1-4}$alkyleneC(=O)$OR^a$, $C_{1-4}$alkyleneOC$_{1-4}$alkyleneC(=O)—$OR^a$, C(=O)$NR^aSO_2R^a$, $C_{1-4}$alkyleneN($R^a$)$_2$, $C_{2-6}$alkenylene-N($R^a$)$_2$, C(=O)$NR^aC_{1-4}$alkyleneOR$^a$, C(=O)$NR^aC_{1-4}$alkyleneHet, OC$_{2-4}$alkyleneN($R^a$)$_2$, OC$_{1-4}$alkyleneCH(OR$^b$)CH$_2$N($R^a$)$_2$, OC$_{1-4}$alkyleneHet, OC$_{2-4}$alkyleneOR$^a$, OC$_{2-4}$alkyleneNR$^aC(=O)—OR^a$, $NR^aC_{1-4}$alkyleneN($R^a$)$_2$, $NR^aC(=O)R^a$, $NR^aC(=O)N(R^a)_2$, N(SO$^2C_{1-4}$alkyl)$_2$, $NR^a(SO_2C_{1-4}$alkyl), $SO_2N(R^a)_2$, $OSO_2CF_3$, $C_{1-3}$alkylenearyl, $C_{1-4}$alkyleneHet, $C_{1-6}$alkyleneOR$^b$, $C_{1-3}$alkyleneN($R^a$)$_2$, C(=O)N($R^a$)$_2$, NHC(=O)$C_1$-$C_3$alkylenearyl, $C_{3-8}$cycloalkyl, $C_{3-8}$heterocycloalkyl, arylOC$_{1-3}$alkylene-N($R^a$)$_2$, arylOC(=O)$R^b$, NHC(=O)$C_{1-3}$alkyleneC$_{3-8}$heterocyclo-alkyl, NHC(=O)$C_{1-3}$alkyleneHet, OC$_{1-4}$alkyleneOC$_{1-4}$alkylene-C(=O)$OR^b$, C(=O)$C_{1-4}$alkyleneHet, and NHC(=O)halo$C_{1-6}$alkyl;

or $R^1$ and $R^2$ are taken together to form a 3- or 4-membered alkylene or alkenylene chain component of a 5- or 6-membered ring, optionally containing at least one heteroatom;

$R^3$ is selected from the group consisting of optionally substituted hydrogen, $C_{1-6}$alkyl, $C_{3-8}$cycloalkyl, $C_{3-8}$heterocycloalkyl, $C_{1-4}$alkylenecycloalkyl, $C_{2-6}$alkenyl, $C_{1-3}$alkylenearyl, aryl$C_{1-3}$alkyl, C(=O)$R^a$, aryl, heteroaryl, C(=O)$OR^a$, C(=O)N($R^a$)$_2$, C(=S)N($R^a$)$_2$, $SO_2R^a$, $SO_2N(R^a)_2$, S(=O)$R^a$, S(=O)N($R^a$)$_2$, C(=O)$NR^aC_{1-4}$alkyleneOR$^a$, C(=O)$NR^aC_{1-4}$alkyleneHet, C(=O)$C_{1-4}$alkylenearyl, C(=O)$C_{1-4}$alkyleneheteroaryl, $C_{1-4}$alkylenearyl substituted with one or more of $SO_2N(R^a)_2$, N($R^a$)$_2$, C(=O)$OR^a$, $NR^aSO_2CF_3$, CN, $NO_2$, C(=O)$R^a$, $OR^a$, $C_{1-4}$alkyleneN($R^a$)$_2$, and OC$_{1-4}$alkyleneN($R^a$)$_2$, $C_{1-4}$alkyleneheteroaryl, $C_{1-4}$alkyleneHet, $C_{1-4}$alkyleneC(=O) $C_{1-4}$alkylenearyl, $C_{1-4}$alkyleneC(=O)—$C_{1-4}$alkyleneheteroaryl, $C_{1-4}$alkyleneC(=O)Het, $C_{1-4}$alkyleneC(=O)N($R^a$)$_2$, $C_{1-4}$alkyleneOR$^a$, $C_{1-4}$alkyleneNR$^aC(=O)R^a$, $C_{1-4}$alkyleneOC$_{1-4}$alkyleneOR$^a$, $C_{1-4}$alkyleneN($R^a$)$_2$, $C_{1-4}$alkyleneC(=O)$OR^a$, and $C_{1-4}$alkyleneOC$_{1-4}$alkyleneC(=O)$OR^a$;

$R^a$ is selected from the group consisting of hydrogen, $C_{1-6}$alkyl, $C_{3-8}$cycloalkyl, $C_{3-8}$heterocycloalkyl, $C_{1-3}$alkyleneN($R^c$)$_2$, aryl, aryl$C_{1-3}$alkyl, $C_{1-3}$alkylenearyl, heteroaryl, heteroaryl$C_{1-3}$alkyl, and $C_{1-3}$alkyleneheteroaryl;

or two $R^a$ groups are taken together to form a 5- or 6-membered ring, optionally containing at least one heteroatom;

$R^b$ is selected from the group consisting of hydrogen, $C_{1-6}$alkyl, hetero$C_{1-3}$alkyl, $C_{1-3}$alkyleneheteroC$_{1-3}$alkyl, arylheteroC$_{1-3}$alkyl, and aryl, heteroaryl, aryl$C_{1-3}$ alkyl, heteroaryl$C_{1-3}$alkyl, $C_{1-3}$alkylenearyl, and $C_{1-3}$alkyleneheteroaryl;

$R^c$ is selected from the group consisting of hydrogen, $C_{1-6}$alkyl, $C_{3-8}$cycloalkyl, aryl, and heteroaryl;

Het is a 5- or 6-membered heterocyclic ring, saturated or partially or fully unsaturated, containing at least one heteroatom selected from the group consisting of oxygen, nitrogen, and sulfur, selected from the group consisting of 1,3-dioxolane, 2-pyrazoline, pyrazolidine, pyrrolidine, piperazine, pyrroline, 2H-pyran, 4H-pyran, morpholine, thiomorpholine, piperidine, 1,4-dithiane, and 1,4-dioxane, and optionally substituted with $C_{1-4}$alkyl or C(=O)$OR^a$;

and pharmaceutically acceptable salts or solvates, in an amount sufficient to inhibit phosphatidylinositol 3-kinase delta activity in said leukocytes.

2. The method according to claim 1 wherein the compound is selected from the group consisting of 2-(6-aminopurin-9-ylmethyl)-3-(2-chlorophenyl)-6,7-dimethoxy-3H-quinazolin-4-one 2-(6-aminopurin-o-ylmethyl)-6-bromo-3-(2-chlorophenyl)-3H-quinazolin-4-one 2-(6-aminopurin-o-ylmethyl)-3-(2-chlorophenyl)-7-fluoro-3H-quinazolin-4-one 2-(6-aminopurin-9-ylmethyl)-6-chloro-3-(2-chlorophenyl)-3H-quinazolin-4-one 2-(6-aminopurin-9-ylmethyl)-3-(2-chlorophenyl)-5-fluoro-3H-quinazolin-4-one 2-(6-aminopurin-o-ylmethyl)-5-chloro-3-(2-chlorophenyl)-3H-quinazolin-4-one 2-(6-aminopurin-9-ylmethyl)-3-(2-chlorophenyl)-5-methyl-3H-quinazolin-4-one
2-(6-aminopurin-9-ylmethyl)-8-chloro-3-(2-chlorophenyl)-3H-quinazolin-4-one
2-(6-aminopurin-9-ylmethyl)-3-biphenyl-2-yl-5-chloro-3H-quinazolin-4-one
5-chloro-2-(9H-purin-6-ylsulfanylmethyl)-3-o-tolyl-3H-quinazolin-4-one
5-chloro-3-(2-fluorophenyl)-2-(9H-purin-6-ylsulfanylmethyl)-3H-quinazolin-4-one
2-(6-aminopurin-9-ylmethyl)-5-chloro-3-(2-fluorophenyl)-3H-quinazolin-4-one
3-biphenyl-2-yl-5-chloro-2-(9H-purin-6-ylsulfanylmethyl)-3H-quinazolin-4-one
5-chloro-3-(2-methoxyphenyl)-2-(9H-purin-6-ylsulfanylmethyl)-3H-quinazolin-4-one
3-(2-chlorophenyl)-5-fluoro-2-(9H-purin-6-ylsulfanylmethyl)-3H-quinazolin-4-one
3-(2-chlorophenyl)-6,7-dimethoxy-2-(9H-purin-6-ylsulfanylmethyl)-3H-quinazolin-4-one
6-bromo-3-(2-chlorophenyl)-2-(9H-purin-6-ylsulfanylmethyl)-3H-quinazolin-4-one
3-(2-chlorophenyl)-8-trifluoromethyl-2-(9H-purin-6-ylsulfanylmethyl)-3H-quinazolin-4-one
3-(2-chlorophenyl)-2-(9H-purin-6-ylsulfanylmethyl)-3H-benzo[g]quinazolin-4-one
6-chloro-3-(2-chlorophenyl)-2-(9H-purin-6-ylsulfanylmethyl)-3H-quinazolin-4-one
8-chloro-3-(2-chlorophenyl)-2-(9H-purin-6-ylsulfanylmethyl)-3H-quinazolin-4-one
3-(2-chlorophenyl)-7-fluoro-2-(9H-purin-6-ylsulfanylmethyl)-3H-quinazolin-4-one
3-(2-chlorophenyl)-7-nitro-2-(9H-purin-6-ylsulfanylmethyl)-3H-quinazolin-4-one
3-(2-chlorophenyl)-6-hydroxy-2-(9H-purin-6-ylsulfanylmethyl)-3H-quinazolin-4-one
5-chloro-3-(2-chlorophenyl)-2-(9H-purin-6-ylsulfanylmethyl)-3H-quinazolin-4-one
3-(2-chlorophenyl)-5-methyl-2-(9H-purin-6-ylsulfanylmethyl)-3H-quinazolin-4-one
3-(2-chlorophenyl)-6,7-difluoro-2-(9H-purin-6-ylsullfanylmethyl)-3H-quinazolin-4-one
3-(2-chlorophenyl)-6-fluoro-2-(9H-purin-6-ylsulfanylmethyl)-3H-quinazolin-4-one
2-(6-aminopurin-9-ylmethyl)-3-(2-isopropylphenyl)-5-methyl-3H-quinazolin-4-one
2-(6-aminopurin-9-ylmethyl)-5-methyl-3-o-tolyl-3H-quinazolin-4-one
3-(2-fluorophenyl)-5-methyl-2-(9H-purin-6-ylsulfanylmethyl)-3H-quinazolin-4-one
2-(6-aminopurin-9-ylmethyl)-5-chloro-3-o-tolyl-3H-quinazolin-4-one
2-(6-aminopurin-9-ylmethyl)-5-chloro-3-(2-methoxyphenyl)-3H-quinazolin-4-one
2-(2-amino-9H-purin-6-ylsulfanylmethyl)-3-cyclopropyl-5-methyl-3H-quinazolin-4-one
3-cyclopropylmethyl-5-methyl-2-(9H-purin-6-ylsulfanylmethyl)-3H-quinazolin-4-one
2-(6-aminopurin-9-ylmethyl)-3-cyclopropylmethyl-5-methyl-3H-quinazolin-4-one
2-(2-amino-9H-purin-6-ylsulfanylrnethyl)-3-cyclopropylmethyl-5-methyl-3H-quinazolin-4-one
5-methyl-3-phenethyI-2-(9H-purin-6-ylsulfanylmethyl)-3H-quinazolin-4-one
2-(2-amino-9H-purin-6-ylsulfanylmethyl)-5-methyl-3-phenethyl-3H-quinazolin-4-one
3-cyclopentyl-5-methyl-2-(9H-purin-6-ylsulfanylmethyl)-3H-quinazolin-4-one
2-(6-aminopurin-9-ylmethyl)-3-cyclopentyl-5-methyl-3H-quinazolin-4-one
3-(2-chloropyridin-3-yl)-5-methyl-2-(9H-purin-6-ylsulfanylmethyl)-3H-quinazolin-4-one
2-(6-aminopurin-9-ylmethyl)-3-(2-chloropyridin-3-yl)-5-methyl-3H-quinazolin-4-one
3-methyl-4-[5-methyl-4-oxo-2-(9H-purin-6-ylsulfanylmethyl)-4H-quinazolin-3-yl]-benzoic acid
3-cyclopropyl-5-methyl-2-(9H-purin-6-ylsulfanylinethyl)-3H-quinazolin-4-one
2-(6-aminopurin-9-ylmethyl)-3-cyclopropyl-5-methyl-3H-quinazolin-4-one
5-methyl-3-(4-nitrobenzyl)-2-(9H-purin-6-ylsulfanylmethyl)-3H-quinazolin-4-one
3-cyclohexyl-5-methyl-2-(9H-purin-6-ylsulfanylmethyl)-3H-quinazolin-4-one
2-(6-aminopurin-9-ylmethyl)-3-cyclohexyl-5-methyl-3H-quinazolin-4-one
2-(2-amino-9H-purin-6-ylsulfanylmethyl)-3-cyclchexyl-5-methyl-3H-quinazolin-4-one
5-methyl-3-(E-2-phenylcyclopropyl)-2-(9H-purin-6-ylsulfanylmethyl)-3H-quinazolin-4-one
3-(2-chlorophenyl)-5-fluoro-2-[(9H-purin-6-ylamino)-methyl]-3H-quinazolin-4-one
2-[(2-amino-9H-purin-6-ylamino)methyl]-3-(2-chlorophenyl)-5-fluoro-3H-quinazolin-4-one
5-methyl-2-[(9H-purin-6-ylamino)methyl]-3-o-tolyl-3H-quinazolin-4-one
2-[(2-amino-9H-purin-6-ylaminomethyl]-5-methyl-3-o-tolyl-3H-quinazolin-4-one
2-[(2-fluoro-9H-purin-6-ylamino)methyl]-5-methyl-3-o-tolyl-3H-quinazolin-4-one
(2-chlorophenyl)-dimethylamino-(9H-purin-6-ylsulfanylmethyl)-3H-quinazolin-4-one
5-(2-benzyloxyethoxy)-3-(2-chlorophenyl)-2-(9H-purin-6-ylsulfanylmethyl)-3H-quinazolin-4-one
6-aminopurine-9-carboxylic acid 3-(2-chlorophenyl)-5-fluoro-4-oxo-3,4-dihydro-quinazolin-2-ylmethyl ester
N-[3-(2-chlorophenyl)-5-fluoro-4-oxo-3,4-dihydroquinazolin-2-ylmethyl]-2-(9H-purin-6-ylsulfanyl)-acetamide
2-[1-(2-fluoro-9H-purin-6-ylamino)ethyl]-5-methyl-3-o-tolyl-3H-quinazolin-4-one
5-methyl-2-[1-(9H-purin-6-ylamino)ethyl]-3-o-tolyl-3H-quinazolin-4-one
2-(6-dimethylaminopurin-9-ylmethyl)-5-methyl-3-o-tolyl-3H-quinazolin-4-one
5-methyl-2-(2-methyl-6-oxo-1,6-dihydro-purin-7-ylmethyl)-3-o-tolyl-3H-quinazolin-4-one
5-methyl-2-(2-methyl-6-oxo-1,6-dihydro-purin-9-ylmethyl)-3-o-tolyl-3H-quinazolin-4-One
2-(amino-dimethylaminopurin-9-ylmethyl)-5-methyl-3-o-tolyl-3H-quinazolin-4-one
2-(2-amino-9H-purin-6-ylsulfanylmethyl)-5-methyl-3-o-tolyl-3H-quinazolin-4-one
2-(4-amino-1,3,5-triazin-2-ylsulfanylmethyl)-5-methyl-3-o-tolyl-3H-quinazolin-4-one 5-methyl-2-(7-methyl-7H-purin-6-ylsulfanylmethyl)-3-o-tolyl-3H-quinazolin-4-one 5-methyl-2-(2-oxo-1,2-dihydro-pyrimidin-4-ylsulfanylmethyl)-3-o-tolyl-3H-quinazolin-4-one 5-methyl-2-purin-7-ylmethyl-3-o-tolyl-3H-quinazolin-4-one 5-methyl-2-purin-9-ylmethyl-3-o-tolyl-3H-quinazolin-4-one 5-methyl-2-(9-methyl-9H-purin-6-ylsulfanylmethyl)-3-o-tolyl-3H-quinazolin-4-one 2-(2,6-Diamino-pyrimidin-4-ylsulfanylniethyl)-5-methyl-3-o-tolyl-3H-quinazolin-4-one 5-methyl-2-(5-methyl-[1,2,4]triazolo[1,5-a]pyrimidifl-7-ylsulfanylmethyl)-3-o-tolyl-3H-quinazolin-4-one 5-methyl-2-(2-methylsulfanyl-9H-purin-6-ylsulfanylmethyl)-3-o-tolyl-3H-quinazolin-4-one 2-(2-hydroxy-9H-purin-6-ylsulfanylmethyl)-5-methyl-3-o-tolyl-3H-quinazolin-4-one 5-methyl-2-(1-methyl-1H-imidazol-2-ylsulfanylmethyl)-3-o-tolyl-3H-quinazolin-4-one 5-methyl-3-o-tolyl-2-(1H-[1,2,4]triazol-3-ylsulfanylmethyl)-3H-quinazolin-4-one 2-(2-amino-6-chloro-purin-9-yimethyl)-5-methyl-3-o-tolyl-3H-quinazolin-4-one 2-(6-aminopurin-7-ylmethyl)-5-methyl-3-o-tolyl-3H-quinazolin-4-one 2-(7-amino-1,2,3-triazolo[4,5-d]pyrimidin-3-ylmethyl)-5-methyl-3-o-tolyl-3H-quinazolin-4-one 2-(7-amino-1,2,3-triazolo[4,5-d]pyrimidin-1-ylmethyl)-5-methyl-3-o-tolyl-3H-quinazolin-4-one 2-(6-amino-9H-purin-2-ylsulfanylmethyl)-5-methyl-3-o-tolyl-3H-quinazolin-4-one 2-(2-amino-6-ethylamino-pyrimidin-4-ylsulfanylmethyl)-5-methyl-3-o-tolyl-3H-quinazolin-4-one 2-(3-amino-5-methylsulfanyl-1,2,4-triazol-1-ylmethyl)-5-methyl-3-o-tolyl-3H-quinazolin-4-one 2-(5-amino-3-methylsulfanyl-1,2,4-triazol-1-ylmethyl)-5-methyl-3-o-tolyl-3H-quinazolin-4-one 5-methyl-2-(6-methylaminopurin-9-ylmethyl)-3-o-tolyl-3H-quinazolin-4-one 2-(6-benzylaminopurin-9-yimethyl)-5-methyl-3-o-tolyl-3H-quinazolin-4-one 2-(2,6-diaminopurin-9-ylmethyl)-5-methyl-3-o-tolyl-3H-quinazolin-4-one 5-methyl-2-(9H-purin-6-ylsulfanylmethyl)-3-o-tolyl-3H-quinazolin-4-one 3-isobutyl-5-methyl-2-(9H-purin-6-ylsulfanylmethyl)-3H-quinazolin-4-one N-{2-[5-Methyl-4-oxo-2-(9H-purin-6-ylsulfanylmethyl)-4H-quinazolin-3-yl]-phenyl}-acetamide 5-methyl-3-(E-2-methyl-cyclohexyl)-2-(9H-purin-6-ylsulfanylmethyl)-3H-quinazolin-4-one 2-[5-methyl-4-oxo-2-(9H-purin-6-ylsulfanylmethyl)-4H-quinazolin-3-yl]-benzoic acid 3-{2-[(2-dimethylaminoethyl)methylamino]phenyl}-5-methyl-2-(9H-purin-6-ylsulfanylmethyl)-3H-quinazolin-4-one 3-(2-chlorophenyl)-5-methoxy-2-(9H-purin-6-ylsulfanylmethyl)-3H-quinazolin-4-one 3-(2-chlorophenyl)-5-(2-morpholin-4-yl-ethylamino)-2-(9H-purin-6-ylsulfanylmethyl)-3H-quinazolin-4-one 3-benzyl-5-methoxy-2-(9H-purin-6-ylsulfanylmethyl)-3H-quinazolin-4-one 2-(6-aminopurin-9-ylmethyl)-3-(2-benzyloxyphenyl)-5-methyl-3H-quinazolin-4-one;

2-(6-aminopurin-9-ylmethyl)-3-(2-hydroxyphenyl)-5-methyl-3H-quinazolin-4-one;

2-(1-(2-amino-9H-purin-6-ylamino)ethyl)-5-methyl-3-o-tolyl-3H-quinazolin-4-one;

5-methyl-2-[1-(9H-purin-6-ylamino)propyl]-3-o-tolyl-3H-quinazolin-4-one;

2-(1-(2-fluoro-9H-purin-6-ylamino)propyl)-5-methyl-3-o-tolyl-3H-quinazolin-4-one;

2-(1-(2-amino-9H-purin-6-ylamino)propyl)-5-methyl-3-o-tolyl-3H-quinazolin-4-one;

2-(2-benzyloxy-1-(9H-purin-6-ylamino)ethyl)-5-methyl-3-o-tolyl-3H-quinazolin-4-one;

2-(6-aminopurin-9-ylmethyl)-5-methyl-3-{2-(2-(1-methylpyrrolidin-2-yl)-ethoxy)-phenyl}-3H-quinazolin-4-one;

2-(6-aminopurin-9-ylmethyl)-3-(2-(3-dimethylaminopropoxy)-phenyl)-5-methyl-3H-quinazolin-4-one;

2-(6-aminopurin-9-ylmethyl)-5-methyl-3-(2-prop-2-ynyloxyphenyl)-3H-quinazolin-4-one; and 2-{2-(1-(6-aminopurin-9-ylmethyl)-5-methyl-4-oxo-4H-quinazolin-3-yl[-phenoxy}-acetamide.

3. A method of inhibiting kinase activity of a phosphatidylinositol 3-kinase delta polypeptide comprising a step of contacting the polypeptide with a compound having a structure

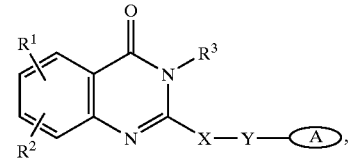

(I)

wherein A is an optionally substituted monocyclic 5-membered heterocyclic ring system containing two or three nitrogen atoms or a bicyclic ring system containing at least two nitrogen atoms, and at least one ring of the bicyclic system is aromatic;

X is selected from the group consisting of $C(R^b)_2$, $CH_2CHR^b$, and $CH=C(R^b)$;

Y is selected from the group consisting of null, S, SO, and $SO_2$, NH, O, C(=O), OC(=O), C(=O)O, and NHC(=O)CH_2S$;

$R^1$ and $R^2$, independently, are selected from the group consisting of hydrogen, $C_{1-6}$alkyl, aryl, heteroaryl, halo, $NHC(=O)C_{1-3}$alkyleneN$(R^a)_2$, $NO_2$, $OR^a$, $CF_3$, $OCF_3$, $N(R^a)_2$, CN, $OC(=O)R^a$, $C(=O)R^a$, $C(=O)OR^a$, aryl$OR^b$, Het, $NR^aC(=O)C_{1-3}$alkyleneC(=O)OR^a$, aryl$OC_{1-3}$alkyleneN$(R^a)_2$, aryl$OC(=O)R^a$, $C_{1-4}$alkyleneC(=O)OR$^a$, $OC_{1-4}$alkyleneC(=O)OR$^a$, $C_{1-4}$alkyleneOC$_{1-4}$alkyleneC(=O)OR$^a$, $C(=O)NR^aSO_2R^a$, $C_{1-4}$alkyleneN$(R^a)_2$, $C_{2-6}$alkenyleneN$(R^a)_2$, $C(=O)NR^aC_{1-4}$alkyleneOR$^a$, $C(=O)NR^aC_{1-4}$alkyleneHet, $OC_{2-4}$alkyleneN$(R^a)_2$, $OC_{1-4}$alkyleneCH(OR$^b$)CH$_2$N$(R^a)_2$, $OC_{1-4}$alkyleneHet, $OC_{2-4}$alkyleneOR$^a$, $OC_{2-4}$alkyleneNR$^a$C(=O)OR$^a$, $NR^aC_{1-4}$alkyleneN$(R^a)_2$, $NR^aC(=O)R^a$, $NR^aC(=O)-N(R^a)_2$, $N(SO^2C_{1-4}$alkyl)$_2$, $NR^a(SO_2C_{1-4}$alkyl), $SO_2N(R^a)_2$, OSO$_2$CF$_3$, C$_{1-3}$alkylenearyl, C$_{1-4}$alkyleneHet, C$_{1-6}$alkyleneOR$^b$, C$_{1-3}$alkyleneN(R$^a$)$_2$, C(=O)N(R$^a$)$_2$, NHC(=O)C$_1$-C$_3$alkylenearyl, C$_{3-8}$cycloalkyl, C$_{3-8}$heterocycloalkyl, arylOC$_{1-3}$alkyleneN(R$^a$)$_2$, arylOC(=O)R$^b$, NHC(=O)C$_{1-3}$alkyleneC$_{3-8}$heterocycloalkyl, NHC(=O)C$_{1-3}$alkyleneHet, OC$_{1-4}$alkyleneOC$_{1-4}$alkyleneC(O)OR$^b$, C(=O)C$_{1-4}$alkyleneHet, and NRC(=O)haloC$_{1-6}$alkyl;

or R$^1$ and R$^2$ are taken together to form a 3-or 4-membered alkylene or alkenylene chain component of a 5- or 6-mernbered ring, optionally containing at least one heteroatom;

R$^3$ is selected from the group consisting of optionally substituted hydrogen, C$_{1-6}$alkyl, C$_{3-8}$cycloalkyl, C$_{3-8}$heterocycloalkyl, C$_{1-4}$alkylenecycloalkyl, C$_{2-6}$alkenyl, C$_{1-3}$alkylenearyl, arylC$_{1-3}$alkyl, C(=O)R$^a$, aryl, heteroaryl, C(=O)OR$^a$, C(=O)N(R$^a$)$_2$, C(=S)N(R$^a$)$_2$, SO$_2$R$^a$, SO$_2$N(R$^a$)$_2$, S(=O)R$^a$, S(=O)N(R$^a$)$_2$, C(=O)NR$^a$C$_{1-4}$alkyleneOR$^a$, C(=O)NR$^a$C$_{1-4}$alkyleneHet, C(=O)C$_{1-4}$alkylenearyl, C(=O)C$_{1-4}$alkyleneheteroaryl, C$_{1-4}$alkylenearyl substituted with one or more of SO$_2$N(R$^a$)$_2$, N(R$^a$)$_2$, C(=O)OR$^a$, NR$^a$SO$_2$CF$_3$, CN, NO$_2$, C(=O)R$^a$, OR$^a$, C$_{1-4}$alkyleneN(R$^a$)$_2$, and OC$_{1-4}$alkyleneN(R$^a$)$_2$, C$_{1-4}$alkyleneheteroaryl, C$_{1-4}$alkyleneHet, C$_{1-4}$alkyleneC(=O)C$_{1-4}$alkylenearyl, C$_{1-4}$alkyleneC(=O)C$_{1-4}$alkyleneheteroaryl, C$_{1-4}$alkyleneC(=O)Het, C$_{1-4}$alkyleneC(=O)N(R$^a$)$_2$, C$_{1-4}$alkyleneOR$^a$, C$_{1-4}$alkyleneNR$^a$C(=O)R$^a$, C$_{1-4}$alkyleneOC$_{1-4}$alkyleneOR$^a$, C$_{1-4}$alkyleneN(R$^a$)$_2$, C$_{1-4}$alkyleneC(=O)OR$^a$, and C$_{1-4}$alkyleneOC$_{1-4}$alkyleneC(=O)OR$^a$;

R$^a$ is selected from the group consisting of hydrogen, C$_{1-6}$alkyl, C$_{3-8}$cycloalkyl, C$_{3-8}$heterocycloalkyl, C$_{1-3}$alkyleneN(R$^c$)$_2$, aryl, arylC$_{1-3}$alkyl, C$_{1-3}$alkylenearyl, heteroaryl, heteroarylC$_{1-3}$alkyl, and C$_{1-3}$alkyleneheteroaryl;

or two R$^a$ groups are taken together to form a 5-or 6-membered ring, optionally containing at least one heteroatom;

R$^b$ is selected from the group consisting of hydrogen, C$_{1-6}$alkyl, heteroC$_{1-3}$alkyl, C$_{1-3}$alkyleneheteroC$_{1-3}$alkyl, arylheteroC$_{1-3}$alkyl, and aryl, heteroaryl, arylC$_{1-3}$ alkyl, heteroarylC$_{1-3}$alkyl, C$_{1-3}$alkylenearyl, and C$_{1-3}$alkyleneheteroaryl;

R$^c$ is selected from the group consisting of hydrogen, C$_{1-6}$alkyl, C$_{3-6}$cycloalkyl, aryl, and heteroaryl;

Het is a 5- or 6-menibered heterocyclic ring, saturated or partially or fully unsaturated, containing at least one heteroatom selected from the group consisting of oxygen, nitrogen, and sulfur; selected from the group consisting of 1,3-dioxolane, 2-pyrazoline, pyrazolidine, pyrrolidine, piperazine, pyrroline, 2H-pyran, 4H-pyran, morpholine, thiomorpholine, piperidine, 1,4-dithiane, and 2,4-dioxane, and optionally substituted with C$_{1-4}$alkyl or C(=O)OR$^a$;

and pharmaceutically acceptable salts or solvates thereof.

4. A compound having a general structural formula

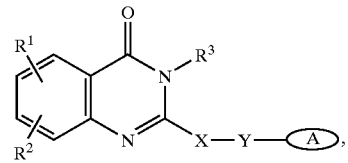

(I)

wherein A is an optionally substituted monocyclic 5-membered heterocyclic ring system containing two or three nitrogen atoms or a bicyclic ring system containing at least two nitrogen atoms, and at least one ring of the cyclic system is aromatic;

X is selected from the group consisting of C(R$^b$)$_2$, CH$_2$CHR$^b$, and CH=C(R$^b$);

Y is selected from the group consisting of null, S, SO, and SO$_2$, NH, O, C(=O), OC(=O), C(=O)O, and NHC(=O)CH$_2$S;

R$^1$ and R$^2$, independently, are selected from the group consisting of hydrogen, C$_{1-6}$alkyl, aryl, heteroaryl, halo, NHC(=O)C$_{1-3}$alkyleneN(R$^a$)$_2$, NO$_2$, OR$^a$, CF$_3$, OCF$_3$, N(R$^a$)$_2$, CN, OC(=O)R$^a$, C(=O)R$^a$, C(=O)OR$^a$, arylOR$^b$, Het, NR$^a$C(=O)C$_{1-3}$alkyleneC(=O)OR$^a$, arylOC$_{1-3}$alkyleneN(R$^a$)$_2$, arylOC(=O)R$^a$, C$_{1-4}$alkyleneC(=O)OR$^a$, OC$_{1-4}$alkyleneC(=O) OR$^a$, C$_{1-4}$alkyleneOC$_{1-4}$alkyleneC(=O)OR$^a$, C(=O)—NR$^a$SO$_2$R$^a$, C$_{1-4}$alkyleneN(R$^a$)$_2$, C$_{2-6}$alkenyleneN(R$^a$)$_2$, C(=O)—NR$^a$C$_{1-4}$alkyleneOR$^a$, C(=O)NR$^a$C$_{1-4}$alkyleneHet, OC$_{2-4}$alkyleneN(R$^a$)$_2$, OC$_{1-4}$alkyleneCH(OR$^b$)CH$_2$N(R$^a$)$_2$, OC$_{1-4}$alkyleneHet, OC$_{2-4}$alkyleneOR$^a$, OC$_{2-4}$alkyleneNR$^a$C(=O)OR$^a$, NR$^a$C$_{1-4}$alkyleneN(R$^a$)$_2$, NR$^a$C(=O)R$^a$, NR$^a$C(=O)N(R$^a$)$_2$, N(SO$_2$C$_{1-4}$alkyl)$_2$, NR$^a$(SO$_2$C$_{1-4}$alkyl), SO$_2$N(R$^a$)$_2$, OSO$_2$CF$_3$, C$_{1-3}$alkylenearyl, C$_{1-4}$alkyleneHet, C$_{1-6}$alkyleneOR$^b$, C$_{1-3}$alkyleneN(R$^a$)$_2$, C(=O)N(R$^a$)$_2$, NHC(=O)C$_1$-C$_3$alkylenearyl, C$_{3-8}$cycloalkyl, C$_{3-8}$heterocycloalkyl, arylOC$_{1-3}$alkyleneN(R$^a$)$_2$, arylOC(=O)R$^b$, NHC(=O)C$_{1-3}$alkyleneC$_{3-8}$heterocycloalkyl, NHC(=O) C$_{1-3}$alkyleneHet, OC$_{1-4}$alkyleneOC$_{1-4}$alkyleneC(=O)OR$^b$, C(=O)C$_{1-4}$alkyleneHet, and NHC(=O)haloC$_{1-6}$alkyl;

or R$^1$ and R$^2$ are taken together to form a 3-or 4-membered alkylene or alkenylene chain component of a 5-or 6-membered ring, optionally containing at least one heteroatom;

R$^3$ is selected from the group consisting of optionally substituted hydrogen, C$_{1-6}$alkyl, C$_{3-8}$cycloalkyl, C$_{3-8}$heterocycloalkyl, C$_{1-4}$alkylenecycloalkyl, C$_{2-6}$alkenyl, C$_{1-3}$alkylenearyl, arylC$_{1-3}$alkyl, C(=O)R$^a$, aryl, heteroaryl, C(=O)OR$^a$, C(=O)N(R$^a$)$_2$, C(=S)N(R$^a$)$_2$, SO$_2$R$^a$, SO$_2$N(R$^a$)$_2$, S(=O)R$^a$, S(=O)N(R$^a$)$_2$, C(=O)NR$^a$C$_{1-4}$alkyleneOR$^a$, C(=O)NR$^a$C$_{1-4}$alkyleneHet, C(=O)C$_{1-4}$alkylenearyl, C(=O)C$_{1-4}$alkyleneheteroaryl, C$_{1-4}$alkylenearyl substituted with one or more of SO$_2$N(R$^a$)$_2$, N(R$^a$)$_2$, C(=O)OR$^a$, NR$^a$SO$_2$CF$_3$, CN, NO$_2$, C(=O)R$^a$, OR$^a$, C$_{1-4}$alkyleneN(R$^a$)$_2$, and OC$_{1-4}$alkyleneN(R$^a$)$_2$, C$_{1-4}$alkyleneheteroaryl, C$_{1-4}$alkyleneHet, C$_{1-4}$alkyleneC(=O)C$_{1-4}$alkylenearyl, C$_{1-4}$alkyleneC(O)—C$_{1-4}$alkyleneheteroaryl, C$_{1-4}$alkyleneC(=O)Het, C$_{1-4}$alkyleneC(=O)N(R$^a$)$_2$, C$_{1-4}$alkyleneOR$^a$, C$_{1-4}$alkyleneNR$^a$C(=O)R$^a$, C$_{1-4}$alkyleneOC$_{1-4}$alkyleneOR$^a$, C$_{1-4}$alkyleneN(R$^a$)$_2$, C$_{1-4}$alkyleneC(=O)OR$^a$, and C$_{1-4}$alkyleneOC$_{1-4}$alkyleneC(=O)OR$^a$;

$R^d$ is selected from the group consisting of hydrogen, $C_{1-6}$alkyl, $C_{3-8}$cycloalkyl, $C_{3-8}$heterocycloalkyl, $C_{1-3}$alkyleneN($R^c$)$_2$, aryl, aryl$C_{1-3}$alkyl, $C_{1-3}$alkylenearyl, heteroaryl, heteroaryl$C_{1-3}$alkyl, and $C_{1-3}$alkyleneheteroaryl;

or two $R^a$ groups are taken together to form a 5-or 6-membered ring, optionally containing at least one heteroatom;

$R^b$ is selected from the group consisting of hydrogen, $C_{1-6}$alkyl, hetero$C_{1-3}$alkyl, $C_{1-3}$alkyleneheteroC$_{1-3}$alkyl, arylhetero$C_{1-3}$alkyl, and aryl, heteroaryl, aryl$C_{1-3}$ alkyl, heteroaryl$C_{1-3}$alkyl, $C_{1-3}$alkylenearyl, and $C_{1-3}$alkyleneheteroaryl;

$R^c$ is selected from the group consisting of hydrogen, $C_{1-6}$alkyl, $C_{3-8}$cycloalkyl, aryl, and heteroaryl;

Het is a 5- or 6-membered heterocyclic ring, saturated or partially or fully unsaturated, containing at least one heteroatom selected from the group consisting of oxygen, nitrogen, and sulfur, selected from the group consisting of 1,3-dioxolane, 2-pyrazoline, pyrazolidine, pyrrolidirie, piperazine, pyrroline, 2H-pyran, 4H-pyran, morpholine, thiomorpholine, piperidine, 1,4-dithiane, and 1,4-dioxane, and optionally substituted with $C_{1-4}$alkyl or C(=O)OR$^a$;

and pharmaceutically acceptable salts or solvates thereof, with the provisos that if X—Y is CH$_2$S, then R$^3$ is different from

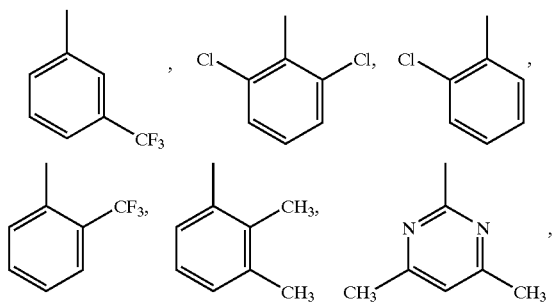

and if X—Y is CH$_2$S, then R$^3$ is different from —CH$_2$CH(OH)CH$_2$OH substituted phenyl.

5. The compound of claim 4 wherein X is selected from the group consisting of CH$_2$, CH$_2$CH$_2$, CH=CH, CH(CH$_3$), CH(CH$_2$CH$_3$), and CH$_2$CH(CH$_3$), and C(CH$_3$)$_2$.

6. The compound of claim 5 wherein Y is selected from the group consisting of null, S, and NH.

7. The compound of claim 5 wherein the A ring system is selected from the group consisting of

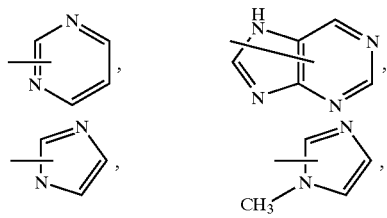

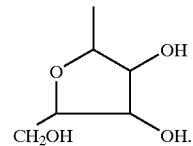, and .

8. The compound of claim 7 wherein the A ring system is substituted with one to three substituents selected from the group consisting of N(R$^a$)$_2$, halo, C$_{1-3}$alkyl, S(C$_{1-3}$alkyl), OR$^a$, and

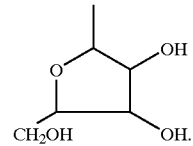

9. The compound of claim 8 wherein the A ring system is substituted with one to three substituents selected from the group consisting of NH$_2$, NH(CH$_3$), N(CH$_3$)$_2$, NHCH$_2$C$_6$H$_5$, NH(C$_2$H$_5$), Cl, F, CH$_3$, SCH$_3$, OH, and

10. The compound of claim 5 wherein R$^1$ and R$^2$, independently, are selected from the group consisting of hydrogen, OR$^a$, halo, C$_{1-6}$alkyl, CF$_3$, NO$_2$, N(R$^a$)$_2$, NR$^a$C$_{1-3}$alkyleneN(R$^a$)$_2$, and OC$_{1-3}$alkyleneOR$^a$, specific substituents include, but are not limited to, H, OCH$_3$, Cl, Br, F, CH$_3$, CF$_3$, NO$_2$, OH, N(CH$_3$)$_2$,

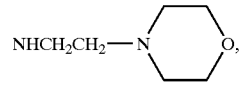

and O(CH$_2$)$_2$OCH$_2$C$_6$H$_5$, or R$^1$ and R$^2$ are taken together to form a five- or six-membered ring.

11. The compound of claim 5 wherein R$^3$ is selected from the group consisting of C$_{1-6}$alkyl, aryl, heteroaryl, C$_{3-8}$cycloalkyl, C$_{3-8}$heterocycloalkyl, C(=O)OR$^a$, C$_{1-4}$alkyleneHet, C$_{1-4}$alkylenecycloalkyl, C$_{1-4}$alkylenearyl, C$_{1-4}$alkyleneC(=O)C$_{1-4}$alkylenearyl, C$_{1-4}$alkyleneC(=O)OR$^a$, C$_{1-4}$alkyleneC(=O)N(R$^a$)$_2$, C$_{1-4}$alkyleneC(=O)Het, C$_{1-4}$alkyleneN(R$^a$)$_2$, and C$_{1-4}$alkyleneNR$^a$C(=O) R$^a$.

12. The compound of claim 5 wherein R$^3$ is selected from the group consisting of OR$^a$, C$_{1-6}$alkyl, aryl, heteroaryl, NO$_2$, N(R$^a$)$_2$, NR$^a$C(=O)R$^a$, C(=O)OC$_2$H$_5$, CH$_2$CH(CH$_3$)$_2$,

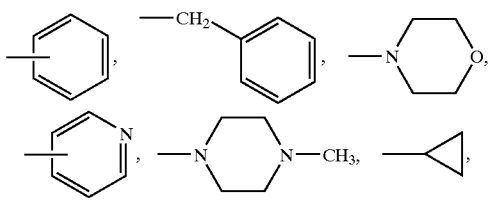

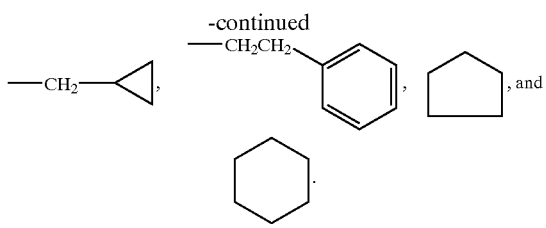

13. The compound of claim 4 wherein $R^3$ is substituted with a substituent selected from the group consisting of halo, $OR^a$, $C_{1-6}$alkyl, aryl, heteroaryl, $NO_2$, $N(R^a)_2$, $NR^aSO_2CF_3$, $NR^aC(=O)R^a$, $C(=O)OR^a$, $SO_2N(R^a)_2$, CN, $C(=O)R^a$, $C_{1-4}$alkyleneN$(R^a)_2$, $OC_{1-4}$alkyleneC≡$CR^a$, $OC_{1-4}$alkyleneC(=O)N$(R^a)_2$, $OC_{1-4}$alkylenearyl, $OC_{1-4}$alkyleneheteroaryl, $OC_{1-4}$alkyleneHet, $OC_{1-4}$alkyleneN$(R^a)_2$, and $N(R^a)C_{1-4}$alkyleneN$(R^a)_2$.

14. The compound of claim 4 wherein $R^3$ is substituted with a substituent selected from the group consisting of Cl, F, $CH_3$, $CH(CH_3)_2$, OH, $OCR^3$, $OCH_2C_6H_5$, $O(CH_2)_3N(CH_3)_2$, $OCH_2C≡CH$, $OCH_2C(=O)NH_2$, $C_6H_5$, $NO_2$, $NH_2$, $NHC(=O)CH_3$, $CO_2H$, and $N(CH_3)CH_2CH_2N(CH_3)_2$, and

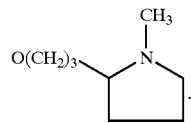

15. The compound of claim 4 selected from the group consisting of:

2-(6-aminopurin-9ylmethyl)-3-(2-benzyloxyphenyl)-5-methyl-3H-quinazolin-4-one;

2-(6-aminopurin-9-ylmethyl)-3-(2-hydroxyphenyl)-5-methyl-3H-quinazolin-4-one;

2-(1-(2-amino-9H-purin-6-ylamino)ethyl)-5-methyl-3-o-tolyl-3H-quinazolin-4-one;

5-methyl-2-[1-(9H-purin-6-ylamino)propyl]-3-o-tolyl-3H-quinazolin-4-one;

2-(1-(2-fluoro-9H-purin-6ylamino)propyl)-5-methyl-3-o-tolyl-3H-quinazolin-4one;

2-(1-(2-amino-9H-purin-6-ylamino)propyl)-5-methyl-3-o-tolyl-3H-quinazolin-4-one;

2-(2-benzyloxy-1-(9H-purin-6-ylamino)ethyl)-5-methyl-3-o-tolyl-3H-quinazolin-4-one;

2-(6-aminopurin-9-ylmethyl)-5-methyl-3-{2-(2-(1-methylpyrrolidin-2-yl)-ethoxy)-phenyl}-3H-quinazolin-4-one;

2-(6-aminopurin-9-ylmethyl)-3-(2-(3-dimethylaminopropoxy)-phenyl)-5-methyl-3H-quinazolin-4-one;

2-(6-aminopurin-9-ylmethyl)-5-methyl-3-(2-prop-2-ynyloxyphenyl)-3H-quinazolin-4-one; and 2-{2-(1-(6-aminopurin-9-ylmethyl)-5-methyl-4-oxo-4H-quinazolin-3-yl)-phenoxy}-acetamide.

* * * * *

UNITED STATES PATENT AND TRADEMARK OFFICE
CERTIFICATE OF CORRECTION

PATENT NO.       : 6,949,535 B2
APPLICATION NO.  : 10/697912
DATED            : September 27, 2005
INVENTOR(S)      : Sadhu et al.

It is certified that error appears in the above-identified patent and that said Letters Patent is hereby corrected as shown below:

Column 1, line 49, "In vitro" should be italicized

Column 3, line 30, "Immunity" should be italicized

Column 5, line 24, "10-told" should be -- 10-fold --

Column 8, line 38, delete "is"

Column 10, line 14, "in vitro," "in vivo," and "ex vivo" all should be italicized Column 10, lines 35, 36, "in vitro," "in vivo," and "ex vivo" all should be italicized Column 10, line 46, "in vivo" should be italicized Column 10, line 50, "ex vivo" should be italicized Column 10, line 51, "In vitro" should be italicized Column 11, line 30, "(IC$_{50}$" should be -- (IC$_{50}$) --

Column 11, line 31, delete second occurrence of "at least"

Column 12, line 50, "(9h" should be -- (9H --

Column 15, line 27, "-3h-" should be -- -3H- --

Column 17, line 16, insert -- O, C(=O), -- between "NH," and "OC(=O)," and delete second occurrence of "OC(=O),"

Column 17, line 20, "C$_3$alkylene" should be -- C$_{1-3}$alkylene --

Column 18, line 24, "decahydro-naphthyl" should be -- decahydronaphthyl --

Column 18, line 56, "tetra-hydronaphthyl" should be -- tetrahydronaphthyl --

Column 22, line 2, "3h" should be -- 3H --

Column 23, line 37, "3h" should be -- 3H --

Column 24, line 61, "in vivo" should be italicized

UNITED STATES PATENT AND TRADEMARK OFFICE
CERTIFICATE OF CORRECTION

PATENT NO.        : 6,949,535 B2
APPLICATION NO.   : 10/697912
DATED             : September 27, 2005
INVENTOR(S)       : Sadhu et al.

It is certified that error appears in the above-identified patent and that said Letters Patent is hereby corrected as shown below:

Column 26, line 46, "than" should be -- that --

Column 26, line 52, "in vitro" (both occurrences) should be italicized

Column 26, line 53, "in vivo" should be italicized

Column 27, line 66, "and or" should be -- and/or --

Column 31, line 40, "in vitro" should be italicized

Column 32, line 38, "in vivo" should be italicized

Column 32, line 39, "in vivo" should be italicized

Column 34, line 28, "in situ" should be italicized

Column 34, line 55, "in situ" should be italicized

Column 35, line 17, "pharmaceutical" should be -- pharmaceutically --

Column 35, line 37, "intra-medullary" should be -- intramedullary --

Column 36, line 16, "inter alia" should be italicized

Column 36, line 40, "in vivo" should be italicized (both occurrences)

Column 36, line 43, "in vitro" and "in vivo" should be italicized

Column 36, line 60, -- "LD50/ED50" should be -- $LD_{50}/ED_{50}$ --

Column 38, line 41, "EcOR1-Not1" should be -- EcoR1-Not1 --

Column 38, line 60, "BamH1-EcOR1" should be -- BamH1-EcoR1 --

Column 38, line 62, "BamH1-EcOR1" should be -- BamH1-EcoR1 --

Column 39, line 13, "HC1," should be -- HCI, --

Column 44, line 32, "U/mL)" should be -- μ/mL) --

UNITED STATES PATENT AND TRADEMARK OFFICE
CERTIFICATE OF CORRECTION

PATENT NO. : 6,949,535 B2
APPLICATION NO. : 10/697912
DATED : September 27, 2005
INVENTOR(S) : Sadhu et al.

It is certified that error appears in the above-identified patent and that said Letters Patent is hereby corrected as shown below:

Column 44, line 43, "ImmunOResearch" should be -- ImmunoResearch -- Spec., page 102, line 20 - PTO Column 44, line 53, "ImmunOResearch" should be -- ImmunoResearch --

Column 47, line 48, "EtOAC" should be -- EtOAc --

Column 47, line 61, "in vacuo" should be italicized

Column 47, line 67, "in vacuo" should be italicized

Column 48, lines 8-9, "in vacuo" should be italicized

Column 49, line 66, "$CH_2CO_2$" should be -- $CH_2Cl_2$ --

Column 50, line 22, "(br S," should be -- (br s, --

Column 50, line 37, "(br S," should be -- (br s, --

Column 52, line 51, "$CH_2Cl_{21}$" should be -- $CH_2Cl_2$, --

Column 52, line 61, "$CH_2Cl_{21}$" should be -- $CH_2Cl_2$, --

Column 54, line 43, "$O_3$." should be -- $O_3$• -- and "O..05KCl" should be -- O•.05KCl --

Column 54, line 61, "O.0.1" should be -- O•0.1 --

Column 55, line 12, "O.0.1" should be -- O•0.1 --

Column 55, line 57, "245.7-246.0©" should be -- 245.7-246.0°C --

Column 55, line 65, "$C_{20H13}$" should be -- $C_{20}H_{13}$ --; "$N_7O.01$" should be -- $N_7$O•0.1 --; and "O.0.05" should be -- O•0.05 --

Column 56, line 16, "$N_7O.H$" should be --$N_7$O•H --

Column 56, line 35, "$N_7O.0.1$" should be -- $N_7$O•0.1 -- and "O.0.6" should be -- O•0.6 --

UNITED STATES PATENT AND TRADEMARK OFFICE
CERTIFICATE OF CORRECTION

PATENT NO. : 6,949,535 B2
APPLICATION NO. : 10/697912
DATED : September 27, 2005
INVENTOR(S) : Sadhu et al.

It is certified that error appears in the above-identified patent and that said Letters Patent is hereby corrected as shown below:

Column 56, line 58, delete "kinases" between "6-" and "mercaptopurine"

Column 57, line 13, "δ" should be -- δ: --

Column 57, line 41, "O.0.05" should be -- O•0.05 --

Column 58, line 12, "S.0.15" should be -- S•0.15 -- and "O.0.05" should be -- O•0.05 --

Column 58, line 32, "S.0.5" should be -- S•0.5 --

Column 58, line 50, "S.0.15" should be -- S•0.15 -- and "O.0.05" should be -- O•0.05 --

Column 59, line 3, "S.0.2" should be -- S•0.2 -- and "O.0.05" should be -- O•0.05 --

Column 59, line 41, "S.0.2" should be -- S•0.2 -- and "O.0.05" should be -- O•0.05 --

Column 59, line 59, "S.0.1" should be -- S•0.1 -- and "O.0.6" should be -- O•0.6 --

Column 60, line 2, "212.7©" should be -- 212.7°C --

Column 60, line 29, "S.0.4" should be -- S•0.4 -- and "O.0.4" should be -- O•0.4 --

Column 60, line 47, "S.0.4" should be -- S•0.4 -- and "O.0.05" should be -- O•0.05 --

Column 60, line 61, "in vacuo" should be italicized

Column 61, line 4, "(2" should be deleted

Column 61, line 4, "S.0.1" should be -- S•0.1 --

Column 61, line 21, "S.C$_2$H$_6$O.0.3" should be -- S•C$_2$H$_6$O•0.3 --

Column 61, line 40, "S.0.65" should be -- S•0.65 -- and "O.0.1" should be -- O•0.1 --

Column 61, line 51, "136(C)" should be -- 136°C --

Column 62, line 12, "S.0.2" should be -- S•0.2 -- and "O.0.1" should be -- O•0.1 --

Column 62, lines 21-22, "in vacuo" should be italicized

UNITED STATES PATENT AND TRADEMARK OFFICE
CERTIFICATE OF CORRECTION

PATENT NO.        : 6,949,535 B2
APPLICATION NO.   : 10/697912
DATED             : September 27, 2005
INVENTOR(S)       : Sadhu et al.

It is certified that error appears in the above-identified patent and that said Letters Patent is hereby corrected as shown below:

Column 62, line 30, "in vacuo" should be italicized

Column 62, line 31, "HOAC" should be -- HOAc --

Column 62, line 32, "chloro-actyl" should be -- chloroacetyl --

Column 62, lines 33-34, "in vacuo" should be italicized

Column 62, line 39, "in vacuo" should be italicized

Column 62, lines 65-66, "in vacuo" should be italicized

Column 63, line 7, "in vacuo" should be italicized

Column 63, line 10, "in vacuo" should be italicized

Column 63, line 15, "were" should be -- was --

Column 63, line 16, "in vacuo" should be italicized

Column 63, lines 41-42, "in vacuo" should be italicized

Column 63, line 50, "were" should be -- was --

Column 63, line 50, "in vacuo" should be italicized

Column 63, lines 53-54, "in vacuo" should be italicized

Column 63, line 58, "were" should be -- was --

Column 63, line 59, "in vacuo" should be italicized

Column 64, line 3, "1H0" should be -- 1H) --

Column 64, line 10, "S.0.15" should be -- S•0.15 --

Column 64, line 31, "O.0.1H$_2$O.0.05" should be -- O•0.1H$_2$O•0.05 --

Column 64, line 51, "O$_2$.0.5H$_2$O.0.04" should be -- O$_2$•0.5H$_2$O•0.04 --

UNITED STATES PATENT AND TRADEMARK OFFICE
CERTIFICATE OF CORRECTION

PATENT NO. : 6,949,535 B2  Page 6 of 10
APPLICATION NO. : 10/697912
DATED : September 27, 2005
INVENTOR(S) : Sadhu et al.

It is certified that error appears in the above-identified patent and that said Letters Patent is hereby corrected as shown below:

Column 67, line 63, "(10" should be -- (100 --

Column 70, line 60, "0.22 um" should be -- 0.22 µM --

Column 70, lines 61-62, "in vacuo" should be italicized

Column 71, line 45, "in vacuo" should be italicized

Column 71, line 50, "in vacuo" should be italicized

Column 71, line 66, "mL) -was" should be -- mL) was --

Column 71, line 67, "in vacuo" should be italicized

Column 72, line 5, "in vacuo" should be italicized

Column 72, line 30, "in vacuo" should be italicized

Column 74, approximately line 58, last structure, "HN" in center of structure should be -- NH --

Column 75, approximately line 23, "HN" in center of structure should be -- NH --

Column 75, line 51, "in vacuo" should be italicized

Column 76, line 2, "in vacuo" should be italicized

Column 76, line 12, "in vacuo" should be italicized

Column 76, line 24, "in vacuo" should be italicized

Column 76, line 47, "Hz.," should be -- Hz, --

Column 76, line 48, "Hz.," should be -- Hz, --, both occurrences

Column 76, line 49, "Hz.," should be -- Hz, --, both occurrences

Column 77, line 7, "Hz.," should be -- Hz, --

UNITED STATES PATENT AND TRADEMARK OFFICE
CERTIFICATE OF CORRECTION

PATENT NO.        : 6,949,535 B2
APPLICATION NO.   : 10/697912
DATED             : September 27, 2005
INVENTOR(S)       : Sadhu et al.

It is certified that error appears in the above-identified patent and that said Letters Patent is hereby corrected as shown below:

Column 77, line 8, "Hz.," should be -- Hz, --, both occurrences

Column 77, line 9, "Hz.," should be -- Hz, --, both occurrences

Column 77, line 10, "Hz.," should be -- Hz, --

Column 77, line 67, "Hz.," should be -- Hz, --

Column 78, line 1, "Hz.," should be -- Hz, --

Column 78, line 2, "Hz.," should be -- Hz, --, both occurrences

Column 78, line 35, "Hz.," should be -- Hz, --

Column 78, line 45, "HN" should be -- S --

Column 78, line 65, "Hz.," should be -- Hz, --, both occurrences

Column 78, line 66, "Hz.," should be -- Hz, --

Column 79, line 28, "500°C" should be -- 50°C --

Column 79, line 66, "Hz.," should be -- Hz, --

Column 80, line 29, "in vacuo" should be italicized

Column 80, line 35, "Hz.," should be -- Hz, --, both occurrences

Column 84, line 8, "in vacuo" should be italicized

Column 84, line 46, "(S," should be -- (s, --, both occurrences

Column 84, line 66, should "(5," be -- (s, --

Column 85, line 14, "1H0" should be -- 1H), --

Column 87, line 34, "3H0," should be -- 3H), --

Column 87, line 48, "7.47 9d," should be -- 7.47 (d, --

UNITED STATES PATENT AND TRADEMARK OFFICE
CERTIFICATE OF CORRECTION

PATENT NO. : 6,949,535 B2
APPLICATION NO. : 10/697912
DATED : September 27, 2005
INVENTOR(S) : Sadhu et al.

It is certified that error appears in the above-identified patent and that said Letters Patent is hereby corrected as shown below:

Column 88, line 11, "7.69 t," should be -- 7.69 (t, --

Column 88, line 61, "7.34 9d," should be -- 7.34 (d, --

Column 89, line 30, "(br s." should be -- (br s, --

Column 89, line 30, "(br s." should be -- (br s, --

Column 89, line 66, "(T," should be -- (t, --

Column 91, line 21, "7.27 9d," should be -- 7.27 (d, --

Column 92, line 33, "in vacuo" should be italicized

Column 92, line 43, "in vacuo" should be italicized

Column 92, line 46, "in vacuo" should be italicized

Column 92, line 66, "0.22 um" should be -- 0.22 μM --

Column 93, line 1, "in vacuo" should be italicized

Column 93, line 35, "in vacuo" should be italicized

Column 93, line 40, "in vacuo" should be italicized

Column 93, line 45, "0.22 um" should be -- 0.22 μM --

Column 93, line 47, "in vacuo" should be italicized

Column 94, line 6, "220x)." should be -- 220λ). --

Column 94, line 7, "in vacuo" should be italicized

Column 94, line 11, "7/43" should be -- 7.43 --

Column 94, line 13, "(5," should be -- (s, --

Column 94, line 31, "in vacuo" should be italicized

UNITED STATES PATENT AND TRADEMARK OFFICE
CERTIFICATE OF CORRECTION

PATENT NO. : 6,949,535 B2
APPLICATION NO. : 10/697912
DATED : September 27, 2005
INVENTOR(S) : Sadhu et al.

It is certified that error appears in the above-identified patent and that said Letters Patent is hereby corrected as shown below:

Column 94, line 60, "in vacuo" should be italicized

Column 95, line 16, "in vacuo" should be italicized

Column 95, line 43, "in vacuo" should be italicized

Column 96, line 5, "in vacuo" should be italicized

Column 96, line 59, delete second occurrence of "4.6x250mm."

Column 96, line 61, "in vacuo" should be italicized

Column 97, line 18, "220x)." should be -- 220λ). --

Column 97, line 19, "in vacuo" should be italicized

Column 97, line 66, "in vacuo" should be italicized

Column 98, line 1, "(S," should be -- (s, --

Column 103, line 8 (line starting with D-047), should "0.3±01." be -- 0.3±0.1 -- ?

Column 103, line 66, "in vivo" should be italicized

Column 104, line 4, "in vivo" should be italicized

Column 104, line 29, "2.5 ng" should be -- 2.5 mg --

Column 104, line 54, "0.5 ng" should be -- 0.5 mg --

Column 123, line 66, "ylsulfanylrnethyl" should be -- ylsulfanylmethyl --

Column 124, line 17, "ylsulfanylinethyl" should be -- ylsulfanylmethyl --

Column 124, line 37, "ylaminomethyl]" should be -- ylamino)methyl] --

Column 125, line 12, "ylsulfanylinethyl" should be -- ylsulfanylmethyl --

Column 125, line 14, "pyrimidifl" should be -- pyrimidin --

UNITED STATES PATENT AND TRADEMARK OFFICE
CERTIFICATE OF CORRECTION

PATENT NO. : 6,949,535 B2
APPLICATION NO. : 10/697912
DATED : September 27, 2005
INVENTOR(S) : Sadhu et al.

It is certified that error appears in the above-identified patent and that said Letters Patent is hereby corrected as shown below:

Column 125, line 25, "yimethyl)" should be -- ylmethyl) --

Column 125, line 46, "yimethyl)" should be -- ylmethyl) --

Column 126, line 28, "3-y([" should be -- 3-yl] --

Column 127, line 7, "C(O)" should be -- C(=O) --

Column 127, line 55, "menibered" should be -- membered --

Column 129, line 1, "$R^d$" should be -- $R^a$ --

Column 130, line 36, ", specific" should be -- . Specific --

Column 131, line 20, "$OCR^3$" should be -- $OCH_3$ --

Column 132, line 1, "9ylmethyl" should be -- 9-ylmethyl --

Column 132, line 11, "6ylamino" should be -- 6-ylamino --

Signed and Sealed this

Fifth Day of February, 2008

JON W. DUDAS
*Director of the United States Patent and Trademark Office*